(12) United States Patent
Butora et al.

(10) Patent No.: US 7,390,803 B2
(45) Date of Patent: Jun. 24, 2008

(54) TETRAHYDROPYRANYL CYCLOPENTYL BENZYLAMIDE MODULATORS OF CHEMOKINE RECEPTOR ACTIVITY

(75) Inventors: Gabor Butora, Martinsville, NJ (US); Sander G. Mills, Scotch Plains, NJ (US); Alexander Pasternak, Princeton, NJ (US); Kothandaraman Shankaran, Kendall Park, NJ (US); Lihu Yang, Edison, NJ (US); Changyou Zhou, Plainsboro, NJ (US); Stephen D. Goble, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 423 days.

(21) Appl. No.: 10/533,326

(22) PCT Filed: Oct. 24, 2003

(86) PCT No.: PCT/US03/33972

§ 371 (c)(1),
(2), (4) Date: May 2, 2005

(87) PCT Pub. No.: WO2004/041161

PCT Pub. Date: May 21, 2004

(65) Prior Publication Data

US 2006/0116421 A1    Jun. 1, 2006

Related U.S. Application Data

(60) Provisional application No. 60/422,451, filed on Oct. 30, 2002.

(51) Int. Cl.
| | |
|---|---|
| *A61K 31/351* | (2006.01) |
| *A61K 31/4523* | (2006.01) |
| *A61K 31/5365* | (2006.01) |
| *C07D 257/04* | (2006.01) |
| *C07D 231/56* | (2006.01) |

(52) U.S. Cl. .............. 514/231.2; 514/318; 514/459; 540/105; 546/207; 546/214; 548/184; 548/253; 548/362.1; 549/415; 549/425

(58) Field of Classification Search ............ 514/231.2, 514/318, 459; 540/105; 546/207, 214; 548/184, 548/253, 362.1; 549/415, 425
See application file for complete search history.

(56) References Cited

FOREIGN PATENT DOCUMENTS

| WO | WO 02/060859 | 8/2002 |
|---|---|---|
| WO | WO 03/093231 | 11/2003 |

OTHER PUBLICATIONS

Samson et al., "Molecular Cloning and Functional Expression of a New Human CC-Chemokine Receptor Gene", Biochemistry, 1996, vol. 35, No. 11, pp. 3362-3367.

*Primary Examiner*—Taofiq Solola
(74) *Attorney, Agent, or Firm*—James L. McGinnis; Mark Daniel

(57) ABSTRACT

The present invention is directed to compounds of the formula (I) (wherein $R^1$, $R^2$, $R^3$, $R^4$, $R^5$, $R^6$, $R^7$, $R^8$, $R^9$, $R^{10}$, $R^{11}$, $R^{27}$, $R^{28}$, $R^{29}$, $R^{30}$, $R^{31}$, X, m, n and the dashed line are defined herein) which are useful as modulators of chemokine receptor activity. In particular, these compounds are useful as modulators of the chemokine receptor CCR-2

(I)

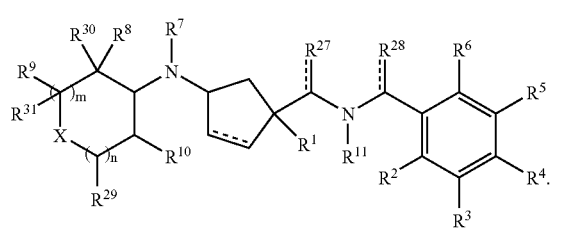

34 Claims, No Drawings

TETRAHYDROPYRANYL CYCLOPENTYL BENZYLAMIDE MODULATORS OF CHEMOKINE RECEPTOR ACTIVITY

RELATED APPLICATION DATA

This is a National filing under 35 USC 371 of PCT/US2003/033972, filed Oct. 24, 2003, which claims priority from U.S. Ser. No. 60/422,451, filed Oct. 30, 2002.

BACKGROUND OF THE INVENTION

The chemokines are a family of small (70-120 amino acids), proinflammatory cytokines, with potent chemotactic activities. Chemokines are chemotactic cytokines that are released by a wide variety of cells to attract various cells, such as monocytes, macrophages, T cells, eosinophils, basophils and neutrophils to sites of inflammation (reviewed in Schall, *Cytokine,* 3, 165-183 (1991) and Murphy, *Rev. Immun.,* 12, 593-633 (1994)). These molecules were originally defined by four conserved cysteines and divided into two subfamilies based on the arrangement of the first cysteine pair. In the CXC-chemokine family, which includes IL-8, GROα, NAP-2 and IP-10, these two cysteines are separated by a single amino acid, while in the CC-chemokine family, which includes RANTES, MCP-1, MCP-2, MCP-3, MIP-1α, MIP-1β and eotaxin, these two residues are adjacent.

The α-chemokines, such as interleukin-8 (IL-8), neutrophil-activating protein-2 (NAP-2) and melanoma growth stimulatory activity protein (MGSA) are chemotactic primarily for neutrophils, whereas β-chemokines, such as RANTES, MIP-1α, MIP-1β, monocyte chemotactic protein-1 (MCP-1), MCP-2, MCP-3 and eotaxin are chemotactic for macrophages, monocytes, T-cells, eosinophils and basophils (Deng, et al., *Nature,* 381, 661-666 (1996)).

The chemokines are secreted by a wide variety of cell types and bind to specific G-protein coupled receptors (GPCRs) (reviewed in Horuk, *Trends Pharm. Sci.,* 15, 159-165 (1994)) present on leukocytes and other cells. These chemokine receptors form a sub-family of GPCRs, which, at present, consists of fifteen characterized members and a number of orphans. Unlike receptors for promiscuous chemoattractants such as C5a, fMLP, PAF, and LTB4, chemokine receptors are more selectively expressed on subsets of leukocytes. Thus, generation of specific chemokines provides a mechanism for recruitment of particular leukocyte subsets.

On binding their cognate ligands, chemokine receptors transduce an intracellular signal though the associated trimeric G protein, resulting in a rapid increase in intracellular calcium concentration. There are at least seven human chemokine receptors that bind or respond to β-chemokines with the following characteristic pattern: CCR-1 (or "CKR-1" or "CC-CKR-1") [MP-1α, MIP-1β, MCP-3, RANTES] (Ben-Barruch, et al., *J. Biol. Chem.,* 270, 22123-22128 (1995); Beote, et al, *Cell,* 72, 415-425 (1993)); CCR-2A and CCR-2B (or "CKR-2A"/"CKR-2A" or "CC-CKR-2A"/"CC-CKR-2A") [MCP-1, MCP-2, MCP-3, MCP-4]; CCR-3 (or "CKR-3" or "CC-CKR-3") [Eotaxin, Eotaxin 2, RANTES, MCP-2, MCP-3] (Rollins, et al., *Blood,* 90,908-928 (1997)); CCR-4 (or "CKR-4" or "CC-CKR-4") [MIP-1α, RANTES, MCP-1] (Rollins, et al., *Blood,* 90, 908-928 (1997)); CCR-5 (or "CKR-5" or "CC-CKR-5") [MIP-1α, RANTES, MIP-1β] (Sanson, et al., *Biochemistry,* 35, 3362-3367 (1996)); and the Duffy blood-group antigen [RANTES, MCP-1] (Chaudhun, et al., *J. Biol. Chem.,* 269, 7835-7838 (1994)). The β-chemokines include eotaxin, MIP ("macrophage inflammatory protein"), MCP ("monocyte chemoattractant protein") and RANTES ("regulation-upon-activation, normal T expressed and secreted") among other chemokines.

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. Humans who are homozygous for the 32-basepair deletion in the CCR-5 gene appear to have less susceptibility to rheumatoid arthritis (Gomez, et al., *Arthritis & Rheumatism,* 42, 989-992 (1999)). A review of the role of eosinophils in allergic inflammation is provided by Kita, H., et al., *J. Exp. Med.* 183, 2421-2426 (1996). A general review of the role of chemokines in allergic inflammation is provided by Lustger, A. D., *New England J. Med.,* 338(7), 426-445 (1998).

A subset of chemokines are potent chemoattractants for monocytes and macrophages. The best characterized of these is MCP-1 (monocyte chemoattractant protein-1), whose primary receptor is CCR2. MCP-1 is produced in a variety of cell types in response to inflammatory stimuli in various species, including rodents and humans, and stimulates chemotaxis in monocytes and a subset of lymphocytes. In particular, MCP-1 production correlates with monocyte and macrophage infiltration at inflammatory sites. Deletion of either MCP-1 or CCR2 by homologous recombination in mice results in marked attenuation of monocyte recruitment in response to thioglycollate injection and *Listeria monocytogenes* infection (Lu et al., *J. Exp. Med.,* 187, 601-608 (1998); Kurihara et al. *J. Exp. Med.,* 186, 1757-1762 (1997); Boring et al. *J. Clin. Invest.,* 100, 2552-2561 (1997); Kuziel et al. *Proc. Natl. Acad. Sci.,* 94, 12053-12058 (1997)). Furthermore, these animals show reduced monocyte infiltration into granulomatous lesions induced by the injection of schistosomal or mycobacterial antigens (Boring et al. *J. Clin. Invest.,* 100, 2552-2561 (1997); Warmington et al. *Am J. Path.,* 154, 1407-1416 (1999)). These data suggest that MCP-1-induced CCR2 activation plays a major role in monocyte recruitment to inflammatory sites, and that antagonism of this activity will produce a sufficient suppression of the immune response to produce therapeutic benefits in immunoinflammatory and autoimmune diseases Accordingly, agents which modulate chemokine receptors such as the CCR-2 receptor would be useful in such disorders and diseases.

In addition, the recruitment of monocytes to inflammatory lesions in the vascular wall is a major component of the pathogenesis of atherogenic plaque formation. MCP-1 is produced and secreted by endothelial cells and intimal smooth muscle cells after injury to the vascular wall in hypercholesterolemic conditions. Monocytes recruited to the site of injury infiltrate the vascular wall and differentiate to foam cells in response to the released MCP-1. Several groups have now demonstrated that aortic lesion size, macrophage content and necrosis are attenuated in MCP-1 −/− or CCR2 −/− mice backcrossed to APO-E −/−, LDL-R −/− or Apo B transgenic mice maintained on high fat diets (Boring et al. *Nature,* 394, 894897 (1998); Gosling et al. *J. Clin. Invest.,* 103, 773-778 (1999)). Thus, CCR2 antagonists may inhibit atherosclerotic lesion formation and pathological progression by impairing monocyte recruitment and differentiation in the arterial wall.

SUMMARY OF THE INVENTION

The present invention is further directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of the formula I:

X is selected from the group consisting of:
—O—, —$NR^{20}$—, —S—, —SO—, —$SO_2$—, and —$CR^{21}R^{22}$—, —$NSO_2R^{20}$—, —$NCOR^{20}$—, —$NCO_2R^{20}$—, —$CR^{21}CO_2R^{20}$—, —$CR^{21}OCOR^{20}$—, —CO—, $C(CH_3)_2$—O—, where $R^{20}$ is selected from: hydrogen, $C_{1-6}$ alkyl, benzyl, phenyl, $C_{3-6}$ cycloalkyl where the alkyl, phenyl, benzyl, and cycloalkyl groups can be unsubstituted or substituted with 1-3 substituents where the substituents are independently selected from: halo, hydroxy, $C_{1-3}$alkyl, $C_{1-3}$alkoxy, —$CO_2H$, —$CO_2$—$C_{1-6}$ alkyl, and trifluoromethyl, where $R^{21}$ and $R^{22}$ are independently selected from: hydrogen, hydroxy, $C_{1-6}$ alkyl, —O—$C_{1-6}$alkyl, benzyl, phenyl, $C_{3-6}$ cycloalkyl where the alkyl, phenyl, benzyl, and cycloalkyl groups can be unsubstituted or substituted with 1-3 substituents are independently selected from: halo, hydroxy, $C_{1-3}$alkyl, $C_{1-3}$alkoxy, —$CO_2H$, —$CO_2$—$C_{1-6}$ alkyl, and trifluoromethyl;

$R^1$ is selected from:
—$C_{1-6}$alkyl, —$C_{0-6}$alkyl-O—$C_{1-6}$alkyl, —$C_{0-6}$alkyl-S—$C_{1-6}$alkyl, —$C_{0-6}$alkyl-$SO_{1-2}$—$C_{1-6}$alkyl, —$C_{0-6}$alkyl-$SO_2$—$NR^{26}$—$C_{1-6}$alkyl, —($C_{0-6}$alkyl)-($C_{3-7}$cycloalkyl)-($C_{0-6}$alkyl), hydroxy, —$CO_2R^{20}$, heterocycle, —CN, —$NR^{20}R^{26}$, —$NR^{26}SO_2R^{20}$, —$NR^{26}COR^{21}$, —$OCOR^{20}$, and phenyl, where $R^{26}$ is selected from: hydrogen, $C_{1-6}$ alkyl, benzyl, phenyl, $C_{3-6}$ cycloalkyl where the alkyl, phenyl, benzyl, and cycloalkyl groups can be unsubstituted or substituted with 1-3 substituents where the substituents are independently selected from: halo, hydroxy, $C_{1-3}$alkyl, $C_{1-3}$alkoxy, —$CO_2H$, —$CO_2$—$C_{1-6}$ alkyl, and trifluoromethyl
where the alkyl and the cycloalkyl are unsubstituted or substituted with 1-7 substituents where the substituents are independently selected from: halo, hydroxy, —O—$C_{1-3}$alkyl, trifluoromethyl, $C_{1-3}$alkyl, —O—$C_{1-3}$ alkyl, —$CO_2R^{20}$, —$SO_2R^{20}$, —$NHCOCH_3$, —$NHSO_2CH_3$, -heterocycle, =O, —CN,
and where the phenyl and heterocycle are unsubstituted or substituted with 1-3 substituents where the substituents are independently selected from: halo, hydroxy, $C_{1-3}$alkyl, $C_{1-3}$alkoxy and trifluoromethyl;

$R^2$ is selected from: hydrogen, $C_{1-6}$alkyl, trifluoromethyl, trifluoromethoxy, chloro, bromo, and phenyl;

$R^3$ is selected from: hydrogen, hydroxy, halo, $C_{1-6}$alkyl, —O—$C_{1-6}$alkyl, —$NR^{20}R^{21}$, —$NR^{20}CO_2R^{21}$, —$NR^{20}CONR^{20}R^{21}$, —$NR^{20}$—$SO_2$—$NR^{20}R^{21}$, —$NR^{20}$—$SO_2$—$R^{21}$, heterocycle, —CN, —$CONR^{20}R^{21}$, —$CO_2R^{20}$, —$NO_2$, —S—$R^{20}$, —SO—$R^{20}$, —$SO_2$—$R^{20}$, and —$SO_2$—$NR^{20}R^{21}$;

$R^4$ is selected from: hydrogen, $C_{1-6}$alkyl, trifluoromethyl, trifluoromethoxy, chloro, bromo, and phenyl;

$R^5$ is selected from: $C_{1-6}$alkyl substituted with 1-6 fluoro and optionally substituted with hydroxyl, —O—$C_{1-6}$alkyl substituted with 1-6 fluoro, —CO—$C_{1-6}$alkyl substituted with 1-6 fluoro, —S—$C_{1-6}$alkyl, -pyridyl, fluoro, chloro, bromo, and phenyl;

$R^6$ is selected from: hydrogen, $C_{1-6}$alkyl, trifluoromethyl, trifluoromethoxy, chloro, bromo, and phenyl;

$R^7$ is selected from: hydrogen, $C_{1-6}$alkyl, and trifluoromethyl;

$R^8$ is selected from: hydrogen, $C_{1-6}$alkyl, where alkyl may be unsubstituted or substituted with 1-6 substituents where the substituents are chosen from the group: fluoro, $C_{1-3}$alkoxy, hydroxy, —$CO_2R^{20}$, fluoro, —O—$C_{1-3}$alkyl, where alkyl may be unsubstituted or substituted with 1-3 fluoro, and $C_{3-6}$ cycloalkyl, —O—$C_{3-6}$cycloalkyl, hydroxy, —$CO_2R^{20}$, —$OCOR^{20}$, phenyl,
or $R^7$ and $R^8$ may be joined together via a $C_{2-4}$alkyl or a $C_{0-2}$alkyl-O—$C_{1-3}$alkyl chain to form a 5-7 membered ring;

$R^9$ is selected from: hydrogen, $C_{1-6}$alkyl, where alkyl may be unsubstituted or substituted with 1-6 substituents where the substituents are chosen from the group: fluoro, $C_{1-3}$alkoxy, hydroxy, —$CO_2R^{20}$, $CO_2R^{20}$, hydroxy, and —O—$C_{1-6}$alkyl, where alkyl may be unsubstituted or substituted with 1-6 substituents where the substituents are chosen from the group: fluoro, $C_{1-3}$alkoxy, hydroxy, —$CO_2R^{20}$,
or $R^8$ and $R^9$ may be joined together by a $C_{1-4}$alkyl chain or a $C_{0-3}$alkyl-O—$C_{0-3}$alkyl chain to form a 3-6 membered ring;

$R^{10}$ is selected from: hydrogen, and $C_{1-6}$alkyl, where alkyl may be unsubstituted or substituted with 1-6 fluoro, fluoro, —O—$C_{3-6}$Cycloalkyl, and —O—$C_{1-3}$alkyl, where alkyl may be unsubstituted or substituted with 1-6 fluoro,
or $R^8$ and $R^{10}$ may be joined together by a $C_{1-3}$alkyl chain or a single bond to form a 3-6 membered ring; where the alkyl are unsubstituted or substituted with 1-3 substituents where the substiuents are independently selected from: halo, hydroxy, —$CO_2R^{20}$, $C_{1-3}$alkyl, and $C_{1-3}$alkoxy,
or $R^8$ and $R^{10}$ may be joined together by a $C_{1-2}$alkyl-O—$C_{1-2}$alkyl chain to form a 6-8 membered ring, where the alkyl are unsubstituted or substituted with 1-3 substituents where the substiuents are independently selected from: halo, hydroxy, —$CO_2R^{20}$, $C_{1-3}$alkyl, and $C_{1-3}$alkoxy,
or $R^8$ and $R^{10}$ may be joined together by a —O—$C_{1-2}$alkyl-O— chain to form a 6-7 membered ring, where the alkyl are unsubstituted or substituted with 1-3 substituents where the substiuents are independently selected from: halo, hydroxy, —CO$_2$R$^{20}$, C$_{1-3}$alkyl, and C$_{1-3}$alkoxy;

R$^{11}$ is selected from: hydrogen, C$_{1-6}$alkyl, and trifluoromethyl;

R$^{27}$ and R$^{28}$ are independently selected from: =O, where R$^{27}$, R$^{28}$, or both, is oxygen and is connected via a double bond, hydrogen, phenyl, and C$_{1-6}$alkyl which may be substituted or unsubstituted with 1-6 of the following substituents: —COR$^{11}$, hydroxy, fluoro, chloro, —O—C$_{1-3}$alkyl;

R$^{29}$, R$^{30}$, and R$^{31}$ are independently selected from: hydrogen, methyl, hydroxyl, trifluoromethyl, methoxy, and trifluoromethoxy;

or R$^{29}$ and R$^9$ are connected by a C$_{1-3}$alkyl bridge;

m is selected from 0, 1, and 2;

n is selected from 0, 1 and 2;

the dashed line represents a single or a double bond;

and pharmaceutically acceptable salts thereof and individual diastereomers thereof.

Preferred compounds of the present invention include those of formula Ia:

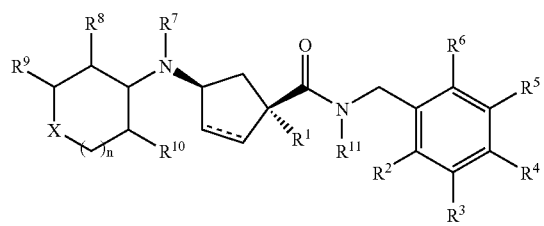

Ia wherein R$^1$, R$^2$, R$^3$, R$^4$, R$^5$, R$^6$, R$^7$, R$^8$, R$^9$, R$^{10}$ and X are defined herein;

and pharmaceutically acceptable salts and individual diastereomers thereof.

Preferred compounds of the present invention also include those of formula Ib:

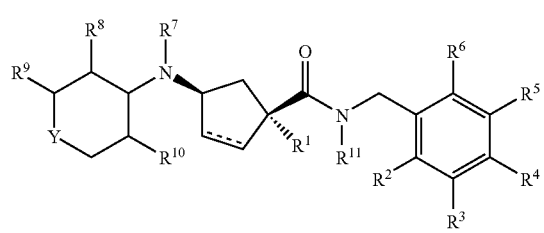

Ib wherein R$^1$, R$^2$, R$^3$, R$^4$, R$^5$, R$^6$, R$^7$, R$^8$, R$^9$, and R$^{10}$ are defined herein, and Y is selected from the group consisting of: —O—, —CH$_2$—, —S—, —SO—, and —SO$_2$—;

and pharmaceutically acceptable salts and individual diastereomers thereof.

More preferred compounds of the present invention also include those of formula Ic:

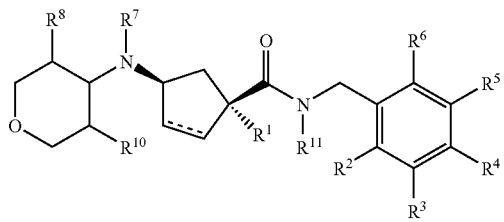

Ic wherein R$^1$, R$^2$, R$^3$, R$^5$ and R$^8$ are defined herein.

More preferred compounds of the present invention also include those of formula Id:

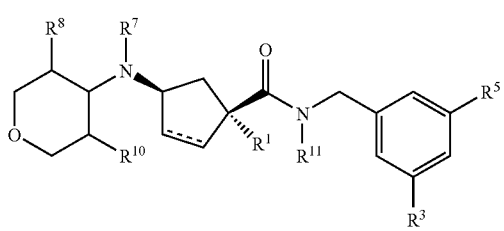

Id wherein:

R$^1$ is selected from: C$_{1-6}$alkyl, C$_{1-6}$alkyl-hydroxy, and C$_{1-6}$alkyl substituted with 1-6 fluoro;

R$^3$ is selected from: C$_{1-6}$alkyl unsubstituted or substituted with 1-6 fluoro, fluoro; chloro, bromo, and phenyl;

R$^5$ is selected from: C$_{1-6}$alkyl unsubstituted or substituted with 1-6 fluoro, fluoro; chloro, bromo, and phenyl;

R$^8$ is selected from: hydrogen, C$_{1-6}$alkyl, C$_{1-6}$alkyl-hydroxy, and C$_{1-6}$alkyl substituted with 1-6 fluoro, and —O—C$_{1-3}$alkyl;

and pharmaceutically acceptable salts and individual diastereomers thereof.

In the present invention it is preferred that X is selected from the group consisting of: —O—, —CH$_2$—, —S—, —SO—, and —SO$_2$—.

In the present invention it is more preferred that X is selected from the group consisting of: —O—, and —CH$_2$—.

In the present invention it is preferred that X is —O—.

In the present invention it is preferred that R$^1$ is selected from:

(1) —C$_{1-6}$alkyl, which is unsubstituted or substituted with 1-6 substituents where the substituents are independently selected from: halo, hydroxy, —O—C$_{1-3}$alkyl, and trifluoromethyl, (2) —C$_{0-6}$alkyl-O—C$_{1-6}$alkyl-, which is unsubstituted or substituted with 1-6 substituents where the substituents are independently selected from: halo, and trifluoromethyl, (3) —C$_{0-6}$alkyl-S—C$_{1-6}$alkyl-, which is unsubstituted or substituted with 1-6 substituents where the substituents are independently selected from: halo, and trifluoromethyl, (4) —(C$_{3-5}$cycloalkyl)-(C$_{0-6}$alkyl), which is unsubstituted or substituted with 1-7 substituents where the substituents are independently selected from: halo, hydroxy, —O—C$_{1-3}$alkyl, and trifluoromethyl.

In the present invention it is more preferred that $R^1$ is $C_{1-6}$alkyl which is unsubstituted or substituted with 1-5 substituents where the substituents are independently selected from: hydroxy, and fluoro.

In the present invention it is more preferred that $R^1$ is selected from: $C_{1-6}$alkyl, $C_{1-6}$alkyl-hydroxy, and $C_{1-6}$alkyl substituted with 1-6 fluoro.

In the present invention it is even more preferred that $R^1$ is selected from: isopropyl, —CH(OH)CH$_3$, and —CH$_2$CF$_3$.

In the present invention it is preferred that $R^2$ is selected from: hydrogen, hydroxy, trifluoromethyl.

In the present invention it is more preferred that $R^2$ is selected from: hydrogen, and hydroxy.

In the present invention it is more preferred that $R^2$ is hydrogen.

In the present invention it is preferred that $R^3$ is selected from: $C_{1-6}$alkyl unsubstituted or substituted with 1-6 fluoro, fluoro, chloro, bromo.

In the present invention it is more preferred that $R^3$ is selected from: trifluromethyl, cyclopropyl, fluoro.

In the present invention it is even more preferred that $R^3$ is trifluromethyl.

In the present invention it is preferred that $R^4$ is selected from: hydrogen, and trifluoromethyl.

In the present invention it is more preferred that $R^4$ is hydrogen.

In the present invention it is preferred that $R^5$ is selected from: $C_{1-6}$alkyl unsubstituted or substituted with 1-6 fluoro, fluoro, chloro, bromo.

In the present invention it is more preferred that $R^5$ is selected from: trifluromethyl, cyclopropyl, and fluoro.

In the present invention it is most preferred that $R^5$ is trifluoromethyl.

In the present invention it is preferred that $R^6$ is hydrogen.

In the present invention it is preferred that $R^7$ is hydrogen.

In the present invention it is preferred that $R^8$ is selected from: hydrogen, $C_{1-3}$alkyl, which is unsubstituted or substituted with 1-6 fluoro, —O—$C_{1-3}$alkyl, fluoro, and hydroxy.

In the present invention it is more preferred that $R^8$ is selected from: hydrogen, methyl, ethyl, trifluoromethyl, fluoro, and —O—CH$_3$.

In the present invention it is preferred that $R^9$ is hydrogen.

In the present invention it is preferred that $R^{10}$ is hydrogen.

In the present invention it is also preferred that $R^8$ and $R^{10}$ are joined together by a —CH$_2$CH$_2$— chain to form a cyclopentyl ring.

In the present invention it is preferred that $R^{27}$ is =O, where $R^{27}$ is O and is joined via a double bond.

In the present invention it is preferred that $R^{29}$, $R^{30}$ and $R^{31}$ are all hydrogen.

Representative compounds of the present invention include the title compounds of the Examples and pharmaceutically acceptable salts and individual diastereomers thereof.

The compounds of the instant invention have at least two asymmetric centers at the 1- and 3-positions of the cyclopentyl ring. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The absolute configurations of the more preferred compounds of this invention are of the orientation where the substituents on the cyclopentyl ring are cis, i.e. as depicted:

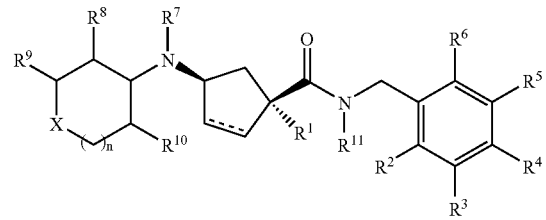

The absolute configurations of the most preferred compounds of this invention are those of the orientation as depicted:

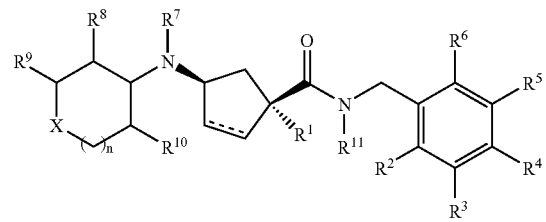

wherein the arido substituent is designated as being of the "R" absolute configuration and the amine substituent is designated as being of the "S" absolute configuration (although the designation for the amido substituent may be specified as "R" if the priority for assignment of the groups at that position differs).

The independent syntheses of diastereomers and enantiomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo. Similarly, $C_{1-8}$, as in $C_{1-8}$alkyl is defined to identify the group as having 1, 2, 3, 4, 5, 6, 7 or 8 carbons in a linear or branched arrangement, such that $C_{1-8}$alkyl specifically includes methyl, ethyl, n-propyl, iso-propyl, n-butyl, iso-butyl, tert-butyl, pentyl, hexyl, heptyl and octyl. Likewise, $C_0$, as in $C_0$alkyl is defined to identify the presence of a direct covalent bond. The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The language "the dashed line represents a single or a double bond" refers to a dashed line used in conjunction with a solid line. Thus a dashed line next to a solid line together represent either a single bond or a double bond. For instance, the depiction

refers to either

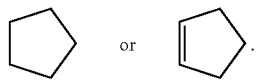

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media such as ether, ethyl acetate, ethanol, isopropanol, or acetonitrile are preferred. Suitable salts are found, e.g. in Remington's Pharmaceutical Sciences, 17th ed., Mack Publishing Company, Easton, Pa., 1985, p. 1418.

Exemplifying the invention is the use of the compounds disclosed in the Examples and herein.

Specific compounds within the present invention include a compound which selected from the group consisting of: the title compounds of the Examples;

and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, in particular CCR-2.

The utility of the compounds in accordance with the present invention as modulators of chemokine receptor activity may be demonstrated by methodology known in the art, such as the assay for chemokine binding as disclosed by Van Riper, et al., *J. Exp. Med.*, 177, 851-856 (1993) which may be readily adapted for measurement of CCR-2 binding.

Receptor affinity in a CCR-2 binding assay was determined by measuring inhibition of $^{125}$I-MCP-1 to the endogenous CCR-2 receptor on various cell types including monocytes, THP-1 cells, or after heterologous expression of the cloned receptor in eukaryotic cells. The cells were suspended in binding buffer (50 mM HEPES, pH 7.2, 5 mM $MgCl_2$, 1 mM $CaCl_2$, and 0.50% BSA) with and added to test compound or DMSO and $^{125}$I-MCP-1 at room temperature for 1 h to allow binding. The cells were then collected on GFB filters, washed with 25 mM HEPES buffer containing 500 mM NaCl and cell bound $^{125}$I-MCP-1 was quantified.

In a chemotaxis assay chemotaxis was performed using T cell depleted PBMC isolated from venous whole or leukophoresed blood and purified by Ficoll-Hypaque centrifugation followed by rosetting with neuraminidase-treated sheep erythrocytes. Once isolated, the cells were washed with HBSS containing 0.1 mg/ml BSA and suspended at $1\times10^7$ cells/ml. Cells were fluorescently labeled in the dark with 2 µM Calcien-AM (Molecular Probes), for 30 min at 37° C. Labeled cells were washed twice and suspended at $5\times10^6$ cells/ml in RPMI 1640 with L-glutamine (without phenol red) containing 0.1 mg/ml BSA. MCP-1 (Peprotech) at 10 ng/ml diluted in same medium or medium alone were added to the bottom wells (27 µl). Monocytes (150,000 cells) were added to the topside of the filter (30 µl) following a 15 min preincubation with DMSO or with various concentrations of test compound. An equal concentration of test compound or DMSO was added to the bottom well to prevent dilution by diffusion. Following a 60 min incubation at 37° C., 5% $CO_2$, the filter was removed and the topside was washed with HEBSS containing 0.1 mg/ml BSA to remove cells that had not migrated into the filter. Spontaneous migration (chemokinesis) was determined in the absence of chemoattractant In particular, the compounds of the following examples had activity in binding to the CCR-2 receptor in the aforementioned assays, generally with an $IC_{50}$ of less than about 1 µM. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, compounds which inhibit or promote chemokine receptor function would be useful in the prevention and/or treatment of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the compounds of the present invention. In a preferred embodiment, the disease or condition is one in which the actions of lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with modulators of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms), (*Trichuriasis, Enterobiasis, Ascariasis, Hookworm, Strongyloidiasis, Trichinosis, filariasis*), trematodes (flukes) (*Schistosomiasis, Clonorchiasis*), cestodes (tape worms) (*Echinococcosis, Taeniasis saginata, Cysticercosis*), visceral worms, visceral larva migraines (e.g., *Toxocara*), eosinophilic gastroenteritis (e.g., *Anisaki* sp., *Phocanema* sp.), and cutaneous larva migraines (*Ancylostona braziliense, Ancylostoma caninum*). In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

The compounds of the present invention are accordingly useful in the prevention and treatment of a wide variety of inflammatory and immunoregulatory disorders and diseases, allergic conditions, atopic conditions, as well as autoimmune pathologies. In a specific embodiment, the present invention is directed to the use of the subject compounds for the prevention or treatment of autoimmune diseases, such as rheumatoid arthritis or psoriatic arthritis.

In another aspect, the instant invention may be used to evaluate putative specific agonists or antagonists of chemokine receptors, including CCR-2. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-2. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of the present compounds in the prevention or treatment of infection by a retrovirus, in particular, herpes virus or the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a preferred aspect of the present invention, a subject compound may be used in a method of inhibiting the binding of a chemokine to a chemokine receptor, such as CCR-2, of a target cell, which comprises contacting the target cell with an amount of the compound which is effective at inhibiting the binding of the chemokine to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism, inverse agonism and/or partial agonism. In a preferred aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

As used herein, the term "treatment" refers both to the treatment and to the prevention or prophylactic therapy of the aforementioned conditions.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, embrel, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antitussive such as codeine, hydrocodone, caramiphen, carbetapentane, or dextramethorphan; a diuretic; and a sedating or non-sedating antihistamine.

Likewise, compounds of the present invention may be used in combination with other drugs that are used in the treatment/prevention/suppression or amelioration of the diseases or conditions for which compounds of the pressent invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO 98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal anti-inflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3, CXCR-3 and CCR-5; (j) cholesterol lowering agents such as HMG-CoA reductase inhibitors (lovastatin, sinvastatin and pravastatin, fluvastatin, atorvastatin, rosuvastatin, and other statins), sequestrants (cholestyramine and colestipol), cholesterol absorption inhibitors (ezetimibe), nicotinic acid, fenofibric acid derivatives (gemfibrozil, clofibrat, fenofibrate and benzafibrate), and probucol; (k) antidiabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, preferably 2.0 to 500, more preferably 3.0 to 200, particularly 1, 5, 10, 15, 20, 25, 30, 50, 75, 100, 125, 150, 175, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made by known procedures or as illustrated.

One of the principal routes used for preparation of compounds within the scope of the instant invention which bear a 1,1,3-trisubstituted cyclopentane framework 1-8 is depicted in Scheme 1A.

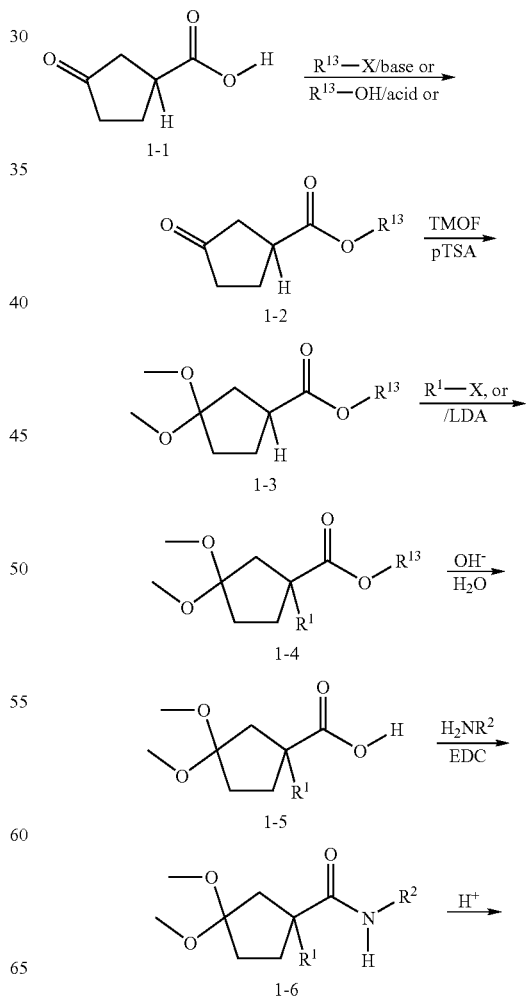

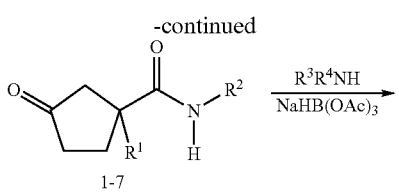

induces usually cleavage of the acetal protecting group as well, and the keto acids 1-9 can be prepared this way in an one-pot procedure. Their conversion to the final modulators of chemokine activity 1-8a can be achieved as described previously.

SCHEME 1B

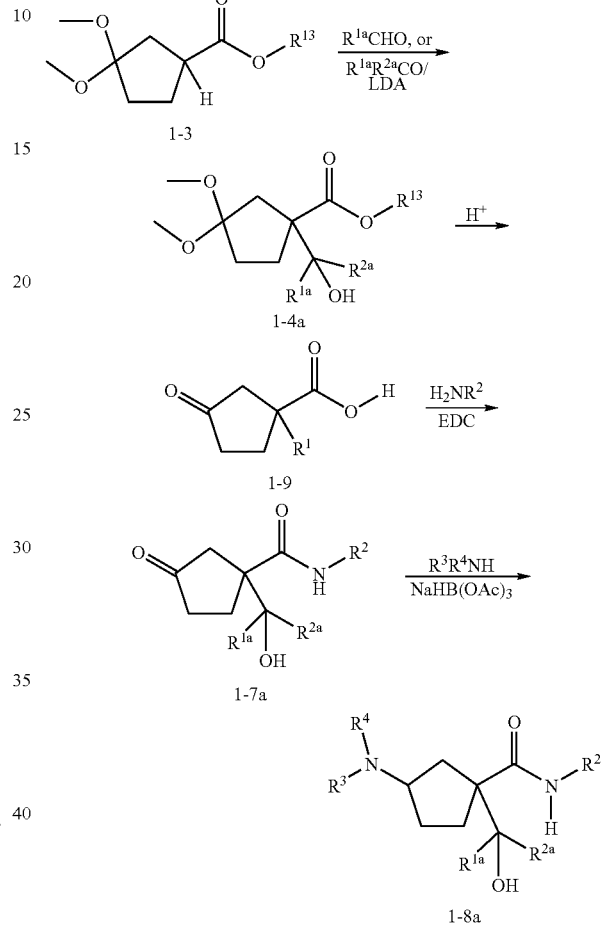

According to this, 3-oxocyclopentanecarboxylic acid (1-1) which was synthesized following a known procedure (Stetter, H., Kuhlman, H., *Liebigs Ann. Chm.*, 1979, 944) is esterified under standard conditions. In the case of $R^{13}$ being a benzyl group the acid is reacted with benzyl chloride in the presence of sodium carbonate in an appropriate solvent, e.g. dimethyl formamide. When $R^{13}$ represents a tert-Butyl group, the respective ester 1-2 can be prepared by reacting the appropriate alcohol in this case tert-Butanol with acid 1-1 in the presence of sulfuric acid. Protection of the oxo-group in 1-2 can be achieved by a number of ways (Greene, T., Wuts, P. G. M., *Protective Groups in Organic Chemistry*, John Wiley & Sons, Inc., New York, N.Y. 1991). The particularly suitable dimethyl acetal protecting group can be introduced using trimethyl orthoformate as a reagent in a suitable solvent such as dichloromethane and methyl alcohol in the presence of an acidic catalyst. Alternatively, in the case of $R^{13}$ being a methyl group, the acid 1-1 can be converted to 1-3 directly by using trimethyl orthoformate and an acidic catalyst, such as para-Toluenesulfonic acid. An alkylation of esters 1-3 with an alkylating agent such as alkyl chloride, bromide or iodide in the presence of an appropriate base such as lithium diisopropylamide, produces intermediates 1-4. The ester protecting group present in 1-4 can be removed by a number of ways, depending on the nature of the ester. Benzyl esters ($R^{13}$=benzyl) can be easily removed by catalytic hydrogenation, methyl esters ($R^{13}$=methyl) can be hydrolyzed in the presence of an acid or base at ambient or elevated temperatures, whereas tert-Butyl esters ($R^{13}$=tert-Butyl) can be easily cleaved under acidic conditions. The amides 1-6 are then prepared by reaction of acids 1-5 with amines $R^2NH_2$ in the presence of a suitable coupling agent, such as 1-[3-(dimethylamino)propyl]-3-ethylcarbodiimide or other agents described in the literature. The acetal protecting group is in general removed under acidic conditions and the final chemokine receptor modulators 1-8 can be then prepared by reaction of ketones 1-7 with appropriate amines $R^3R^4NH$ in a presence of a reducing agent such as sodium triacetoxyborohydride or sodium cyanoborohydride.

The enolate generated from ester 1-3 ($R^{13}$ being a benzyl or tert-Butyl group) in the presence of a strong base such as lithium diisopropylamide can be reacted with aldehydes ($R^{1a}$CHO) or ketones ($R^{1a}R^{2a}$CO) to produce the appropriate hydroxyalkyl substituted intermediates 1-4a as indicated in Scheme 1B. Once again the ester protecting group is removed under conditions suitable for the particular protecting group: the cleavage of the benzyl esters can be achieved hydrogenolytically, and the acids can be converted to the final products 1-8a as described in Scheme 1, or, in the case of the tert-Butyl esters, under acidic conditions. The latter The compounds, Which can be synthesized according to the chemistry described in Schemes 1A and 1B represent diastereoisomeric mixtures (Eliel, E. E., Wilen, S. H., *Stereochemistry of Organic Compounds*, John Wiley & Sons, Inc., New York), and these can be separated into their components by chromatography using normal phase, reverse phase or chiral columns, depending on the nature of the separation. The chiral chromatographic separations are particularly suitable to obtain single isomers.

An alternative route for preparation of compounds 1-8 and 1-8a is detailed in Schemes 2A, 2B and 2C.

SCHEME 2A

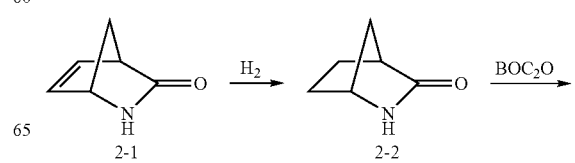

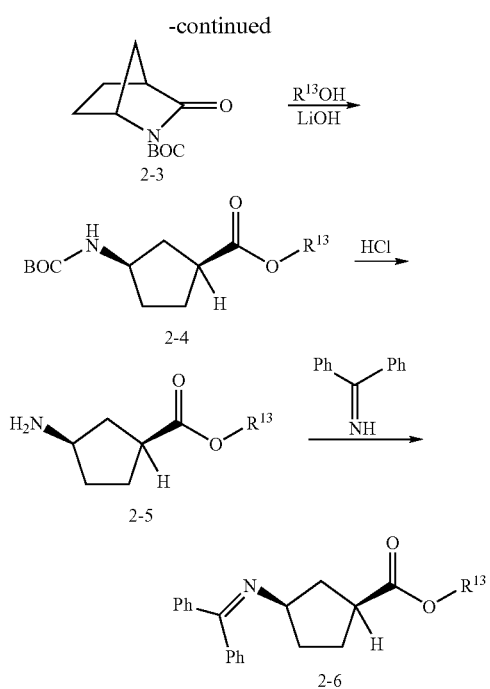

According to this, the commercially available homochiral lactam 2-1 is hydrogenated and the saturated 2-2 is treated with $BOC_2O$ in the presence of a suitable catalyst, e.g. N,N-dimethylamino pyridine. A base catalyzed cleavage of the amide bond in the presence of a suitable alcohol $R^{13}$—OH provides then the respective ester 2-4. The BOC-protecting group is removed, preferably with an acid such as HCl in a aprotic solvent, such as dioxane, to yield the amine 2-5 in a form of a salt. When this amine is mixed with benzophenone imine, the respective Schiff base 2-6 is formed, which can be obtained in pure form by simple filtration to remove ammonium chloride.

The enolate formed from ester 2-6 with a strong base, such as LDA can be reacted with alkyl halides $R^1$—X, as well as aldehydes $R^{1a}CHO$ or ketones $R^{1a}R^{2a}CO$ to obtain intermediates 2-7a, 2-7b and 2-8a, 2-8b respectively, Scheme 2B. These reactions produce a mixture of the respective cis-(2-7a and 2-8a) and trans-(2-7b and 2-8b) diastereoisomers, which can be separated by a suitable chromatography. In most cases, normal phase flash chromatography on deactivated silica gel can be applied with success.

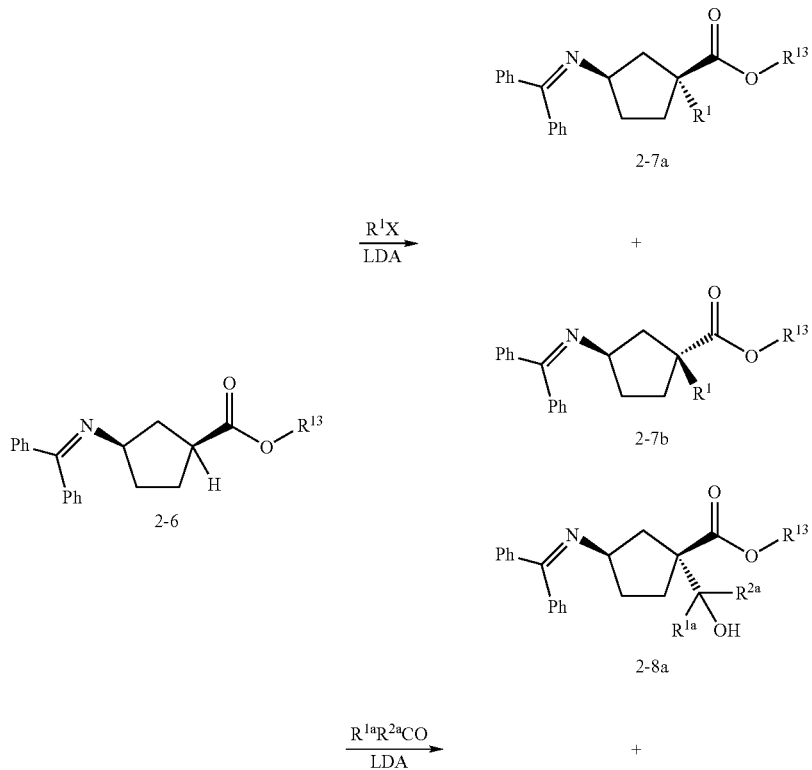

SCHEME 2B

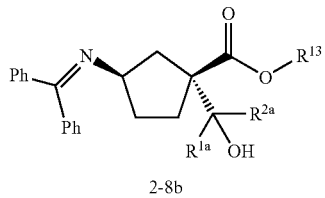
2-8b

The desired cis diastereoisomers 2-7a and 2-8a are then treated with an acid such as HCl to aid hydrolysis of the imine group and the resulting amino group is suitably protected e.g. in a form of a tert-butoxycarbonyl amide (Scheme 2C). The ester group present in intermediates 2-10a is then cleaved. The applied procedure depends on the nature of the ester: e.g. a benzyl ester can be cleaved by hydrogenolysis, an tert-Butyl ester under aprotic acidic conditions and a alkyl ester can be hydrolyzed under either acidic or basic conditions. The formed acids are then coupled with suitable amines as described before and the BOC protecting group is removed with an acid. A reductive alkylation of amines 2-13a with suitable ketones $R^{3a}R^{3b}CO$ or aldehydes $R^{3a}CHO$. If necessary, a second reductive alkylation to introduce the $R^4$ substituent is then performed to yield the final modulators of chemokine activity 1-8b.

SCHEME 2C

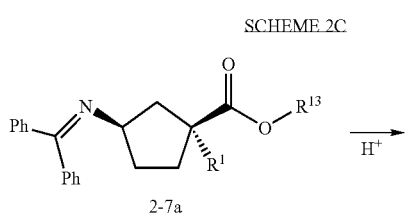

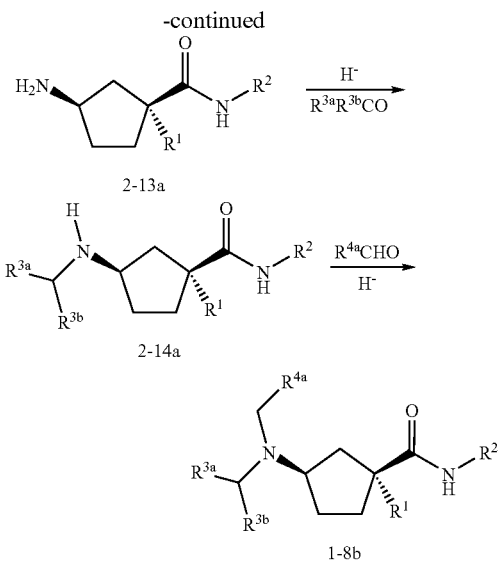

Intermediates 2-8a can be transformed into final products 1-8a in a sequence of steps (Scheme 2D) analogous to those described in Scheme 2C except that a base catalyzed hydrolysis of the ester group was found not to be suitable for the desired transformation.

The chemistry described in Schemes 2A-D offers a considerable advantage in that following these transformations products 1-8 are obtained in a homochiral form, rendering the separation step described in Scheme 1 unnecessary.

SCHEME 2D

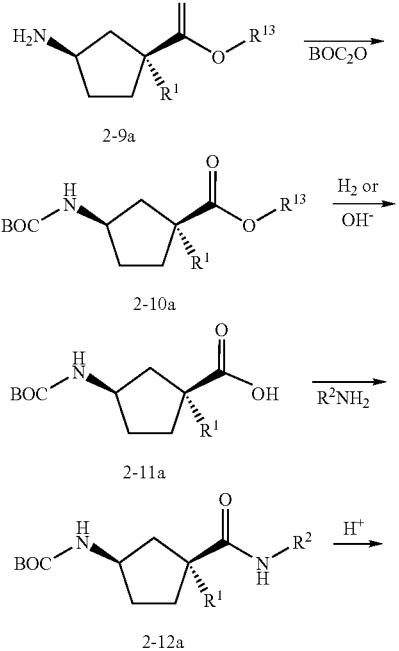

The third principal route to synthesize compounds within the scope of the instant invention is detailed in Scheme 3A and 3B.

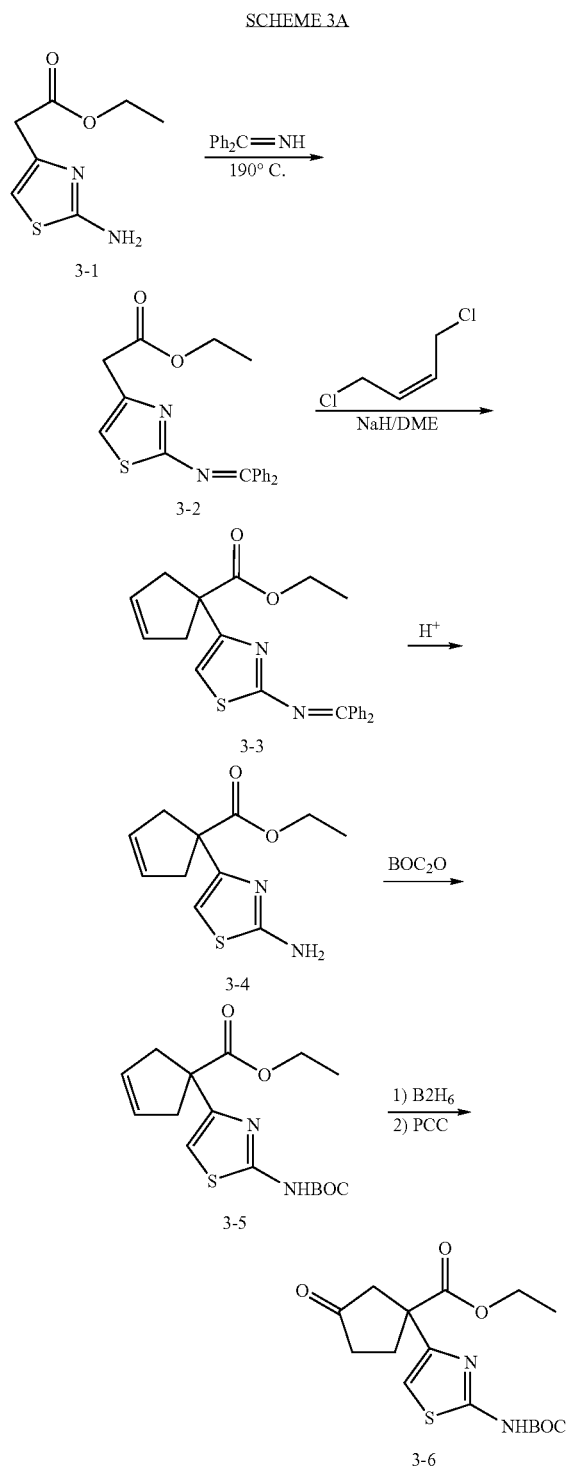

According to this, the commercially available ethyl aminothiazole acetate 3-1 is treated with benzophenone imine, preferably at elevated temperature. The enolate, generated from ester 3-2 with a strong base, e.g. sodium hydride is then double alkylated with 1,4-dichloro-2-butene in a suitable solvent, such as dimethoxyethane preferably in the presence of an additional co-solvent (e.g. DMPU) to suppress undesired side-reactions. The cleavage of the Schiff base 3-3 is accomplished as described previously and the amino group in 3-4 is protected by treatment with $BOC_2O$ in the presence of a catalytic amount of DMAP 3-5. Addition of borane to the double bond (see March, J. *Advanced Organic Chemistry*, 4th edition, John Wiley & Sons Inc., New York, p. 702-707) is followed by a direct pyridinium chlorochromate mediated oxidation of the formed adduct to produce ketones 3-6 directly, in fair yield.

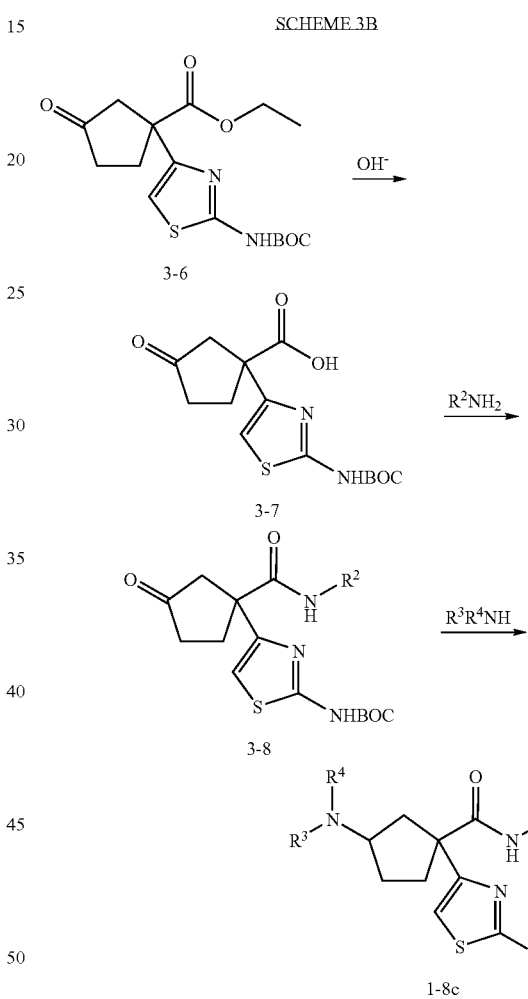

The ester group present in intermediates 3-6 is then removed by a base catalyzed hydrolysis, and the acids 3-7 are coupled to amines $R^2NH_2$ as discussed previously. The last step in preparation of final compounds 1-8c is a reductive amination of ketones 3-8 with amines $R^3R^4NH$ as detailed above. Similarly to the case described in Scheme 1A and 1B this synthetic sequence produces mixtures of diastereoisomers, and their separation can be accomplished using chromatography on normal-, reverse-, or chiral phases.

The previously described synthetic sequence can be used to obtain other modulators of chemokine activity, which carry an aromatic or heteroaromatic ring, as well as other groups which can not be introduced by direct alkylation (e.g. cyano). The required chemical transformations are detailed in Scheme 3C.

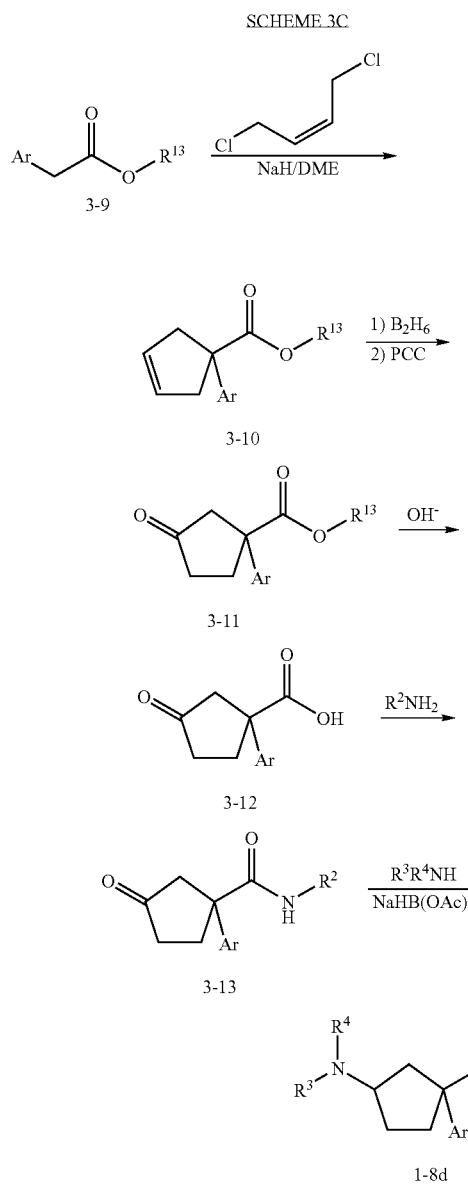

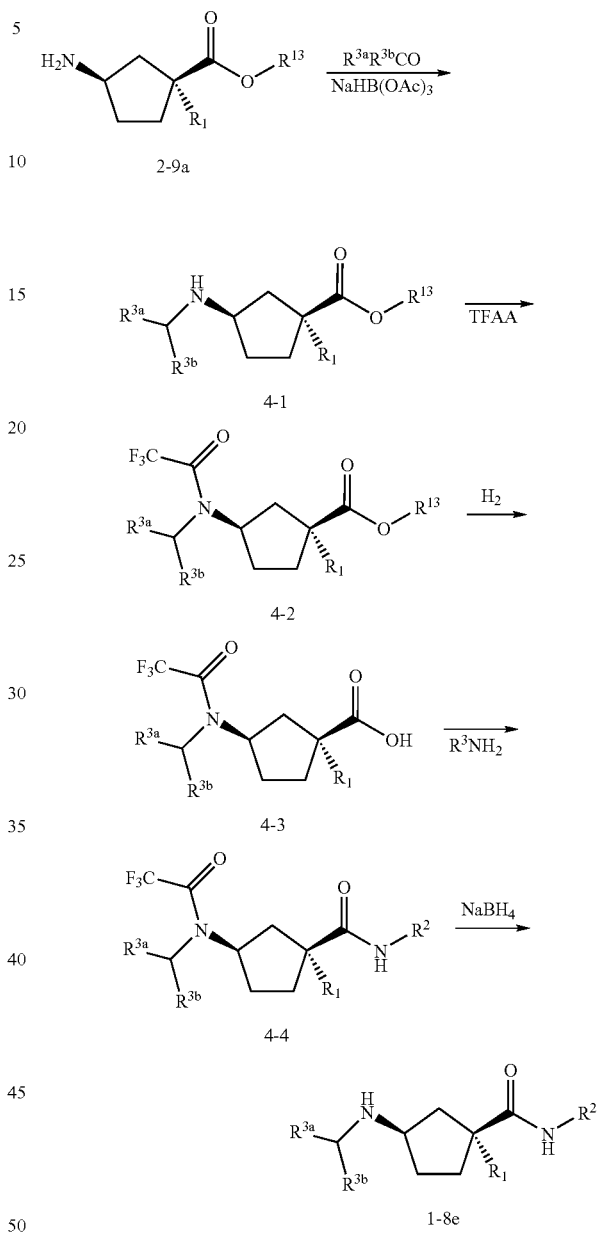

According to this, an alkyl arylacetate is reacted with 1,4-dichloro-2-butene, the olefin is hydroborated and the adduct oxidized to yield 3-11 as discussed previously. A base catalyzed hydrolysis is followed by an amide forming step, and the final amines 1-8c are then prepared in an reductive amination step analogous to that, described above. Similarly to chemistry depicted in Schemes 3A and 3B, the sequence described in Scheme 3C yields a mixture of diastereoisomers. These are then separated into single isomers by means described previously.

In the cases discussed so far, the formation of the amide bond always preceded the reductive amination step. In some instances, however, it was advantageous to reverse this order (Scheme 4).

According to this, the amine intermediate 2-9a is reductively alkylated with an appropriate ketone $R^{3a}R^{3b}CO$ and the resultant secondary amine is protected e.g., as a trifluoroacetamide. The ester group is now cleaved (hydrogenolysis if $R^{13}$ is a benzyl group) and the amide is attached as described above. A reductive or base catalyzed removal of the trifluoroacetyl protecting group then affords the desired modulators of chemokine activity 1-8e.

The amines 5-1 incorporated into the amide portion of 1-8 often contain a substituted benzyl group (Scheme 5). Some of these, e.g. the 3,5-bistrifluoromethylbenzylamine ($R^5$=$CF_3$), 3-fluoro-5-trifluoromethylbenzylamine ($R^5$=F), or others can be obtained commercially, others are available through synthesis, Schemes 6, 7.

SCHEME 5

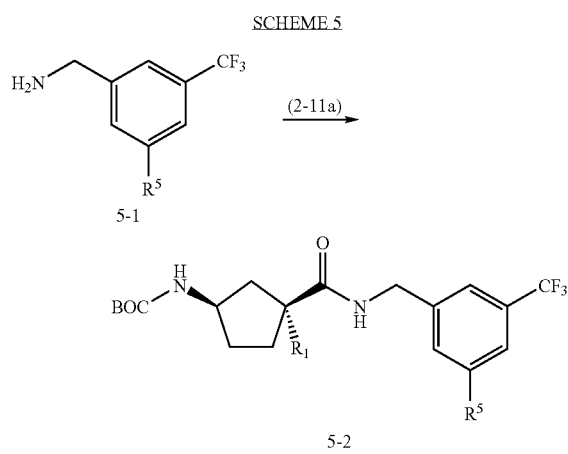

An example of such a synthesis is depicted in Scheme 6. According to this, the commercially available 3-trifluoromethyl-5-amino bromobenzene (6-1) is converted to the corresponding nitrile using zinc cyanide in the presence of palladium, and a Sandmeyer reaction is then used to produce the respective halide 6-3, $R^5$=Cl, I. The reduction of the nitrile in the presence of an aromatic halide to the corresponding amine can be successfully accomplished e.g. with borane in THF.

SCHEME 6

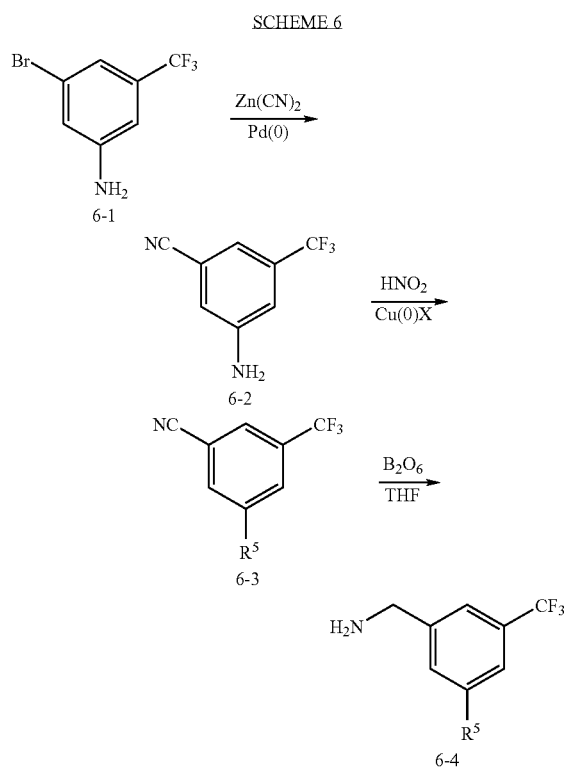

Additional examples of benzyl amines incorporated into the amide portion of compounds within the scope of the instant invention, as well as their syntheses are further described in the Experimental section.

The amine portion of the target compounds 1-8 can be, as detailed above, prepared either from reductive amination of the corresponding ketones 1-7 and 1-7a with appropriate amines 7-1, or by a reductive alkylation of amines 2-9a and 2-13a with the corresponding ketones 7-3, Scheme 7. The amines 7-1 as well as ketones 7-3 typically represent alicyclic structures, some of which, e.g. tetrahydropyran-4-one and a number of lower both cyclic and alicyclic ketones, can be obtained commercially, others have to be synthesized either by known or newly developed procedures.

SCHEME 7

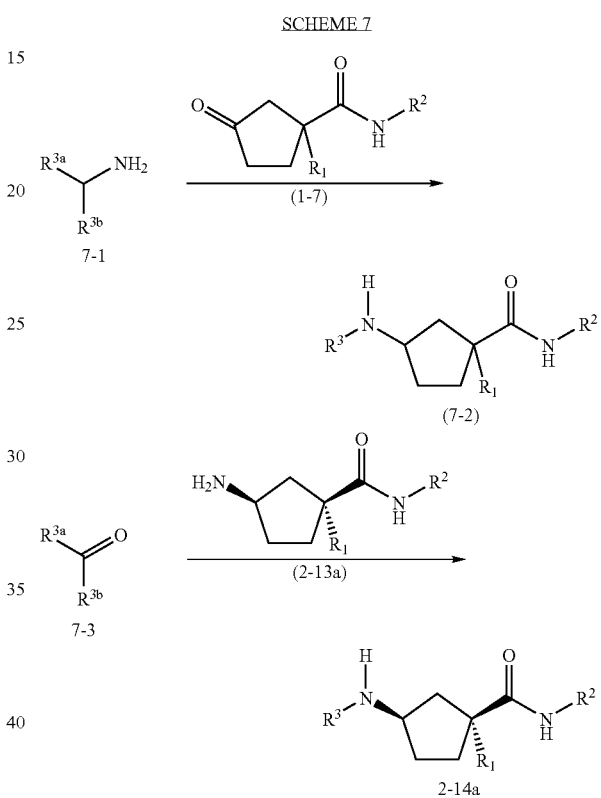

A synthesis of some of the ketones 7-3 is detailed in Scheme 8. According to this, a commercially available 5,6-dihydro-4-methoxy-2H-pyran (8-1) is treated with m-chloroperbenzoic acid to affect epoxidation of the double bond. This in turn reacts with the formed chlorobenzoic acid and the epoxide ring opening furnishes the ketone 8-2. Its protection in the form of an acetal is followed by removal of the ester. An alkylation of the secondary alcohol with an appropriate alkyl halide $R^6X$ in a presence of a base affords the ether 8-5. Deprotection of the acetal under acidic conditions affords the desired ketones 8-6. In this manner, besides the 3-hydroxy-tetrahydropyran-4-one, a number of 3-alkoxyderivatives can be synthesized. Further details, as well as examples are described in the Experimental section.

An example of preparation of amines 7-1, in this case 3-methyl-4-amino-tetrahydropyrane is detailed in Scheme 9. According to this, 3-methyltetrahydropyran-4-one, which can be synthesized from tetrahydropyran-4-one following a previously published procedure (*J. Am. Chem. Soc.*, 1991, 113, 2079-2089) is reacted with benzhydrylamine under reductive amination conditions.

SCHEME 8

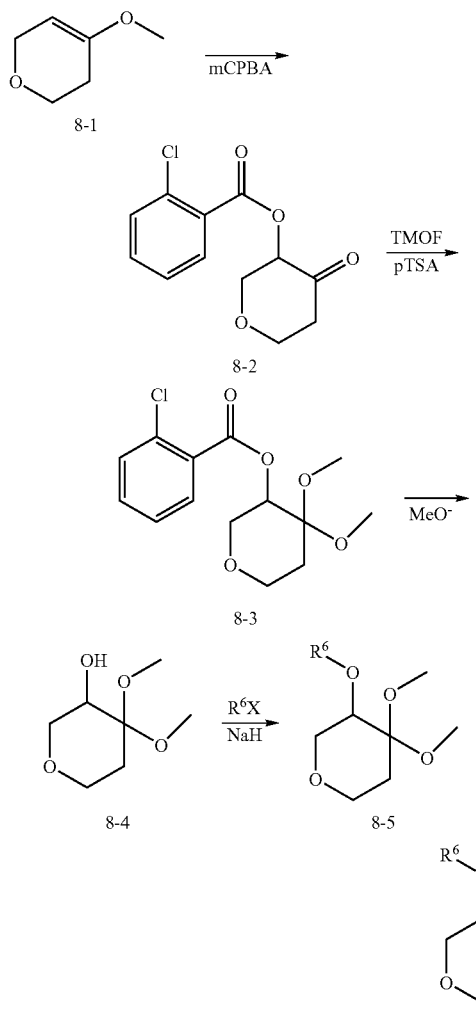

SCHEME 9

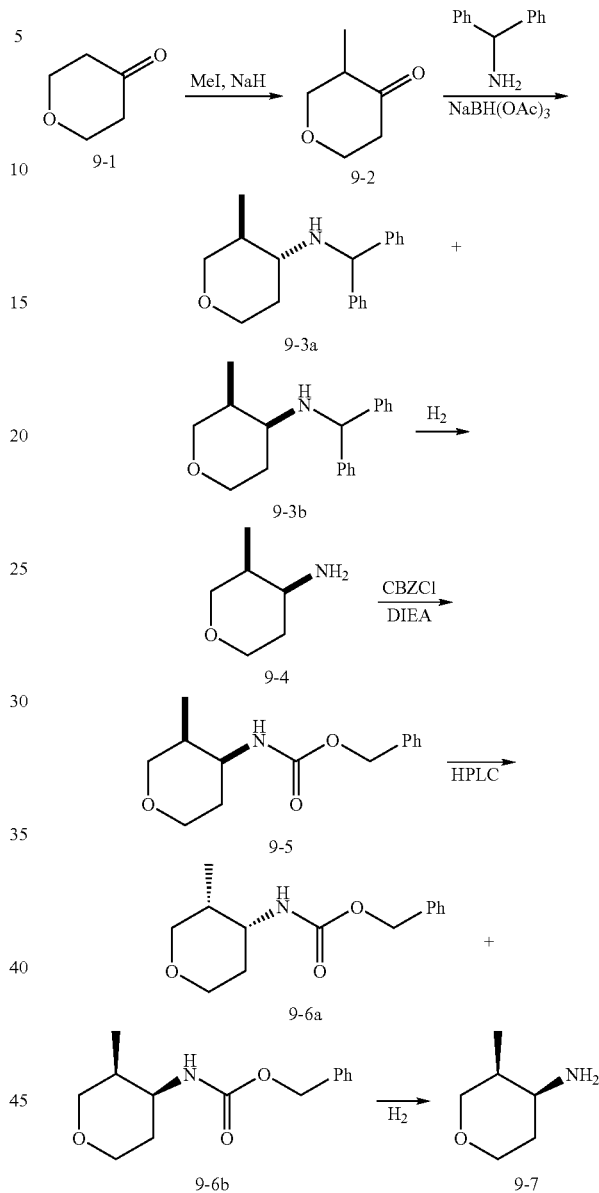

This transformation yields the two respective diastereoisomeric pairs with trans-(9-3a) and cis (9-3b) relative stereochemistry in a ratio of approximately 1 to 9. The major cis-racemic pair (9-3b) is subjected to hydrogenolysis to aid removal of the benzhydryl group (Greene, T., Wuts, P. G. M., *Protective Groups in Organic Chemistry*, John Wiley & Sons, Inc., New York, N.Y. 1991) and the free amine 9-4 is then reacted with benzyloxycarbonyl chloride in the presence of a suitable base, e.g. diisopropylethylamine. The two enantiomers contained within the racemate 9-5 can be then separated using chiral preparative chromatography. A DAICEL® Chiralpak AD polysacharide type preparative column (Chiral Technologies, 730 Springdale Drive, P.O. Box 564, Exton, Pa. 19341) can be used for the desired separation with great success. The faster eluting enantiomer 9-6b was shown to have the absolute stereochemistry (3R, 4S) by derivatization and NMR analysis as well as single crystal X-Ray diffraction analysis (Eliel, E. E., Wilen, S. H., *Stereochemistry of Organic Compounds*, John Wiley & Sons, Inc., New York). The CBZ protecting group is then removed hydrogenolytically to yield 9-7 in excellent yield.

Additional details as well as examples of preparation of amines 7-1 can be found in the Experimental section.

In some cases the order of carrying out the foregoing reaction schemes may be varied to facilitate the reaction or to avoid unwanted reaction products. The following examples are provided for the purpose of further illustration only and are not intended to be limitations on the disclosed invention.

Concentration of solutions was generally carried out on a rotary evaporator under reduced pressure. Flash chromatography was carried out on silica gel (230-400 mesh). MPLC refers to medium pressure liquid chromatography and was carried out on a silica gel stationary phase unless otherwise noted. NMR spectra were obtained in CDCl₃ solution unless otherwise noted. Coupling constants (J) are in hertz (Hz). Abbreviations: diethyl ether (ether), triethylamine (TEA), N,N-diisopropylethylamine (DIEA) saturated aqueous (sat'd), room temperature (rt), hour(s) (h), minute(s) (min).

Intermediate 1

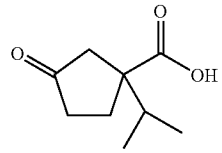

Step A

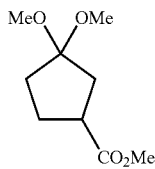

A solution of 3-oxo-cyclopentanecarboxylic acid (20 g, 160 mmol, Stetter, H., Kuhlman, H., *Liebigs Ann. Chemie,* 1979, 7, 944-9) in MeOH (200 mL) and trimethyl orthoformate (85 mL, 780 mmol) followed by TsOH (3.0 g, 16 mmol) was added. The reaction mixture was stirred at room temperature for 4 h and concentrated in vacuo. The residue was diluted with ether, washed with saturated NaHCO$_3$, brine, and dried over anhydrous MgSO$_4$. The crude product was purified by flash chromatography (ether:pentane/25:75,) to yield the desired product (21.52 g, 73%). $^1$H NMR (500 MHz, CDCl$_3$): 3.68 (s, 3H), 3.21 (d, J=9.9 Hz, 6H), 2.89 (p, J=8.5 Hz, 1H), 2.14-2.05 (m, 2H), 2.02-1.80 (m, 4H).

Step B

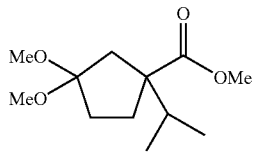

A flame-dried 500 mL round-bottomed flask, was charged with dry THF (150 mL) and diisopropylamine (19.2 mL, 137 mmol) was added. The solution was cooled to −78° C. and n-butyllithium (55 mL, 140 mmol, 2.5 M solution in hexanes) was added via syringe, followed by neat ester from the previous step (21.52 g, 114.4 mmol). The reaction mixture was stirred at −78° C. for 30 minutes and 2-iodopropane (34.3 mL, 343.2 mmol) was added. After the reaction was stirred for another 20 minutes at −78° C., it was kept in a refrigerator (+5° C.) overnight. The reaction was quenched with 10% citric acid and extracted with ether (3×). The combined organic layers were washed with H$_2$O, brine, dried over anhydrous MgSO$_4$, and concentrated. The residue was purified by flash chromatography (ether:pentane/20:80) to yield the desired product (16.74 g, 63.6%). $^1$H NMR (400 MHz, CDCl$_3$): 3.69 (s, 3H), 3.18 (d, J=20.5 Hz, 6H), 2.57 (d, J=13.9 Hz, 1H), 2.29 (m, 1H), 1.90 (p, J=6.8 Hz, 1H), 1.81 (m, 2H), 1.65 (m, 2H), 0.89 (q, J=11.9 Hz, 6.8 Hz, 6H).

Step C

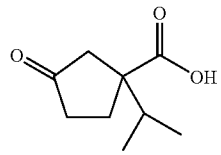

The ester from the previous step (16.7 g, 72.7 mmol) was dissolved in ethanol (30 mL) and a solution of NaOH (11 g, 280 mmol) in H$_2$O (30 mL) was added. The reaction mixture was refluxed for 3 days, cooled to room temperature and acidified with concentrated HCl. The alcohol was evaporated under reduced pressure and the residue was extracted with dichloromethane (5×). The combined organic layers were dried over anhydrous MgSO$_4$ and concentrated in vacuo to yield 11.07 g (89%) of the desired acid Intermediate 1. $^1$H NMR (500 MHz, CDCl$_3$): 2.70 (d, J=18.1 Hz, 1H), 2.44-2.39 (m, 1H), 2.30-2.15 (m, 2H), 2.14 (dd, J=18.1 Hz, 1.0 Hz, 1H), 2.06 (p, J=6.9 Hz, 1H), 1.98 (m, 1H), 0.98 (dd, J=11.4 Hz, 6.9 Hz, 6H).

Intermediate 2

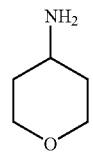

Step A

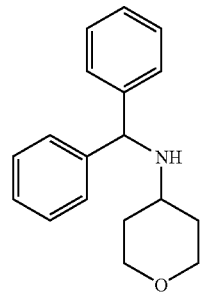

To a solution of tetrahydro-4H-pyran-4-one (5 g, 50 mmol) and diphenylmethylamine (8.4 mL, 50 mmol) in DCM (250 mL) was added 4 Å powdered molecular sieves followed by NaB(OAc)$_3$H (32 g, 150 mmol). The reaction mixture was stirred at room temperature overnight. It was filtered through celite, the filtrate was washed with saturated NaHCO$_3$ (4×), dried over MgSO$_4$, and concentrated in vacuo to yield a crude product (13.25 g, 99.9%). $^1$H NMR (400 MHz, CDCl$_3$): 7.42 (bd, J=7.0 Hz, 4H), 7.32 (bt, J=7.2 Hz, 4H), 7.24 (bt, J=7.3 Hz, 2H), 5.07 (s, 1H), 3.96 (dt, J=11.1 Hz, 3.5 Hz, 2H), 3.33 (td, J=11.5 Hz, 2.1 Hz, 2H), 2.66 (m, 1H), 1.93 (m, 2H), 1.54 (bs, 1H), 1.44 (m, 2H).

Step B

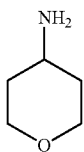

A mixture of the amine from previous step (13.2 g, 49.4 mmol), 4N HCl/dioxane (12.5 mL, 49.4 mmol), Pd/C 10% (1.1 g), dioxane (30 mL), and ethanol (120 mL) was hydrogenated at 35 psi pressure overnight on a Parr apparatus. The catalyst was filtered off and the filtrate was concentrated to dryness. The residue was triturated with DCM, and the precipitate was filtered, and dried to yield 4.91 g (72%) of Intermediate 2 in a form of a hydrochloride salt. $^1$H NMR (400 MHz, CD$_3$OD): 3.99 (dd, J=12.1 Hz, 5.1 Hz, 2H), 1.89 (td, J=11.9 Hz, 2.1 Hz, 2H), 3.38-3.32 (m, 1H), 1.96-1.92 (m, 2H), 1.70-1.59 (m, 2H).

Intermediate 3

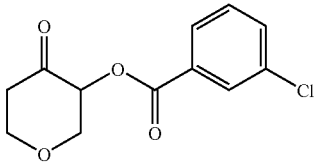

A flame-dried 250 mL round-bottomed flask was charged with 5,6-dihydro-4-methoxy-2H-pyran (5.00 g, 43.8 mmol) and dry DCM (150 mL). Na$_2$HPO$_4$ (22.4 g, 158 mmol) was added and the mixture was cooled to 0° C. in an ice-bath. A solution of m-CPBA (13.6 g, 78.8 mmol) in DCM (30 mL) was added slowly via syringe. The reaction mixture was then allowed to warm up to room temperature. Upon completion of reaction, the mixture was diluted with DCM, washed with H$_2$O (3×) and saturated NaCl, dried over Na$_2$SO$_4$, and concentrated in vacuo to yield the desired Intermediate 3 (8.36 g, 75.0%). $^1$H NMR (500 MHz, CDCl$_3$): 8.06 (t, J=1.7 Hz, 1H), 7.97 (dt, J=0.8 Hz, 1.4 Hz, 1H), 7.58 (dq, J=8.0 Hz, 1.1 Hz, 1H), 7.42 (t, J=7.8 Hz, 1H), 5.53 (ddd, J=10.6 Hz, 7.1 Hz, 1.0 Hz, 1H), 4.48 (ddd, J=10.8 Hz, 6.9 Hz, 1.4 Hz, 1H), 4.34 (m, 1H), 3.74 (m, 2H), 2.67 (m, 1H), 2.62 (dt, J=14.4 Hz, 1.8 Hz, 1H).

Intermediate 4

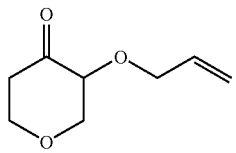

Step A

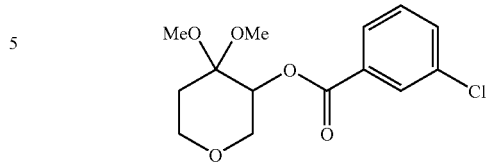

Intermediate 3 (200 mg, 0.787 mmol) was dissolved in DCM (5 mL) and MeOH (5 mL) before trimethyl orthoformate (8.68 mL, 7.87 mmol) and TsOH (15 mg, 0.0787 mmol) were added. The reaction mixture was stirred at room temperature for two days, concentrated to dryness and purified by preparative TLC to yield the desired acetal (161 mg, 68.2%). $^1$H NMR (500 MHz, CDCl$_3$): 8.07 (t, J=1.7 Hz, 1H), 7.99 (dt, J=7.8 Hz, 1.3 Hz, 1H), 7.56 (dq, J=8.0 Hz, 1.1 Hz, 1H), 7.41 (t, J=8.0 Hz, 1H), 7.12 (d, J=1.9 Hz, H), 4.00 (dd, J=12.8 Hz, 1.8 Hz, 1H), 3.93 (dd, J=11.5 Hz, 3.9 Hz, 1H), 3.83 (dd, J=12.9 Hz, 1.4 Hz, 1H), 3.58 (m, 1H), 3.29 (s, 3H), 3.19 (s, 1H), 2.13 (m, 1H), 1.95 (dd, J=14.1 Hz, 2.0 Hz, 1H).

Step B

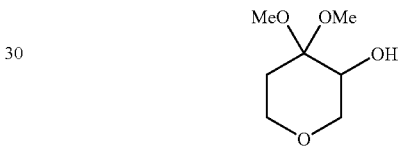

The ester from previous step (160 mg, 0.533 mmol) was dissolved in MeOH (2 mL) and a solution of NaOMe (0.5 M in MeOH, 1.3 mL) was added. The reaction was stirred for 1.5 h. The mixture was concentrated in vacuo and the crude product was used in the next step without further purification Step C

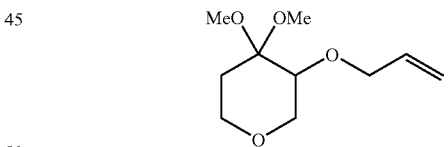

NaH (50 mg, 1.1 mmol) was suspended in THF (5 mL), and the crude alcohol from previous step (90 mg, 0.53 mmol) was added, followed by allyl bromide (461 µL, 5.33 mmol). The reaction mixture was stirred at room temperature overnight, and concentrated to dryness. The residue was diluted with ether, washed with saturated NaCl, dried over MgSO4, and concentrated in vacuo. The crude product was purified by preparative TLC to yield 81 mg, (75% for last two steps) of the desired product. $^1$H NMR (400 MHz, CDCl$_3$): 5.97 (m, 1H), 5.32 (dq, J=17.2 Hz, 1.6 Hz, 1H), 5.21 (dd, J=10.1 Hz, 1.2 Hz, 1H), 4.21 (m, 1H), 4.08 (m, 1H), 3.94 (dd, 12.1 Hz, 2.9 Hz, 1H), 3.80 (td, J=11.1 Hz, 3.9 Hz, 1H), 3.61 (dd, J=12.3 Hz, 1.6 Hz, 1H), 3.51 (dt, J=11.5 Hz, 2.7 Hz, 1H), 3.39 (m, 1H), 3.26 (s, 3H), 3.24 (s, 3H), 2.02 (m, 1H), 1.75 (md, J=14.0 Hz, 1H).

Step D

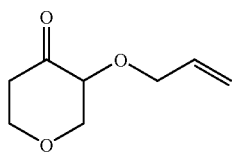

The previously described acetal (80 mg, 0.40 mmol) was dissolved in a 10% solution of TFA in DCM and stirred at room temperature for 1.5 h. The solvent was removed in vacuo and the concentrate was diluted with ether and washed with saturated $NaHCO_3$ (5×). The combined aqueous layer was back extracted with ether (1×). The combined organic layers were dried over $MgSO_4$ and concentrated in vacuo to yield Intermediate 4 (61 mg, 98%). $^1$H NMR (400 MHz, $CDCl_3$) δ 5.92 (m, 1H), 5.27 (m, 2H), 4.29 (tq, J=0.5 Hz, 1.6 Hz, 1H), 4.23 (dq, J=6.3 Hz, 1.6 Hz, 1H), 4.14 (m, 1H), 4.05 (tq, J=6.1 Hz, 1.4 Hz, 1H), 3.99 (m, 1H), 3.73 (m, 1H), 3.58 (app. q, 1H), 3.61 (m, 2H).

Intermediate 5

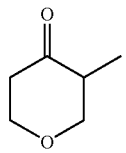

Intermediate 5 was prepared according to the procedure described in *J. Am. Chem. Soc.*, 1991, 113, 2079-2089.

Intermediate 6

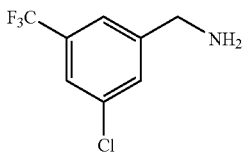

Step A

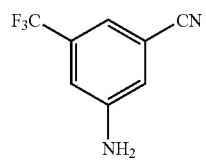

DMF (10 mL) was deoxygenated (nitrogen purge, 30 minutes) and 3-amino-5-bromobenzotrifluoride (500 mg, 2.08 mmol) in DMF was added. The solution was purged with nitrogen for another 10 minutes and zinc cyanide (147 mg, 1.25 mmol) was added followed by tetrakis(triphenylphospine)palladium (96 mg, 0.083 mmol). Nitrogen was passed through for another 15 minutes then it was heated to 80° C. in a sealed tube overnight. The reaction mixture was diluted with ethyl acetate, washed with an ammonium hydroxide solution (2×), and concentrated in vacuo. The crude product was purified by preparative LC (ethyl acetate:hexanes/30:70) to yield 289 mg (74%) of the desired product $^1$H NMR (400 MHz, $CDCl_3$): 7.25 (d, J=0.6 Hz, 1H), 7.08 (s, 1H), 7.06 (d, J=0.9 Hz, 1H). L-C-MS for $C_{10}H_8F_3N_3$ $[M+CH_3CN]^+$ calculated 227.07, found 227.8.

Step B

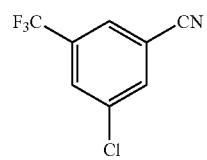

A mixture of Copper(II) chloride (250 mg, 1.34 mmol), tert-butylnitrite (217 µL, 1.61 mmol), and anhydrous acetonitrile (7 mL), was cooled to 0° C. and the nitrile from previous step (415 mg, 1.55 mmol) in anhydrous acetonitrile (2 mL) was slowly added. The reaction mixture was heated to 65° C. and monitored by TLC. When the reaction was complete, the mixture was cooled to room temperature, poured into 20% aqueous HCl and extracted with ether. The organic layer was washed with 20% aqueous HCl, dried over anhydrous $MgSO_4$, and concentrated in vacuo. The crude product was used in next step without further purification.

Step C

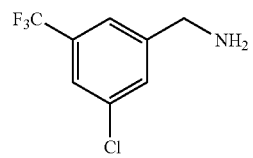

The nitrile from previous step (270 mg, 1.34 mmol) was dissolved in THF (1 mL) and 1M Borane in THF (6.70 mL, 6.70 mmol) was added. The mixture was stirred at room temperature overnight and concentrated in vacuo. The residue was picked up in a solution of 1% HCl (4N in dioxane) in methanol and heated at 50° C. overnight. Solvent was stripped off and the residue was dissolved in 1% HCl in methanol. This process was repeated three times to yield crude Intermediate 6 (212 mg, 64.4%). $^1$H NMR (400 MHz, $CDCl_3$): 7.80 (m, 3H), 4.22 (s, 2H).

Intermediate 7

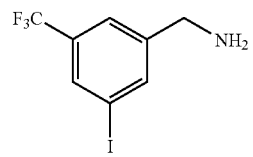

Step A

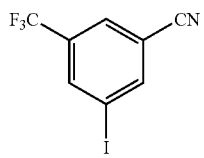

3-Amino-5-trifluoromethylbenzonitrile (500 mg, 2.69 mmol) was added to a mixture of concentrated HCl (5 mL) and water (5 mL) (solution A). Sodium nitrite (342 mg, 4.95 mmol) was dissolved in water (5 mL) (solution B). The two solutions were cooled to 0° C. separately before solution B was added slowly to solution A. At end of addition, KI-starch paper was used to test presence of nitrous acid. A solution of KI (765 mg, 4.61 mmol) in water (5 mL) was added and stirred for 30 minutes followed by heating to 100° C. until no nitrogen gas evolution was seen. The mixture was allowed cool to room temperature and extracted with ether (2×), dried over anhydrous NaSO$_4$, and concentrated in vacuo. Crude product was purified by preparative TLC (ethyl acetate:hexanes/40:60,) to yield 580 mg (72%) of the desired product. $^1$H NMR (300 MHz, CDCl$_3$): 8.18 (d, J=1.38 Hz, 2H), 7.89 (t, J=0.73 Hz, 1H).

Step B

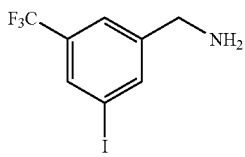

Intermediate 7 was prepared as detailed in Intermediate 6, Step 3. $^1$H NMR (400 MHz, CD$_3$OD): 8.16 (s, 1H), 8.09 (s, 1H), 7.83 (s, 1H), 4.19 (s, 2H).

Intermediate 8

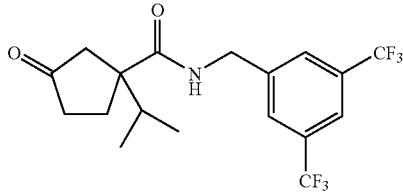

Intermediate 1 (2.5 g, 15 mmol), bis(trifluoromethyl)benzylamine (4.11 g, 14.7 mmol), DIEA (3.8 mL, 22 mmol), 1-hydroxy-7-azabenzotriazole (2.0 g, 15 mmol) and EDC (4.23 g, 22.0 mmol) were dissolved in DCM (100 mL) and stirred at room temperature overnight. The reaction mixture was washed with 1N HCl (2×), saturated NaHCO$_3$, H$_2$O (2×) and brine (1×). It was dried over anhydrous MgSO$_4$, and concentrated in vacuo. The crude product was purified by flash chromatography (EtOAc:Hexanes/40:60) to yield Intermediate 8 (3.87 g, 66.6%). $^1$H NMR (500 MHz, CDCl$_3$): 7.81 (s, 1H), 7.74 (s, 2H), 6.16 (bs, 2H), 2.78 (bd, J=18.07 Hz, 1H), 2.40 to 2.20 (bm, 4H), 2.08 to 1.98 (m, 2H), 0.99 (d, J=6.86 Hz, 3H), 0.97 (d, J=6.87 Hz, 3H).

Intermediate 9

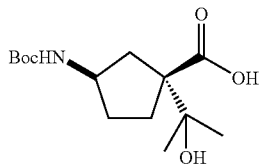

Step A

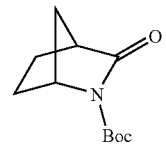

50 g (0.46 mol) of (1S,4R)-(+)-2-azabicyclo[2.2.1]hept-5-en-3-one in 200 mL of methanol containing 2.5 g of Pd/C (10%) was hydrogenated on a Parr shaker under 50 psi of hydrogen for 1 h. The catalyst was removed by filtration through a pad of celite. The filtrates were evaporated and the residue was dried in vacuum. The resulting white solid (50 g) was dissolved in 200 mL of methylene chloride and 110 g (0.50 mol) of di-tert-butyl dicarbonate and 1.0 g of DMAP were added. The reaction mixture was stirred at room temperature overnight and then loaded on a silica gel column, eluted with 10% EtOAc/Hexane. The title compound (83 g, 86%) was obtained as a white solid. $^1$NMR (400 MHz, CDCl$_3$): 1.40 (d, 1H), 1.51 (s, 9H), 1.70-1.95 (m, 5H), 2.84 (m, 1H), 4.50 (m, 1H).

Step B

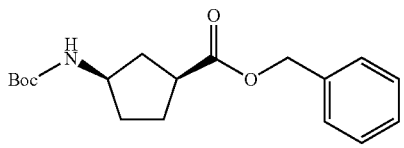

To a stirred mixture of 63.0 g (0.30 mol) of (1S,4R)-(+)-N-BOC-2-azabicyclo[2.2.1]hept-3-one and 32 g (0.30 mol) of benzyl alcohol in 200 mL of THF under nitrogen was added 2.8 g (0.30 mol) of lithium hydride in multiple portions. The resulting mixture was stirred overnight. TLC showed a complete conversion. The entire mixture was poured into a stirred mixture of ice-water/EtOAc (500 mL). The organic phase was separated and washed with water (2×200 mL), dried over Na$_2$SO$_4$, evaporated and Dried in vacuum. The title compound (95.5 g, 100%) was obtained as a white solid. $^1$H NMR (400 MHz, CDCl$_3$): 1.44 (s, 9H), 1.60 (m, 1H), 1.72 (m, 1H), 1.95 (m, 3H), 2.24 (m, 1H), 2.90 (m, 1H), 4.08 (m, 1H), 4.98 (broad, 1H), 5.13 (s, 2H), 7.38 (m, 5H).

Step C

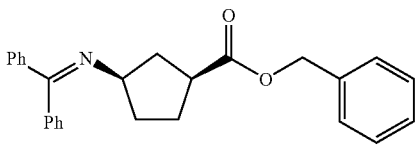

A mixture of 96 g (0.30 mol) of (1S,3R)-benzyl-(N-BOC-3-amino)-cyclopentanecarboxylate and 300 mL of 4N HCl in dioxane was stirred for 1 h. The solvent was removed under reduced pressure, and the residue was dried under high vacuum overnight and then suspended in 300 mL of $CH_2Cl_2$. To this suspension was added 54.4 g of benzophenone imine. The resulting mixture was stirred overnight. The precipitate was removed by filtration and the filtrates were washed with brine, dried over $Na_2SO_4$, evaporated and dried in vacuum.

The title compound was obtained as a light yellow oil (116.0 g, 100%). $^1$H NMR (400 MHz, CDCl$_3$): 1.80 (m, 1H), 1.95 (m, 2H), 2.15 (m, 2H), 2.50 (m, 1H), 2.89 (m, 1H), 3.61 (m, 1H), 5.20 (s, 2H), 7.18 (d, 2H), 7.38 (m, 8H), 7.47 (m, 3H), 7.64 (d, 2H).

Step D

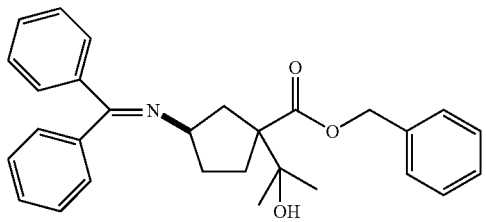

To a flame-dried 500 mL round-bottomed flask, was added dry THF (130 mL). The solvent was cooled to −78° C. before diisopropylamine (10.5 mL, 75.2 mmol), 2.5 M n-butyl-lithium (30 mL, 75 mmol), and a solution of the product prepared in Step C (25 g, 65 mmol) in THF (20 mL), were added sequentially. The reaction mixture was stirred at −78° C. for 30 minutes before acetone (14.4 mL, 196 mmol) was added. After the reaction was stirred for another h, the mixture was quenched with saturated NH$_4$Cl, extracted with ether, dried over MgSO$_4$, and concentrated. The crude product was purified by MPLC (EtOAc:Hexanes/25:75). Cis and trans isomers were resolved with cis being the desired isomer (cis, 6.8 g; trans, 3.47 g). %). Cis isomer: $^1$H NMR (400 MHz, CDCl$_3$): 7.58 (m, 2H), 7.48-7.28 (m, 11H), 7.14 (m, 2H), 5.22 (s, 2H), 3.78 (p, J=12.1 Hz, 6.2 Hz, 1H), 3.46 (s, 1H), 2.56-2.50 (m, 1H), 2.27 (dd, J=13.9 Hz, 5.9 Hz, 1H), 2.08 (dd, J=13.8 Hz, 6.6 Hz, 1H), 1.92 (m, 1H), 1.83-1.69 (m, 2H), 1.09 (d, J=14.0 Hz, 6H).

Step E

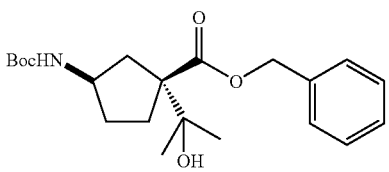

The imine from previous step (6.8 g, 15 mmol) was dissolved in THF (50 mL) before 2 N aqueous HCl (50 mL) was added. The reaction mixture was stirred and monitored by TLC. After completion of reaction, the mixture was concentrated in vacuo to remove THF. The aqueous layer was basisified to pH 9.0 with saturated Na$_2$CO$_3$ solution and extracted with DCM. The organic layer was dried over MgSO$_4$ and di-tert-butyl dicarbonate (4.4 g, 20 mmol) was added. The reaction was stirred at room temperature overnight before being extracted with DCM, dried over MgSO$_4$, and concentrated in vacuo. The crude product was purified by column chromatography to yield (2.9 g, 50%). $^1$H NMR (400 MHz, CDCl$_3$) 7.39 (m, 5H), 5.20 (s, 2H), 4.62 (bs, 1H), 4.13 (b, 1H), 3.40 (s, 1H), 2.25 (dd, J=14.5 Hz, 8.1 Hz, 1H), 2.16 (m, 1H), 2.01 (m, 2H), 1.89 (m, 1H), 1.44 (s, 9H), 1.18 (s, 6H).

Step F

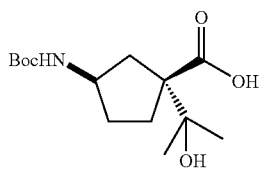

A mixture of the benzyl ester form previous step (2.9 g), Pd/C (300 mg), and ethanol (50 mL) were placed on a Parr-shaker under 50 psi pressure overnight. The mixture was filtered through celite and concentrated in vacuo to yield the desired product (2.01 g, 91.0%). $^1$H NMR (500 MHz, CDCl$_3$): 6.56 (s, ½H), 5.17 (s, ½H), 4.00 (d, J=43.3 Hz, 1H), 2.40-1.70 (m, 6H), 1.46 (b, 9H), 1.27 (b, 6H).

Intermediate 10

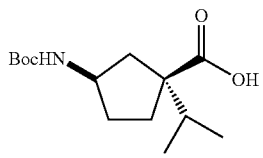

Step A

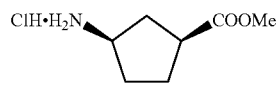

A mixture of (1S)-(+)-2-azabicyclo[2.2.1]hept-5-en-3-one (10.3 g, 94.4 mmol) in EtOAc (200 mL) and 10% Pd/C (0.5 gm), was hydrogenated at room temperature under a hydrogen balloon. After 24 h the reaction mixture was filtered and evaporated leaving behind 10.4 g (100%) of a product that was taken in 250 mL methanol and HCl (12M, 6 mL). The resultant mixture was stirred at RT, until the reaction was complete (72 h). Evaporation of methanol followed by drying under high vacuum, yielded the title compound as an off white solid (16.0 g, 96%).

$^1$H NMR (D$_2$O, 500 MHz): 3.70 (s, 3H), 3.01 (m, 1H), 2.38 (m, 1H), 2.16-1.73 (m, 6H).

Step B

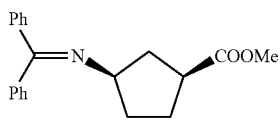

To a suspension of the intermediate from step A (10.2 g, 56.8 mmol) in dry dichloromethane (200 mL) was added benzophenone imine (10.2 g, 56.8 mmol) at room temperature and the resultant mixture was stirred for 24 h. The reaction mixture was filtered and the filtrate was evaporated, to leave behind a yellow oil that was triturated with ether (100 mL), filtered and evaporated. This operation was repeated twice to ensure that the product was free of ammonium chloride impurities. The resultant oil was thoroughly dried under vacuum to yield the title compound (18.03 g, >100%) and required no further purification. $^1$H NMR (CDCl$_3$, 500 MHz): 7.5-7.18 (m, 10H), 3.75 (m, 1H), 3.7 (s, 3H), 2.78 (m, 1H), 2.26-1.71 (m, 6H).

Step C

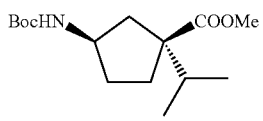

To a solution of LDA (prepared from diisopropylamine (7.7 g, 76.1 mmol) and n-butyllithium (30.4 mL, 2.5 M in hexane, 76 mmol) in THF (120 mL) at −78° C. was added the ester from Step B (18.0 g, 58.6 mmol). The resultant burgundy colored solution was stirred for 20 min. after which it was quenched with 2-iodopropane (14.9 gm, 88.0 mmol). The reaction mixture was gradually warmed over 3 h to 0° C. and this temperature was maintained for an additional 3 h. Reaction was quenched with water and extracted with EtOAc. The organic layer was washed with water, brine, dried (anhydrous magnesium sulfate) and concentrated to yield an oil. To the solution of the crude Schiff base (20.0 g) in THF (100 mL) was added HCl (5.0 mL, 12 M) and was allowed to stir at room temperature for 3 h. After the removal of all volatiles, the hydrochloride salt was taken up into dichloromethane (250 mL), and a saturated solution of sodium bicarbonate (250 mL) and di-tert-butyl dicarbonate (26.0 g, 1.4 Eq.) were added. The resultant mixture was vigorously stirred overnight at RT. The organic layer was separated and washed with water, brine, dried (anhydrous magnesium sulfate) and concentrated to yield an oil. Purification by flash column chromatography (eluent:hexane:EtOAc/19:1) gave the desired product (4.91 g, 30%). $^1$H NMR (500 MHz, CDCl$_3$): 4.79 (br, 1H), 4.01 (m, 1H), 3.71 (s, 3H), 2.18-1.60 (m, 6H), 1.44 (s, 9H), 0.87 (d, J=6.9 Hz, 3H), 0.86 (d, J=6.9 Hz, 3H).

Step D

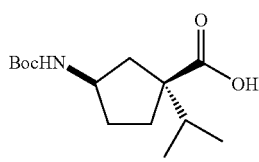

To a solution of the ester from the previous step (4.91 g, 17.2 mmol) in MeOH (100 mL) was added a solution of LiOH (3.6 g, 85 mmol) in water (20 mL) and THF (10 mL). The resultant mixture was heated at 80° C. until the reaction was complete (18 h). Methanol was removed in vacuo and the crude product was taken up with water/EtOAc (200 mL, 1:4) and cooled to 0° C. The acidity of the mixture was adjusted to pH 6. The EtOAc layer was separated, washed with water, brine, dried (anhydrous magnesium sulfate) and concentrated to yield an oil. Purification by flash column chromatography (eluent:hexane:EtOAc/1:1+2% AcOH) gave Intermediate 10 (3.9 g, 84%). $^1$H NMR (500 MHz, CDCl$_3$): 11.36 (br, 1H), 6.49 (br, 1H), 4.83 (m, 1H), 3.71 (s, 3H), 2.30-1.55 (m, 6H), 1.46 (s, 9H), 0.94 (d, J=6.9 Hz, 3H), 0.933 (d, J=6.9 Hz, 3H).

Intermediate 11

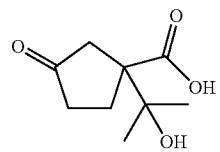

Step A

Procedure A

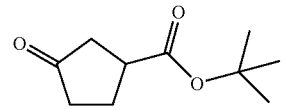

A solution of 3-oxo-cyclopentane carboxylic acid (Stetter, H., Kuhlmann, H. Liebigs Ann. Chem., 1979, 7, 944-9) (5.72 g, 44.6 mmol) in dichloromethane (30 mL) was treated with N,N'-di-iso-propyl-O-tert-Butyl-iso-urea (21.2 mL, 89.3 mmol) and the reaction mixture was stirred at ambient temperature overnight. The precipitated N,N'-di-iso-propyl urea was filtered off, the filtrate concentrated in vacuo and the residue was purified by distillation (b.p.: 125-129° C. @ 18 mmHg) to yield 4.7446 g (58%) of the pure product. $^1$H NMR (500 MHz, CDCl$_3$): 3.02 (p, J=7.8 Hz, 1H), 2.05-2.50 (m, 6H), 1.45 (s, 9H). $^{13}$C NMR (125 MHz, CDCl$_3$): 217.00, 173.47, 80.99, 41.88, 41.14, 27.94, 26.57.

Procedure B

A 2 L round RBF was charged with anhydrous magnesium sulfate (113 g, 940 mmol) and dichloromethane (940 mL). While stirring, the suspension was treated with concentrated sulfuric acid (12.5 mL, 235 mmol) followed after 15 minutes by 3-oxo-cyclopentane carboxylic acid (30.1 g, 235 mmol). After stirring for 15 minutes, tert-butanol (87 g, 1.2 mol) was added. The reaction vessel was closed with a stopper to aid retention of isobutylene, and stirred at ambient temperature for 72 h The solid was filtered off through a plug of Celite and the volume of the filtrate was reduced to approximately 500 mL, and washed with a saturated solution of sodium bicarbonate (2×150 mL). The organic phase was dried with anhydrous magnesium sulfate, filtered, and the solvent was removed by distillation at reduced pressure (180 mmHg). The crude product was purified by distillation to yield 39.12 g (90%) of pure product.

Step B

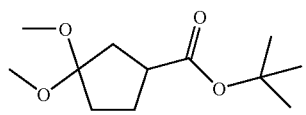

A solution of tert-Butyl 3-oxocyclopentane carboxylate (11.54 g, 62.64 mmol) in dichloromethane (200 mL) was treated with trimethyl orthoformate (41.4 mL, 251 mmol) in the presence of p-toluenesulfonic acid (400 mg) and stirred at room temperature for 48 h. The dark reaction mixture was poured onto a saturated solution of sodium bicarbonate, and the crude product was extracted with dichloromethane. The combined organic extracts were dried with anhydrous magnesium sulfate, the solvent was removed in vacuo, and the crude product was purified by distillation (b.p.: 104° C. @ 4 mmHg) to yield 12.32 g (85%) of the desired product. $^1$H NMR (500 MHz, CDCl$_3$): 3.21 (s, 3H), 3.20 (s, 3H), 2.80 (m, 1H), 2.10 to 1.80 (bm, 6H), 1.46 (s, 9H). $^{13}$C NMR (125 MHz, CDCl$_3$): 174.9, 111.2, 80.3, 67.8, 49.2, 42.5, 37.4, 33.8, 28.3, 22.0.

Step C

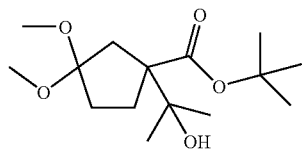

A solution of diisopropylaamine (5.6 mL, 40 mmol) in dry tetrahydrofuran (40 mL) was cooled to −78° C. and it was treated with n-butyllithium (16 mL, 40 mmol, 2.5M solution in hexanes). The neat ester from the previous step (5.8 g, 25 mmol) was added via syringe, and the enolate was allowed to form for 30 minutes at −15° C. The temperature of the reaction mixture was lowered to −78° C. once again, and acetone (5.5 mL, 75 mmol) was added via syringe. The reaction was allowed to proceed at −15° C. overnight, and it was quenched by pouring the mixture onto 150 mL of 10% aqueous citric acid. The crude product was extracted into diethyl ether, the combined extracts were dried and the solvent was removed in vacuo. The crude product (8.31 g) was further purified by column chromatography (Silica gel, ethyl acetate+hexanes/1:1) to yield 4.31 g (60%) of pure product. $^1$H NMR (500 MHz, CDCl$_3$): 3.21 (s, 3H), 3.18 (s, 3H), 2.46 (d, J=14.2 Hz, 1H), 2.20 (m, 1H), 1.99 (d, J=13.96 Hz), 1.85 (m, 3H), 1.50 (s, 9H), 1.21 (bs, 6H). $^{13}$C NMR (125 MHz, CDCl$_3$): 175.9, 110.4, 81.8, 73.3, 60.6, 49.5, 49.0, 39.5, 33.6, 28.2, 27.9, 26.7, 25.6.

Step D

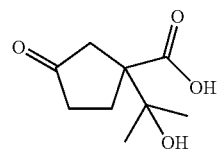

The solution of the ester-acetal (4.31 g, 14.9 mmol) from the previous step in dichloromethane (4 mL) was treated with trifluoroacetic acid (4.0 mL) and stirred at room temperature overnight. The solvent was evaporated in vacuo, and the residue was co distilled several times with hexane to yield 4.14 g of the desired acid. $^1$H NMR (500 MHz, CDCl$_3$): 2.84 (d, J=18.31 Hz), 2.26 (d, J=18.76 Hz), 2.48 to 2.28 (m, 4H), 1.41 (s, 3H), 1.37 (s, 3H).

Intermediate 12

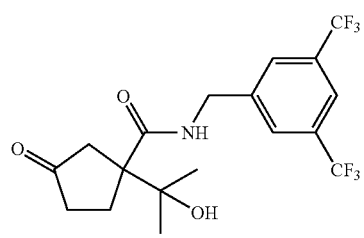

A solution of Intermediate 11 (2.00 g, 10.7 mmol), 3,5-bistrifluoromethylbenzyl anime 3.00 g, 10.7 mmol), 1-hydroxy-7-azabenzotriazole (1.46 mg, 10.7 mmol) and dissopropylamine pylamine (1.87 mL, 10.7 mmol) in dichloromethane (10 mL) was treated with 1-[3-dimethylamino)propyl]-3-ethylcarbodiimide EDC (3.09 g, 16.1 mmol) and the reaction mixture was stirred at room temperature overnight. It was diluted with dichloromethane, washed with water, dried with anhydrous magnesium sulfate and the solvent was removed in vacuo. The crude residue was further purified by column chromatography (Silica gel, ethyl acetate: hexanes/4:1) to yield 1.52 g (36%) of the pure product. $^1$H NMR (500 MHz, CDCl$_3$): 8.10 (bt, J=5.72 Hz, 1H), 7.77 (s, 1H), 7.75 (s, 2H), 4.61 (dd, J=15.56, 6.18.Hz, 1H), 4.56 (dd, J=6.18 Hz, 15.33 Hz, 1H), 2.86 (d, J=18.07 Hz, 1H), 2.40 to 2.18 (m, 4H), 1.32 (s, 3H), 1.25 (s, 3H). $^{13}$C NMR (125 MHz, CDCl$_3$): 216.6, 175.8, 141.6, 131.9, 131.7, 127.5, 121.9, 73.8, 58.5, 44.6, 42.7, 36.8, 28.5, 27.2, 26.5. LC-MS for C18H19F6NO3 [M+H]$^+$ calc. 412.13, found 412.15.

Intermediate 13

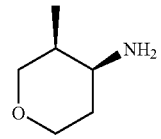

Step A

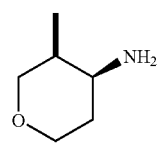

The cis-racemate of 3-methyl-4-amino-tetrahydropyrane was obtained from 3-methyltetrahydropyran-4-one (Intermediate 5) in a procedure analogous to that described under preparation of Intermediate 2.

Step B

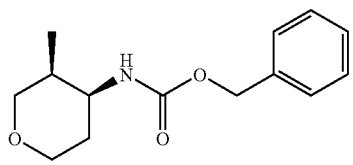

A solution of the racemic cis-amine (1.54 g, 10.3 mmol), the preparation of which is described in the previous step, and diisopropylethylamine (4.46 mL, 25.6 mmol) in dry dichloromethane, under $N_2$ at ambient temperature, was treated with neat carbobenzoxy chloride (1.61 mL, 11.3 mmol) and the resulting mixture was stirred at room temperature for 2 h. It was diluted with dichloromethane and extracted with 10% aqueous solution of citric acid. The aqueous phase was back extracted with dichloromethane, and the combined organic extracts were washed with saturated aqueous sodium bicarbonate. After drying (anhydrous magnesium sulfate), the solvent was removed in vacuo and column chromatography (Silica gel, ethyl acetate:hexane/2:3) gave 1.8347 g (72%) of the pure product. The respective enantiomers were obtained by chiral HPLC using a ChiralPak AD semi-preparative column. The absolute configuration of the faster eluting isomer (Tr=13.0 minutes, Hexane:EtOH/93:7, 9 mL/min) was shown to be (3R,4S) by both derivatization of the free amine followed by NMR spectroscopy, as well as single crystal X-ray diffraction analysis. $^1$H NMR (500 MHz, CDCl$_3$): 7.47 (bm, 5H), 5.12 (bs, 2H), 4.65 (bd, J=8.7 Hz, 1H), 3.98 (dd, J=11.44, 3.43 Hz, 1H), 3.87 (dd, J=11.4, 4.3 Hz, 1H), 3.45 (m, 2H), 3.08 (t, J=11.40 Hz, 1H), 1.95 (d, J=11.60 Hz, 1H), 1.50 (m, 2H), 0.90 (d, J=6.63 Hz, 3H).

Step C

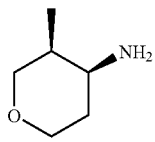

The solution of the CBZ-protected amine from the previous step (284 mg, 1.14 mmol) in ethanol (15 mL) was hydrogenated using 133 mg of Pd/C (10%) under an ambient hydrogen pressure of a balloon for 30 minutes. The catalyst was filtered off, and the solution was concentrated in vacuo to leave 158 mg (91%) of the desired product.

Intermediate 14

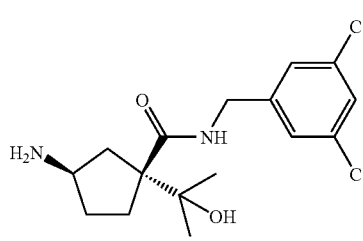

Step A

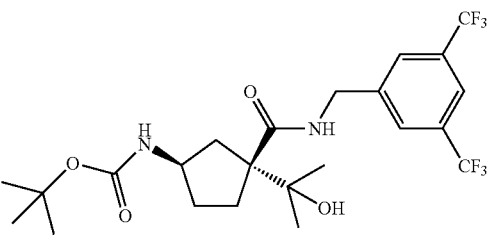

A solution of the acid Intermediate 9 (3.72 g, 13.0 mmol), 3,5-bistrifluoromethylbenzylamine hydrochloride (3.62 g, 13.0 mmol), diisopropylethylamine (2.26 mL, 13.0 mmol), 1-hydrozy-7-azabenzotriazole (1.76 g, 13.0 mmol) in dichloromethane (30 mL) was treated with EDC (3.72 g, 19.4 mmol) and the reaction mixture was stirred at room temperature for 2 h. It was poured onto water (50 mL) and extracted with dichloromethane. The combined organic extracts were washed with brine, dried with anhydrous. magnesium sulfate and the solvent was removed in vacuo to leave 4.80 g of an oily crude product. This was further purified by column chromatography (Silica gel, ethyl acetate hexanes/2:3) to yield 3.18 g (48%) of the pure product. $^1$H NMR (500 MHz, CDCl$_3$): 8.40 (bs, 1H), 7.76 (s, 1H), 7.75 (s, 2H), 5.34 (d, J=6.18 Hz, 1H), 4.56 (m, 2H), 4.0 (m, 1H), 3.21 (s, 1H), 2.15 (dd, J=14.2, 4.81 Hz, 1H), 2.05 to 1.85 (m, 4H), 1.62 (m, 1H), 1.41 (bs, 9H), 1.26 (s, 3H), 1.23 (s, 3H). $^{13}$C NMR (125 MHz, CDCl$_3$): 178.4, 155.7, 141.8, 131.9 (m), 127.5, 121.0, 79.1, 74.6, 52.3, 42.7, 37.8, 33.4, 31.6, 28.3, 27.0, 26.3.

Step B

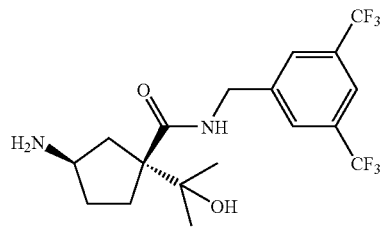

The solution of the BOC-protected amine from the previous step (3.18 g, 6.20 mmol) was stirred at room temperature in dioxane/HCl (4.0 N) for 1 h. The solvent was removed in vacuo to yield the pure hydrochloride (2.63 g, 94%). LC MS for C$_{18}$H$_{22}$F$_6$N$_2$O$_2$ for [M+H]$^+$ calc. 413.16, found 413.20.

Intermediate 15

Step A

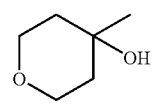

A solution of tetrahydro-4H-pyran-4-one (10.0 g, 99.9 mmol) in dry tetrahydrofuran (200 mL) was cooled to 0° C. and a solution of methylmagnesium chloride (3.0 M, in THF) was added via syringe. After stirring at 0° C. for 30 minutes the cooling bath was removed, and the reaction was allowed to proceed at room temperature for another 30 minutes. It was quenched by pouring onto a saturated aqueous solution of ammonium chloride, and extracted with diethyl ether. After drying with magnesium sulfate the solvent was removed in vacuo (100 mmHg), and the crude product (11.07 g) was further purified by distillation (b.p.: 87° C. @ 20 mmHg) to yield 4.36 g (38%) of the desired alcohol. $^1$H NMR (500 MHz, CDCl$_3$): 3.75 (ddd, J=14.2, 11.2, 2.8 Hz, 2H), 3.65 (dt, J=8.7, 4.4 Hz, 2H), 1.98 (bs, 1H), 1.63 (ddd, J=14.2, 10.3, 4.6 Hz, 2H), 1.50 (bd, J=13.0 Hz, 2H), 1.24 (s, 3H).

Step B

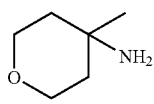

A solution of 4-hydroxy-4-methyltetrahydropyran (5.86 g, 50.5 mmol) in acetonitrile (25 mL) was cooled to 0° C. and concentrated sulfuric acid (10.5 g) was added. The reaction mixture was stirred at room temperature for another 1 h, after which time it was poured onto ice (~50 g) and extracted with dichloromethane. The combined organic phases were washed with a saturated solution of sodium bicarbonate, dried with anhydrous magnesium sulfate, and the solvent was evaporated to dryness in vacuo. The crude product (7.15 g) was dissolved in a solution consisting of 20 g of sodium hydroxide and 30 mL of ethylene glycol in 20 mL of water, and was heated to 125° C. for 72 h. The reaction mixture was allowed to cool to room temperature, and the pH was made strongly acidic with concentrated sulfuric acid (~70 mL). The entire mixture was evaporated to dryness under reduced pressure and allowed to dry at high vacuum overnight. The amine was liberated from the sulfate form with aqueous sodium hydroxide, and extracted into dichloromethane. The combined extracts were dried with anhydrous sodium sulfate, and the dichloromethane was evaporated to dryness in vacuo. The pure amine was obtained by distillation at reduced pressure: b.p.: 90-91° C. @ 100 mmHg; 3.3983 g (59%) of the product was obtained in a form of a mobile liquid. $^1$H NMR (500 MHz, CDCl$_3$): 3.71 (ddd, J=11.44, 8.01, 3.20 Hz, 2H), 3.58 (ddd, J=10.52, 6.40, 3.89 Hz, 2H), 1.56 (bs, 2H), 1.36 (m, 2H), 1.12 (s, 3H). $^{13}$C NMR (125 MHz, CDCl$_3$): δ4.3, 46.3, 40.6, 27.0.

Intermediate 16

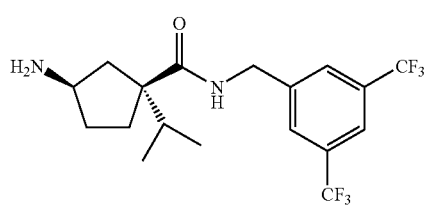

Step A

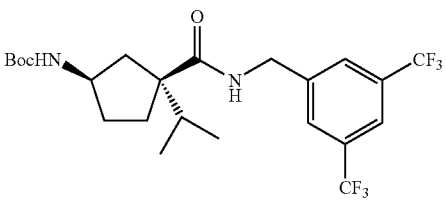

To a stirred solution of Intermediate 10 (2.09 g, 7.71 mmol), 1-ethyl-3-(3-dimethyl-aminopropyl)carbodiimide (2.96 g, 15.4 mmol) in DCM (100 mL), was added 3,5-bistrifluorobenzylamine hydrochloride (2.26 g, 8.10 mmol), diisopropylethylamine (1.05 g, 8.10 mmol), and 1-hydroxy-7-azabenzotriazole (1.15 g, 8.48 mmol). The reaction was stirred at room temperature for 18 h before being diluted with DCM and washed twice with aqueous 1 N HCl, once with saturated aqueous sodium bicarbonate, and once with brine. The organic layer was dried over MgSO$_4$, filtered and concentrated under reduced pressure. The product was purified by medium pressure liquid chromatography (silica gel, 60% EA/Hexanes) to give 2.23 g of a colorless oil which was used directly in Step B.

Step B

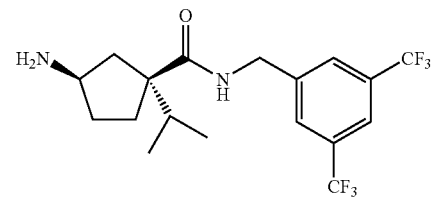

The product from Step A was dissolved in hydrogen chloride (4 N solution in dioxane, 25 mL) and stirred at room temperature. After 1.5 h the reaction was concentrated under reduced pressure to give 1.79 g of a white solid (54% over 2 steps). ESI-MS calc. for C18H22F6N2O: 396.4; found 397.2 (M+H).

Intermediate 17

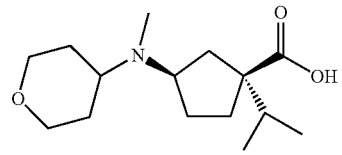

Step A

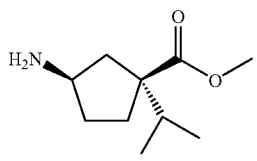

To a cooled (0° C.) solution of Intermediate 10 (1.0 g, 3.7 mmol) in methanol (50 mL) was added thionyl chloride (1.1 mL, 15 mmol) dropwise and the resulting solution was allowed to warm to room temperature. After 18 h, an additional amount of thionyl chloride (2.1 mL, 30 mmol) was added and the reaction was allowed to stir at room temperature. After 18 h, the reaction was concentrated under reduced pressure and the product was used directly in Step B.

Step B

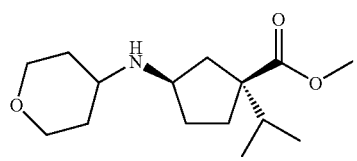

The crude product from Step A was combined with tetrahydro-4H-pyran-4-one (730 mg, 7.3 mmol), triethylamine (1.0 mL, 7.3 mmol), 4 Å powdered molecular sieves (~1 g), and sodium triacetoxyborohydride (5.1 g, 24 mmol) in 50 mL DCM. The reaction mixture was stirred at room temperature for 4 days, then filtered through celite, diluted with DCM, and washed with saturated NaHCO$_3$ solution twice and then once with brine. The organic layer was dried over anhydrous MgSO$_4$, filtered and concentrated to give 1.0 g of a slightly yellow oil (99+% over 2 steps). ESI-MS calc. for C15H27NO3: 269, found 270 (M+H).

Step C

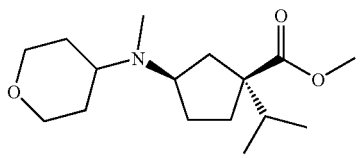

The product from Step B (1.0 g, 3.7 mmol) was combined with formaldehyde (37% solution in water) (3.0 mL, 37 mmol), 4 Å powdered molecular sieves (1 g), and sodium triacetoxyborohydride (3.9 g, 19 mmol) in 50 mL DCM. The reaction mixture was stirred at room temperature for 1 h, then filtered through celite, diluted with DCM, and washed with saturated NaHCO$_3$ and brine. The organic layer was dried over anhydrous MgSO$_4$, filtered and concentrated to give 1.0 g of a slightly yellow oil (95%). ESI-MS calc. for C16H29NO3: 283; found 284 (M+H).

Step D

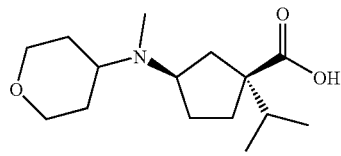

The product from Step C (1.0 g, 3.5 mmol) was dissolved in a solution of THF (10 mL) and methanol (10 mL) and treated dropwise with a solution of lithium hydroxide monohydrate (730 mg, 17 mmol) in water (10 mL) over 10 min. The reaction was allowed to stir at room temperature for 1 h before being heated to reflux. After 36 h at reflux the reaction was cooled to room temperature, neutralized with 3N hydrochloric acid and concentrated under reduced pressure to dryness. The resultant crude product was triturated with a 50% solution of methanol/DCM to give 950 mg of a white solid (99%). ESI-MS calc. for C15H27NO3: 269: found 270 (M+H).

Intermediate 18

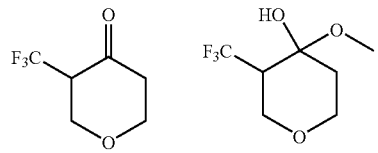

Step A

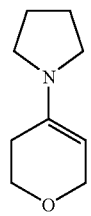

A mixture of tetrahydro-4H-pyran-4-one (10 g, 100 mmol) and pyrrolidine (11 g, 150 mmol) was stirred at room temperature for 1 h. The excess pyrrolidine was removed on the vacuum pump and the residue was dried under high vacuum overnight. The enamine was obtained as a yellow liquid (14.7 g) which was used in next step without further purification.

Step B

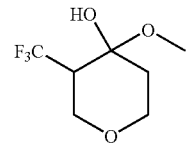

The enamine from step A (1.54 g, 10.0 mmol) and 4-N,N-dimethylpyridine (1.22 g) were treated with DMF (25 mL).

The mixture was cooled to 0° C. and solid 5-(trifluoromethyl) dibenzo-thiophenium trifluoromethanesulfonate (4.02 g, 10.0 mmol) was added. The resulting mixture was stirred at 0° C. for 1 h, quenched with 30 mL of concentrated aqueous HCl, stirred for 2 h, and extracted with ether (4×70 mL). The combined ether layers were washed with water (50 mL) and brine (50 mL), dried over Na₂SO₄, evaporated. The residue was purified by flash chromatography on silica gel (10% ethyl ether/Hexane) to yield two components. The more polar component (200 mg) was the desired material. 1H-NMR showed it might exist in semi ketal form. $^1$H NMR (400, CDCl₃): 4.43-3.38 (m, 5H), 3.24, 3.18 (ss, 3H), 2.52 (m, 1H), 1.82 (m, 1H). The less polar product (100 mg) was confirmed as alpha-alpha' di-trifluoromethyl tetrahydro-2H-pyran-4-one. $^1$H NMR (400 MHz, CDCl₃): 4.59 (dd, 2H), 3.24, 3.80 (t, J=11.3, 2H), 3.42 (m, 2H).

Intermediate 19

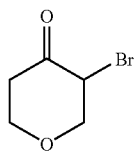

To a cooled (−78° C.) solution of lithium diisopropylamide (2.0 M solution in heptane/THF/ethylbenzene, 65 mL, 200 mmol) in THF (300 mL) was added trimethylsilyl chloride (70 mL, 500 mmol) dropwise. After 5 minutes at −78° C. tetrahydro-4H-pyran-4-one (10 g, 100 mmol) in THF (120 mL) was added. The reaction was stirred for 1 minutes before triethylamine (200 mL) was added and the reaction was quenched with saturated aqueous sodium bicarbonate. The solution was extracted twice with diethyl ether and the combined organic layers where washed with 0.1 N aqueous citric acid, dried over K₂CO₃, filtered and concentrated under reduced pressure. The resultant silyl ether was dissolved in THF (90 mL) and cooled to 0° C. N-bromosuccinimide (19.6 g, 110 mols) was added portionwise and the resulting solution was stirred 5 minutes at 0° C. The ice bath was removed and the solution was stirred for 30 minutes at room temperature before being quenched with saturated aqueous sodium bicarbonate and extracted twice with diethyl ether. The combined organic layers where washed with brine, dried over MgSO₄, filtered and concentrated under reduced pressure. The product was purified by flash chromatography (silica gel, 20-50% diethyl ether/petroleum ether) to give 8.75 g of a white solid (49%).

H NMR (CDCl₃, 500 MHz): 4.46 (t, J=6.5 Hz, 1H), 4.30 (m, 1H), 4.09 (m, 1H), 3.91 (m, 2H), 2.99 (m, 1H), 2.65 (m, 1H).

Intermediate 20

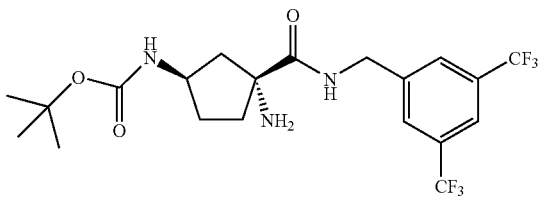

Step A

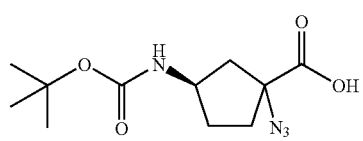

This intermediate was prepared in an analogous fashion to that of Intermediate 10, except 2,4,6-triisopropylbenzene-sulfonylazide was used in place of 2-iodopropane. The cis and trans isomers were not separated; therefore, the compound was used as a mixture of two diastereomers. FT-IR: 3310, 2939, 2568, 2110, 1711, 1680.

Step B

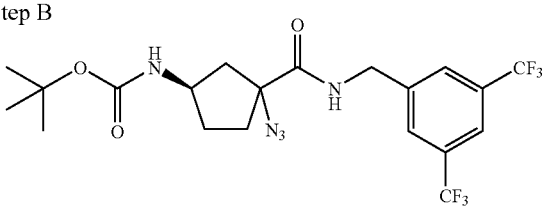

A mixture of the acid described in step A, Intermediate 20 (250 mg, 0.93 mmol), 3,5-bis(trifluoromethyl)benzylamine hydrochloride (260 mg, 0.93 mmol), DMAP (12.7 mg, 0.093 mmol), N,N-diisopropylethylamine (160 □l, 0.93 mmol) in dichloromethane (20 mL) was treated with 1-[3-(dimethylamino)propyl]-3-ethylcarbodiimide hydrochloride (EDC, 356 mg, 1.86 mmol) and stirred at room temperature overnight. The reaction mixture was diluted with dichloromethane (20 mL), washed with water (2×20 mL), brine (1×30 mL), dried over anhydrous sodium sulfate and the solvent was evaporated. Purification by preparative TLC (eluant: 25% ethyl acetate/75% hexane) afforded two separate single isomers (isomer 1, less polar cis, 72 mg, 18%; isomer 2, more polar trans, 140 mg, 31%). LC-MS calculated for $C_{20}H_{23}F_6N_5O_3$ is 495.17, found (MH)⁺ 495.2 for both isomer 1 and isomer 2. FT-IR still exhibited 2109 cm⁻ for the azide.

$^1$H NMR (CDCl₃, 500 MHz) (for isomer 1): 7.84 (s, 1H), 7.72 (s, 2H), 7.15 (br s, 1H), 5.58 (br s, 1H), 4.61 (dd, J=6.0, 15.56 Hz, 1H), 4.58 (dd, J=6.0, 15.56 Hz, 1H), 4.37 (br s, 1H), 2.44 (ddd, J=8.1, 8.9, 13.8 Hz, 1H), 2.34 (dd, J=7.3, 14.6 Hz, 1H), 2.24 (dd, J=4.6, 14.5 Hz, 1H), 2.16-2.02 (m, 2H), 1.96-1.88 (m, 1H), 1.46 (s, 9H).

$^1$H NMR (CDCl₃, 500 MHz) (for isomer 2): 7.83 (s, 1H), 7.73 (s, 2H), 7.02 (br s, 1H), 4.67 (br s, 1H), 4.62 (dd, J=6.2, 15.3 Hz, 1H), 4.57 (dd, J=6.0, 15.3 Hz, 1H), 4.27 (br s, 1H), 2.68 (dd, J=8.0, 14.5 Hz, 1H), 2.40-2.29 (m, 2H), 2.11-2.03 (m, 1H), 1.92 (br d, J=12.1 Hz, 1H), 1.73-1.65 (m, 1H), 1.44 (s, 9H).

Step C

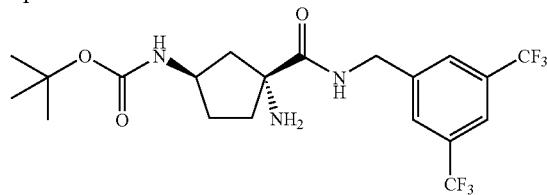

To a solution of the less polar cis isomer (isomer 1) described in step B, intermediate 20 (70 mg, 0.141 mmol) in THF/water (2 mL/0.1 mL) was added triphenyl-phosphine (111 mg, 0.423 mmol) and the resulting solution stirred for 5 h at room temperature. The reaction was evaporated under reduced pressure and the residue was purified by preparative TLC (eluant: 90% ethyl acetate/10% hexane) to afford Intermediate 20 (50 mg, 60%) as a yellow foam. LC-MS calculated for $C_{20}H_{25}F_6N_3O_3$ is 469.18, found $(MH)^+$ 470.2

Intermediate 21

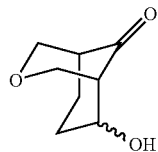

A mixture of 9.70 g (0.0970 mol) of tetrhydro-4H-pyran-4-one and 10.5 g (150 mmol) of pyrrolidine was stirred at room temperature for 1.5 h. The excess of pyrrolidine was removed on vacuum pump. The residue was dissolved in 90 mL of ether, cooled to 0° C. and 7.4 mL of acrolein was added. The resulting mixture was stirred at room temperature overnight. 67 mL of water was added, followed by a solution of 14 g of sulfuric acid (98%) in 33 mL of water. The ether and 10 mL of water were removed under reduced pressure, the remaining mixture was refluxed for 0.3 h and then cooled to room temperature. The resulting dark mixture was extracted with DCM (4×100 mL), and the combined organics where dried over anhydrous $Na_2SO_4$ and evaporated. The residue was purified on MPLC (30% ethyl acetate/hexane). A mixture (6.6 g) of endo/exo isomers (~1/1) was obtained together with pure fast isomer (1.0 g, endo) and pure slow isomer (0.8 g, exo). $^1$H NMR (400 MHz, $CDCl_3$): endo: 4.58 (d, J=11.6 Hz, 1H), 4.20 (d, J=11.2 Hz, 1H), 4.17 (d, J=11.2 Hz, 1H), 3.91 (d, J=11.3 Hz, 1H), 3.72 (d, J=11.5 Hz, 1H), 2.60-2.30 (m, 4H), 2.13 (m, 1H), 2.02 (m, 1H), 1.80 (m, 1H). Exo: 4.54 (d, J=1.1 Hz, 1H), 4.10 (dd, J=11.4 Hz, 2H), 3.80 (dd, J=11.5 Hz, 2H), 2.86 (s, 1H), 2.70 (m, 1H), 2.50 (s, 1H), 2.38 (m, 2H), 2.10 (m, 1H), 1.78 (m, 1H).

Intermediate 22

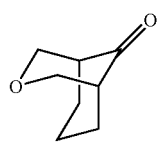

Step A

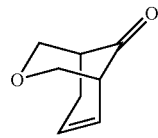

To a mixture of Intermediate 21 (endo/exo: ~1:1, 3.12 g, 20 mmol) and DBU (9.0 g, 60 mmol) in benzene (25 mL) at 0° C. was added dropwise a neat solution of trifluoromethane sulfonic acid anhydride. An exothermic reaction was observed. The reaction mixture was stirred for 1 h, dumped onto a silica gel column, eluted with 20% $Et_2O$/hexane. The desired product was obtained as a light yellow oil (1.80 g).). $^1$H NMR (400 MHz, $CDCl_3$): 5.98 (m, 1H), 5.65 (m, 1H), 4.10 (dd, 1H), 3.90 (dd, 1H), 3.78 (dd, 1H), 3.65 (dd, 1H), 2.80 (m, 3H), 2.50 (d, J=11.5).

Step B

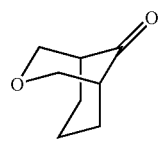

A mixture of the Intermediate 21 (9.0 g) and 10% Pd/C (0.9 g) in 50 mL of ethyl acetate was hydrogenated on a Parr-shaker for 2 h under 50 psi of hydrogen. The catalyst was removed by filtration. The filtrate was evaporated. Intermediate 22 was obtained as a light yellow solid (6.817 g). $^1$H NMR (400 MHz, $CDCl_3$): 4.24 (d, J=11.5 Hz, 2H), 3.90 (d, J=11.60 Hz, 2H), 2.58 (m, 1H), 2.38 (br S, 2H), 2.25 (m, 2H), 2.08 (m, 2H), 1.58 (m, 1H).

Intermediate 23

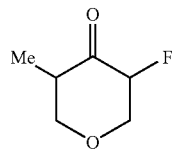

Step A

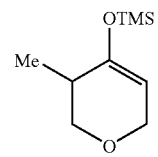

To a flame-dried, 125 mL flask under nitrogen was placed diisopropylamine (4.7 g, 33 mmol) and 20 mL of anhydrous THF at −78° C. A solution of n-butyllithium (1.6 M, 20.5 mL, 33 mmol) was added. The cooling bath was removed and the reaction mixture was warmed to room temperature for 10 minutes, then recooled to −78° C. A solution of trimethylsilyl chloride (10 mL, 150 mmol) in 20 mL of THF at −78° C. was cannulated into the reaction flask. Then a solution of the Intermediate 5 (3.5 g, 30 mmol) in 20 mL of THF was cannulated into the reaction. A large amount of white precipitate was formed. 30 mL of triethylamine was added. The reaction mixture was quenched with saturated aqueous sodium bicarbonate and extracted with pentane (2×250 mL). The pentane layers were washed with water (250 mL), 5% aqueous citric acid (2×250 mL) and dried over anhydrous sodium sulfate. The crude product was used in next step without further purification. $^1$H NMR (400 MHz, CDCl$_3$): 4.74 (s, 1H), 4.18 (s, 2H), 3.84 (dd, J=4.6 Hz, 1H), 3.42 (dd, J=4.5 Hz, 1H), 2.20 (m, 1H), 1.03 (d, J=7.0 Hz, 3H), 0.19 (s, 9H).

Step B

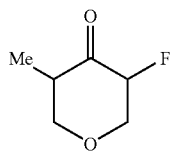

Diflurotriethylenediammonium tetrafluroborate (10.6 g, 30.0 mmol) was placed in a 100 mL flask under nitrogen. 50 mL of anhydrous acetonitrile was added. The mixture was stirred at 0° C., then a neat solution of the enol trimethylsilyl ether (entire material from step A, intermediate 23) was added dropwise. The reaction was stirred until all the enol ether was consumed (~30 min). Acetonitrile was then removed and the residual solid was washed with a mixture of ether and hexane (1/9, 5×). The filtrates were evaporated and the residue was purified on MPLC. Two components were obtained. The proton NMR of the slow-eluted material was consistent with that of the desired product (250 mg). $^1$H NMR (400 MHz, CDCl$_3$): 4.79; 4.67 (m, 1H), 4.19 (m, 1H), 4.08 (m, 1H), 3.84 (m, H), 3.40 (t, J=1.0 Hz, 1H), 3.16 (m, 1H), 1.06 (d, J=6.9 Hz, 3H). The fast-eluted compound (200 mg) was alpha-alpha' difluoro ketone.

Intermediate 24

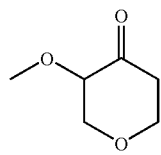

Step A

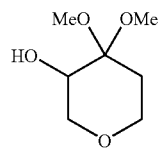

To a cooled (0° C.) mixture of 5,6-dihydro-4-methoxy-2H-pyran (10.0 g, 87.5 mmol) in methanol (200 mL) was added dropwise a solution of m-CPBA (30.2 g, 175 mmol) in methanol (50 mL) via addition funnel. The resulting solution was stirred for 5 h allowing to warm to room temperature. The methanol was removed under reduced pressure affording a white solid. The material was dissolved in 500 mL of dichloromethane and cooled to 0° C. To the mixture, while stirring vigorously, was added in portions an excess of solid calcium hydroxide (50-60 grams). After stirring an additional 30 minutes, the mixture was filtered through a plug of celite and the filtrate evaporated under reduced pressure to afford 11.62 g (82%) of the desired product as a clear oil. $^1$H NMR (CDCl$_3$, 500 MHz) δ 3.88-3.80 (m, 2H), 3.73-3.68 (m, 2H), 3.54-3.48 (m, 1H), 3.28 (s, 3H), 3.27 (s, 3H), 2.00-1.93 (m, 1H), 1.82-1.77 (m, 1H).

Step B

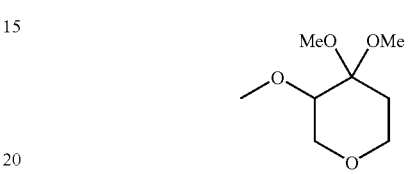

To a cooled (0° C.) solution of the product from Step A (9.40 g, 58.0 mmol) in THF (200 mL), under nitrogen, was slowly added NaH (2.32 g, 58.0 mmol) and the resulting slurry was stirred for 1 h at 0° C. Iodomethane (7.22 mL, 116 mmol) was then added via syringe to the slurry and the resulting mixture was stirred overnight allowing to warm to room temperature. The reaction was quenched with a saturated solution of ammonium chloride (200 mL) and the organic layer was then removed using a separatory funnel. The aqueous layer was extracted with ether (3×150 mL) and all the organics were combined, dried over anhydrous sodium sulfate, filtered, and evaporated in vacuo. Purification was done by flash column using a stepwise gradient eluant of 10-60% ether/hexane to afford 8.46 g (83%) of the desired product as a clear oil. $^1$H NMR (CDCl$_3$, 500 MHz) 3.98 (dd, J=2.5, 12.4 Hz, 1H), 3.77 (ddd, J=3.5, 7.1, 10.8 Hz, 1H), 3.57 (dd, J=1.4, 12.4 Hz, 1H), 3.50 (dd, J=2.5, 11.7 Hz, 1H), 3.46 (s, 3H), 3.25 (s, 3H), 3.22 (s, 3H), 3.22-3.20 (m, 1H), 1.96 (ddd, J=4.7, 11.8, 16.5 Hz, 1H), 1.75 (br dd, J=1.7, 14.2 Hz, 1H).

Step C

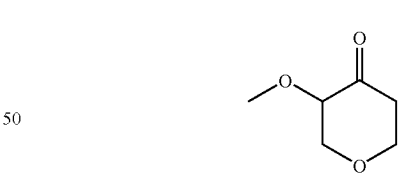

A solution of product from step B, intermediate 24 (3.0 g, 17 mmol) in THF/water (60 mL/10 mL) was treated with concentrated hydrochloric acid (6 mL) and the resulting solution stirred at room temperature for 1 h. The mixture was concentrated in vacuo to remove the THF and the aqueous layer then extracted with ether (6×50 mL). The organics were combined, dried over anhydrous sodium sulfate, filtered, and evaporated under reduced pressure to afford intermediate 24 (1.75 g, 79%) as a clear oil. $^1$H NMR (CDCl$_3$, 500 MHz) 4.23 (ddd, J=1.2, 11.4, 12.4 Hz, 1H), 4.15-4.09 (m, 1H), 3.82 (dd, J=5.95, 8.7 Hz, 1H), 3.74 (ddd, J=5.5, 8.5, 13.6 Hz, 1H), 3.56 (dd, J=8.8, 11.3 Hz, 1H), 3.50 (s, 3H), 2.61 (app dd, J=5.0, 8.9 Hz, 2H).

Intermediate 25

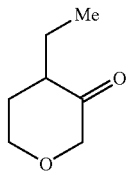

Procedure A

To a solution of terahydro-4H-pyran-4-one (700 mg, 7.00 mmol) and HMPA (1.2 mL) in THF (14 mL) was added slowly a solution of LDA (3.5 mL, 2 M solution) in 14 mL THF at −78° C. The mixture was stirred for 5 minutes before iodoethane (0.56 mL, 7.0 mmol) was added and the solution was gradually warned to 0° C. over 2 h. The reaction mixture was quenched with a saturated solution of $NH_4Cl$ and then extracted with ether (4×50 mL). The ether layer was washed with brine, dried over anhydrous magnesium sulfate, concentrated and purified by flash column chromatography. Eluting with hexane:EtOAc (19:1) afforded intermediate 25 (0.07 g, 8%).

Procedure B

Step A

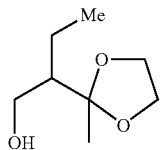

A mixture of ethyl 2-ethylacetoacetate (3.0 g, 19 mmol), ethylene glycol (1.4 g, 23 nmol), CSA (100 mg) and benzene (80 mL) was refluxed in a Dean-Stark apparatus, with continuos removal of water. After ensuring the completion of the reaction (by TLC) it was diluted with water and extracted with ether (100 mL). The ether layer was washed with brine, dried (anhydrous magnesium sulfate) and concentrated to afford the desired compound (4.2 g). This was taken in ether (50 mL) and was slowly added to LAH (1.2 g, 32 mmol) at 0° C. The reaction was warmed to room temperature and stirred for 12 h. The reaction mixture was then quenched sequentially with water (1.5 mL), 15% NaOH (1.5 mL) and water (4.5 mL). The resultant heterogeneous mixture was vigorously stirred and filtered. Evaporation of the filtrate gave 3.1 g of the title compound that required no further purification.

Step B

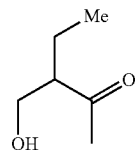

To a stirring slurry of silica (12 g, 230-400 mesh) in methylene chloride (100 mL) was added a 10% aqueous solution of oxalic acid followed by the acetal from Step A (1.6 g, 10 mmol) in methylene chloride (5 mL). The resultant mixture was stirred at room temperature until the reaction was complete. Upon the completion of the reaction, $NaHCO_3$ (1.0 g) was added, stirred (10 minutes) and filtered. The filtrate was evaporated to give the 0.96 g of the title compound that required no purification.

Step C

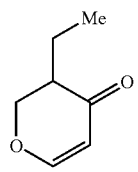

To a premixed solution of triethyl orthoformate (2.4 g, 16 mmol) and tin (IV) chloride (16.3 mL 1.0 M solution in dichloromethane, 16 mmol) at 40° C. was added the hydroxy ketone from Step B (0.95 g, 8.1 mmol) in dichloromethane (3 mL). The reaction mixture was warmed to −5° C. over 1.5 h before being quenched with a saturated $NaHCO_3$ solution and extracted with ether (2×50 mL). The ether layer was washed with brine, dried over anhydrous magnesium sulfate, concentrated and purified by flash column chromatography on silica gel. Eluting with hexane:ether (9:1) to give the title compound (0.58 g, 57%).

Step D

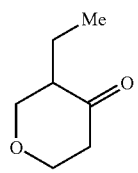

The intermediate from Step C (0.56 g) in hexane (10 mL) and Pd/C (5%, 50 mg) was hydrogenated at room temperature until the TLC indicated the completion of reaction. The reaction mixture was filtered and the filtrate was carefully evaporated (volatile product!) to yield the mixtures of the desired intermediate 25 and the over reduction product. The recovery of intermediate 25 was further facilitated by a subsequent TPAP/NMMO/DCM oxidation of the mixture, which after 1 h was filtered to yield 410 mg of the title compound that required no further purification.

1H NMR ($CDCl_3$, 500 MHz): 4.15 (m, 2H), 3.80 (m, 1H), 3.48 (m, 1H), 2.61 (m, 1H), 2.44 (m, 2H), 1.82 (m, 1H), 1.31 (s, 1H), 0.72 (m, 1H), 0.94 (t, J=7.4 Hz, 3H).

Intermediate 26

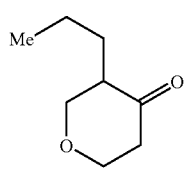

To a solution of terahydro-4H-pyran-4-one (700 mg, 7.0 mmol) and HMPA (1.2 mL) in THF (14 mL) was added slowly a solution of LDA (3.5 mL, 2 M solution) in 14 mL

Intermediate 27

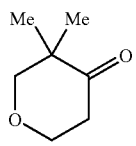

Following the Steps A-D given for the preparation of Intermediate 25 (Procedure 2) and starting from methyl 2,2-dimethylacetoacetate, gave the title compound. $^1$H NMR (CDCl$_3$, 500 MHz): 3.98 (m, 2H), 3.58 (s, 2H), 2.56 (m, 2H), 1.15 (s, 6H).

Intermediate 28

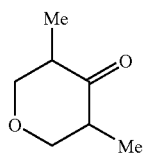

Following the Steps A-D given for the preparation of Intermediate 25 (procedure 2) and starting from methyl 2,4-dimethyl-3-oxobutyrate, gave the title compound. $^1$H NMR (CDCl$_3$, 500 MHz): 4.22 (m, 1H), 3.99 (m, 1H), 3.62 (m, 1H), 3.28 (m, 1H), 2.72 (m, 1H), 1.16 (d, J=6.8 Hz, 3H), 0.97 (d, J=6.8 Hz, 3H).

Intermediate 29

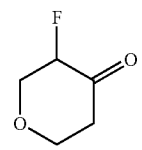

To a mixture of 5.6-dihydro-4-methoxy-2H-pyran (500 mg, 4.4 mmol) in acetonitrile/water (15 mL, 1:1) at room temperature was added [1-(chloromethyl)-4-fluoro-1,4-diazoniabicyclo[2.2.2.] octane bis(tetrafluoroborate)] (1.5 g, 4.4 mmol, SELECTFLUOR™) in one lot and the reaction stirred to completion. Solid NaCl was added to the reaction mixture, and then extracted with ether (4×50 mL). The ether layer was dried (anhydrous magnesium sulfate) and concentrated to yield 0.34 g (65%) of the title compound that required no further purification. $^1$H NMR (CDCl$_3$, 500 MHz): 4.95 (m, 1H), 4.4-4.21 (m, 2H), 3.72-3.65 (m, 2H), 2.75 (m, 2H).

Intermediate 30

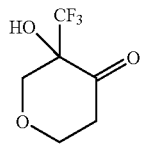

Step A

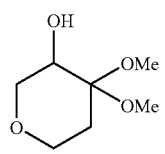

To a mixture of 5.6-dihydro-4-methoxy-2H-pyran (2.0 g, 18 mmol) in methanol (40 mL) at 0° C. was added m-CPBA (6.0 g, 35 mmol). After stirring for 10 min. at 0° C., the reaction mixture was allowed to warm to room temperature and stirred for 1 h. The solvent was removed under vacuum and the crude mixture was chromatographed on a silica column. Eluting with hexane:EtOAc (7:3) gave 2.8 g (95%) of the title compound.

1H NMR (CDCl$_3$, 500 MHz): 3.83 (m, 2H), 3.70 (m, 2H), 3.50 (m, 1H), 3.28 (s, 3H), 3.27 (s, 3H), 1.96 (m, 1H), 1.77 (m, 1H).

Step B

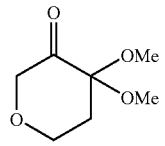

To a mixture of the acetal from Step A (2.8 g, 17 mmol) in dichloromethane (30 mL) was added 4 Å powdered molecular sieves (~5 g), 4-methylmorpholine N-oxide (5.0 g, 43 mmol) and finally TPAP (0.2 g). The resultant mixture was stirred vigorously for 3 h at which point the reaction was complete. It was filtered, evaporated, and purified by flash column chromatography on silica gel. Eluting with hexane:ether (1:4) gave the title compound (2.67 g, 96%).

Step C

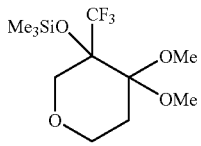

To the ketone from Step B (2.8 g, 18 mmol) in THF (20 mL) at 0° C. was added TBAF (28 mg) followed by neat trimethyl (trifluoromethyl)silane (4.0 g, 28 mmol). After stirring for 10 min. at 0° C., the reaction mixture was allowed to warm to room temperature and stirred for 12 h. THF was removed under vacuum and the crude passed through a silica gel column. Eluting with hexane:EtOAc (4:1) gave 4.1 g (77%) of the title compound.

Step D

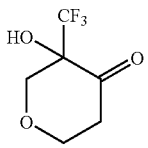

To the silylether from Step C (4.0 g, 13.3 mmol) at room temperature was added TFA (2.0 mL) and the mixture was stirred for 36 h. The TFA was removed under vacuum and the crude was purified by flash silica gel column chromatography. Eluting with hexane:ether (4:1) gave 1.5 g (65%) of the title compound.

1H NMR (CDCl$_3$, 500 MHz): 4.49 (m, 1H), 4.41 (m, 1H), 4.34 (br, 1H), 3.72 (m, 1H), 3.39 (m, 1H), 3.07 (m, 1H), 2.72 (m, 1H).

Intermediate 31

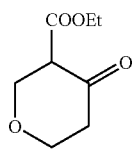

Prepared according to *J. Am. Chem. Soc.*, 1997, 119, 4285, except that the reaction was performed on the ethyl ester.

Intermediate 32

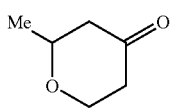

Step A

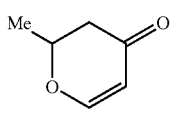

To a solution of trans-1-methoxy-3 (trimethylsilyloxy)-1, 3-butadiene (1.62 g, 9.4 mmol) and acetaldehyde (0.63 mL, 11 mmol) in ether (25 mL) at −78° C. was added slowly a solution of boron trifluoride diethyletherate (1.36 mL, 10.7 mmol). After stirring for 3 h at the same temperature, the reaction mixture was quenched with a saturated solution of sodium bicarbonate, warmed to room temperature and then extracted with ether (2×50 mL). The ether layer was washed with brine, dried (anhydrous magnesium sulfate), and concentrated followed by purification by silica flash column chromatography. Eluting with hexane:diethyl ether (8:2) gave the desired product (0.6 g, 57%).

Step B

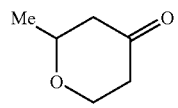

The intermediate from Step A (0.59 g) in EtOAc (10 mL) with Pd/C (50 mg) was hydrogenated at room temperature under a hydrogen filled balloon, until the reaction was complete as indicated by TLC. The reaction mixture was filtered and the filtrate was carefully concentrated (volatile product!) followed by purification by silica gel flash column chromatography. Elution with hexane:diethyl ether (7:3) gave 0.2 g (33%) of the desired compound (Intermediate 30).

1H NMR (CDCl$_3$, 500 MHz): 4.28 (m, 1H), 3.75 (m, 1H), 3.69 (m, 1H), 2.63-2.27 (m, 4H), 1.34 (d, J=6.1 Hz, 3H).

Intermediate 33

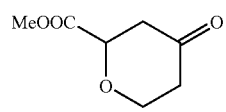

Step A

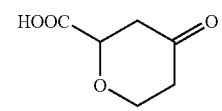

To comanic acid (0.25 g) in EtOAc (5 mL) was added Pd/C (25 mg) and the resulting solution was hydrogenated at room temperature under a hydrogen filled balloon, until the reaction was complete as indicated by TLC. The reaction mixture was filtered and the filtrate was concentrated to give the desired product (0.25 g, 97%), which required no further purification.

Step B

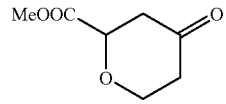

To a solution of the intermediate from Step A (0.1 g, 0.7 mmol) in THF:hexane (4 mL, 1:1) at room temperature, was added (trimethylsilyl) diazomethane (451 1, 1.3 eq, 2 M solution in hexane) and the mixture was stirred for 24 h. The solvent was carefully concentrated (volatile product!) followed by purification by silica gel flash column chromatography. Elution with hexane:EtOAc (4:1) gave the desired product (0.02 g, 16%).

Intermediate 34

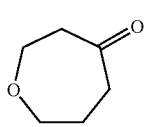

Prepared according to *Chem. Ber.*, 1959, 91, 1589.

Intermediate 35

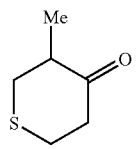

Prepared according to *Synlett*, 1991, 783.

Intermediate 36

Prepared according to *Synlett*, 1991, 783.

Intermediate 37

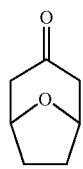

Step A

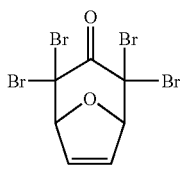

To a solution of furan (20 mL, 720 mmol) in benzene (600 mL) was added tetrabromoacetone (11 g, 30 mmol). The solution was cooled to 0° C. and 1.0 M diethyl zinc solution in hexane (30 mL, 30 mmol) was added dropwise. The solution was stirred at 0° C. for 2.5 h then at room temperature for 60 h. The reaction was quenched with a saturated aqueous solution of dibasic EDTA (15 mL) and extracted with ethyl acetate (150 mL). The organic layer was washed three times with saturated aqueous dibasic EDTA then with brine and was dried over MgSO$_4$, filtered and concentrated under reduced pressure.

Step B

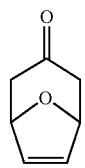

The resultant oil from Step A was dissolved in a saturated solution of NH$_4$Cl in methanol (120 mL) which was then added dropwise to Zn—Cu couple (20 g wet with diethyl ether). The mixture was stirred at room temperature for 2.5 h. The reaction was filtered through celite and concentrated to remove the methanol. The product was dissolved in DCM and washed twice with saturated aqueous dibasic EDTA. The organic layer was dried over MgSO$_4$, filtered and concentrated under reduced pressure. The product was purified by flash chromatography (silica, 33% PE/Et$_2$O) to give 1.7 g of a colorless solid (46%). $^1$H NMR (CDCl$_3$, 500 MHz): 6.25 (s, 2H), 5.03 (d, J=5.0 Hz, 2H), 2.75 (dd, J=5.0 Hz, 17.0 Hz, 2H), 2.32 (d, J=16.5 Hz, 2H).

Step C

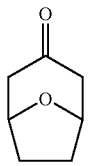

To a solution of the product from Step B (780 mg, 6.4 mmol) in ethyl acetate (25 mL) was added 78 mg of Pd(OH)$_2$ (20% on activated carbon) catalyst. A hydrogen balloon was placed over the reaction and it was stirred at room temperature for 3 h. The reaction was filtered through celite, washed with ethyl acetate and concentrated to give 754 mg of a colorless oil (97%). $^1$H NMR(CDCl$_3$, 500 MHz): 4.68 (bs, 2H), 2.65 (dd, J=5.0 Hz, 15.0 Hz, 2H), 2.23 (d, J=15.0 Hz, 2H), 2.20-1.98 (m, 2H), 1.76-1.69 (m, 2H).

Intermediate 38

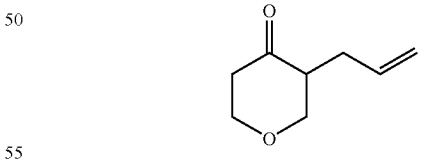

A solution of tetrahydro-4H-pyran-4-one (9.87 g, 98.5 mmol) and HMPA (18 mL, 99 mmol) in THF (50 mL) was added dropwise under argon to a solution of 1.5 M LDA.THF in cyclohexane diluted with THF (250 mL) at −78° C. The mixture was stirred for 20 min, then allyl bromide (17.0 mL, 197 mmol) in THF (50 mL) was added dropwise. The reaction mixture was warmed to 0° C. and stirred for 1.5 h. Then the reaction mixture was further warmed to room temperature and stirred for 30 min. The reaction was quenched by pouring into ice water. This mixture was extracted with ether three times. The combined ethereal layers were washed with brine, dried over MgSO₄, filtered, and concentrated. Purification by flash chromatography (silica, 35% ether/pet ether) provided 4.26 g of a colorless liquid (31%). ¹H NMR (CDCl₃, 400 MHz): 5.76 (m, 1H), 5.04-5.10 (m, 2H), 4.16-4.22 (m, 2H), 3.77 (dt, J=10.8, 3.6 Hz, 1H), 3.44 (dd, J=11.2, 9.2 Hz, 1H), 2.53-2.66 (m, 3H), 2.44 (dt, J=14.4, 3.6 Hz, 1H), 2.04 (m, 1H).

Intermediate 39

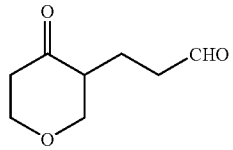

Step A

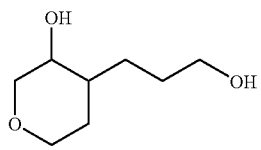

To a cooled (0° C.) solution of olefin INTERMEDIATE 38 (1.98 g, 14.1 mmol) in THF (70 mL) was added dropwise 1.0 M BH₃.THF in THF (8.46 mL, 8.46 mmol). The reaction mixture was warmed to room temperature and stirred for 1 h. Then a second portion of 1.0 M BH₃.THF in THF (8.46 mL, 8.46 mmol) was added and the reaction mixture was stirred over the weekend. The reaction was quenched by the addition of water (70 mL), then was treated with NaBO₃.4H₂O (7.80 g, 50.8 mmol). The resulting suspension was vigorously stirred for 4.25 h, then was concentrated to dryness. The residue was purified by flash chromatography (silica, 5% methanol/DCM, then 8% methanol/DCM, then 10% methanol/DCM) to give 1.92 g (85%) of diol as a mixture of isomers.

Step B

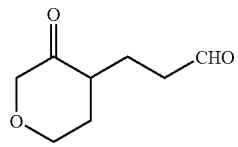

Oxalyl chloride (110 □L, 1.26 mmol) was dissolved in DCM (8 mL), precooled to −78° C. Then a solution of DMSO (179 □L, 2.52 mmol) in DCM (1.5 mL) was added dropwise. After 5 min, a solution of the diol from Step A immediately above (50.5 mg, 0.315 mmol) in DCM (1.5 mL) was added dropwise. The reaction mixture was stirred at −78° C. for 20 min, then triethylamine (702 □L, 5.04 mmol) was added dropwise. The reaction mixture was stirred for an additional 10 min, then was warmed to room temperature. After 45 min, the reaction mixture was poured into 2 N HCl solution and extracted three times with DCM. The combined organic layers were washed with brine, dried over MgSO₄, filtered, and concentrated, giving 45.4 mg of crude product.

Intermediate 40

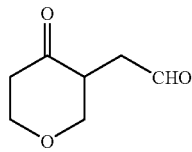

Olefin INTERMEDIATE 38 (2.00 g, 14.3 mmol) was dissolved in DCM (70 mL), cooled to −78° C., and treated with ozone gas (via pipet) until the reaction mixture appeared blue in color. Nitrogen gas was then bubbled through the reaction mixture until the blue color had disappeared (colorless). Triphenylphosphine (3.90 g, 14.9 mmol) was added and the reaction mixture was allowed to warm to room temperature and stir for 1.25 h. The reaction mixture was concentrated and 50% ethyl acetate/hexane was added to precipitate the triphenylphosphine oxide. The mixture was filtered and purified by MPLC (silica, ethyl acetate) to give 832 mg of the desired product. ¹H NMR (CDCl₃, 500 MHz): 9.78 (s, 1H), 4.20-4.31 (m, 2H), 3.67 (dt, J=12.5, 3.0 Hz, 1H), 3.37 (t, J=11 Hz, 1H), 3.21 (m, 1H), 2.89 (dd, J=18.5, 7.0 Hz, 1H), 2.72 (m, 1H), 2.40 (m, 1H), 2.25 (dd, J=18.5, 5.5 Hz, 1H).

Intermediate 41

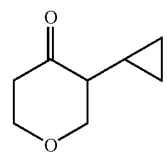

Step A

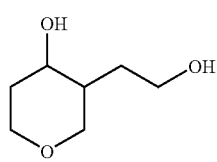

Through a cooled (−78° C.) solution of the allyl pyranone INTERMEDIATE 38 (659 mg, 4.70 mmol) in methanol (10 mL) was bubbled ozone gas until the reaction appeared blue. Nitrogen gas was then bubbled through the solution until the blue color disappeared. Sodium borohydride (267 mg, 7.05 mmol) was added and the reaction mixture was permitted to warm to rt. The reaction mixture was then concentrated and purified by flash chromatography (silica, 10% methanol/DCM) to afford 571 mg of diol as a mixture of diastereomers.

Step B

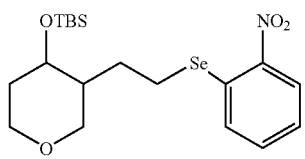

To a solution of the diol prepared as described in Step A (780 mg, 5.33 mmol) and 2-nitrophenyl selenocyanate (1.33 g, 5.87 mmol) in THF (17 mL) at 0° C. was added dropwise tri-n-butylphosphine (1.59 mL, 6.40 mmol). The reaction mixture was warmed to rt, stirred for 45 min, and concentrated. Purification by flash chromatography (silica, 80% ethyl acetate/hexane) gave 1.30 g of hydroxyselenide intermediate (74%) which was combined with imidazole (671 mg, 9.85 mmol) in DMF (10 mL) and treated with t-butyldimethylsilyl chloride (653 mg, 4.33 mmol) in DMF (5 mL). The reaction mixture was stirred at room temperature for overnight. Although incomplete by TLC, the reaction was diluted with ether and washed five times with water and once with brine. The ethereal phase was dried over anhydrous MgSO$_4$, filtered, and concentrated. Purification by MPLC (silica, 40% ethyl acetate/hexane) provided 1.53 g of desired product (87%).

Step C

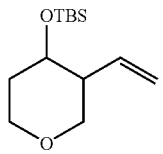

A cooled (0° C.) solution of the selenide prepared as described in Step B (1.50 g, 3.37 mmol) in THF (10 mL) was treated with 30% aqueous H$_2$O$_2$ (2.92 mL, 33.7 mmol), allowed to warm to rt, and stirred for 2.5 h. The reaction mixture was poured into 100 mL of 10% Na$_2$S$_2$O$_3$ solution, and the resulting mixture was extracted twice with ether. The combined ethereal layers were washed with saturated NaHCO$_3$ solution, then brined, dried over anhydrous MgSO$_4$, filtered, and concentrated. Purification by MPLC (silica, 20% ethyl acetate/hexane then 50% ethyl acetate/hexane) afforded 671 mg of olefin product as a mixture of isomers (~4:1, 82%). $^1$H NMR (CDCl$_3$, 500 MHz, major isomer): 5.69 (m, 1H), 5.07-5.14 (m, 2H), 3.95 (dt, J=11.5, 4.0 Hz, 1H), 3.89 (dd, J=4.0, 11.5 Hz, 1H), 3.57 (dt, J=4.5, 9.0 Hz, 1H), 3.44 (dt, J=2.5, 11.0H, 1H), 3.26 (dd, J=9.5, 11.5 Hz, 1H), 2.24 (m, 1H), 1.84 (m, 1H), 1.61 (m, 1H), 0.90 (s, 9H), 0.066 (s, 3H), 0.059 (s, 3H).

Step D

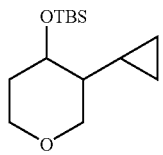

Nitroso methylurea (4.42 g, 42.8 mmol) was added in portions to a precooled (0° C.) two phase mixture of 40% KOH solution (18 mL) and ether (52 mL). The mixture was swirled by hand until all of the solids had dissolved and the ether layer had become deep yellow. This mixture was cooled to −78° C. to freeze the aqueous layer, then the ethereal layer was decanted into a container with KOH pellets (~5 g). The resulting diazomethane solution was stored in the freezer for 0.5 h. The olefin prepared as described in Step C (519 mg, 2.14 mmol) was dissolved in ether (5 mL), cooled to 0° C., and combined with about ½ of the diazomethane solution. Then palladium acetate (12 mg) was added. Gas evolution and a color change from yellow to colorless was observed. After occasionally swirling this mixture for 15 min, MgSO$_4$ was added, and the mixture was filtered and concentrated to give 592 mg of cyclopropyl product which required no further purification. $^1$H NMR (CDCl$_3$, 500 MHz, major isomer): 3.91 (m, 2H), 3.70 (m, 1H), 3.48 (m, 1H), 3.29 (dd, J=10.5, 14.5 Hz, 1H), 1.87 (m, 1H), 1.49-1.57 (m, 1H), 0.92 (s, 9H), 0.72 (m, 1H), 0.54 (m, 2H), 0.39 (m, 1H), 0.31 (m, 1H), 0.087 (s, 6H), 0.028 (m, 1H).

Step E

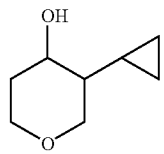

A solution of the cyclopropyl-TBS-ether prepared as described in Step D (590 mg, 2.14 mmol) in THF (8 mL) was treated with 1.0 M tetrabutylammonium fluoride solution in THF (2.57 mL, 2.57 mmol). The resulting reaction mixture was stirred at room temperature for 24 h, then was concentrated and purified by MPLC (silica, 20% acetone/ether) to give 332 mg of product, which was contaminated by a small amount of solvent. $^1$H NMR (CDCl$_3$, 500 MHz, major isomer): 3.98 (m, 1H), 3.93 (dd, J=4.5, 12.0 Hz, 1H), 3.68 (dt, J=4.5, 9.5 Hz, 1H), 3.44 (dt, J=2.5, 12.0 Hz, 1H), 3.19 (dd, J=11.0, 11.5 Hz, 1H), 1.94 (m, 1H), 1.81 (m, 1H), 1.58 (m, 1H), 0.77 (m, 1H), 0.62 (m, 1H), 0.44 (m, 1H), 0.37 (m, 1H), 0.090 (m, 1H).

Step F

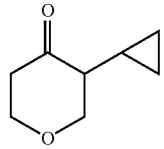

To a cooled (−78° C.) solution of oxalyl chloride (0.373 mL, 4.28 mmol) in DCM (15 mL) was added dropwise DMSO (0.607 mL, 8.56 mmol) in DCM (2 mL). After stirring at room temperature for 3 min, the alcohol prepared as described in Step E (2.1 mmol) in DCM (4 mL) was added dropwise. After an additional 15 min, triethylamine (2.39 mL, 17.1 mmol) was added dropwise and the reaction mixture was permitted to warm to room temperature and stir for 1 h. The reaction mixture was diluted with DCM and washed in turn with 3N HCl solution and saturated NaHCO$_3$ solution, dried over anhydrous MgSO$_4$, filtered, and concentrated. Purification by MPLC (silica, ether) gave 272 mg of ketone product. $^1$H NMR (CDCl$_3$, 500 MHz): 4.10 (m, 2H), 3.87 (m, 1H), 3.68 (dd, J=8.0, 11.5 Hz, 1H), 2.49-2.60 (m, 2H), 1.75 (m, 1H), 0.94 (m, 1H), 0.67 (m, 1H), 0.51 (m, 1H), 0.22 (m, 1H), 0.14 (m, 1H).

Intermediate 42

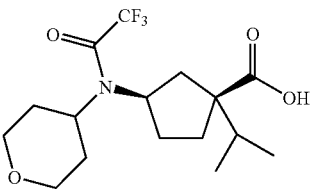

Step A

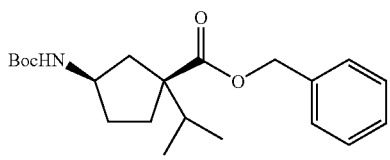

This Intermediate was prepared following the procedures described in Intermediate 9 A-E, except that in Step D 2-iodopropane was used as the alkylating agent instead of acetone. Resolution of cis/trans diastereomers: Flash chromatography (silica gel, 8% EA/hexanes) H NMR (500 MHz, CDCl$_3$): 7.36 (m, 5H), 5.14 (s, 2H), 4.77 (m, 1H), 4.01 (d, J=1H), 2.17 (m, 1H), 1.99-1.53 (m, 5H), 1.42 (m, 9H), 0.85 (d, J=7.0 Hz, 6H).

Step B

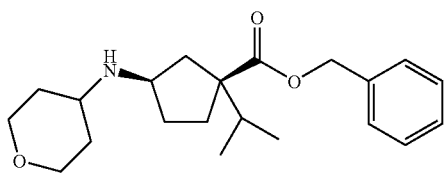

The BOC-amine from Step A (7.3 g, 20 mmol) was treated with hydrogen chloride (4N solution in dioxane). The reaction was allowed to stir for 1.5 h at room temperature before being concentrated to remove the dioxane. The resultant solid was dissolved in DCM (150 mL) and treated with tetrahydro-4H-pyran-4-one (2.4 g, 24 mmol) and triethylamine (2.8 mL, 20 mmol). The resulting solution was stirred at room temperature for 5 minutes before 4 Å powdered molecular sieves (~5 g) and sodium triacetoxyborohydride (17 g, 80 mmol) where added. The mixture was stirred for 2 h at room temperature. The reaction was filtered through celite and washed with a saturated aqueous sodium bicarbonate solution then brine. The organic layer was dried over MgSO$_4$, filtered, and concentrated under reduced pressure. To give 6.7 g of a colorless oil (97%). ESI-MS calc. for C21H31NO3: 345; Found: 346 (M+H).

Step C

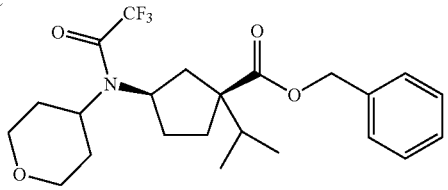

The amine from Step B (6.6 g, 19.1 mmol) was added to a solution of DCM (100 mL) and triethylamine (2.9 mL, 21 mmol). Trifluoroacetic anhydride (3.0 mL, 21 mmol) was added to the solution dropwise at room temperature and the resulting solution was allowed to stir at room temperature for 2.5 h. The reaction was diluted with DCM (100 mL) and washed with hydrochloric acid (1N aqueous solution) followed by brine. The organic layer was dried over MgSO$_4$, filtered and concentrated under reduced pressure. The crude yellow oil was purified by MPLC (silica gel, 0 to 30% EA/Hexanes) to give 4.9 g of a colorless oil (58%). $^1$H NMR (CDCl$_3$, 500 MHz): 7.37 (m, 5H), 5.18 (m, 2H), 4.20-3.88 (m, 4H), 3.64 (m, 1H), 3.42 (t, J=12.0 Hz, 1H), 3.26 (t, J=11.5 Hz, 1H), 3.18 (t, J=11.5 Hz, 1H), 2.81-2.65 (m, 2H), 2.26 (m, 1H), 1.89-1.80 (m, 3H), 1.64-1.40 (m, 3H), 0.874 (m, 6H).

Step D

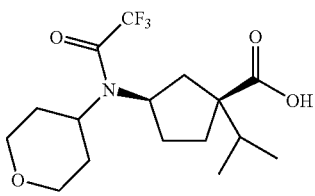

The product from Step C (3.5 g, 7.9 mmol) was dissolved in methanol (60 mL) and treated with 20% palladium hydroxide on activated carbon (350 mg). This mixture was placed under a hydrogen atmosphere (1 atm) and allowed to stir at room temperature for 1.2 h. the reaction was filtered through celite and concentrated under reduced pressure to give 2.63 g of a white solid (95%).

EXAMPLE 1

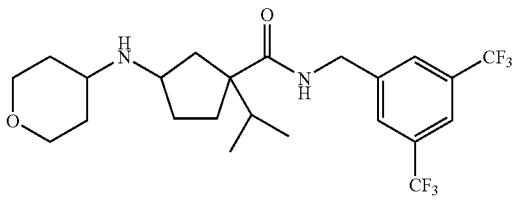

A solution of Intermediate 8 (50 mg, 0.13 mmol) and Intermediate 2 (18 mg, 0.13 mmol) in DCM (5 mL) was treated with DIEA (35 µL, 0.19 mmol), 4 Å powdered molecular sieves and sodium triacetoxyborohydride (108 mg, 0.508 mmol) and stirred at room temperature overnight. The reaction was quenched with saturated NaHCO$_3$ and extracted with DCM (5×). The combined organic phases were dried over Na$_2$SO$_4$ and concentrated. The crude product was purified by preparative TLC (MeOH:DCM:NH$_4$OH/94.5:5:0.5) to yield the desired product (28 mg, 46%). Cis and trans pairs were further resolved by preparative TLC. The respective cis-racemate was further resolved by a chiral HPLC using a ChiralCel OD column. LC-MS for C$_{23}$H$_{31}$F$_6$N$_2$O$_2$ [M+H]$^+$ calculated 481.22, found 481.30.

EXAMPLE 2

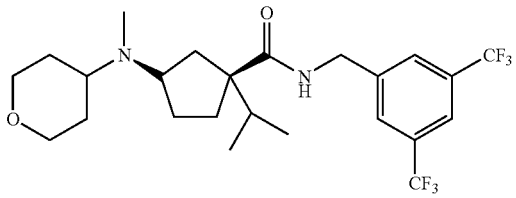

To a solution of the amine from Example 1 (cis-racemate, 25 mg, 0.052 mmol), formaldehyde (37% aqueous solution, 12 μL, 0.16 mmol), DIEA (13 μL, 0.078 mmol), TFA (5 μL) and MeOH (1.5 mL) was added NaCNBH$_3$ (17 mg, 0.26 mmol). The reaction mixture was stirred at room temperature overnight and concentrated in vacuo. Purification by preparative TLC (MeOH:DCM:NH$_4$OH/3:96.7:0.3) gave 17 mg (66%) of the desired product. The cis-racemate was resolved by a ChiralPak AD semi-preparative HPLC column. LC-MS for $C_{24}H_{32}F_6N_2O_2$ [M+H]$^+$ calculated 495.24, found 495.25.

EXAMPLE 3

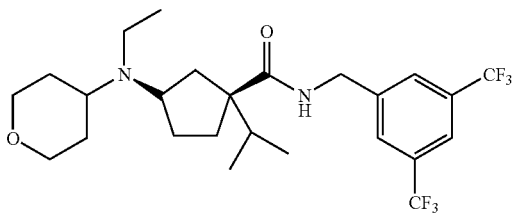

This amine was synthesized in 38% yield starting from the secondary amine preparation of which was described in Example 1 according the procedure described in Example 2, except that acetaldehyde was used instead of the formaldehyde. LC-MS for $C_{25}H_{34}F_6N_2O_2$ [M+H]$^+$ calculated 509.25, found 509.35.

EXAMPLE 4

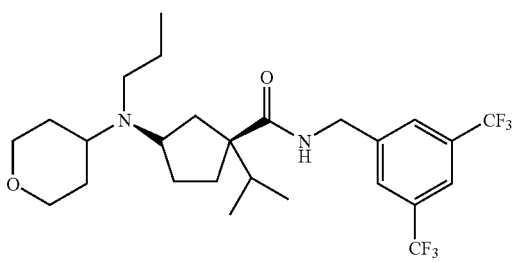

This amine was prepared starting from the secondary amine preparation of which was described in Example 1 according the procedure described in Example 2, except that propionaldehyde was used instead of the formaldehyde. LC-MS for $C_{26}H_{36}F_6N_2O_2$ [M+H]$^+$ calculated 523.27, found 523.20.

EXAMPLE 5

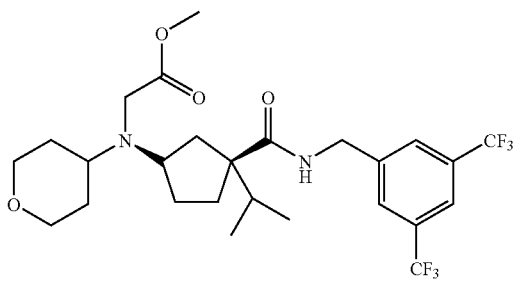

The amine from Example 1 (cis-racemate, 50 mg, 0.10 mmol) and methyl bromoacetate (30 μL, 0.31 mmol) were dissolved in DCM (1 mL) and a saturated solution of NaHCO$_3$ (1 mL) was added. The reaction mixture was stirred at room temperature overnight. Purified by preparative TLC (MeOH:DCM:NH$_4$OH (4:95.6:0.4) gave the desired product (43 mg, 74%). LC-MS for $C_{26}H_{34}F_6N_2O_4$ [M+H]$^+$ calculated 553.24, found 553.25.

EXAMPLE 6

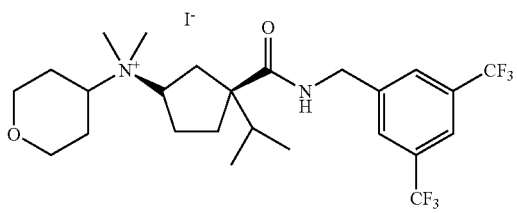

A solution of the amine from Example 2 (55 mg, 0.089 mmol), methyl iodide (56 μL, 0.89 mmol), and THF (2 mL) was heated to 50° C. in a sealed tube for 4.5 days and concentrated to dryness (74 mg, 99+%). L-C-MS for $C_{25}H_{35}F_6N_2O_2$ [M]$^+$ calculated 509.26, found 509.35.

EXAMPLE 7

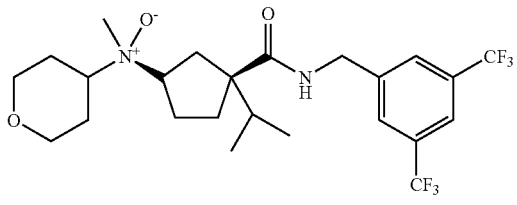

A mixture of the amine from Example 2 (50 mg, 0.089 mmol), H$_2$O$_2$ (30% aqueous solution, 3 mL), and MeOH (5 mL) was stirred at room temperature for a week before being concentrated to yield Example 7. L-C-MS for $C_{24}H_{32}F_6N_2O_3$ [M]$^+$ calculated 510.23, found 511.3.

EXAMPLE 8

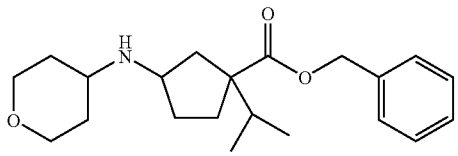

Step A

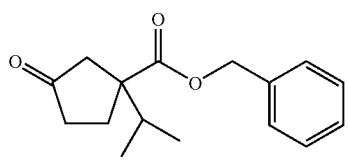

Intermediate 1 (2.00 g, 11.8 mmol), benzyl alcohol (6.22 mL, 57.6 mmol), DMAP (145 mg, 1.18 mmol), EDC (3.38 g, 17.6 mmol) and DCM (75 mL) were mixed together and stirred at room temperature. After completion of reaction, the mixture was washed with H$_2$O (3×). The combined aqueous layers were back extracted with DCM (1×). The combined organic layers were washed with brine (1×), dried over MgSO$_4$, and concentrated to dryness. The crude product was purified by flash chromatography (EtOAc:Hexanes/15:85) to yield the desired ester (900 mg, 29%). $^1$H NMR (500 MHz, CDCl$_3$): 7.39-7.34 (m, 5H), 5.16 (d, J=2.8 Hz, 2H), 2.85 (d, J=18.3 Hz, 1H), 2.50-2.44 (m, 1H), 2.32-2.05 (m, 4H), 1.97-1.90 (m, 1H), 0.94 (t, J=6.6 Hz, 6H).

Step B

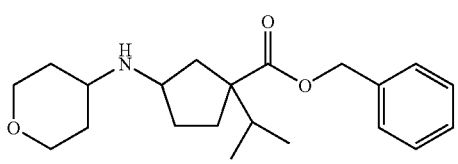

This compound was synthesized following the procedure described in Example 1. LC-MS for C$_{21}$H$_{32}$NO$_3$ [M+H]$^+$ calculated 346.23, found 346.

EXAMPLE 9

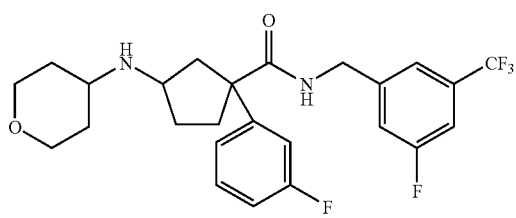

Step A

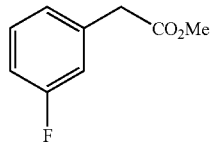

Thionyl chloride (9.5 mL, 130 mmol) was added dropwise to methanol (225 mL) and 3-fluorophenyl acetic acid (20 g, 130 mmol) was dumped into the solution. The reaction mixture was refluxed for 1 h before being concentrated in vacuo to yield the desired product (23.4 g, >100%). $^1$H NMR (400 MHz, CDCl$_3$): 7.30 (m, 1H), 7.02 (m, 3H), 3.73 (s, 3H), 3.64 (s, 2H).

Step B

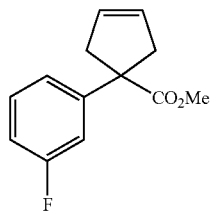

The ester from Step A (23.25 g, 138.0 mmol) and 1,4-dichloro-cis-butene (15 mL, 0.14 mol) were dissolved in DME (200 mL) at 0° C. under nitrogen and NaH (60% dispersion in mineral oil, 14 g, 350 mmol) was added. The reaction mixture was stirred for 12 h, quenched in ice water and extracted with ether (3×). The combined organic layers were washed with water and brine, dried over anhydrous MgSO$_4$, and concentrated in vacuo. The crude product was purified by vacuum distillation (b.p.: 92-101° C. @ 0.11 mmHg) to yield the desired product (20 g, 60%), and about 20% of the corresponding cyclopropane product. $^1$H NMR (500 MHz, CDCl$_3$): 7.29 (m, 1H), 7.10 (m, 2H), 6.97 (m, 1H), 5.78 (s, 2H), 3.68 (s, 3H), 3.41 (d, J=15.1 Hz, 2H), 2.78 (d, J=14.6 Hz, 2H).

Step C

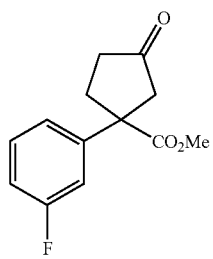

The olefin from Step B (12.5 g, 56.8 mmol), Borane (1 M in THF, 28.4 mL, 28.4 mmol), and THF (100 mL) were mixed together and stirred at room temperature under nitrogen. Upon disappearance of the starting material, the reaction mixture was concentrated to dryness in vacuo and dissolved again in DCM. Anhydrous MgSO$_4$ (75 g) and PCC (49 g, 230 mmol) were added. The reaction mixture was stirred for 24 h and filtered through silica gel. The precipitate was suspended in DCM and ethyl acetate. The solution was refluxed for 20 minutes and filtered hot through silica gel to recover the product. The combined filtrate was concentrated in vacuo and purified by flash column chromatography (ethyl acetate:hexanes/30:70) to yield the desired ketone (6.46 g, 48%). $^1$H NMR (400 MHz, CDCl$_3$): 7.35 (m, 1H), 7.14-7.00 (m, 4H), 3.69 (s, 3H), 3.25 (dd, J=17.9 Hz, 2.1 Hz, 1H), 2.98 (m, 1H), 2.61 (d, J=17.9 Hz, 1H), 2.41-2.28 (m, 3H).

Step D

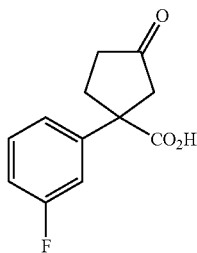

Lithium hydroxide (2.05 g, 25.4 mmol) was dissolved in water (5 mL) and a solution of ester from Step C (3.0 g, 13 mmol) in methanol (25 mL) was added. The reaction mixture was stirred at room temperature for 5 h before being concentrated in vacuo. The concentrate was dissolved in water and washed with ether. The aqueous layer was acidified to pH 2-3 by addition of 2 N aqueous HCl and extracted with ether (4×). The combined organic layers were dried over anhydrous MgSO$_4$, filtered, and concentrated in vacuo to yield the desired acid (2.678 g, 94%). The crude product was used in the next step without any additional purification.

Step E

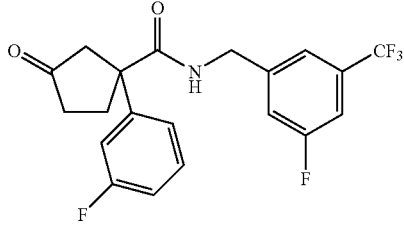

The above described acid (1.34 g, 6.57 mmol), 3-fluoro-5-trifluoromethyl benzylamine (972 μL, 6.57 mmol), HOAT (895 mg, 6.57 mmol) and EDC (1.9 g, 9.85 mmol) were dissolved in DCM and stirred for 16 h at room temperature. The reaction mixture was diluted with methylene chloride, washed with 1 N HCl solution, saturated NaHCO$_3$, water, and brine. It was dried over anhydrous MgSO$_4$ and concentrated in vacuo. The crude product was purified by MPLC (ethyl acetate:hexanes/50:50) to yield the desired amide (1.156 g, 44%). $^1$H NMR (400 MHz, CDCl$_3$): 7.44 (m, 1H), 7.21 (d, J=8.0 Hz, 1H), 7.17 (m, 4H), 6.99 (d, J=9.0 Hz, 1H), 5.64 (s, 1H), 4.41 (t, J=5.9 Hz, 2H), 3.21 (d, J=17.6 Hz, 1H), 2.80 (m, 1H), 2.64-2.44 (m, 3H), 2.35 (m, 1H).

Step F

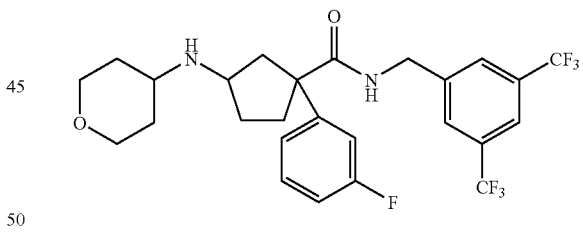

The ketone from Step E (200 mg, 0.50 mmol), Intermediate 2 (70 mg, 0.50 mmol), DIEA (130 μL, 0.76 mmol), sodium triacetoxyborohydride (534 mg, 2.52 mmol), and 4 Å powdered molecular sieves were mixed together in DCM and stirred at room temperature for 24 h. The reaction was filtered through celite, concentrated, and purified by preparative TLC (methanol:NH$_4$OH:DCM (4:0.4:96.6) to yield the final product (156 mg, 64%). LC-MS for C$_{25}$H$_{28}$F$_5$N$_2$O [M+H]$^+$ calculated 483.20, found 483.25.

EXAMPLE 10

This compound was synthesized starting from the acid preparation which was described in Example 9, Step D and bis-trifluoromethylbenzylamine hydrochloride using the same procedure detailed in Example 9, Step E-F. LC-MS for C$_{26}$H$_{28}$F$_7$N$_2$O$_2$ [+H]$^+$ calculated 533.20, found 533.2.

A number of additional compounds containing various aromatic groups attached to C1 of the cyclopentane ring (R$_1$) in both the 3,5-bistrifluoromethyl- as well as in the 3-trifluoro-5-fluorobenzylamide series were prepared using procedures analogous to those described in Example 9. Table 1 summarizes the structures and the calculated and observed MS characteristics of these compounds.

TABLE 1

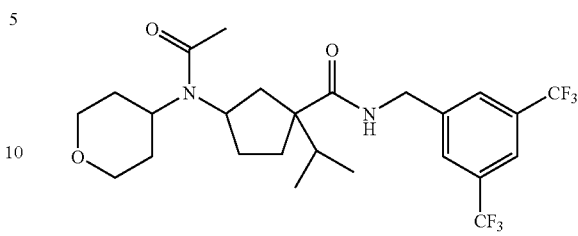

| Example | R₁ | R₇ | Molecular Formula | Calculated [M + H⁺] | Found [M + H⁺] |
|---|---|---|---|---|---|
| 11 | 3-methoxyphenyl | F | $C_{26}H_{31}F_4N_2O_3$ | 495.22 | 495.22 |
| 12 | 3-methoxyphenyl | CF₃ | $C_{27}H_{31}F_6N_2O_3$ | 545.22 | 545.20 |
| 13 | 2-thienyl | F | $C_{23}H_{27}F_4N_2O_2S$ | 471.17 | 471.25 |
| 14 | 2-thienyl | CF₃ | $C_{27}H_{31}F_6N_2O_2S$ | 521.16 | 521.15 |
| 15 | 3-thienyl | F | $C_{23}H_{27}F_4N_2O_2S$ | 471.17 | |
| 16 | 3-thienyl | CF₃ | $C_{24}H_{27}F_6N_2O_2S$ | 521.16 | 521.20 |
| 17 | phenyl | F | $C_{25}H_{29}F_6N_2O_2$ | 465.21 | 465.25 |
| 18 | phenyl | CF₃ | $C_{26}H_{29}F_6N_2O_2$ | 515.21 | 515.20 |

Note:
The respective cis- and trans- and trans diastereoisomeric pairs of Example 12 were resolved by preparative TLC and the more polar cis- racemate was further resolved using chiral HPLC.

EXAMPLE 19

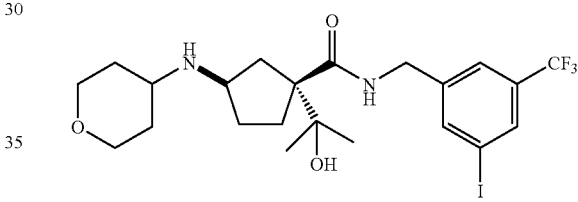

The amine from Example 1 (20 mg, 0.042 mmol), neat acetic anhydride (0.5 mL), and pyridine (0.5 mL) were mixed and stirred at room temperature. Upon completion of the reaction, the mixture was concentrated, dissolved in ether, washed with H₂O (3×), dried over MgSO₄, and concentrated to dryness. The crude product was purified by preparative LC (EtOAc:Hexanes/50:50) to yield the desired product (5.5 mg, 25%). LC-MS for $C_{25}H_{33}F_6N_2O_3$ [M+H]⁺ calculated 523.23, found 523.3.

EXAMPLE 20

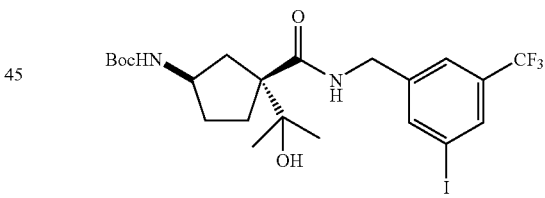

Step A

A solution of Intermediate 9 (400 mg, 1.39 mmol), Intermediate 7 (470 mg, 1.39 mmol), DIEA (365 µL, 2.09 mmol), and HOAT (190 mg, 1.39 mmol) in DCM (20 mL) was treated with EDC (400 mg, 2.09 mmol). The resulting mixture was stirred overnight, washed with saturated NaHCO₃, water (2×), brine, dried (anhydrous magnesium sulfate) and concentrated in vacuo. The crude product was purified by Preparative TLC (EtOAc:Hexanes/40:60) to yield the desired product (500 mg, 63%). ¹H NMR (500 MHz, CDCl₃): 8.15 (bs, 1H), 7.84 (s, 1H), 7.53 (s, 1H), 5.26 (bs, 1H), 4.47 (d, J=6.1 Hz, 2H), 4.01 (m, 1H), 2.60 (bs, 1H), 2.17 (dd, J=14.4 Hz, 5.4 Hz, 1H), 2.07 (m, 1H), 2.00-1.87 (m, 3H), 1.61 (m, 1H), 1.43 (s, 9H), 1.27 (d, J=16.3 Hz, 6H). LC-MS for $C_{22}H_{31}F_3N_2O_4$[M+H]⁺ calculated 571.12, found 571.2.

Step B

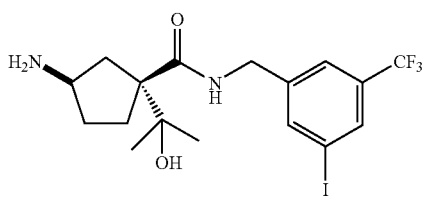

The BOC-protected amine from the previous step (100 mg) was treated with HCl in dioxane (4 N, 6 mL) and was stirred at room temperature for 1 h. It was concentrated in vacuo to yield the desired amine hydrochloride (97 mg, 99%). LC-MS for $C_{17}H_{23}F_3IN_2O_2[M+H]^+$ calculated 470.07, found 471.1.

Step C

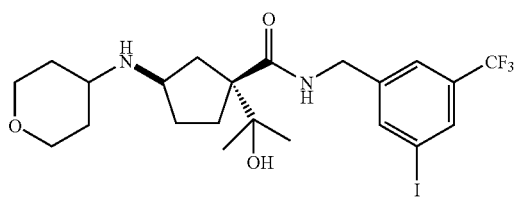

The amine from the previous step (400 mg, 0.851 mmol), tetrahydro-4H-pyran-4-one (170 μL, 1.70 mmol), and DIEA (225 μL, 1.28 mmol) were dissolved in DCM (30 mL). Molecular sieves (4 Å, powdered) and sodium triacetoxyborohydride (900 mg, 4.26 mmol) were added. The reaction mixture was stirred at room temperature overnight and the reaction was quenched with saturated $NaHCO_3$. The solution was heated at 80° C. for 4 h to break up borane complexes, cooled to room temperature and extracted with DCM (5×). The combined organic extracts were dried over $Na_2SO_4$ and concentrated to dryness. The crude product was purified by preparative TLC (MeOH:DCM:$NH_4$OH/5:94.5:0.5) to yield 270 mg (61%) of the desired product. L-C-MS for $C_{22}H_{31}IF_3N_2O_3$ $[M+H]^+$ calculated 554.13, found 555.1.

Starting from Intermediates 9 and/or 10 a number of additional compounds were synthesized. The applied procedures were analogous to those described in Example 20 varying the benzylamine in Step A as well as the ketone in Step C. Their structure and MS characteristics are summarized in Table 2.

TABLE 2

| Ex. | R1 | R2 | R3 | R4 | Molecular Formula | Calc'd [M+H+] | Found [M+H+] |
|---|---|---|---|---|---|---|---|
| 21 | tetrahydropyran-4-yl | OH | Cl | $CF_3$ | $C_{22}H_{31}ClF_3N_2O_3$ | 463.19 | 463.15 |
| 22 | tetrahydropyran-4-yl | OH | H | Ph | $C_{27}H_{37}N_2O_3$ | 437.27 | 437.35 |
| 23 | tetrahydropyran-4-yl | OH | H | $OCF_3$ | $C_{22}H_{32}F_2N_2O_4$ | 445.22 | 445.3 |
| 24 | tetrahydropyran-4-yl | OH | H | 1-methyl-5-(trifluoromethyl)-1H-tetrazol-... | $C_{22}H_{32}F_3N_6O_3$ | 497.24 | 497.2 |
| 25 | tetrahydropyran-4-yl | OH | F | $CF_3$ | $C_{22}H_{31}F_4N_2O_3$ | 447.22 | 445.25 |

TABLE 2-continued

| Ex. | R1 | R2 | R3 | R4 | Molecular Formula | Calc'd [M+H+] | Found [M+H+] |
|---|---|---|---|---|---|---|---|
| 26 | 3-methyltetrahydropyran | OH | Cl | Cl | $C_{21}H_{31}Cl_2N_2O_3$ | 429.16 | 429.25 |
| 27 | 3-methyl-4-methyl-tetrahydropyran | OH | F | $CF_3$ | $C_{23}H_{33}F_4N_2O_3$ | 461.23 | 461.25 |
| 28 | 3-chlorobenzoate of 4-methyl-tetrahydropyran-3-ol | OH | F | $CF_3$ | $C_{29}H_{34}ClF_4N_2O_5$ | 601.20 | 601.3 |
| 29 | 3-fluoro-4-methyl-tetrahydropyran | OH | F | $CF_3$ | $C_{22}H_{30}F_5N_2O_3$ | 465.21 | 465.25 |
| 30 | 3-trifluoromethyl-4-methyl-tetrahydropyran | OH | F | $CF_3$ | $C_{23}H_{30}F_7N_2O_3$ | 515.21 | 515.2 |
| 31 | 4-methylcyclohexyl | OH | F | $CF_3$ | $C_{23}H_{33}F_4N_2O_4$ | 445.24 | 445.3 |
| 32 | ethyl 4-methylcyclohexanecarboxylate | H | $CF_3$ | $CF_3$ | $C_{27}H_{37}F_6N_2O_3$ | 551.26 | 551.35 |
| 33 | 2-methylcyclohexyl ether | H | $CF_3$ | $CF_3$ | $C_{24}H_{33}F_6N_2O_2$ | 495.24 | 495.25 |
| 34 | methyl 3-methylcyclopentanecarboxylate | H | $CF_3$ | $CF_3$ | $C_{25}H_{33}F_6N_2O_3$ | 523.23 | 523.3 |

TABLE 2-continued

[Structure: cyclopentane core with R1-NH substituent, C(=O)NH-CH2-aryl(R3,R4) group, and R2/tert-butyl substituent]

| Ex. | R1 | R2 | R3 | R4 | Molecular Formula | Calc'd [M+H+] | Found [M+H+] |
|---|---|---|---|---|---|---|---|
| 35 | [tert-butyl ester cyclobutyl group] | H | CF3 | CF3 | $C_{27}H_{37}F_6N_2O_3$ | 551.26 | 551.2 |
| 36 | [N-methyl-4-methylpiperidinyl] | H | CF3 | CF3 | $C_{24}H_{34}F_6N_3O$ | 494.25 | 494.3 |
| 37 | [N-acetyl-4-methylpiperidinyl] | H | CF3 | CF3 | $C_{25}H_{34}F_6N_3O_2$ | 522.25 | 522.25 |

Notes:

Example 27: The mixture of cis- and trans- racemates was separated by preparative TLC (the less polar racemate having the cis-relative stereochemistry).

Example 30: The single enantiomers contained within the cis and trans racemic pairs derived from the pyran ring were resolved using a semi-preparative ChiralCel OD column.

Example 32: Cis and trans isomers on the cyclohexane ring were separated by preparative TLC (MeOH:NH4OH:DCM/1.5:0.15:98.35).

EXAMPLE 38

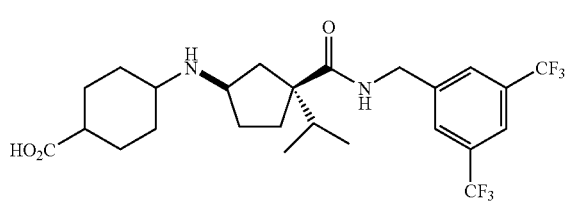

The ester described in Example 32 (25 mg, 0.043 mmol) was dissolved in MeOH (3 mL) and 5 N NaOH (1 mL) was added. After completion of reaction, the mixture was concentrated to dryness, the residue was dissolved in water, acidified to pH 7, and extracted with DCM (6×). The combined organic phases were dried over $Na_2SO_4$ and concentrated in vacuo to yield the desired acid. It was further purified by reverse phase preparative HPLC to afford 21.7 mg (91%) of the pure product. LC-MS for $C_{25}H_{33}F_6N_2O_3$ [M+H+] calculated 523.23, found 523.2.

EXAMPLE 39

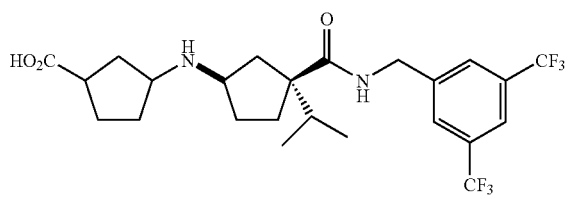

The compound in Example 39 was prepared as detailed in Example 38 using the ester described in Example 34 as starting material. LC-MS for $C_{24}H_{31}IF_6N_2O_3$ [M+H$^+$] calculated 509.22, found 509.2.

EXAMPLE 40

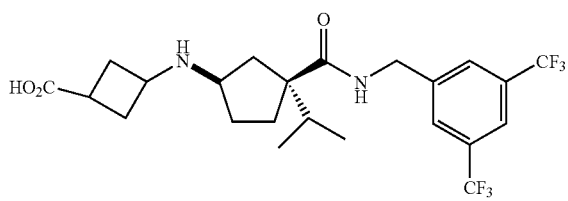

The solution of the ester described in Example 35 (50 mg) in TFA (2.5 mL) and DCM (2.5 mL) was stirred at room temperature. After completion of reaction, the reaction mixture was concentrated in vacuo and purified by reverse phase HPLC to yield the desired acid (0.64 mg). LC-MS for $C_{23}H_{29}F_6N_2O_3$ [M+H$^+$] calculated 495.20, found 495.25.

EXAMPLE 41

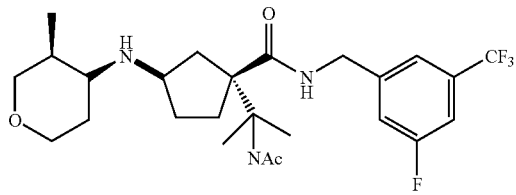

Concentrated sulfuric acid (3 mL) was cooled to 0° C. before a solution of the cis-racemate (50 mg) from Example 27 in acetonitrile (2 mL) was added. The mixture was stirred at room temperature overnight. The reaction was poured onto ice, the solution was made basic with 5 N NaOH, and extracted with ether (3×). The combined organic phases were dried over anhydrous MgSO$_4$ and concentrated in vacuo. The crude product was purified by reverse phase HPLC to yield the desired acetamide (1.7 mg). LC-MS for $C_{25}H_{36}F_{43}O_3$ [M+H$^+$] calculated 502.26, found 502.3.

EXAMPLE 42

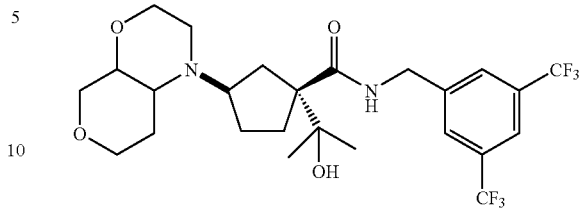

A solution of Intermediate 4 (110 mg, 0.698 mmol) in DCM (10 mL) was cooled to −78° C. and O$_3$ was passed though until a permanent blue color indicated completion of the reaction. The excess ozone was removed with nitrogen and the reaction mixture was warmed up to room temperature. This solution was dried over anhydrous MgSO$_4$ and after removal of the drying agent by filtration, the corresponding amine Intermediate 14 (250 mg, 0.558 mmol), DIEA (146 µL, 0.837 mmol), molecular sieves, and sodium triacetoxyborohydride (590 mg, 2.79 mmol) were added. The resulting mixture was stirred at room temperature overnight and filtered through celite. Saturated NaHCO$_3$ solution was added and the mixture was heated to 60° C. for 3 h to break down the borane adducts. The product was extracted with DCM (5×) and the combined organic layers were dried over Na$_2$SO$_4$, filtered, and concentrated in vacuo, and the product was purified by preparative TLC (MeOH:DCM:NH$_4$OH/4:95.6:0.4) to yield the desired product (23.3 mg). The two isomers were resolved by preparative TLC. LC-MS for $C_{25}H_{33}F_6N_2O_4$ [M+H$^+$] calculated 539.23, found 539.2.

EXAMPLE 43

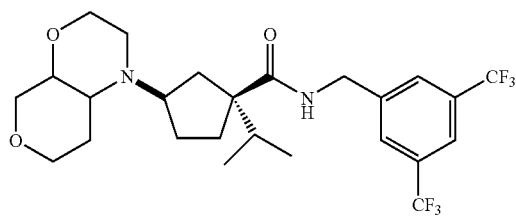

This compound was prepared as described in Example 42. LC-MS for $C_{25}H_{33}F_6N_2O_3$ [M+H$^+$] calculated 523.23, found 523.3.

EXAMPLE 44

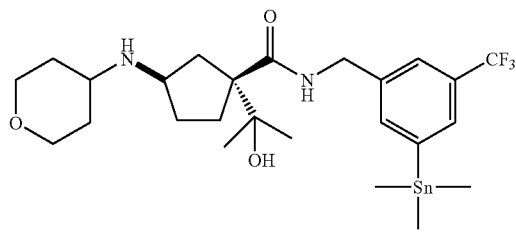

The iodide described in Example 20 (100 mg, 0.18 mmol) and Pd(Ph$_3$P)$_4$ (22 mg, 0.018 mmol) was dissolved in THF (10 mL) and Me$_6$Sn$_2$ (120 mg, 0.36 mmol) was added. The reaction was complete after refluxing for 3 h. The mixture was allowed to cool to room temperature, diluted with EtOAc, washed with saturated NaHCO$_3$, dried over Na$_2$SO$_4$, and concentrated in vacuo. The crude product was purified by preparative TLC (MeOH:DCM:NH4OH/5:94.5:0.5) to yield the desired product (63.3 mg, 59.4%). LC-MS for C$_{25}$H$_{40}$F$_3$N$_2$O$_3$Sn [M+H$^+$] calculated 591.19, found 593.2.

EXAMPLE 45

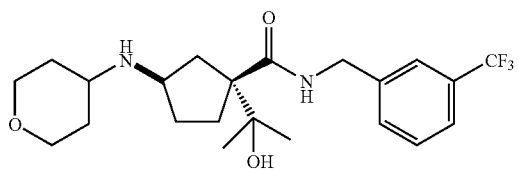

The tin-derivative described in Example 44 was stirred in 4 N HCl. LC-MS for C$_{22}$H$_{32}$F$_3$N$_2$O$_3$ [M+H$^+$] calculated 429.23, found 429.25.

EXAMPLE 46

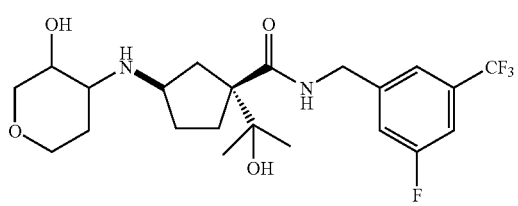

The ester described in Example 28 (170 mg, 0.283 mmol) was dissolved in MeOH (2 mL) and sodium methoxide (0.5 M in MeOH, 640 μL, 0.3 mmol) was added. After completion of reaction, the mixture was concentrated in vacuo and purified by preparative LC (MeOH:DCM:NH$_4$OH/6:93.4:0.6) to yield 79.7 mg (60%) of the desired product. LC-MS for C$_{22}$H$_{31}$F$_4$N$_2$O$_4$ [M+H$^+$] calculated 463.21, found 463.3.

EXAMPLE 47

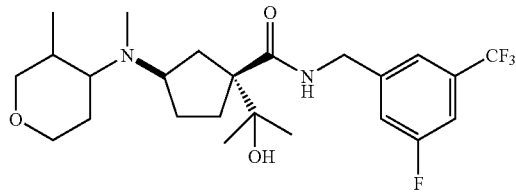

This compound was prepared as detailed in Example 20, Step G starting with the secondary amine from Example 27 and formaldehyde. LC-MS for C$_{24}$H$_{35}$F$_4$N$_2$O$_3$ [M+H$^+$] calculated 475.25, found 475.3.

EXAMPLE 48

Step A

Iodine (2 crystals) was added to a suspension of magnesium (18.5 g, 761 mmol) in anhydrous THF (240 mL) followed by cyclopropyl bromide (3 mL). The mixture was heated at 60° C. until the reaction initiated where upon cyclopropyl bromide (105 g, 868 mmol) was added at such a rate that a gentle reflux was maintained. After complete addition the mixture was heated at reflux for an additional 1 h. To the cooled (ice-bath) mixture was added tin (IV) chloride (15 mL, 130 mmol) and the reaction heated at reflux for 1 h. The reaction mixture was cooled and water (200 mL) was added cautiously, and the resulting mixture was extracted with Et$_2$O (3×400 mL). The combined Et$_2$O layers were dried over Na$_2$SO$_4$, filtered and concentrated in vacuo. The residue was purified by vacuum distillation (b.p. 94° C. @ 1 mm Hg to give the desired product (19 g, 52%).

Step B

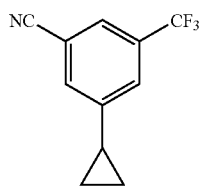

A mixture of the product from step A (4.0 g, 14 mmol), potassium carbonate (700 mg, 5 mmol), intermediate 20 (1.5 g, 5.0 mmol), and Pd(PPh$_3$)$_4$ (300 mg, 0.25 mmol) in anhydrous N,N-dimethylformamide (50 mL) was heated at reflux for 1 h. The cooled reaction mixture was poured into water (350 mL) and extracted with EtOAc (3×200 mL). The combined EtOAc layers were washed with water (3×300 mL), saturated NaCl (100 mL), dried over Na$_2$SO$_4$, filtered and evaporated. The residue was purified by MPLC (Biotage Flash 40) eluting with 2% EtOAc in hexanes to give the desired product (650 mg, 62%); $^1$H NMR 500 MHz (CDCl$_3$): 0.81 (2H, m), 1.16 (2H, m), 2.02 (1H, m), 7.52 (1H, s), 7.54 (1H, s), 7.69 (1H,s).

Step C

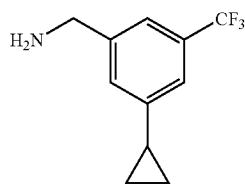

A solution of the product from step B (650 mg, 3.1 mmol) in a mixture of ethyl alcohol (25 mL) and ammonium hydroxide (5 mL) was hydrogenated at 50 psi over Raney nickel (200 mg) for 7 h on a Parr apparatus. The catalyst was removed by filtration, and the filtrate evaporated. The residue was purified by MPLC (Biotage Flash 40) elution with 2% CH$_3$OH in CH$_2$Cl$_2$ containing 0.5% NH$_4$OH to give the desired product (336 mg, 51%); $^1$H NMR 500 MHz (CDCl$_3$): 0.74 (2H, m), 1.02 (2H, m), 1.95 (1H, m), 3.90 (2H,s), 7.19 (1H, s), 7.22 (1H, s), 7.36 (1H,s).

Step D

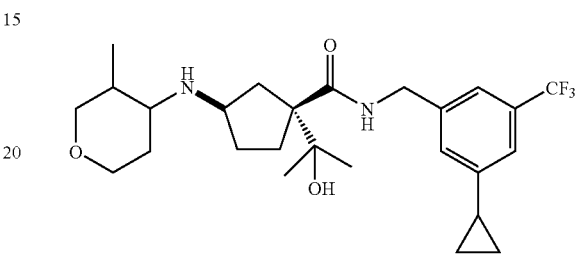

This compound was synthesized according to the procedure described in Example 146, except that Intermediate 9 was used instead of Intermediate 10 and the previously described cyclopropylbenzylamine (Step C) instead of the pyridylbenzylamine. The respective single diastereoisomers were obtained by semi-preparative chiral HPLC using a ChiralCel OD column (eluent:hexane:ethanol/95:5, 9.0 mL/minutes. LC-MS for C$_{26}$H$_{37}$F$_3$N$_2$O$_3$ [M+H]$^+$ calculated 483.28, found 483.30.

EXAMPLE 49

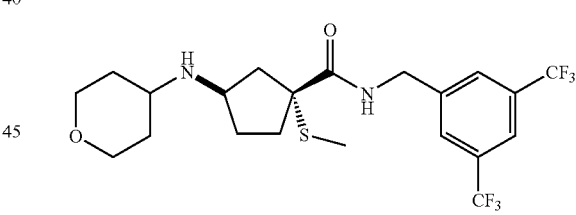

Step A

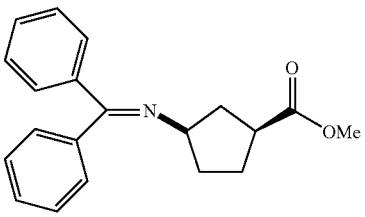

This ester was synthesized as described in Intermediate 10, Step B.

Step B

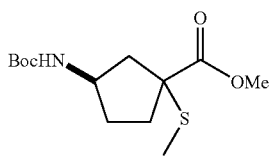

This intermediate was synthesized starting from the ester described in the previous step according to the procedure detailed under the description of Intermediate 10, Step C, except that dimethyl disulfide was used as alkylating agent instead of acetone. LC-MS for $C_{21}H_{24}NO_2S$ [M+H$^+$] calculated 354.14, found 354.25.

Step C

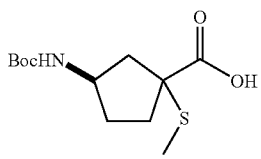

The ester described in the previous step (2.10 g, 7.27 mmol) was dissolved in MeOH (10 mL) and THF (10 mL) and a solution of lithium hydroxide (1.5 g, 36 mmol) in $H_2O$ (10 mL) was added. The mixture was heated to 60° C. overnight and concentrated in vacuo. The aqueous layer was washed with hexanes, acidified to pH 4, and extracted with DCM (3×). The combined organic layers were dried over anhydrous $MgSO_4$ and concentrated to dryness. The crude product was used in the following step without any additional purification.

Step D

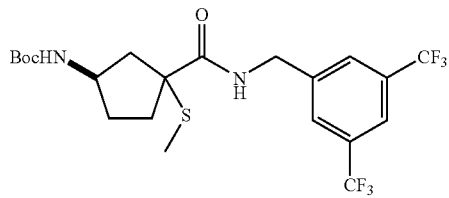

The amide group was attached in a procedure analogous to that described in Example 20, Step A. LC-MS for $C_{21}H_{27}N_2O_3S$ [M+H$^+$] calculated 501.16, found 445.15 (loss of the t-butyl group).

Step E

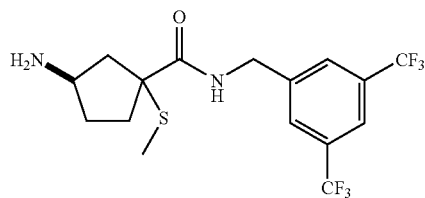

The BOC-protecting group was removed as described in Example 20, Step B. LC-MS for $C_{16}H_{18}F_6N_2OS$ [M+H$^+$] calculated 401.10, found 401.2.

Step F

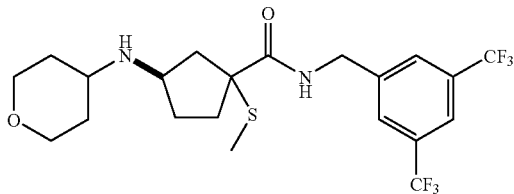

The final amine was prepared as detailed in Example 20, Step C. The respective cis and trans isomers were resolved using preparative TLC (MeOH:DCM:NH$_4$OH/4:95.6: 0.4) with cis- being the desired isomer. LC-MS for $C_{21}H_{27}F_6N_2O_2S$ [M+H$^+$] calculated 485.16, found 485.2.

EXAMPLE 50

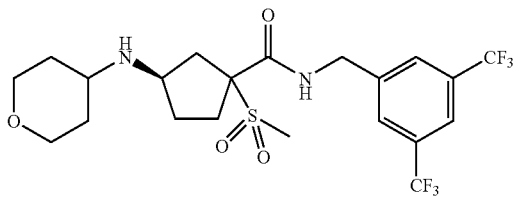

Step A

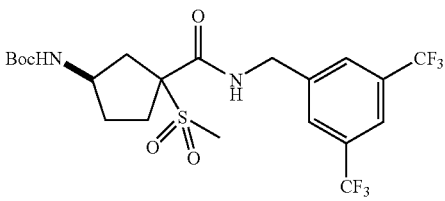

The sulfide, preparation of which was described in Example 49, Step E (200 mg, 0.4 mmol) was dissolved in isopropanol (7 mL) before a solution of oxone (500 mg, 0.8 mmol) in $H_2O$ (7 mL) was added. The mixture was stirred at room temperature for 2 h before being concentrated to dryness. The concentrate was diluted with ether, washed with $H_2O$ (3×), dried over anhydrous $MgSO_4$, and concentrated in vacuo to yield 207 mg (97%) of the desired compound. LC-MS for $C_{21}H_{27}F_6N_2O_5S$ [M+H$^+$] calculated 533.15, found 433.15 (-BOC-group).

Step B

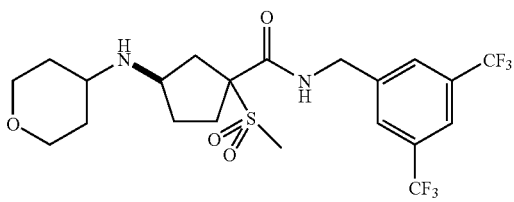

This compound was prepared starting from the previously described sulfone using the procedures detailed in Example 49, Steps E and F. The cis- and trans-isomers were separated by preparative TLC with the less polar compound being the cis isomer. LC-MS for $C_{21}H_{27}F_6N_2O_4S$ [M+H$^+$] calculated 517.15, found 517.15.

EXAMPLE 51

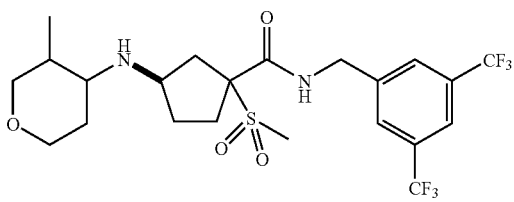

This compound was prepared as detailed in Example 50 using Intermediate 5 instead of tetrahydro-4H-pyranone. The two pairs of isomers were separated by preparative TLC (MeOH:DCM:NH$_4$OH/3:96.7:0.3). LC-MS for $C_{22}H_{29}F_6N_2O_4S$ [M+H$^+$] calculated 531.17, found 531.25.

EXAMPLE 52

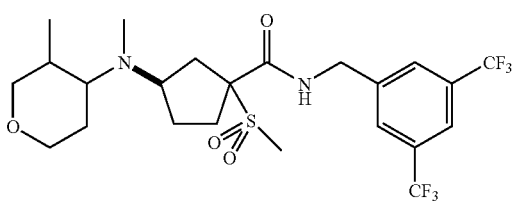

A mixture of the product described in Example 51 (more polar isomer, 30 mg, 0.058 mmol), formaldehyde (37% wt in H$_2$O, 15 µL, 0.17 mmol), TFA, NaCNBH$_3$ (20 mg, 0.29 mmol), and MeOH (5 mL) was stirred at room temperature overnight before being concentrated in vacuo and purified by preparative TLC (MeOH:DCM:NH$_4$OH/4:95.6:0.4) to yield Example 52 (11 mg, 35.7%). LC-MS for $C_{23}H_{31}F_6N_2O_4S$ [M+H$^+$] calculated 545.18, found 545.2.

EXAMPLE 53

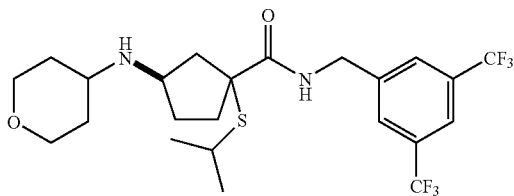

The compound listed under Example 53 was prepared as detailed in Example 49 except that diisopropyl sulfide was used instead of dimethyl sulfide and the cis and trans isomers were resolved in Step D instead of Step F. LC-MS for $C_{23}H_{31}F_6N_2O_2S$ [M+H$^+$] calculated 513 19, found 513.2.

EXAMPLE 54

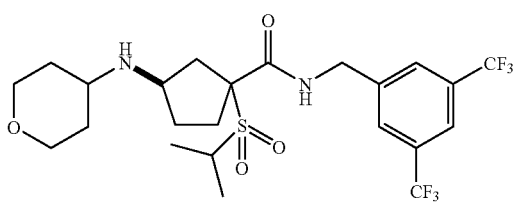

The compound described under Example 54 was prepared as detailed in Example 50. LC-MS for $C_{23}H_{31}F_6N_2O_4S$ [M+H]$^+$ calculated 545.18, found 545.2.

EXAMPLE 55

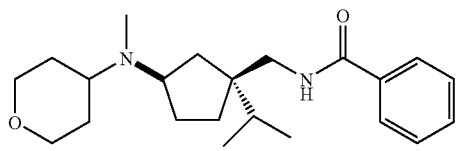

Step A

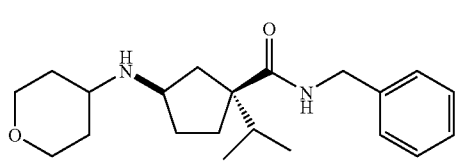

This compound was synthesized following the procedure detailed in Example 1.

Step B

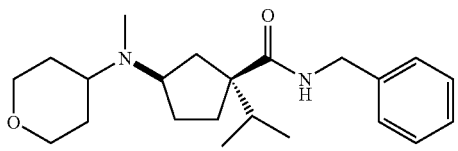

This compound was synthesized by reductive methylation of the secondary amine from Step A following the procedure described in Example 52. LC-MS for $C_{22}H_{35}N_2O_2$ [M+H$^+$] calculated 359.26, found 359.35.

Step C

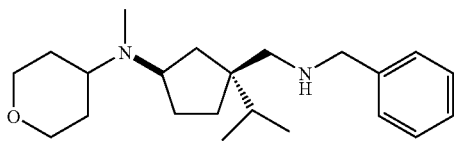

Under $N_2$, the amide from the previous step (2.1 g, 5.9 mmol) was dissolved in THF (20 mL) and a 1 M solution of borane in THF (29 mL, 29 mmol) was added. The reaction mixture was refluxed overnight and concentrated to dryness. The residue was dissolved in an 1% solution of HCl in MeOH and heated to 50° C. overnight. The mixture was concentrated again and dissolved in 1% HCl in MeOH solution to break down the excess borane. The crude product was used in the next step. LC-MS for $C_{22}H_{37}N_2O_2$ [M+H$^+$] calculated 345.28, found 345.25.

Step D

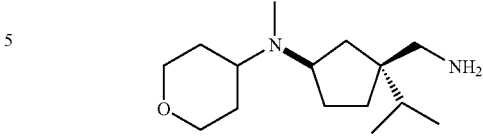

A mixture of the benzylamine from the previous step (2 g, 6 mmol), Pd(OH)$_2$ (500 mg), concentrated HCl (3 mL), and ethanol (50 mL) was hydrogenated at 40 psi for 2 days on a Parr apparatus. The reaction mixture was filtered through celite and concentrated in vacuo to yield 2.15 g, (99%) of the desired product.

Step E

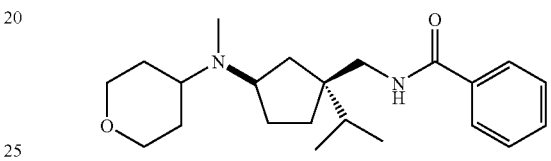

The final compound was prepared as detailed in Intermediate 8, except that trifluoromethylbenzylamine was replaced by the amine from the previous step and Intermediate 1 was replaced by benzoic acid. The crude product was purified by preparative TLC (MeOH:DCM:NH$_4$OH/4:95.6:0.4). LC-MS for $C_{22}H_{35}N_2O_2$ [M+H$^+$] calculated 359.26, found 359.35.

Following the procedure described in Example 55, by varying the structure of the acids used in the last step of Example 55, a number of analogous amides were prepared. Their structure and MS characteristics are summarized in Table 3.

TABLE 3

| Ex. | R | Molecular Formula | Calculated [M$^+$H$^+$] | Found [M$^+$H$^+$] |
|---|---|---|---|---|
| 56 | (3-CF$_3$-benzoyl) | $C_{23}H_{33}F_3N_2O_2$ | 427.25 | 427.3 |
| 57 | (3,5-bis-CF$_3$-benzoyl) | $C_{24}H_{32}F_6N_2O_2$ | 495.24 | 495.25 |

TABLE 3-continued

| Ex. | R | Molecular Formula | Calculated [M+H+] | Found [M+H+] |
|---|---|---|---|---|
| 58 | (2-CF3-phenyl ketone) | C23H33F3N2O2 | 427.25 | 427.3 |
| 59 | (3,5-F,CF3-phenyl ketone) | C23H32F4N2O2 | 445.24 | 445.3 |
| 60 | (2-OH-pyridin-3-yl ketone) | C21H33N3O3 | 376.25 | 376.3 |
| 61 | (5-I-2-OH-phenyl ketone) | C22H33IN2O3 | 501.15 | 501.25 |

EXAMPLE 62

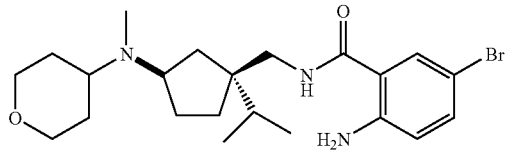

A mixture of the amine described in Example 55, Step D (100 mg, 0.307 mmol), DIEA (107 µL, 0.614 mmol), 5-bromoisatoic anhydride (75 mg, 0.31 mmol), and DCM (20 mL) was stirred at room temperature overnight. The final compound was obtained by preparative TLC (MeOH:DCM:NH4OH/4:95.6:0.4) to yield 132 mg (82%) of the final product. LC-MS for C22H35BrN3O2 [M+H+] calculated 452.18, found 452.2.

EXAMPLE 63

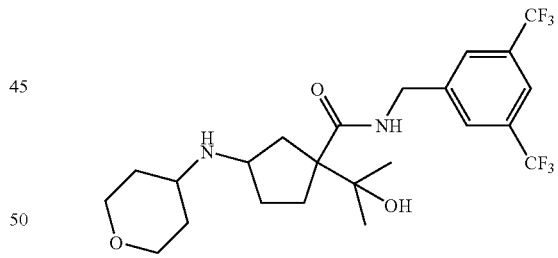

A solution of the ketone Intermediate 12 (764 mg, 1.92 mmol), amine Intermediate 2 (264 mg of the hydrochloride, 1.92 mmol), 1.96 g of 4 Å powdered molecular sieves and diisopropylethylamine (335 µL, 1.92 mmol) in dichloromethane (10 mL) was treated with sodium triacetoxyborohydride (2.03 g, 9.62 mmol) and the stirring at room temperature was continued overnight. The reaction was quenched with a saturated aqueous solution of sodium bicarbonate, and the crude product was extracted with dichloromethane. The combined organic extracts were washed with brine and dried with anhydrous sodium sulfate. The solvent was removed in vacuo, and the residue (1.07 g) was purified by preparative TLC (six plates, Silica gel, 1,000 micron, eluted with ethyl acetate:ethanol:ammonium hydroxide/90:8:2) to yield 654 mg of homogenic product. The respective cis and trans racemates were separated using preparative TLC (eluent:dichloromethane:methanol:ammonium hydroxide (90:9:1). 317 mg (33%) of the higher eluting cis-racemate and 305 mg (32%) of the lower eluting trans racemic mixture were obtained. The single enantiomers contained within the cis-racemic mixture were obtained using a ChiralPak AD semi-preparative chiral HPLC column (eluent:hexane:ethanol/9:1, 9.0 mL/minute, Tr=6.99 min, and 11.12 min, respectively). cis-Isomer: $^1$H NMR (500 MHz, CDCl$_3$): 10.0 (bs, 1H), 7.78 (s, 1H), 7.73 (s, 2H), 4.53 (bd, J=15.10 Hz, 1H), 4.43 (bd, J=15.34 Hz, 1H), 3.93 (bd, J=11.67 Hz, 1H), 3.82 (11.21 Hz, 1H), 3.57 (bs, 1H), 3.31 (dt, J=11.89, 1.83 Hz, 1H), 3.25 (dt, J=12.13, 1.60 Hz, 1H), 2.65 (m, 1H), 2.26 (m, 1H), 2.0 (m, 5H), 1.80 (bd, J=~13 Hz), 1.28 (s, 3H), 1.20 (m, 2H), 1.17 (s, 3H). LC-MS for $C_{23}H_{30}F_6N_2O_3$ [M+H]$^+$ calc. 497.22, found 497.35.

EXAMPLE 64

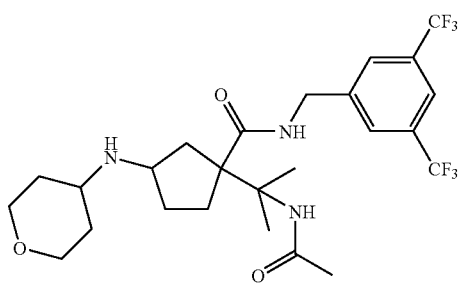

A solution of the alcohol described under Example 63 (cis-isomer, 80 mg, 0.16 mmol) in 1.0 mL of acetonitrile was cooled to 0° C. and concentrated sulfuric acid (380 mg, 3.88 mmol) were added. The solution was allowed to warm up to room temperature, and the reaction was completed by stirring at 50° C. for 1 h. Ice was then added, and the product was extracted into dichloromethane. After drying (anhydrous sodium sulfate), the solvent was removed in vacuo, and the residue was purified by preparative TLC (eluent:dichloromethane:methanol:ammonium hydroxide/90:9:1) to get 29.8 mg (34%) of the pure product. LC-MS for $C_{25}H_{33}F_6N_3O_3$ [M+H]$^+$ calc. 538.24, found 538.30.

EXAMPLE 65

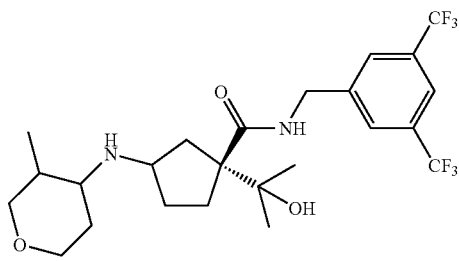

Procedure A

A solution of the ketone Intermediate 12 (429 mg, 1.04 mmol), amine Intermediate 13 (as a hydrochloride salt, 158 mg, 1.04 mmol), diisopropylethylamine (182 µL, 1.04 mmol), 4 Å molecular sieves (766 mg) in 10 mL of dry dichloromethane was treated with sodium triacetoxyborohydride (1.10 g, 5.21 mmol) and the reaction mixture was stirred at room temperature for 48 h. The crude reaction mixture was poured onto a saturated solution of sodium bicarbonate (50 mL), and the organic solvent was slowly evaporated under mildly reduced pressure (250 torr) and slight heating (40° C.). HPLC analysis of the aqueous phase indicated complete breakdown of the initial borane adduct (LC MS for $C_{24}H_{31}BF_6N_2O_4$ for [M+H]$^+$ calc. 537.23, found 537.25) after approximately 30 minutes. The crude product was extracted into dichloromethane, dried (anhydrous magnesium sulfate) and the solvent was removed in vacuo. The residue was further purified by preparative TLC to afford 243 mg (46%) of the higher eluting cis-isomeric mixture and 45.3 mg (8.5%) of the corresponding lower eluting trans-isomeric pair. The cis-isomeric pair was separated into single isomers by chiral semi-preparative HPLC using a ChiralPak AD column, eluted by a mixture of hexanes and ethyl alcohol (95:5) at 9 mL/minutes. The retention time of the isomers under the corresponding analytical conditions (1.0 mL/minutes flow rate) were 7.69 and 12.33 minutes, for the biologically less and more active isomer, respectively. $^1$H NMR (500 MHz, CDCl$_3$): 10.14 (s, 1H), 7.80 (s, 1H), 7.73, s 2H), 5.80 (bs, 1H), 4.50 (bd, J=4.81 2H), 3.91 (bd, J=11.7 Hz, 1H), 3.63 (bd, J=11.44 Hz, 1H), 3.56 (bs, 1H), 3.40 (dd, J=11.4, 2.3 Hz. 1H), 3.33 (dt, J=11.45, 2.75 Hz, 1H), 2.72 (bs, 1H), 2.30 (m, 1H), 2.05 to 1.85 (bm, 4H), 1.60 (m, 2H), 1.48 (m, 2H), 1.31 (s, 3H), 1.18 (s, 3H), 0.88 (d, J=6.86 Hz, 3H). LC MS for $C_{24}H_{32}F_6N_2O_3$ for [M+H]$^+$ calc. 511.23, found 511.30.

Procedure B

A solution containing the ketone Intermediate 5 (667 mg, 5.84 mmol), Intermediate 14 (2.62 g, 5.84 mmol), diisopropylethylamine (1.02 mL, 5.84 mmol) and crushed 4 Å molecular sieves (3.53 g) in dichloroethane (10 mL) was treated with sodium triacetoxyborohydride (6.18 g, 29.2 mmol) and stirred at room temperature overnight. The workup was identical to that described under Procedure A of this example. The 2.39 g of the product mixture was separated into single diastereomers using a ChiralCel OD and ChiralPak AD columns. The obtained material (888 mg, 30%) was identical in all respects to that obtained under Procedure A of this example.

EXAMPLE 66

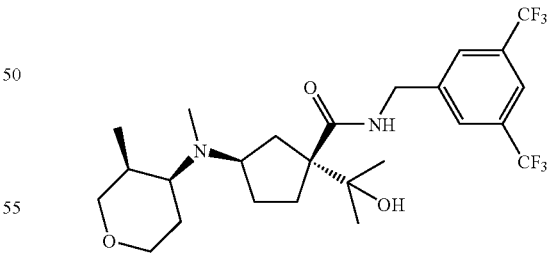

A solution of the amine hydrochloride from Example 65 (slower eluting cis-isomer, in the form of a hydrochloride salt, 55 mg, 0.1 mmol), crushed 4 Å molecular sieves (226 mg) in dichloromethane (4 mL) was treated with an aqueous solution of formaldehyde (210 µL, 37%, 2.0 mmol) followed by sodium triacetoxyborohydride (212 mg, 1.00 mmol) and the mixture was stirred at room temperature overnight. It was poured onto saturated aqueous sodium bicarbonate (20 mL), extracted with dichloromethane. The combined extracts were dried (anhydrous magnesium sulfate), and the solvent was evaporated in vacuo. The residue was purified by preparative TLC (eluent ethyl acetate:ethanol:ammonium hydroxide/90:8:2) to afford 44 mg (87%) of the pure product. $^1$H NMR (500 MHz, CDCl$_3$): 9.18 (bs, 1H), 7.78 (s, 1H), 7.74 (s, 2H), 4.56 (dd, J=15.33, 6.17 Hz, 1H), 4.50 (dd, J=15.33, 5.49 Hz, 1H), 4.00 (dd, J=11.21, 4.58 Hz, 1H), 3.66 (d, J=11.44 Hz, 1H), 3.48 (dd, J=11.44, 2.06 Hz, 1H), 3.30 (m, 2H), 2.75 (bd, J=12.12 Hz, 1H), 2.18 (s, 3H), 2.20 (m, 3H), 1.80 (m, 5H), 1.37 (d, J=12.36 Hz, 1H), 1.29 (s, 3H), 1.21 (s, 3H), 1.04 (d, J=7.09 Hz, 3H). LC MS for C$_{25}$H$_{34}$F$_6$N$_2$O$_3$ for [M+H]$^+$ calc. 525.25, found 525.25.

EXAMPLE 67

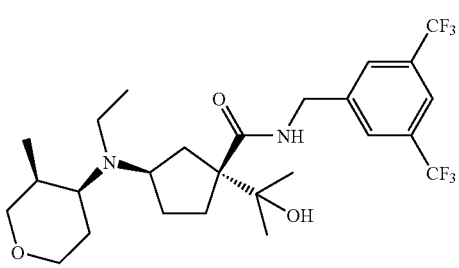

This compound was synthesized starting from the secondary amine described under Example 65 by a procedure analogous to that described under Example 66, except that formaldehyde was replaced by acetaldehyde. LC MS for C$_{26}$H$_{36}$F$_6$N$_2$O$_3$ for [M+H]$^+$ calc. 539.26, found 539.25.

EXAMPLE 68

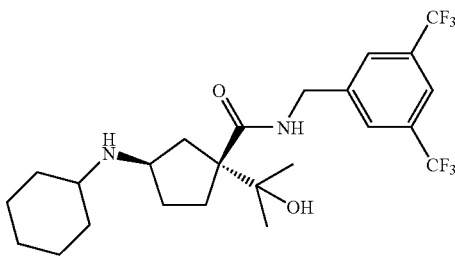

This compound was synthesized starting from amine Intermediate 14 and cyclohexanone in a procedure analogous to that described under Example 65, Procedure B. LC MS: C$_{24}$H$_{32}$F$_6$N$_2$O$_2$ for [M+H]$^+$ calc. 495.24, found 495.20.

EXAMPLE 69

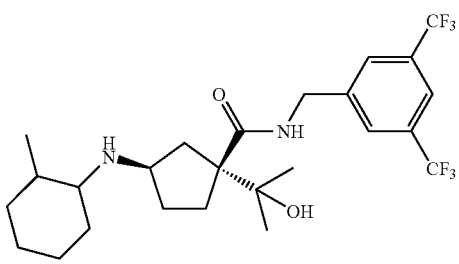

This compound was synthesized starting from amine Intermediate 14 and 2-methylcyclohexanone in a procedure analogous to that described under Example 65, Procedure B. LC MS: C$_{25}$H$_{34}$F$_6$N$_2$O$_2$ for [M+H]$^+$ calc. 509.25, found 509.40. Single diastereomers were obtained using a ChiralCel OD and ChiralPak AD semi-preparative columns.

EXAMPLE 70

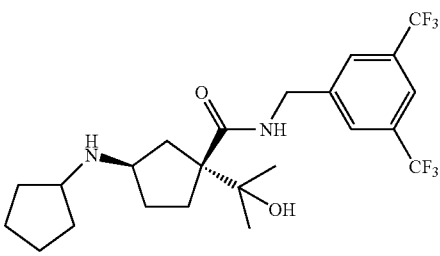

This compound was synthesized starting from amine Intermediate 14 and 3-cyclopentenone in a procedure analogous to that described under Example 65, Procedure B. LC MS: C$_{23}$H$_{30}$F$_6$N$_2$O$_2$ for [M+H]$^+$ calc. 481.22, found 481.30.

EXAMPLE 71

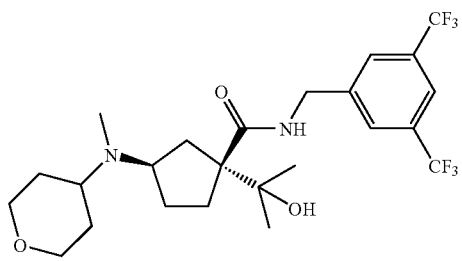

This compound was synthesized starting from the secondary amine described under Example 63 by a procedure analogous to that described under Example 66. LC MS: C$_{24}$H$_{32}$F$_6$N$_2$O$_3$ for [M+H]$^+$ calc. 511.23, found 511.23.

EXAMPLE 72

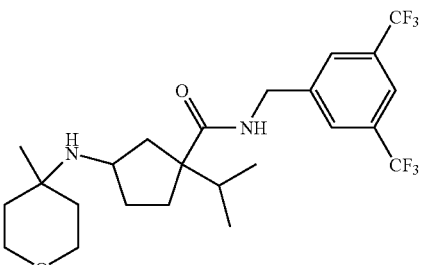

A solution of the ketone Intermediate 8 (983 mg, 2.48 mmol) and the amine Intermediate 15 (429 mg, 3.72 mmol) in neat Ti(OiPr)$_4$ (6 mL) was stirred at room temperature overnight. Methanol (10 mL) was then added via syringe, followed by sodium borohydride (150 mg, 3.96 mmol) and the stirring at ambient temperature was continued for another 2 h. The reaction mixture was then poured onto aqueous NaOH (0.1 N, 75 mL) and the precipitate was filtered through a plug of Celite, which was then washed with methanol. The combined filtrates were concentrated in vacuo and the residue was extracted with ethyl acetate. The combined extracts were dried (anhydrous sodium sulfate) and the solvent was removed in vacuo to leave 1.0092 g of crude product. Purification by preparative TLC (six plates, 1000 micron, eluted with dichloromethane:methanol:ammonium hydroxide/92:8:1) afforded 574 mg (47%) of the higher eluting cis-racemic pair and 159 mg (13%) of the lower eluting trans-racemic product. LC MS: $C_{24}H_{32}F_6N_2O_2$ for $[M+H]^+$ calc. 495.24, found 495.35.

EXAMPLE 73

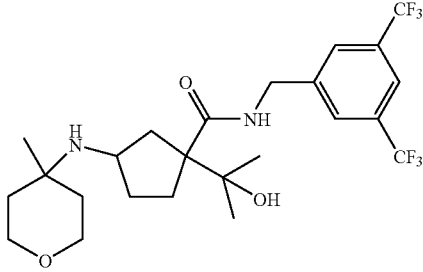

This compound was obtained starting from Intermediate 12 according to a procedure described under Example 72. The single diastereomers contained within the cis-racemic pair were isolated using a ChiralPak AD semi-preparative HPLC column. LC MS: $C_{24}H_{32}F_6N_2O_3$ for $[M+H]^+$ calc. 511.23, found 511.30.

EXAMPLE 74

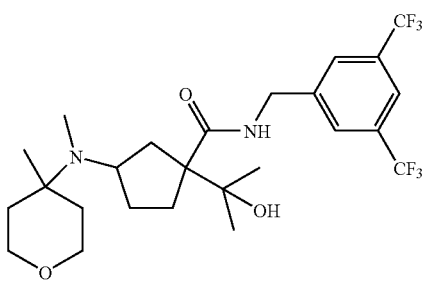

This compound was obtained starting from the secondary amine described under Example 73 according to a procedure analogous to that described under Example 66. LC MS: $C_{25}H_{34}F_6N_2O_3$ for $[M+H]^+$ calc. 525.25, found 525.40.

EXAMPLE 75

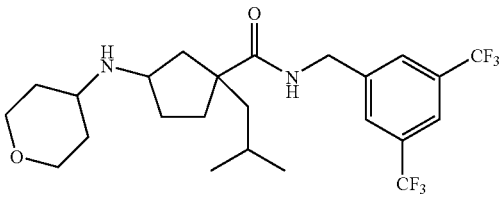

Step A

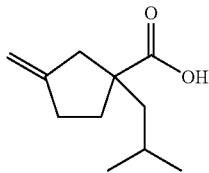

A solution of methyl 3-methylene-1-isobutyl-cyclopentanecarboxylate (see Intermediate 6, Step A, 3.92 g, 20.0 mmol) in a mixture of dioxane (50 mL) and water (50 mL) containing 2.79 g (116 mmol) of lithium hydroxide monohydrate was heated to reflux overnight. The solvent was removed in vacuo, the residue was dissolved in water and the solution was made acidic with 2 N HCl. The product was extracted from the aqueous phase with chloroform (6×30 mL). The combined organic extracts were dried (anhydrous magnesium sulfate) and the solvent was removed in vacuo to yield 3.10 g (85%) of the desired product.

Step B

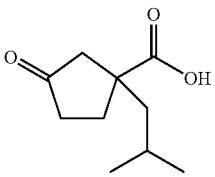

A solution of the 3-methylene-1-isobutyl-cyclopentanecarboxylate (3.10 g, 17.0 mmol) in dichloromethane was cooled to −78° C. and a stream of ozone was passed through the stirred solution until a permanent blue color indicated complete consumption of the olefin. The excess ozone was purged with nitrogen, and triphenylphosphine (4.90 g, 18.7 mmol) was added. The cooling bath was removed, and the reaction mixture was stirred at ambient temperature overnight. The solvent was evaporated in vacuo, the residue was diluted with diethyl ether, and the triphenylphosphine oxide was filtered off. The organic solution was washed with aqueous 10% potassium carbonate (1×150 mL). The aqueous phase was washed with diethyl ether (3×50 mL), and made acidic with 2 N HCl. The desired acid was extracted into diethyl ether (4×50 mL), dried (magnesium sulfate) and the solvent was removed in vacuo to yield 2.72 g (87%) of the desired acid. $^1$H NMR (CDCl$_3$, 500 MHz): 2.87 (dd, J=18.31, 1.83 Hz, 1H), 2.43 (dp, J=6.64, 1.83 Hz), 2.30 (d, J=16.0 Hz, 1H), 2.30 (d, 2.74 Hz, 1H), 2.15 (d, J=18.07 Hz, 1H), 1.94 (m, 2H), 1.70 (h, J=6.40 Hz, 1H), 1.57 (dd, J=13.96, 6.64 Hz, 1H), 0.93 (d, 6.63 Hz, 3H), 0.92 (d, J=6.63 Hz, 1H).

Step C

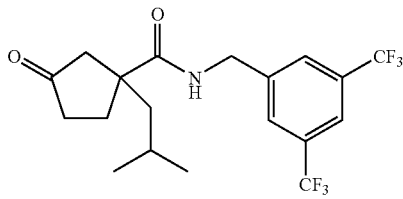

A mixture of the acid (750 mg, 4.07 mmol), 3,5-bistrifluoromethylbenzylamine hydrochloride (1.138 g, 0.2180 mmol), diisopropylethylamine (710 µL, 4.07 mmol), 4-N,N-dimethylaminopyridine (60.0 mg 0.491 mmol) in dichloromethane (15 mL) was treated with 1-[3-(dimethylamino)propyl]-3-ethylcarbodiimide hydrochloride (EDC, 1.56 g, 8.14 mmol) and stirred at room temperature for 24 h. The reaction mixture was diluted with dichloromethane (20 mL), washed with water (3×30 mL), brine (1×30 mL), dried over anhydrous sodium sulfate and the solvent was evaporated under reduced pressure to yield 1.25 g (75%) of the desired product which was further purified by column chromatography (silica gel, ethyl acetate:hexanes (1:1) to yield 583 mg (35%) of the pure desired product. LC-MS for $C_{19}H_{22}F_6NO_2$ [M+H]$^+$ calculated 410.15, found 410.20.

Step D

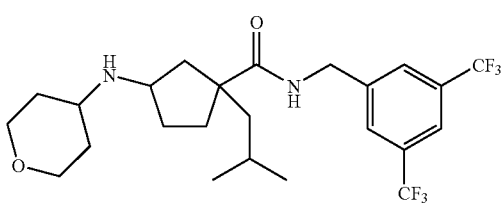

The final amine was synthesized starting from Intermediate 2 and the ketone described in the previous step according to the procedure described under Example 1. LC-MS for $C_{24}H_{32}F_6N_2O_2$ [M+H]$^+$ calculated 495.24, found 495.30.

EXAMPLE 76

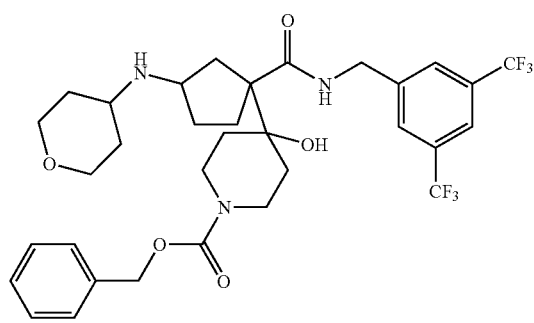

Step A

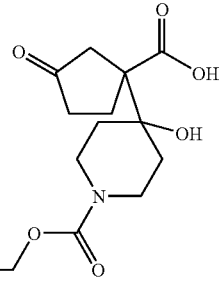

This acid was synthesized in a procedure analogous to that described for the preparation of Intermediate 11, except that the acetone in Step C was replaced by N-Benzyloxycarbonylpiperidin-4-one. LC-MS for $C_{19}H_{23}NO_6$ [M+H]$^+$ calculated 362.15, found 362.15.

Step B

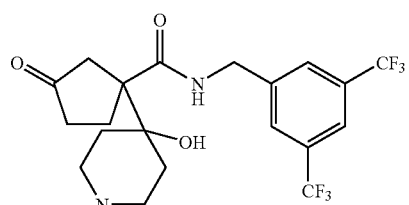

This keto amide was synthesized starting from the previously described acid and 3,5-bistrifluoromethyl-benzylamine according to the procedure described for the preparation of Intermediate 12. $^1$H NMR (CDCl$_3$, 500 MHz): 7.78 (m, 2H), 7.72 (s, 2H), 7.35 (bm, 4H), 5.12 (s, 2H), 4.58 (dd, J=15.6, 6.0 Hz, 1H), 4.52 (dd, J=15.3, 5.7 Hz, 1H), 4.08 (bs, 2H), 3.05 (s, 2H), 2.74 (d, J=18 Hz, 1H), 2.40 to 2.15, bm, 5H), 1.9 to 1.4 (bm, 6H). LC-MS for $C_{28}H_{28}N_2F_6O_5$ [M+H]$^+$ calculated 587.19, found 587.35.

Step C

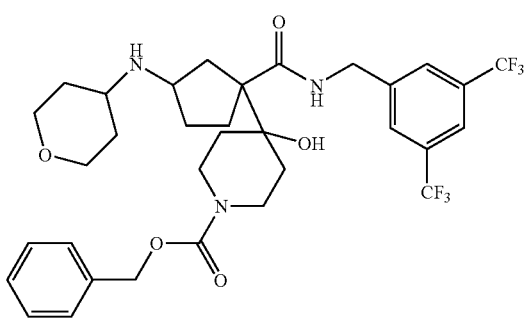

The final amine was synthesized starting from the Intermediate ketone described in the previous step and Intermediate 2 according to a procedure analogous to that described for the preparation of Example 63. The respective single diastereomers were obtained by a chiral HPLC separation using a ChiralPak AD semi-preparative column, eluent:hexane:ethanol/80: 20, flow rate of 9.0 ml/minutes. LC-MS for $C_{33}H_{39}F_6N_3O_5$ [M+H]$^+$ calculated 672.28, found 672.30.

EXAMPLE 77

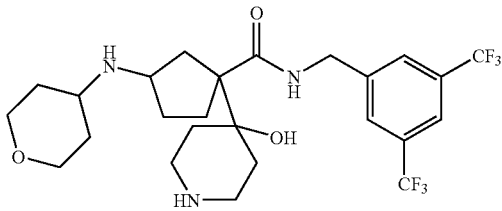

A solution of the CBZ-Protected amine, the synthesis of which was described under Example 76 (109 mg, 0.154 mmol), was dissolved in ethanol (15 mL), and Pd/C (10%, 27 mg) was added, and the resulting mixture was hydrogenated under a hydrogen filled balloon at room temperature for 24 h. The catalyst was filtered off, and the solvent was removed in vacuo to yield 87.7 mg (93%) of the desired product. LC-MS for $C_{35}H_{33}F_6N_3O_3$ [M+H]$^+$ calculated 538.24, found 538.30.

EXAMPLE 78

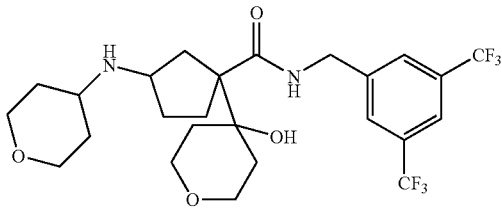

The compound described under this example was synthesized using a procedure analogous to that described for preparation of Example 76, except that in Step A the N-CBZ-piperidin-4-one was replaced by tetrahydro-4H-pyran-4-one. The respective single diastereomers were obtained by a chiral HPLC separation using a ChiralPak AD semi-preparative column, eluent:hexane:ethanol/90:10, flow rate of 9.0 mL/minutes. LC-MS for $C_{25}H_{32}F_6N_2O_4$ [M+H]$^+$ calculated 539.23, found 539.35.

EXAMPLE 79

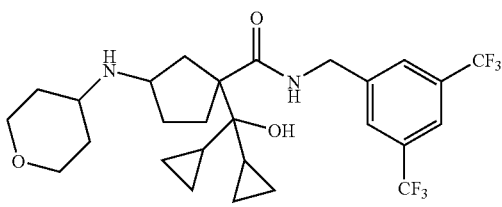

The compound described under this example was synthesized using a procedure analogous to that described for preparation of Example 76, except that in Step A the N-CBZ-piperidin-4-one was replaced by dicyclopropylketone. LC-MS for $C_{27}H_{34}F_6N_2O_3$ [M+H]$^+$ calculated 549.25, found 549.40.

EXAMPLE 80

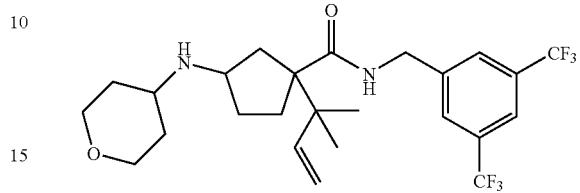

Step A

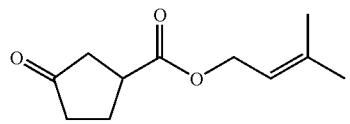

A solution of 3-oxocyclopentanecarboxylic acid (6.20 g, 48.4, Stetter, H., Kuhlman, H., *Liebigs Ann. Chemie,* 1979, 7, 944-9) and 3-methyl-2-buten-1-ol (5.90 mL, 58.1 mmol) and DMAP (140 mg) in dichloromethane (50 mL) was treated with EDC and stirred at room temperature overnight. The reaction was quenched by pouring onto 100 mL of water, and the product was extracted with dichloromethane. The combined organic extracts were washed with brine and dried with anhydrous magnesium sulfate. Evaporation of the solvent in vacuo gave 10.51 g (100%) of the desired ester. $^1$H NMR (CDCl$_3$, 500 MHz): 5.33 (bt, J=7.33 Hz, 1H), 4.62 (d, J=7.32 Hz, 2H), 3.12 (ddd, J=14.9, 8.0, 6.9 Hz, 1H), 2.55 to 2.10 (m, 6H0, 1.77 (s, 3H), 1.72 (s, 3H).

Step B

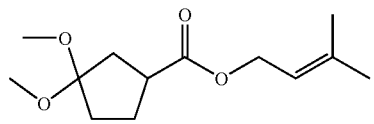

A solution of the ester from the previous step (10.50 g, 53.78 mmol) and TsOH (500 mg) in dichloromethane (50 mL) was treated with trimethyl orthoformate (24 mL, 220 mmol) and stirred at room temperature overnight. The reaction was quenched by pouring onto a saturated solution of sodium bicarbonate and the crude product was extracted with dichloromethane. The combined organic layers were washed with brine, dried with anhydrous magnesium sulfate, and the solvent was evaporated in vacuo. The residue was further purified by distillation (b.p.: 123° C. @ 4 mm Hg) to give 8.27 g (63%) of the desired acetal. $^1$H NMR (CDCl$_3$, 500 MHz): 5.33 (bt, J=7.09 Hz, 1H), 4.57 (d, J=7.32 Hz, 2H), 3.21 (s, 3H), 3.19 (s, 3H), 2.87 m, 1H), 2.15 to 1.80 (bm, 6H), 1.76 (s, 3H), 1.70 (s, 3H).

Step C

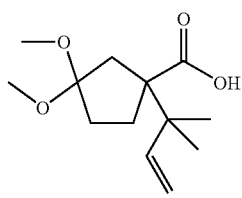

A solution of diisopropylamine (14.28 mL, 101.9 mmol) in THF (200 mL) was cooled to −78° C. and n-butyllithium (40.76 mL, 2.5 M in hexane, 110 mmol) was added via syringe. After 10 minutes, the neat ester from the previous step (12.34 g, 50.94 mmol) was added via syringe, followed after 20 minutes by neat chloro trimethylsilane (12.93 mL, 101.9 mmol). The solution was allowed to warm up to room temperature over 3 h, after which time it was quenched by pouring onto a 10% aqueous solution of citric acid. The crude product (19.75 g) was obtained by extraction with diethyl ether, drying (magnesium sulfate) and evaporation of the solvent in vacuo. It was further purified by flash chromatography (silica gel, ethyl acetate:hexane/2:3) to yield 5.25 g (43%) of the pure product. $^1$H NMR (CDCl$_3$, 500 MHz): 5.95 (dd, J=17.2, 10.8 Hz, 1H), 5.07 (dd, J=10.75, 0.9 Hz, 1H), 5.25 (dd, J=17.40, 0.9 Hz, 1H), 3.21 (s, 3H), 3.14 (s, 3H), 2.58 (d, J=13.73 Hz, 1H), 2.28 (m, 1H), 1.88 to 1.76 (bm, 3H), 1.73 to 1.66 (bm, 2H), 1.084 (s, 3H), 1.00 (s, 3H). $^{13}$C NMR (CDCl$_3$, 125 MHz): 174.7, 143.9, 113.1, 112.3, 58.7, 53.8, 50.7, 41.4, 36.5, 31.4, 24.7, 23.1, 22.0.

Step D

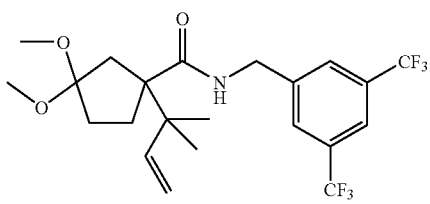

A solution of the crude acid, the preparation of which was described in the previous step (1.0 g, 4.2 mmol). 3,5-bistrifluoromethylbenzyl amine hydrochloride (1.15 g, 4.13 mmol), diisopropylethylamine (0.72 mL, 4.13 mmol) in dichloromethane (12 mL) was treated with EDC (1.18 g, 6.19 mmol) and stirred at room temperature overnight. The reaction mixture was diluted with dichloromethane, washed with water and brine, dried with magnesium sulfate and the solvent was evaporated in vacuo to leave 2.00 g of crude product. Flash chromatography (silica gel, ethyl acetate:hexanes/1:1) gave 1.38 g (72%) of the pure amide. $^1$H NMR (CDCl$_3$, 500 MHz): 7.78 (s, 3H), 6.30 (bt, J=5.72 Hz, 1H), 17.4, 10.8 Hz, 1H), 5.06 (dd, J=10.8, 1.1 Hz, 1H), 5.00 (dd, J=17.4, 0.9 Hz, 1H), 4.57 (dd, J=15.6, 6.2 Hz, 1H), 4.53 (dd, J=15.3, 6.0 Hz, 1H), 3.20 (s, 3H), 3.08 (s, 3H), 2.47 (d, J=14.2 Hz, 1H), 2.14 (m, 1H), 1.95 to 1.70 (bm, 4H), 1.07 (s, 3H), 1.06 (s, 3H).

Step E

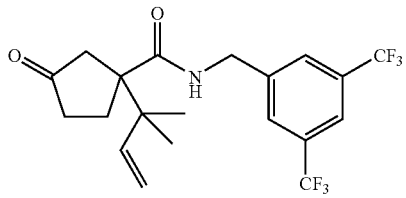

A solution of the acetal from previous step (407 mg, 0.871 mmol) was dissolved in dichloromethane (6.0 mL) and treated with TFA (1.0 mL). The solution was stirred at room temperature overnight. The reaction mixture was poured onto aqueous saturated sodium bicarbonate and extracted with dichloromethane. Drying (magnesium sulfate) and evaporation of the solvent in vacuo gave 326 mg (89%) of the pure ketone. $^1$H NMR (CDCl$_3$, 500 MHz): 7.79 (s, 1H), 7.72 (s, 2H), 6.58 (t, J=5.26 Hz, 1H), 6.02 (dd, J=17.40, 10.75 Hz, 1H), 5.16 (d, J=10.76 Hz, 1H), 5.08 (d, J=17.60 Hz, 1H), 4.52 (d, J=5.95 Hz, 2H), 2.78 (dd, J=18.08, 1.37 Hz, 1H), 2.35 (m, 3H), 2.12 (m, 2H), 1.09 (s, 6H). $^{13}$C NMR (CDCl$_3$, 125 MHz): 216.2, 174.4, 144.7, 141.3, 128.1, 121.7, 114.9, 58.9, 44.5, 43.4, 40.6, 37.0, 28.7, 24.3, 23.5. LC-MS for $C_{20}H_{21}F_6NO_2$ [M+H]$^+$ calculated 422.15, found 422.20.

Step F

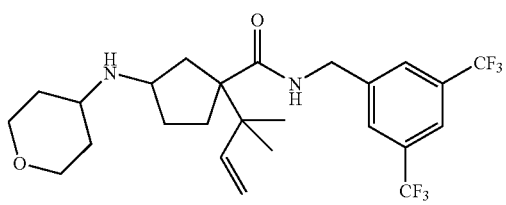

The final amine listed under this example was synthesized starting from the ketone from the previous step and Intermediate 2 in a procedure analogous to that described under Example 1. LC-MS for $C_{25}H_{32}F_6N_2O_2$ [M+H]$^+$ calculated 507.24, found 507.40.

EXAMPLE 81

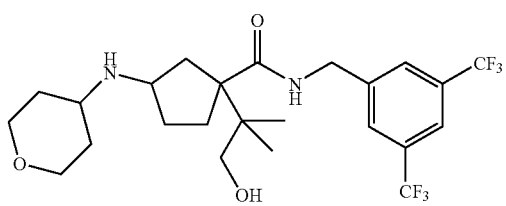

A solution of the olefin, the preparation of which was described under Example 80 (89 mg, 0.16 mmol), in ethanol (20 mL) was treated with perchloric acid (500 μL), cooled to −78° C. and ozone was passed through until a permanent blue color indicated completion of the reaction. The excess ozone was purged with a stream of nitrogen, and sodium borohydride (150 mg) was added. The temperature was allowed to rise to room temperature overnight, another 400 mg of sodium borohydride was added, and the reaction was stirred at ambient temperature another 2 h. The solvent was removed in vacuo, and the residue was treated with an aqueous saturated solution of sodium bicarbonate. The crude product was extracted into dichloromethane, dried with anhydrous sodium sulfate, and the solvent was removed in vacuo. The respective cis- (higher eluting, 18.7 mg, 22%) and trans- (lower eluting, 10.0 mg, 12%) racemic pairs were obtained by preparative TLC (dichloromethane:methanol:ammonium hydroxide/90:9:1). LC-MS for $C_{24}H_{32}F_6N_2O_3$ $[M+H]^+$ calculated 511.23, found 511.40. The respective single diastereomers contained within the cis-pair were separated by semi-preparative HPLC (ChiralPak AD, 93% hexane:7% ethanol, 9 mL/min). The retention times of an analogous analytical run (1.0 mL/min) were Tr=7.65 and 9.98 minutes.

EXAMPLE 82

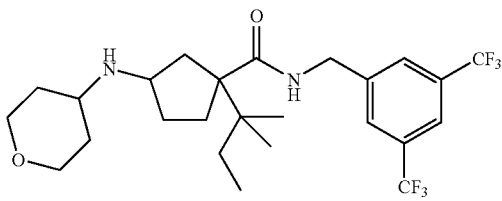

A solution of the olefin, the preparation of which was described under Example 80 (82 mg, 0.151 mmol), and Pd/C (50 mg, 10%) in ethanol (10 mL) was placed under a hydrogen balloon at room temperature for 30 minutes. The catalyst was filtered off, and the solvent was removed in vacuo to yield 61.8 mg (75%) of the pure product. LC-MS for $C_{25}H_{34}F_6N_2O_2$ $[M+H]^+$ calculated 509.25, found 509.35.

EXAMPLE 83

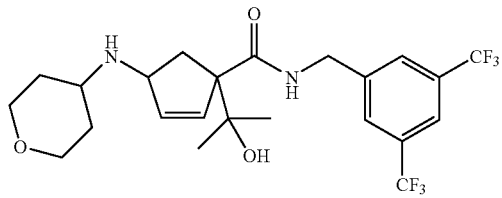

Step A

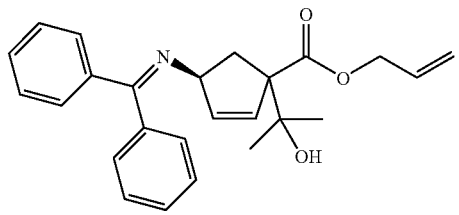

A solution of diisopropylamine (2.71 mL, 19.3 mmol) in diethyl ether (60 mL) was cooled to −78° C. and n-butyl-lithium (7.73 mL, 19 mmol, 2.5 M solution in hexane) was added drop-wise, via syringe. A solution of the allyl ester (5.86 g, 17.58 mmol, prepared from (3R,1S)-3-benzhydryli- monocyclopent-4-ene-carboxylic acid and allyl bromide as described under Preparation of Intermediate 9, Step A) in diethyl ether (30 mL) was then added and the solution was stirred at −78° C. 2.5 h. At this point a solution of zinc chloride in diethyl ether (19.33 mL, 1.0 M, 19 mmol) was added dropwise, followed by 2.58 mL (35.1 mmol) of neat acetone. The reaction mixture was stirred at −78° C. for another 45 minutes, after which it was quenched by the addition of 300 mL of an aqueous saturated solution of ammonium chloride. The aqueous layer was separated and washed with ether three more times. The combined organic extracts were dried with anhydrous sodium sulfate and the solvent was evaporated in vacuo. The obtained mixture of the cis- and trans-diastereoisomer (6.35 g) was used without purification in the next step.

Step B

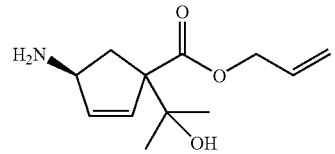

The crude Schiff base from the previous step (6.35 g) was dissolved in THF (30 mL) and 2 N aqueous HCl (10 mL) was added and the mixture was stirred at room temperature overnight. The solvent was evaporated to dryness under reduced pressure, and the obtained mixture of the desired amines and benzophenone (7.51 g) was used in the next step without any further purification.

Step C

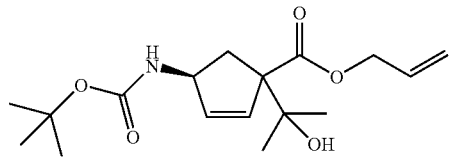

A solution of the crude amine from the previous step (7.51 g) in dichloromethane (50 mL) was treated with di-tert-butyl dicarbonate (5.35 g, 24.5 mmol) and a saturated aqueous solution of sodium bicarbonate (50 mL) was added. The biphasic reaction mixture was vigorously stirred for 1 hr, and the organic layer was separated. The aqueous phase was extracted two more times with dichloromethane, and the combined organic extracts were dried, and the solvent was removed in vacuo. The residue (9.44 g) was further purified by gradient column chromatography (eluent:ethyl acetate: hexanes, 15% to 100%). 744 mg (14%, three steps) of the first eluting 1,3-trans-isomer, 405 mg (8%) of the second eluting 1,3-cis-isomer and 658 mg of mixed fractions where obtained in an overall yield of 34% for three steps.

Higher Eluting 1,3-trans-Isomer: $^1$H NMR (CDCl$_3$, 500 MHz): 5.93 (m, 3H), 5.37 (dd, J=17.2, 1.2 Hz, 1H), 5.30 (dd, J=10.3, 0.7 Hz, 1H), 4.70 (m, 3H), 2.63 (dd, J=14.5, 8.2 Hz, 1H), 1.95 (dd, J=14.7, 4.6 Hz, 1H), 1.45 (s, 9H), 1.17 (s, 6H).

Lower Eluting 1,3-trans-Isomer: $^1$H NMR (CDCl$_3$, 500 MHz): 5.90 (m, 3H), 5.35 (dd, J=17.2, 1.1 Hz, 1H), 5.25 (dd, J=10.5, 0.7 Hz, 1H), 4.85 (bs, 1H), 0.72 (bs, 1H), 4.60 (d, J=5.72 Hz, 2H), 2.80 (dd, J=14.0, 8.24 Hz, 1H), 1.77 (dd, J=14.4, 5.5 Hz, 2H), 1.46 (s, 9H), 1.23 (s, 3H), 1.22 (s, 3H).

Step D

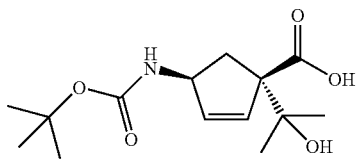

A solution of the ester from previous step (lower eluting cis-isomer, 640 mg, 1.96 mmol) and morpholine (1.71 mL, 19.6 mmol) in THF (20 mL), was thoroughly degassed (vacuum/nitrogen cycle) and Pd(Ph$_3$P)$_4$ (237 mg) was added. The reaction mixture was stirred at room temperature for 2 h, after which time it was diluted with dichloromethane and washed with 2 N aqueous HCl. The organic phases were dried (magnesium sulfate) and the solvent was removed in vacuo to yield 685 mg of crude product. It was used in the next step without further purification.

Step E

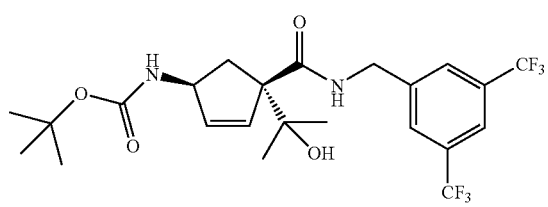

A solution of the crude acid from the previous step (685 mg, max 1.96 mmol), 3,5-bistrifluoromethylbenzylamine hydrochloride (1.64 g, 5.88 mmol), diisopropylethylamine (993 µL, 5.88 mmol), HOAT (800 mg, 5.88 mmol) in dichloromethane (40 mL) was treated with EDC (1.13 g, 5.88 mmol) and the reaction mixture was stirred at room temperature overnight. It was diluted with dichloromethane and washed with water. After drying (anhydrous sodium sulfate) the solvent was evaporated to dryness. The residue was further purified by column chromatography (silica gel, ethyl acetate:hexane/2:3) to yield 555.6 mg (54%, two steps) of the pure amide. $^1$H NMR (CDCl$_3$, 500 MHz): 7.85 (bs, 1H), 7.78 (s, 1H), 7.75 (s, 2H), 5.98 (dd, J=5.5, 2.1 Hz, 1H), 5.84 (dd, J=5.50, 1.83 Hz, 1H), 4.98 (bs, 1H), 4.55 (m, 3H), 4.2 (bs, 1H), 2.75 (dd, J=14.9, 9.2 Hz, 1H), 2.02 (dd, J=14.6, 4.6 Hz, 1H), 1.38 (s, 9H), 1.28 (s, 3H), 1.15 (s, 3H).

Step F

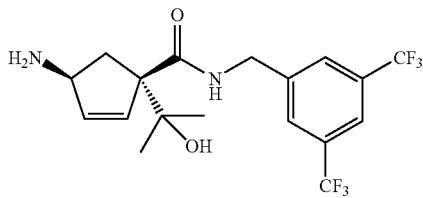

The BOC-Protected amine from the previous step (516 mg, 1.01 mmol) was dissolved in 8 mL of 4 N HCl solution in dioxane. After 30 minutes of stirring at room temperature the solvent was removed in vacuo, and the crude hydrochloride (454 mg, 100%) was used in the next step without further purification.

Step G

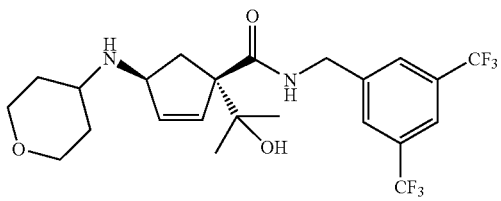

The final product was obtained from the previously described amine and tetrahydro-4H-pyran one as described in the procedure from Example 65, Procedure B. $^1$H NMR (CDCl$_3$, 500 MHz): 9.82 (bs, 1H), 7.79 (s, 1H), 7.68 (s, 2H), 6.24 (d, J=5.72 Hz, 1H), 6.03 (bs, 1H), 5.94 (dd, J=5.72, 2.52 Hz, 1H), 4.58 (dd, J=15.6, 6.2 Hz, 1H), 4.40 (dd, J=15.6, 5.04 Hz, 1H), 4.16 (bd, J=7.32 Hz, 1H), 3.90 (bd, J=11.7 Hz, 2H), 3.30 (m, 2H), 2.67 (m, 1H), 2.20 (dd, J=14.41, 7.3 Hz, 1H), 1.95 (d, J=14.42 Hz, 1H), 1.70 (bd, J=12.8 Hz, 1H), 1.63 (bd, J=13.0 Hz, 1H), 1.30 (s, 3H), 1.25 (bm, 2H), 1.12 (s, 3H). LC-MS for C$_{23}$H$_{29}$F$_6$N$_2$O$_3$ [M+H]$^+$ calculated: 495.20, found 495.25.

EXAMPLE 84

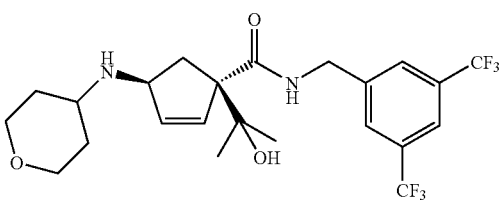

This compound was synthesized starting from the trans-isomeric ester intermediate, described under Step C, Example 83, following the procedures described under Example 83, Steps D-G. LC-MS for C$_{23}$H$_{28}$F$_6$N$_2$O$_3$ [M+H]$^+$ calculated: 495.20, found 495.30.

EXAMPLE 85

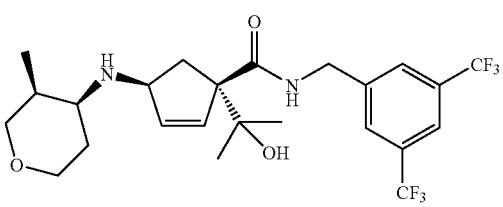

This compound was prepared following the procedure described for the preparation of the compound under Example 83, except that in Step G tetrahydro-4H-pyran-4-one was replaced by Intermediate 5. The respective cis- and trans-diastereoisomeric pairs (THP ring) were separated using preparative TLC (ethyl acetate:ethanol:ammonium hydroxide/85: 4:1) and the respective isomers contained within the higher eluting cis-pair were obtained by separation on a semi-preparative chiral HPLC column: ChiralPak AD, 95% hexanes, 9.0 ml/minutes. The respective retention times of an analogous analytical run (1.0 mL/min) were 11.8 and 15.0 minutes, respectively. LC-MS for $C_{23}H_{28}F_6N_2O_3$ [M+H]$^+$ calculated: 495.20, found 495.30.

The slower (Tr=15.0 minutes) eluting cis-diastereoisomer: $^1$H NMR (CDCl$_3$, 500 MHz): 9.9 (bs, 1H), 7.78 (s, 1H), 7.67 (s, 2H), 6.27 (m, 1H), 5.95 (m, 1H), 4.60 (m, 1H), 4.40 (m, 1H), 4.10 (d, J=18.1 Hz, 1H), 3.85 (bt, J=11.9 Hz, 1H), 3.65 (bt, J=13.0, 2.8 Hz, 2H), 3.42 (bd, J=11.44 Hz, 1H), 3.32 (m, 1H), 2.82 (m, 1H), 2.20 (m, 1H), 1.98 (m, 1H), 1.76 (bs, 1H), 1.40 (m, 1H), 1.30 (s, 3H), 1.10 (s, 3H), 0.82 (d, J=7.10 Hz, 3H).

EXAMPLE 86

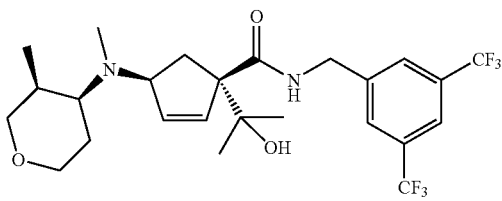

This compound was prepared from the amine, the synthesis of which was described under Example 86 and formaldehyde following the procedure described in Example 66. $^1$H NMR (CDCl$_3$, 500 MHz): 7.80 (s, 1H), 7.71 (s, 2H), 6.05 (dd, J=5.72, 2.29 Hz, 1H), 5.92 (bd, J=4.81 Hz, 1H), 5.30 (bs, 1H), 4.56 (d, J=5.95 Hz, 1H), 4.2 (bs, 1H), 4.0 (dd, J=12, 4.5 Hz, 1H), 3.73 (d, J=11.44 Hz, 1H), 3.47 (dd, J=11.44, 1.83 Hz, 1H), 3.32 (dt, J=12.1, 2.3 Hz, 1H), 2.57 (dt, J=11.9, 4.1 Hz, 1H), 2.32 (dd, J=14.6, 8.2 Hz, 1H), 2.02 (s, 3H), 1.97 (dd, J=14.9, 4.6 Hz, 1H), 1.85, (bs, 1H), 1.75 (m, 2H), 1.52 (bd, J=11.44 Hz, 1H), 1.21 (s, 3H), 1.14 (s, 3H), 1.02 (d, J=6.86 Hz, 3H). LC-MS for $C_{25}H_3F_6N_2O_3$ [M+H]$^+$ calculated: 523.23, found 523.30.

EXAMPLE 87

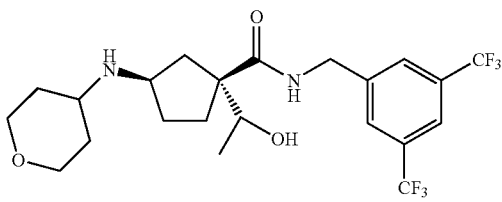

Step A

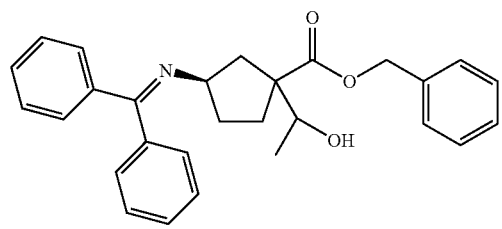

A solution of diisopropylamine (2.70 mL, 19.3 mmol) in tetrahydrofuran (20 mL) was cooled to −78° C. and a solution of n-butyllithium in hexanes (7.70 mL, 2.5M, 19.3 mmol) was added via syringe, followed by a solution of the Schiff base, the preparation of which was described in Intermediate 9, Steps A to C (5.685 g, 14.82 mmol), in THF (10 mL). The enolate was allowed to form for 3 h at −78° C., after which time the neat acetaldehyde (1.00 mL, 29.7 mmol) was added. The reaction was quenched with the addition of aqueous citric acid (200 mL, 10%) and the crude product was extracted into diethyl ether. Drying (anhydrous magnesium sulfate) and evaporation of the solvent gave the crude desired product (6.16 g). This was further purified by flash chromatography (deactivated silica gel, ethyl acetate:hexanes/3:7) to yield the desired cis-isomer (2.32 g, 54%). This Schiff base was found to be unstable, and was used in the next step without delay. LC-MS for $C_{29}H_{29}NO_3$ [M+H]$^+$ calculated: 428.21, found 428.20.

Step B

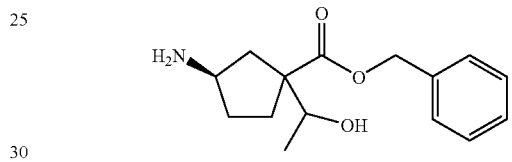

The Schiff base prepared in the previous step (2.323 g, 5.433 mmol) was dissolved in THF (20 mL) and 2 N aqueous HCl was added. The reaction mixture was stirred at room temperature 2 h, after which time the volatiles were removed in vacuo. The resulting mixture of the desired amine hydrochloride and benzophenone was used in the next step without further purification.

Step C

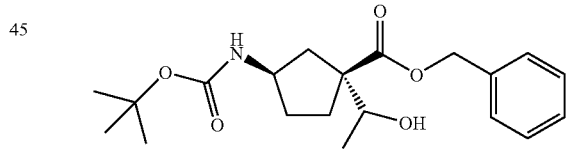

The crude product from the previous step (max 5.433 mmol) was dissolved in dichloromethane (50 mL) and di-tert-butyl dicarbonate (2.371 g, 10.86 mmol) was added followed by 50 mL of a saturated solution of sodium bicarbonate. The reaction mixture was vigorously stirred at root temperature for 1 h. The layers were separated and the aqueous phase was washed with dichloromethane. The combined organic extracts were dried (anhydrous magnesium sulfate) and the solvent was evaporated in vacuo. Final purification by gradient flash chromatography (ethyl acetate:hexanes/0% to 40%) gave the desired BOC-protected amine (619 mg, 32%, two steps) as a diastereoisomeric mixture (3:2) of two isomers. LC-MS for $C_{20}H_{29}NO_5$ [M+H]$^+$ calculated: 364.20, found 264.20 (loss of the BOC group).

Step D

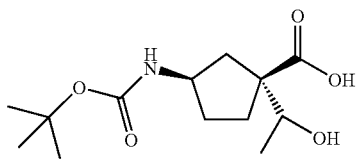

This acid was prepared following the procedure described in Intermediate 9, Step F, and was used in the next step without further purification.

Step E

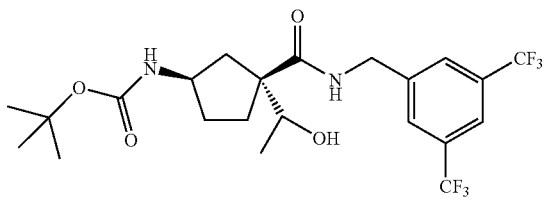

The solution of the acid from the previous step (63 mg, 0.23 mmol) and 3,5-bistrifluoromethylbenzyl amine hydrochloride (77 mg, 0.28 mmol), 1-hydroxy-7-azobenzotriazole (31.5 mg, 0.231 mmol) in dichloromethane (6 mL) was treated with EDC (66 mg, 0.35 mmol) and the resulting mixture was stirred at room temperature overnight. The reaction was quenched with water, and the product was extracted into dichloromethane. The combined organic extracts were dried (anhydrous magnesium sulfate) and the solvent was removed in vacuo. The residue (112.7 mg) was further purified by preparative TLC (ethyl acetate:hexanes/3:2) to yield the desired product (41 mg, 36%) as a mixture of two diastereoisomers. These were separated by preparative TLC (DCM: acetone/9:1) to yield single isomers (the hydroxyethyl sidechain) of unknown absolute stereochemistry. LC-MS for $C_{22}H_{28}F_6N_2O_4$ [M+H]$^+$ calculated: 499.20, found 443.05 (loss of the t-butyl group). Higher eluting diastereoisomer: $^1$H NMR (CDCl$_3$, 500 MHz): 7.76 (s, 1H), 7.75 (s, 2H), 4.86 (bs, 1H), 4.62 (dd, J=15.6, 6.4 Hz, 1H), 4.49 (dd, J=15.6, 5.0 Hz, 1H), 3.98 (m, 1H), 3.82 (dd, J=12.6, 6.2 Hz, 1H), 2.41 (m, 2H), 2.01 (m, 1H), 1.79 (dd, J=13.7, 6.6 Hz, 1H), 1.64 (m, 1H), 1.41 (s, 9H), 1.32 (m, 1H), 1.17 (d, J=6.18 Hz, 3H).

Step F

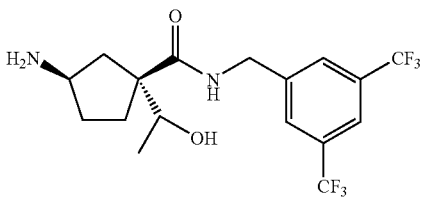

A solution of the of the higher eluting diastereoisomer from the previous step (92 mg, 0.19 mmol) in dichloromethane (3 mL) was treated with TFA (3 mL) and the resulting mixture was stirred at room temperature for 2 h. The volatiles were removed in vacuo to yield 86.9 mg (93%) of the crude product. LC-MS for $C_{17}H_{20}F_6N_2O_2$ [M+H]$^+$ calculated: 399.14, found 399.15. A similar procedure was applied to the lower eluting BOC-protected amine described in the previous step to obtain the respective amine.

Step G

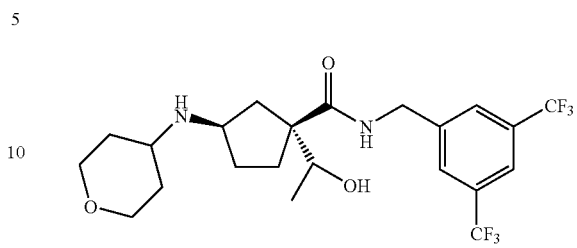

The amide trifluoroacetate, the preparation of which was described in the previous step (87 mg, 0.17 mmol), tetrahydro-4H-pyran-4-one (52 mg, 0.52 mmol), crushed 4 Å molecular sieves (1.0 g) and diisopropylethylamine were combined in dichloromethane and sodium triacetoxyborohydride (185 mg, 0.87 mmol) was added. The reaction mixture was stirred at room temperature overnight, after which time it was quenched by pouring onto a saturated solution of sodium bicarbonate. The crude product was extracted with dichloromethane and the combined organic extracts were backwashed with brine, dried (anhydrous magnesium sulfate) and the solvent was removed in vacuo. The residue (89.2 mg) was further purified by preparative TLC (DCM:MeOH:ammonium hydroxide/90:9:1) to yield 65.8 mg of the pure product. LC-MS for $C_{12}H_{28}F_6N_2O_3$ [M+H]$^+$ calculated: 483.20, found 483.25. Similarly prepared was the final product derived from the lower eluting BOC-protected amine as described in Step E of this Example.

EXAMPLE 88

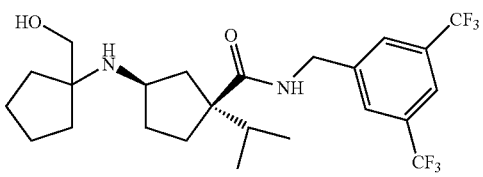

This compound was synthesized according to the procedure described in Example 63, except that 1-hydroxymethyl-cyclopentylamine was used instead of Intermediate 2. The respective single diastereoisomers were separated by preparative TLC. LC-MS for $C_{22}H_{32}F_3N_3O_3$ [M+H]$^+$ calculated 444.24, found 444.24.

EXAMPLE 89

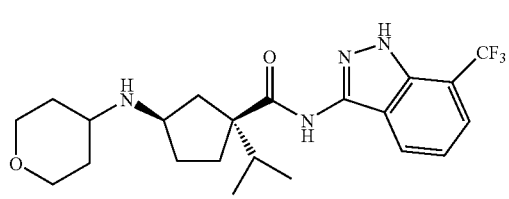

Step A

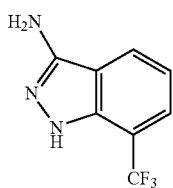

3-Cyano-2-fluorobenzotrifluoride (2.0 g, 11 mmol) was combined with hydrazine monohydrate (10 mL, 200 mmol) in n-butyl alcohol (40 mL) and heated to reflux. After 2.5 h the reaction was cooled to room temperature and concentrated to dryness to give 2.2 g of a white solid. ESI-MS calc. for C8H6F3N3: 201; found 202 (M+H).

Step B

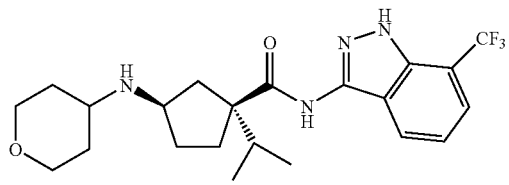

To a cooled (0° C.) solution of Intermediate 42 (63 mg, 0.18 mmol) in DCM (5 mL) was added oxalyl chloride (54 μL, 0.53 mmol) and 1 drop of DMF and the resulting solution was allowed to warm to room temperature. After 2 h the reaction was concentrated to dryness and dried for 1.5 h under high vacuum. The resulting acid chloride was dissolved in DCM (5 mL) and added dropwise to a stirred solution of the product from Step A (55 mg, 0.25 mmol) in triethylamine (10 mL). After 30 minutes the reaction was concentrated under reduced pressure and the crude intermediate was dissolved in ethyl alcohol and treated with sodium borohydride (20 mg). After 20 h at room temperature the reaction was concentrated to dryness and the product was purified by reverse phase HPLC (C18, 25-100% MeCN/H2O) and converted to its hydrochloride salt by the addition of hydrogen chloride (2 N solution in ethyl ether) to give 1.3 mg of product. ESI-MS calc. for C22H29F3N4O2: 438; found 439 (M+H).

EXAMPLE 90

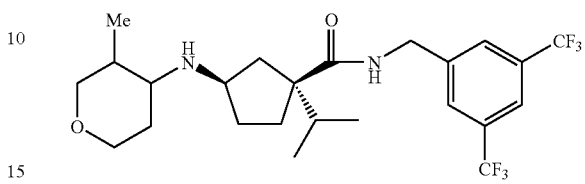

To a mixture of Intermediate 16 (0.95 g, 2.2 mmol) in dichloroethane (10 mL) was added successively Intermediate 5 (0.276 g, 2.42 mmol), DIEA (0.31 g, 2.4 mmol) and 4 Å powdered molecular sieves (2.0 g) and the resulting mixture was stirred for 30 minutes at room temperature. To the stirred mixture was added sodium triacetoxyborohydride (0.7 g, 3 mmol) and the reaction was stirred at room temperature for 24 h. The mixture was filtered and the filtrate was stirred with a saturated solution of sodium bicarbonate (2.0 mL) for 10 minutes and then taken in ethyl acetate (50 mL). The organic layer was washed with brine, dried (anhydrous magnesium sulfate), concentrated, and purified by flash column chromatography (hexane:EtOAc/1:1+15% MeOH), to give the title compound (1.02 g, 94%) as a mixture of diastereoisomers. Preparative HPLC (ChiralCel OD column) was used to facilitate further separation of diastereoisomers. Thus, 60 mg of the above mixture was separated (elution with hexane and 5% ethanol) to yield 4 mg, 8 mg and 18 mg of three isomers shown below. All three isomers were then transformed to the HCl salts.

Following Example 90 and starting from other appropriate intermediates, a variety of compounds were prepared. Reverse phase preparative HPLC accomplished the separation of selected compounds, which were subsequently transformed to the HCl salts. Their structures (Examples 90 to 131) and MS characteristics are listed in the Table 4.

TABLE 4

(Examples 90 to 131)

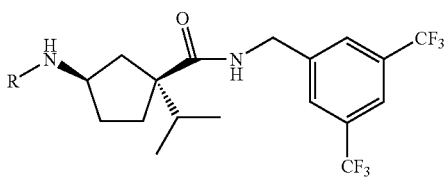

| Ex. | R | Molecular Formula | Calculated [M + H+] | Found [M + H+] |
|---|---|---|---|---|
| 90 | 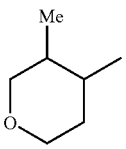 isomer A | C24H32F6N2O2 | 495.24 | 495.30 |

TABLE 4-continued (Examples 90 to 131)

| Ex. | R | Molecular Formula | Calculated [M + H+] | Found [M + H+] |
|---|---|---|---|---|
| 91 | Me, tetrahydropyran, isomer B | $C_{27}H_{31}F_6N_2O_2$ | 495.24 | 495.30 |
| 92 | Me, tetrahydropyran, isomer C | $C_{24}H_{32}F_6N_2O_2$ | 495.24 | 495.30 |
| 93 | Me-CH2-tetrahydropyran, isomer A | $C_{25}H_{34}F_6N_2O_2$ | 509.26 | 509.40 |
| 94 | Me-CH2-tetrahydropyran, isomer B | $C_{25}H_{34}F_6N_2O_2$ | 509.26 | 509.40 |
| 95 | Me-CH2-tetrahydropyran, isomer C | $C_{25}H_{34}F_6N_2O_2$ | 509.26 | 509.40 |
| 96 | F-tetrahydropyran, isomer A | $C_{23}H_{29}F_7N_2O_2$ | 499.22 | 499.20 |
| 97 | F-tetrahydropyran, isomer B | $C_{23}H_{29}F_7N_2O_2$ | 499.22 | 499.20 |
| 98 | F-tetrahydropyran, isomer C | $C_{23}H_{29}F_7N_2O_2$ | 499.22 | 499.20 |

TABLE 4-continued
(Examples 90 to 131)
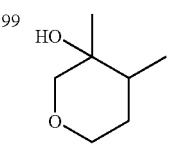
| Ex. | R | Molecular Formula | Calculated [M + H+] | Found [M + H+] |
|---|---|---|---|---|
| 99 | 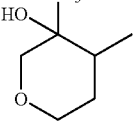 isomer B | C₂₄H₂₉F₉N₂O₃ | 565.21 | 565.30 |
| 100 | 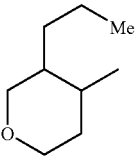 isomer A | C₂₄H₂₉F₉N₂O₃ | 565.21 | 565.30 |
| 101 | 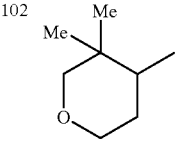 | C₂₆H₃₆F₆N₂O₂ | 523.28 | 523.30 |
| 102 | 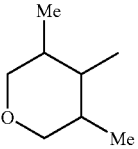 | C₂₅H₃₄F₆N₂O₃ | 509.26 | 509.20 |
| 103 | 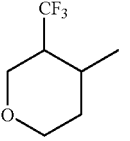 | C₂₅H₃₄F₉N₂O₂ | 509.26 | 509.20 |
| 104 | 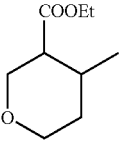 | C₂₄H₂₉F₉N₂O₃ | 549.26 | 549.40 |
| 105 | 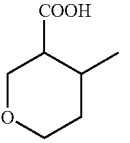 | C₂₆H₃₄F₆N₂O₄ | 553.25 | 553.40 |
| 106 | COOH | C₂₆H₃₄F₆N₂O₄ | 525.22 | 525.30 |

TABLE 4-continued (Examples 90 to 131)

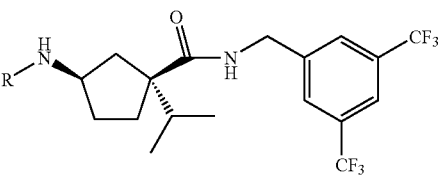

| Ex. | R | Molecular Formula | Calculated [M + H$^+$] | Found [M + H$^+$] |
|---|---|---|---|---|
| 107 | (3-methyl tetrahydropyran) | $C_{23}H_{30}F_6N_2O_2$ | 481.23 | 481.20 |
| 108 | (4-methyl tetrahydrothiopyran) | $C_{23}H_{30}F_6N_2OS$ | 497.21 | 497.20 |
| 109 | (4-methyl tetrahydrothiopyran 1,1-dioxide) | $C_{23}H_{30}F_6N_2O_3S$ | 529.20 | 529.20 |
| 110 | (4-methyl oxepane) | $C_{24}H_{32}F_6{}_2O_2$ | 495.24 | 495.30 |
| 112 | (3-methyl tetrahydrofuran) | $C_{22}H_{29}F_6N_2O_2$ | 497.21 | 467.20 |
| 113 | (3-ethyl tetrahydrofuran) | $C_{22}H_{29}F_6N_2O_2$ | 467.21 | 467.20 |
| 114 | (3-methyl tetrahydrothiophene) | $C_{22}H_{30}F_6N_2OS$ | 483.19 | 483.20 |
| 115 | (3-methyl oxetane) | $C_{21}H_{26}F_6N_2O_2$ | 453.20 | 453.15 |
| 116 | (methyl cyclohexane) | $C_{24}H_{32}F_6N_2O$ | 479.25 | 479.30 |
| 117 | Me (dimethyl cyclohexane) | $C_{25}H_{34}F_6N_2O$ | 493.27 | 493.30 |
| 118 | (methyl cycloheptane) | $C_{25}H_{34}F_6N_2O$ | 493.27 | 493.30 |

TABLE 4-continued
(Examples 90 to 131)
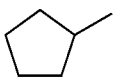
| Ex. | R | Molecular Formula | Calculated [M + H+] | Found [M + H+] |
|---|---|---|---|---|
| 119 |  | C₂₃H₃₀F₆N₂O | 453.20 | 453.15 |
| 120 | 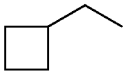 | C₂₂H₂₈F₆N₂O | 451.22 | 451.30 |
| 121 | 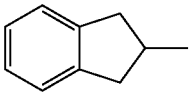 | C₂₃H₃₀F₆N₂O | 465.23 | 465.30 |
| 122 | 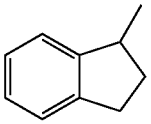 | C₂₇H₃₀F₆N₂O | 513.23 | 513.30 |
| 123 | 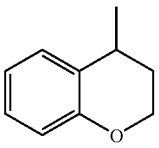 | C₂₇H₃₀F₆N₂O | 513.23 | 513.40 |
| 124 | 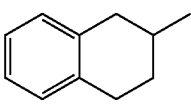 | C₂₇H₃₀F₆N₂O₂ | 529.23 | 529.30 |
| 125 | 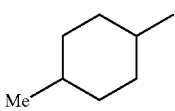 | C₂₈H₃₂F₆N₂O | 527.25 | 527.30 |
| 126 | 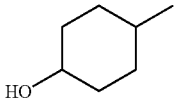 | C₂₄H₃₄F₆N₂O | 493.27 | 493.30 |
| 127 | 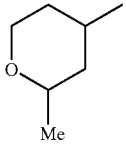 | C₂₄H₃₂F₆N₂O₂ | 495.24 | 495.40 |
| 128 |  | C₂₅H₃₂F₆N₂O₂ | 495.24 | 495.40 |

TABLE 4-continued

(Examples 90 to 131)

![Structure with R-NH, cyclopentane, isopropyl, amide, and 3,5-bis(trifluoromethyl)benzyl groups]

| Ex. | R | Molecular Formula | Calculated [M + H⁺] | Found [M + H⁺] |
|-----|---|-------------------|---------------------|----------------|
| 129 | (4-methyl-2-methoxycarbonyl-tetrahydropyran) | $C_{25}H_{32}F_6N_2O_4$ | 539.23 | 539.30 |
| 130 | (2,2,5-trimethyl-1,3-dioxane) | $C_{24}H_{32}F_6N_2O_3$ | 511.24 | 511.30 |
| 131 | (4-methylpiperidine) | $C_{23}H_{32}F_6N_2O$ | 480.24 | 480.30 |

EXAMPLE 132

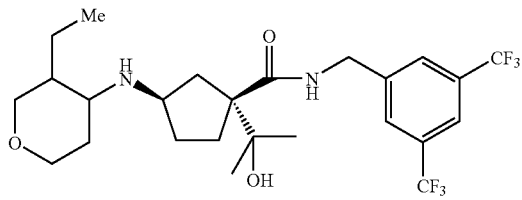

To a mixture of Intermediate 14 (0.5 g, 1.1 mmol) in dichloroethane (20 mL) was added successively intermediate 25 (0.41 g, 3.2 mmol), DIEA (0.31 g, 2.42 mmol) and 4 Å powdered molecular sieves (2.0 g) and the mixture was stirred for 30 minutes at room temperature. To this stirred mixture was added sodium triacetoxyborohydride (0.45 g, 2.1 mmol) and the resultant mixture was stirred at room temperature for 24 h. The mixture was filtered and the filtrate was stirred with a saturated solution of sodium bicarbonate (2.0 mL) for 10 minutes and then taken in ethyl acetate (50 mL). The solvent layer was washed with brine, dried (anhydrous magnesium sulfate), concentrated, and purified by flash column chromatography. Eluting with DCM+10% MeOH, gave the title compound (0.42 g, 75%) as a mixtures of diastereomers. Reverse phase HPLC (ChiralCel OD column) was used to facilitate further separation of the diastereomers discussed above. Elution with heptane containing 8% ethanol gave two major compounds 74 mg and 132 mg of two isomers shown below. Both isomers were then transformed to the HCl salt.

Following Example 132 and starting from other appropriate intermediates, a variety of compounds were prepared and are shown in Table 5. Preparative reverse phase HPLC accomplished the separation of selected compounds, which were subsequently transformed to the HCl salts. Their structures (Examples 132 to 140) and MS characteristics are summarized in Table 5.

TABLE 5

(Examples 132 to 140)

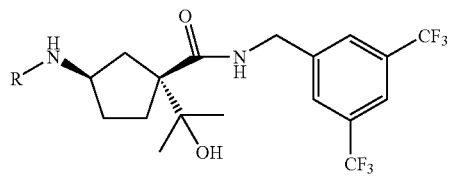

| Ex. | R | Molecular Formula | Calculated [M + H⁺] | Found [M + H⁺] |
|---|---|---|---|---|
| 132 | Me, tetrahydropyran-3-ylmethyl (4-Me), isomer A | $C_{25}H_{34}F_6N_2O_3$ | 525.26 | 525.40 |
| 133 | Me, tetrahydropyran-3-ylmethyl (4-Me), isomer B | $C_{25}H_{34}F_6N_2O_3$ | 525.26 | 525.40 |
| 134 | F, 4-methyltetrahydropyran-3-yl, isomer A | $C_{23}H_{29}F_7N_2O_3$ | 515.21 | 515.40 |
| 135 | F, 4-methyltetrahydropyran-3-yl, isomer B | $C_{23}H_{29}F_7N_2O_3$ | 515.21 | 515.40 |
| 136 | 3-cyclopropyl-4-methyltetrahydropyran | $C_{26}H_{34}F_6N_2O_3$ | 537.26 | 537.40 |
| 137 | 3-methyltetrahydropyran | $C_{23}H_{30}F_6N_2O_3$ | 497.22 | 497.20 |
| 138 | 4-methyltetrahydrothiopyran | $C_{23}H_{30}F_6N_2O_2S$ | 513.20 | 513.20 |
| 139 | 2,2,5-trimethyl-1,3-dioxane | $C_{24}H_{32}F_6N_2O_4$ | 527.23 | — |

TABLE 5-continued (Examples 132 to 140)

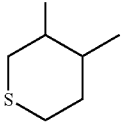

| Ex. | R | Molecular Formula | Calculated [M + H+] | Found [M + H+] |
|---|---|---|---|---|
| 140 | 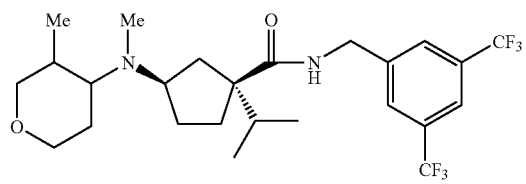 | C24H32F6N2O2S | 527.22 | 527.40 |

EXAMPLE 141

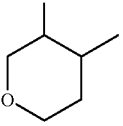

To a solution of amine from Example 91 (0.028 g, 0.057 mmol) in MeOH (2.0 mL) was added formalin (40 μL, 37% solution in water) followed by sodium cyanoborohydride (0.010 g, 0.17 mmol) and the reaction was stirred at room temperature for 16 h. After the evaporation of the volatiles, the crude was purified by silica column chromatography. Elution with hexane:EtOAc (1;1)+ 2% MeOH gave the desired product.

Starting from Examples 92, 96 and 97 and following the procedure given for Example 141 the products listed below were obtained. The synthesized compounds (Examples 141 to 144) and MS characteristics are summarized in Table 6.

TABLE 6

(Examples 141 to 144)

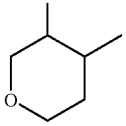

| Ex. | R | Molecular Formula | Calculated [M + H+] | Found [M + H+] |
|---|---|---|---|---|
| 141 | Me | C25H34F6N2O2 | 509.26 | 509.30 |

TABLE 6-continued (Examples 141 to 144)

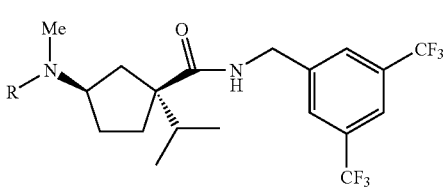

| Ex. | R | Molecular Formula | Calculated [M + H+] | Found [M + H+] |
|---|---|---|---|---|
| 142 | 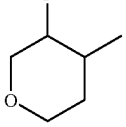 Me | C25H34F6N2O2 | 509.26 | 509.30 |
| 143 | 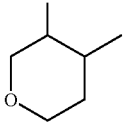 F | C24H31F7N2O2 | 513.24 | 513.30 |
| 144 | F | C24H31F7N2O2 | 513.24 | 513.30 |

EXAMPLE 145

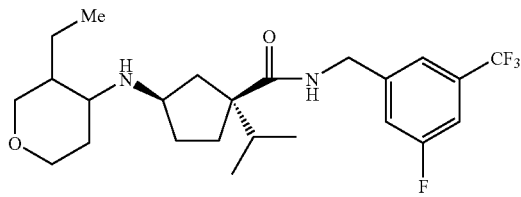

Step A

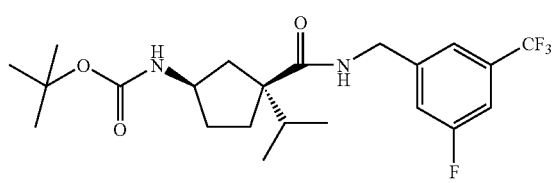

To intermediate 10 (0.27 g, 1.0 mmol) and 3-fluoro-5-trifluromethyl benzylamine (0.23 g, 1.2 mmol) in DCM (8.0 mL) was added PyBOP (0.75 g, 1.5 mmol) and the resulting mixture was stirred at room temperature for 24 h. The reaction mixture was quenched with water and the solvent layer was washed with brine, dried (anhydrous magnesium sulfate), concentrated, and purified by flash column chromatography. Eluting with hexane:EtOAc (10:1) gave the title compound (0.14 g, 32%).

Step B:

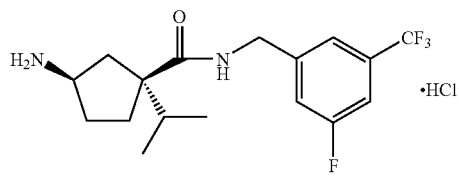

To a solution of the product from Step A (0.14 g) in EtOAc (4.0 mL) was added a saturated solution of HCl in EtOAc (1.0 mL) and the mixture stirred. After 1 h at room temperature, the volatiles were removed under vacuum to leave behind the title compound (0.12 g, 100%) as a white solid. LC-MS for $C_{17}H_{22}F_4N_2O$ $[M+H]^+$ calculated 346.17, found 346.2.

Step C

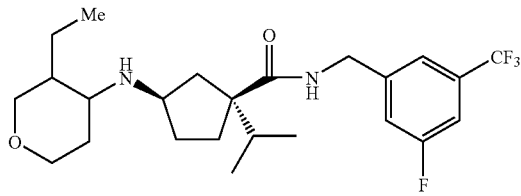

A mixture of the intermediate from Step B (0.035 g, 0.090 mmol), intermediate (0.018 g, 0.14 mmol), DIEA (0.013 g, 0.101 mmol) and 4 Å powdered molecular sieves (0.1 g) in dichloroethane (2 mL) was stirred for 30 minutes at room temperature. To the stirred mixture was added sodium triacetoxyborohydride (0.029 g, 0.14 mmol) and the resultant mixture was stirred at room temperature for 24 h. The mixture was filtered and the filtrate was evaporated and purified by flash column chromatography. Eluting with hexane:EtOAc (1:1)+ 10% MeOH, gave Example 145 as a mixture of diastereomers which was subsequently transformed to its HCl salt (0.018 g). LC-MS for $C_{24}H_3F_4N_2O_2$ $[M+H]^+$ calculated 459.26, found 459.4.

EXAMPLE 146

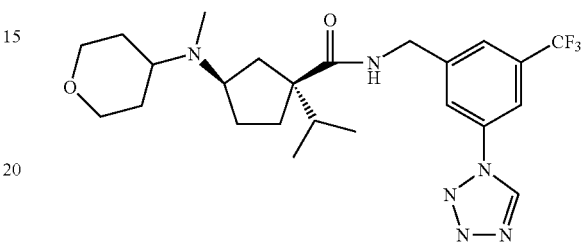

Step A

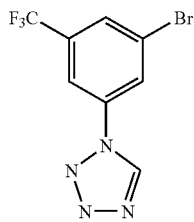

A mixture of 3-bromo-5-trifluoromethylbenzonitrile (1.0 g, 4.2 mmol), triethyl orthoformate (1.3 mL, 8.1 mmol) and sodium azide (490 mg, 7.5 mmol) in glacial acetic acid (10 mL) was heated to reflux for 8 h. The reaction was poured onto crushed ice and extracted 4 times with ethyl ether. The combined organic layers where washed with brine, dried over MgSO$_4$, filtered and concentrated under reduced pressure. The residue was purified by medium pressure liquid chromatography (silica gel, 0-60% EA/hexanes) to give 510 mg of product (41%). ESI-MS calc. for C8H4BrF3N4: 292; found 293 (M+H).

Step B

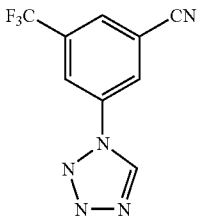

The product from Step A (440 mg, 1.3 mmol) was combined with tetrakis(triphenylphosphine) palladium (90 mg, 0.078 mmol) and zinc cyanide (300 mg, 2.6 mmol) in DMF (deoxygenated, 3 mL) and heated to reflux. After 22 h, the reaction was cooled to room temperature and partitioned between ethyl ether and aqueous 2 N NH$_4$OH. The organic layer was washed twice with 2 N NH$_4$OH, then with brine, dried over MgSO₄, filtered and concentrated under reduced pressure to give 340 mg of a product which was used directly in the next step. ESI-MS calc. for C9H4F3N5: 239; found 240 (M+H).

Step C

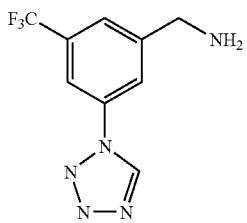

The product from Step B (340 mg) was dissolved in THF (10 mL) and treated with borane (1.0 M solution in THF, 7.0 mL, 7.0 mmol). After 20 h at room temperature, the reaction was quenched with a 1% hydrogen chloride solution in methanol (20 mL) and heated to 50° C. After 3 h. the reaction was concentrated under reduced pressure and the residue was re-dissolved in a 1% hydrogen chloride solution in methanol (20 mL). After 18 h the solution was concentrated under reduced pressure and the resulting residue was dissolved in aqueous 1N HCl, and washed successively with DCM and ethyl ether. The aqueous layer was concentrated under reduced pressure to give 300 mg of a white hydrochloride salt (73% over 2 steps). ESI-MS calc. for C9H8F3N5: 243; found 244 (M+H).

Step D

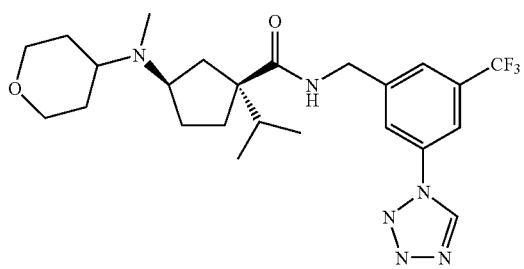

Intermediate 17 (700 mg, 2.6 mmol) was dissolved in DCM (10 mL) and treated with oxalyl chloride (500 µL, 5.5 mmol) and 1 drop of DMF. After 2 h at room temperature the reaction was concentrated to dryness and dried for 1.5 under high vacuum. 35 mg of this acid chloride (0.12 mmol) was dissolved in DCM (1 mL) and added dropwise to a stirred solution of the product from Step C (16 mg, 0.057 mmol) in triethylamine (1 mL). After 3.5 h the reaction was concentrated under reduced pressure and passed through a Spe-ed SCX column, washing with methanol and eluting with 2 M NH₃ solution in methanol. This crude product was further purified by reverse phase HPLC (C18, 25-100% MeCN/H₂O) and converted to its hydrochloride salt by addition of hydrogen chloride (2 N solution in ethyl ether) to give 2.5 mg of a white solid (8%). ESI-MS calc. for C24H33F3N6O2: 494; found 495 (M+H).

EXAMPLE 147

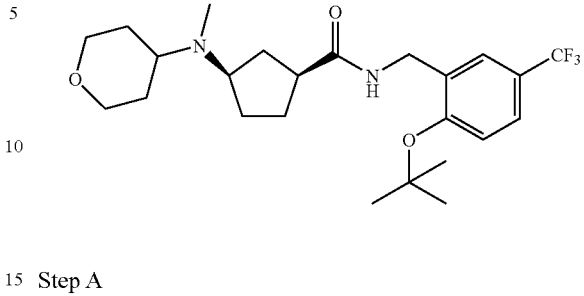

Step A

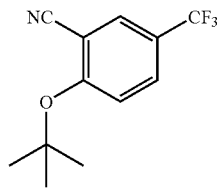

To a cooled (0° C.) solution of 2-fluoro-5-trifluoromethyl-benzonitrile (5.23 g, 27.7 mmol) in 140 mL of THF was added dropwise at a rapid pace a suspension of potassium t-butoxide (3.88 g, 34.6 mmol) in 35 mL of THF. The reaction mixture was permitted to slowly warm to room temperature and stir overnight. The reaction mixture was concentrated under reduced pressure then ethyl ether and 1 N HCl solution were added and the layers were separated. The ethereal layer was washed with saturated NaHCO₃ solution, then brine, dried over anhydrous MgSO₄, filtered, and concentrated. Purification by MPLC (silica, 25% ethyl acetate/hexane) afforded 5.25 g (78%) of a white crystalline solid. ¹H NMR (CDCl₃, 500 MHz): 7.84 (d, J=2.0 Hz, 1H), 7.73 (dd, J=8.5, 2.0 Hz, 1H), 7.27 (d, J=9.0 Hz), 1.55 (s, 9H).

Step B

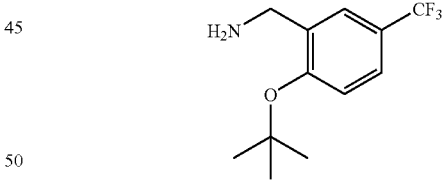

To a solution of the nitrile prepared as described in Step A (7.6 g, 31 mmol) in ethanol (100 mL) was added ammonium hydroxide solution (28-30%, 25 mL) and Raney® 2800 nickel (slurry in water, ~3.5 g). The resulting mixture was agitated under 50 psi of hydrogen gas for 24 h using a Parr apparatus. The reaction mixture was then filtered through celite washing with ethanol and then water. The filtrate was concentrated to dryness under reduced pressure and the residue so obtained was purified by flash chromatography [silica, 5 to 10% gradient (1% increments) of (10% ammonium hydroxide solution (28-30%)/methanol) in DCM] to afford 5.5 g (71%) of desired amine as a colorless oil which crystallized upon storage in the freezer. ¹H NMR (CDCl₃, 500 MHz): 7.56 (d, J=2.0 Hz, 1H), 7.44 (dd, J=8.5, 2.0 Hz, 1H), 7.12 (d, 8.5 Hz, 1H), 3.90 (s, 2H), 2.70 (bs, 2H), 1.51 (s, 9H).

Step C

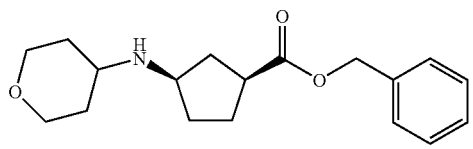

Intermediate 42 (10 g, 39 mmol) was combined with tetrahydro-4H-pyran-4-one (4.3 g, 43 mmol), triethylamine (5.4 mL, 39 mmol), 4 Å powdered molecular sieves (5 g), and sodium triacetoxyborohydride (41 g, 190 mmol) in 200 mL DCM. The reaction mixture was stirred at room temperature for 4 days, then filtered through celite, diluted with DCM, and washed with saturated NaHCO$_3$ solution twice and then once with brine. The organic layer was dried over anhydrous MgSO$_4$, filtered and concentrated to give 10 g of product (85%). ESI-MS calc. for C18H25NO3: 303; found 304 (M+H).

Step D

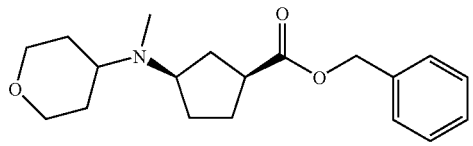

The product from Step C (10 g, 33 mmol) was combined with formaldehyde (37% solution in water) (27 mL, 330 mmol), 4 Å powdered molecular sieves (10 g), and sodium triacetoxyborohydride (35 g, 170 mmol) in 350 mL DCM. The reaction mixture was stirred at room temperature for 4 h, then filtered through celite, diluted with DCM, and washed with saturated NaHCO$_3$ and brine. The organic layer was dried over anhydrous MgSO$_4$, filtered and concentrated to give 8.4 g of product (81%). ESI-MS calc. for C19H27NO3: 317; found 318 (M+H).

Step E

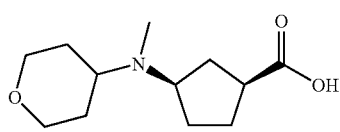

The product from Step D (1.1 g, 3.4 mmol) was hydrogenolyzed over Pd(OH)$_2$ (20%, 110 mg) in methanol under a hydrogen filled balloon. After 90 minutes the reaction was filtered through celite and concentrated under reduced pressure to give 900 mg of product.

Step F

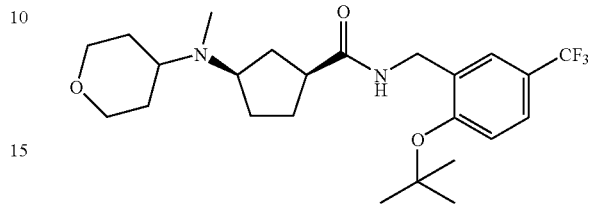

To a stirred solution of the product from Step E (50 mg, 0.22 mmol) and 1-ethyl-3-(3-dimethylaminopropyl)carbodiimide (62 mg, 0.32 mmol) in DCM (10 mL), was added the product from Step B (80 mg, 0.32 mmol). The reaction was stirred at room temperature for 18 h before being diluted with DCM and washed with saturated aqueous sodium bicarbonate and brine. The organic layer was dried over MgSO$_4$, filtered and concentrated under reduced pressure. The product was purified preparative TLC (silica gel, 0.3% NH$_4$OH (3.7% MeOH (97% DCM) to give 68 mg of a colorless oil (67%). 1.3 mg of this oil was converted to its hydrochloride salt by addition of hydrogen chloride (2 N solution in ethyl ether) to give 1.4 mg of a white solid. ESI-MS calc. for C24H35F3N2O3: 456; found 457 (M+H).

EXAMPLE 148

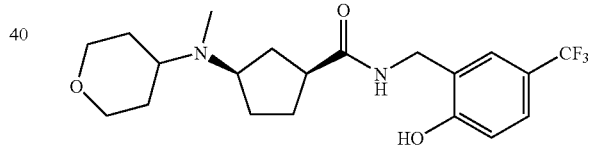

The free base from Example 147 (66 mg, 0.14 mmol) was dissolved in trifluoroacetic acid (3 mL) and treated with 3 drops of water. After 72 h at room temperature, the reaction was concentrated under reduced pressure and converted to its hydrochloride salt by the addition of hydrogen chloride (2 N solution in ethyl ether) to give 62 mg of a white solid. ESI-MS calc. for C20H27F3N2O3: 400; found 401 (M+H).

EXAMPLE 149

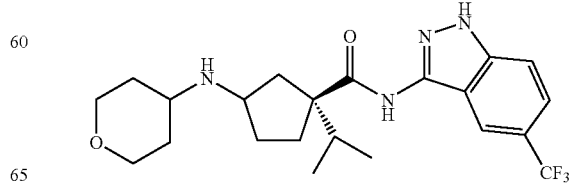

Step A

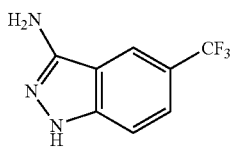

3-Cyano-4-fluorobenzotrifluoride (2.0 g, 11 mmol) was combined with hydrazine monohydrate (10 mL, 200 mmol) in n-butyl alcohol (40 mL) and heated to reflux. After 2 h the reaction was cooled to room temperature and concentrated to dryness to give 2.6 g of a white solid. ESI-MS calc. for C8H6F3N3: 201; found 202 (M+H). $^1$H NMR (CDCl$_3$, 500 MHz): δ 8.18 (s, 1H), 7.45 (d, 1H), 7.35 (d, 1H), 5.60 (m, 3H).

Step B

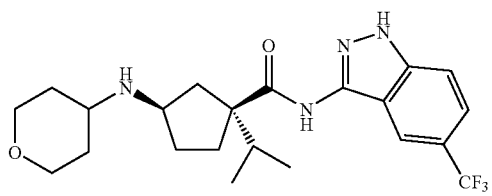

Intermediate 42 (200 mg, 0.6 mmol) was dissolved in DCM (5 mL) and THF (10 mL) and was treated with oxalyl chloride (110 µL, 1.2 mmol) and 1 drop of DMF. After 2 h at room temperature the reaction was concentrated to dryness and dried for 1.5 h under high vacuum. 100 mg of this acid chloride (0.3 mmol) was dissolved in DCM (5 mL) and added dropwise to a stirred solution of the product from Step A (180 mg, 0.90 mmol) in triethylamine (3 mL). After 72 h the reaction was concentrated under reduced pressure and the crude product was dissolved in a solution of THF (3 mL) and methanol (3 mL) and treated with a solution of lithium hydroxide (20 mg) in water (3 mL). This solution was stirred at room temperature for 72 h and concentrated to dryness. This crude product was further purified by reverse phase HPLC (C18, 25-100% MeCN/H$_2$O) and converted to its hydrochloride salt by the addition of hydrogen chloride (2 N solution in ethyl ether) to give 0.8 mg of product. ESI-MS calc. for C22H29F3N4O2: 438; found 439 (M+H).

EXAMPLE 150

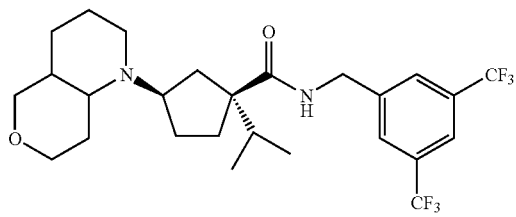

The dicarbonyl Intermediate 39 (36 mg, 0.23 mmol) was combined with optically pure amine Intermediate 16 (100 mg, 0.231 mmol), triethylamine (32 µL, 0.23 mmol), 4 Å powdered molecular sieves (~100 mg), and sodium triacetoxyborohydride (245 mg, 1.16 mmol) in DCM (3 mL). The resulting mixture was stirred at room temperature for 16 h. The reaction mixture was filtered through a celite plug, washing with more DCM. The filtrate was washed with saturated NaHCO$_3$ solution, then brine. The organic layer was dried over anhydrous MgSO$_4$, filtered, and concentrated. Purification by flash chromatography (silica, gradient from 0.25/2.25/97.5 to 1/9/90 of NH$_4$OH/methanol/DCM) gave three bands, each having the correct mass for the product (4 possible isomers separated into three bands). Mixed fractions obtained from the first purification were subjected to further purification by preparative TLC (silica, 0.6/5.5/94 of NH$_4$OH/methanol/DCM) and the bands were combined with the corresponding bands purified by flash chromatography giving 34 mg, 42 mg, and 12 mg of the 1$^{st}$, 2$^{nd}$, and 3$^{rd}$ bands to elute, respectively. Analysis by chiral HPLC (ChiralPak AD and OD columns) indicated that the first two bands were single isomers, while the third band was a mixture of two isomers. All three products were converted to their HCl salts by dissolving in DCM (~1 mL), adding excess 4 N HCl in dioxane (~6 drops) and concentrating to give white solids.

Spot 1, single isomer: ESI-MS calc. for C26H34F6N2O2: 520; Found: 521 (M+H).

Spot 2, single isomer: ESI-MS calc. for C26H34F6N2O2: 520; Found: 521 (M+H).

Spot 3, two isomers: ESI-MS calc. for C26H34F6N2O2: 520; Found: 521 (M+H).

EXAMPLE 151

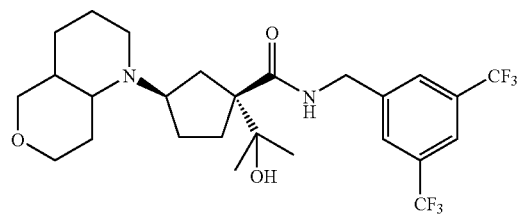

The dicarbonyl Intermediate 39 (34 mg, 0.22 mmol) was combined with optically pure amine Intermediate 14 (100 mg, 0.223 mmol), triethylamine (31 µL, 0.22 mmol), 4 Å powdered molecular sieves (~200 mg), and sodium triacetoxyborohydride (236 mg, 1.12 mmol) in DCM (4 mL). The resulting mixture was stirred at room temperature for 24 h. The reaction mixture was filtered through a celite plug, washing with methanol. The filtrate was concentrated. Saturated NaHCO$_3$ solution (30 mL) and methanol (~5 mL) was added and the reaction mixture was stirred at 50° C. for 0.5 h (to break up boron complex with product as seen in HPLC-MS). The mixture was partially concentrated to remove methanol, and then was extracted twice with DCM. The combined organic layers were washed with brine, dried over MgSO$_4$, filtered, and concentrated. Purification by preparative TLC (silica, 0.7/6.3/93 of NH$_4$OH/methanol/DCM) permitted separation of four bands, each with a mass corresponding to product (resolved all four possible isomers). The top spot (spot 1) required further purification by reverse phase HPLC (YMC column) to eliminate a side product and obtain the pure isomer. All four pure isomers were converted to their HCl salts by dissolving in DCM (~1 mL), adding excess 4 N HCl in dioxane (~6 drops) and concentrating to give white solids.

Spot 1: ESI-MS calc. for C26H34F6N2O3: 536; Found: 537 (M+H).

Spot 2: ESI-MS calc. for C26H34F6N2O3: 536; Found: 537 (M+H).

Spot 3: ESI-MS calc. for C26H34F6N2O3: 536; Found: 537 (M+H).

Spot 4: ESI-MS calc. for C26H34F6N2O3: 536; Found: 537 (M+H).

EXAMPLE 152

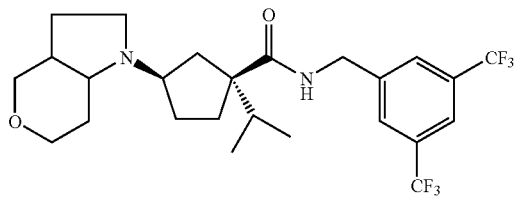

The dicarbonyl Intermediate 40 (33 mg, 0.23 mmol) was combined with optically pure amine Intermediate 16 (100 mg, 0.231 mmol), triethylamine (32 µL, 0.23 mmol), 4 Å powdered molecular sieves (~200 mg), and sodium triacetoxyborohydride (244 mg, 1.16 mmol) in DCM (20 mL). The resulting mixture was stirred under nitrogen at room temperature for 16 h. The reaction mixture was filtered through a celite plug, washing with more DCM. The filtrate was washed with saturated NaHCO3 solution, then brine. The organic layer was dried over anhydrous MgSO4, filtered, and concentrated. Purification by flash chromatography (silica, gradient from 0.1/0.9/99 to 1.5/13.5/85 of NH4OH/methanol/DCM) gave a single spot presumed to be the 2 cis-product isomers. Purification by chiral HPLC (ChiralPak OD column, 5% ethanol/hexane) afforded two pure single isomers: peak 1 gave 18 mg, and peak 2 gave 16 mg. ESI-MS calc. for C25H32F6N2O2: 506; Found: 507 (M+H).

EXAMPLE 153

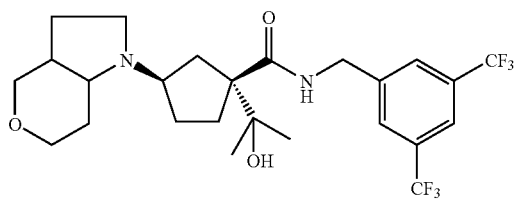

The dicarbonyl Intermediate 40 (210 mg, 1.48 mmol) was combined with optically pure amine Intermediate 14 (610 mg, 1.48 mmol), triethylamine (205 µL, 1.48 mmol), 4 Å powdered molecular sieves (~1 g), and sodium triacetoxyborohydride (1.57 g, 7.40 mmol) in DCM (50 mL). The resulting mixture was stirred at room temperature for 3 days. The reaction mixture was filtered through a celite plug, washing with methanol. The filtrate was concentrated. Saturated NaHCO3 solution (100 mL) was added and the reaction mixture was agitated at 50° C. for 3 h (to break up boron complex with product as seen in HPLC-MS). The aqueous mixture was extracted six times with DCM, then the organic layers were combined and washed with brine, dried over MgSO4, filtered, and concentrated to give 653 mg of crude product. Separation of the two cis-isomers and further purification was accomplished by a combination of preparative TLC (silica, 0.5/4.5/95 of NH4OH/methanol/DCM) and chiral HPLC (ChiralPak OD column, 7% ethanol/hexane) afforded the resolved single cis-isomers, which were converted to their HCl salts by dissolving in DCM, adding excess 4 N HCl in dioxane and concentrating to give white solids (180.3 mg of peak 1 off of the OD column, and 147.6 mg of peak 2). ESI-MS calc. for C25H32F6N2O3: 522; Found: 523 (M+H).

EXAMPLE 154

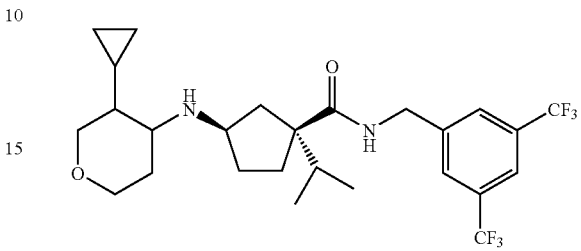

The ketone Intermediate 41 (43 mg, 0.31 mmol) was combined with optically pure amine Intermediate 16 (133 mg, 0.307 mmol), triethylamine (43 µL, 0.31 mmol), 4 Å powdered molecular sieves (~200 mg), and sodium triacetoxyborohydride (260 mg, 1.23 mmol) in DCM (4 mL). The resulting mixture was stirred at room temperature overnight. The reaction mixture was filtered through a celite plug, washing with more DCM. The filtrate was washed with saturated NaHCO3 solution, then brine. The organic layer was dried over anhydrous MgSO4, filtered, and concentrated. Purification by preparative TLC (silica, 5% of 1:9 NH4OH/methanol in DCM) gave two bands corresponding to product (74 mg top spot, 60 mg bottom spot).

Top spot-ESI-MS calc. for C26H34F6N2O2: 520; Found: 521 (M+H).

Bottom spot-ESI-MS calc. for C26H34F6N2O2: 520; Found: 521 (M+H).

EXAMPLE 155

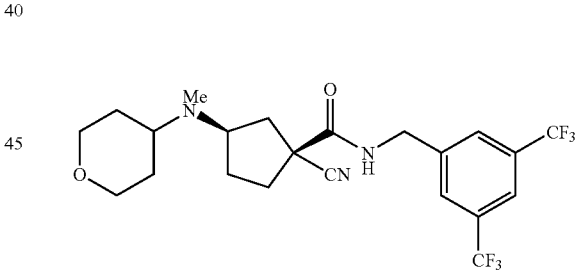

Step A

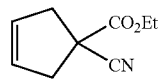

A solution of ethyl cyanoacetate (40.9 g, 0.361 mol) in 400 mL DMF was cooled to 0° C. and treated under a steady stream of N2 with lithium hydride (7.18 g, 0.903 mol) in multiple portions. After hydrogen evolution subsided, cis-1,4-dichloro-2-butene (51.9 g, 0.415 mol) was added dropwise by addition funnel. The reaction became very thick during the addition, requiring the addition of 200 mL of DMF to aid in stirring. The reaction mixture was permitted to warm to room temperature and was stirred for 1 h. The reaction mixture was then poured into a 1:1 mixture of water/ice, which was in turn extracted twice with ether. The ethereal layers were combined and washed five times with water, and once with brine. The ethereal phase was then dried over MgSO$_4$, filtered and concentrated. The resulting crude product was distilled using a short path distillation apparatus (1 mm Hg, bath temperature=100° C., head temperature=75° C.), giving 25.8 g of the desired product (43%). $^1$H NMR (CDCl$_3$, 500 MHz): 5.70 (s, 2H), 4.27 (q, J=7 Hz, 2H), 3.10 (m, 4H), 1.34 (t, J=7 Hz, 3H).

Step B

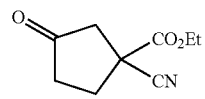

A solution of the cyclopentene prepared in Step A above (17.5 g, 0.106 mol) in 100 mL of THF was cooled to −78° C. and treated with BH$_3$·THF (1.0 M solution in THF, 63.5 mL, 64 mmol) dropwise. The reaction mixture was stirred at −78° C. for 0.5 h, then warmed to room temperature and stirred for an additional 1 h. TLC indicated that the reaction was incomplete so the mixture was cooled back to −78° C. and treated with more BH$_3$-THF solution (1.0 M solution in THF, 42 mL, 42 mmol). The reaction mixture was then warmed to room temperature and stirred for 2 h. After storing overnight in a freezer, the reaction mixture was concentrated at room temperature and redissolved in DCM (500 mL). Then while stirring with an overhead mechanical stirring apparatus, premixed PCC (137 g, 0.635 mol) and magnesium sulfate (130 g) were added in portions over 15 minutes. The resulting exotherm was controlled with an ice bath. After stirring at room temperature for 3 h, the reaction mixture was filtered through a 3" plug of silica, washing the remaining solids three times with acetone. The filtrate was concentrated and filtered a second time through a 3" silica plug washing through with 50% ethyl acetate/hexane. The filtrate was concentrated and the residue was purified by flash chromatography (silica, 50% ethyl acetate/hexane) giving 4.63 g (24%) of product. $^1$H NMR (CDCl$_3$, 500 MHz) δ 4.35 (q, J=8.5 Hz, 2H), 2.94 (d, J=23 Hz, 1H), 2.78 (d, J=23 Hz, 1H), 2.51-2.70 (m, 4H), 1.38 (t, J=9 Hz, 3H).

Step C

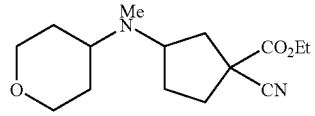

The ketone intermediate from Step B above (1.02 g, 5.64 mmol) was combined with Intermediate 2 (931 mg, 6.77 mmol), sodium triacetoxyborohydride (4.78 g, 22.6 mmol), triethylamine (0.94 mL, 6.8 mmol), and 4 Å powdered molecular sieves (~2 g) in 30 mL of DCM. The reaction mixture was permitted to stir at room temperature for 4 days. Then 37% aqueous formaldehyde (4.58 g, 56.4 mmol) was added, followed by more 4 Å powdered molecular sieves (~5 g). After stirring the mixture for five minutes, more sodium triacetoxyborohydride (5 g, 23 mmol) was added and the resulting mixture was stirred for 2.5 h. The reaction mixture was then filtered through celite, washing with DCM. The filtrate was then washed with saturated NaHCO$_3$ solution, water, and brine, dried over anhydrous MgSO$_4$, filtered, and concentrated. Purification by flash chromatography (silica, 10% methanol/DCM) afforded 1.12 g of target amine (75% yield). ESI-MS calc. for C15H24N2O3: 280; Found: 281 (M+H).

Step D

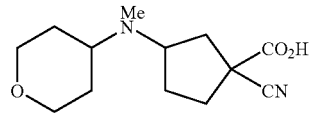

A solution of the aminoester from Step C above (1.07 g, 3.82 mmol) in 1:1 THF/methanol (16 mL) was treated with a solution of LiOH.H$_2$O (0.80 g, 19 mmol) in water (8 mL). The resulting mixture was stirred at room temperature for 2 h, then was neutralized with 2 N HCl solution, and partially concentrated to remove the organic solvents. Attempts to extract the product into chloroform failed as the product remained in the aqueous layer. Therefore the aqueous mixture was concentrated to dryness (2.06 g crude mixture) and used as is in the following step. ESI-MS calc. for C13H20N2O3: 252; Found: 253 (M+H).

Step E

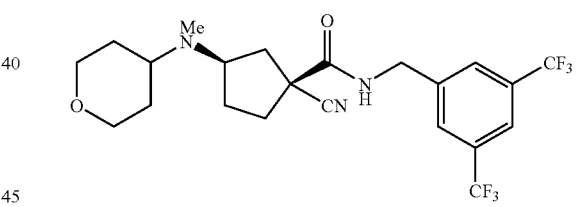

A solution of the crude amino-acid from Step D above (~3.17 mmol) and 3,5-Bis(trifluoromethyl)-benzylamine hydrochloride (1.33 g, 4.76 mmol) in DCM was treated with EDC (1.22 g, 6.34 mmol). The resulting reaction mixture was stirred at room temperature over night. HPLC-MS analysis indicated low conversion. 4 N HCl in 1,4-dioxane (0.79 mL, 3.2 mmol) was added followed by DMF (10 mL) and the reaction mixture was stirred for another 48 h. The reaction mixture was then partially concentrated to remove the DCM and partitioned between EtOAc and saturated NaHCO$_3$ solution. The aqueous layer was extracted again with ethyl acetate and the combined organic layers were washed with water five times and once with brine. The organic layer was then dried over anhydrous MgSO$_4$, filtered, and concentrated. Purification by preparative TLC allowed separation of the cis (top spot) and trans (bottom spot) isomers, although approximately ⅓ of the material was lost accidentally. 198 mg Of the desired cis isomer was obtained as a mixture of two enantiomers. ESI-MS calc. for C22H25F6N3O2: 477; Found: 478 (M+H).

EXAMPLE 156

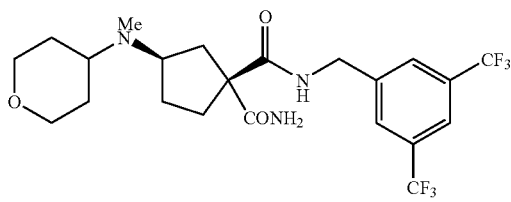

To a solution of the final product in Example 155 (87.6 mg, 0.183 mmol) in DMSO (1 mL) was added $K_2CO_3$ (5 mg) followed by 30% $H_2O_2$ solution (24 µL). The resulting mixture was stirred at room temperature for 30 minutes, then was quenched with excess 10% $Na_2SO_3$ solution. The mixture was then extracted three times with ethyl acetate and the combined organic layers were washed successively with 10% $Na_2SO_3$ solution, water (four times) and brine. The organic layer was then dried over anhydrous $MgSO_4$, filtered, and concentrated to afford 76.6 mg of crude product. Purification by preparative TLC (silica, 8% of 1/9 $NH_4OH$/methanol in DCM) gave 49.1 mg of target compound.

EXAMPLE 157

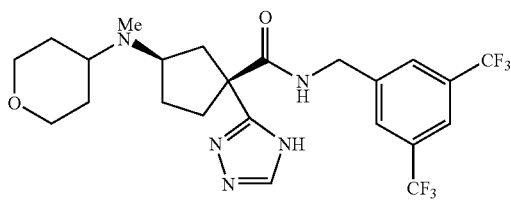

A solution of the final product from Example 156 (47.6 mg, 0.0961 mmol) in N,N-dimethylformamide dimethylacetal (1.5 mL) was stirred at 120° C. for 3 h, then was concentrated and stored under vacuum until the next day. The residue was dissolved in AcOH (1 mL), hydrazine hydrate (6 mg) was added, and the mixture was stirred at 90° C. for 3 h. The reaction mixture was concentrated and the crude product was purified by reverse phase HPLC, followed by preparative TLC (silica, 10% of 1/9 $NH_4OH$/methanol in DCM) to give the target compound as a mixture of two enantiomers. ESI-MS calc. for C23H27F6N5O2: 519; Found: 520 (M+H).

EXAMPLE 158

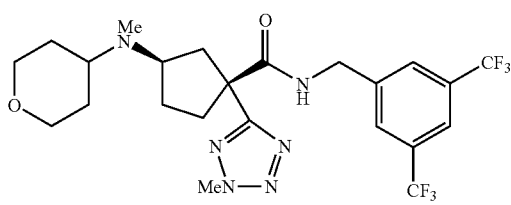

Step A

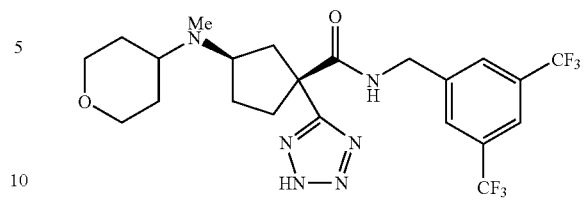

The final product from Example 155 (87 mg, 0.18 mmol) was combined with triethylamine hydrochloride (75 mg, 0.55 mmol) and sodium azide (71 mg, 1.1 mmol) in 1-methyl-2-pyrrolidinone (3 mL) and stirred at reflux for 5.5 h, then at room temperature overnight. An aqueous workup failed because of the product's high aqueous solubility. The aqueous product mixture was therefore concentrated (1-2 mm Hg and ~70° C. were required to remove the 1-methyl-2-pyrrolidinone). The crude product was purified by preparative TLC (silica, 30% methanol/DCM) to give 58 mg of the tetrazole product. ESI-MS calc. for C22H26F6N6O2: 520; Found: 521 (M+H).

Step B

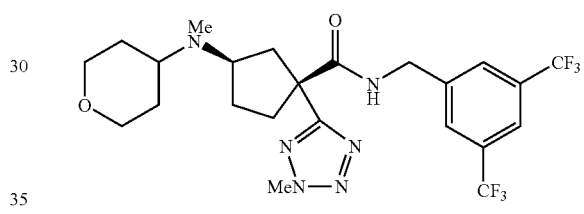

The tetrazole intermediate prepared in Step A above (15.1 mg, 0.0290 mmol) was combined with triphenylphosphine (19 mg, 0.073 mmol) and methanol (3 µL, 0.07 mmol) in DCM under a nitrogen atmosphere. Diethyl azodicarboxylate (12 µL, 0.073 mmol) was added and the reaction mixture was stirred at room temperature overnight. The reaction mixture was applied onto an ion exchange column (Super Spe-ed benzenesulfonic SCX, 5 g/35 mL from Applied Separations) and the column was rinsed with 10% methanol/ethyl acetate (50 mL) to remove neutral impurities. Then the column was rinsed with 1:1 of 2 N $NH_3$ in methanol/DCM (40 mL) and the filtrate was concentrated and further purified by preparative TLC (silica, 10% methanol in DCM) to give 8.9 mg of desired product (mixture of two enantiomers). ESI-MS calc. for C23H28F6N6O2: 534; Found: 535 (M+H).

EXAMPLE 159

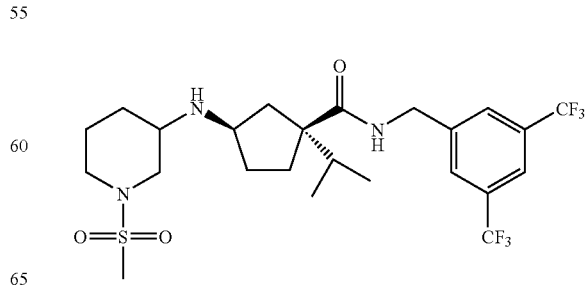

Step A

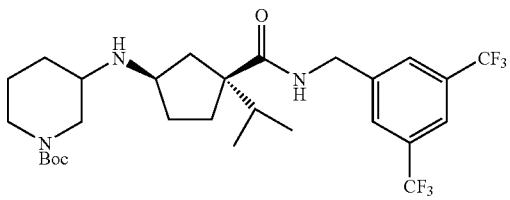

Intermediate 8 (115 mg, 0.290 mmol) was combined with 3-amino-1-N-t-butoxycarbonylpiperidine (87 mg, 0.44 mmol) and sodium triacetoxyborohydride (246 mg, 1.16 mmol) in 5 mL DCM and stirred at room temperature overnight. The reaction mixture was diluted with DCM and washed with saturated NaHCO$_3$ solution, and brine, dried over anhydrous MgSO$_4$, filtered, and concentrated. Purification by preparative TLC (silica, 8% of 1/9 NH$_4$—OH/methanol in DCM) allowed separation of two bands with the top band corresponding to a mixture of 4 cis-cyclopentyl isomers (74 mg). ESI-MS calc. for C28H39F6N3O3: 579; Found: 580 (M+H).

Step B

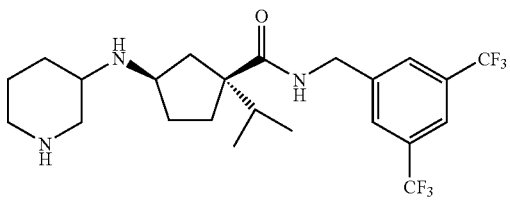

The product from Step A above (72 mg, 0.12 mmol) was dissolved in 5 mL of 4 N HCl in 1,4-dioxane and stirred at room temperature for 1.5 h. The reaction mixture was then concentrated to afford 69.5 mg of product (as a mixture of four isomeric salts). ESI-MS calc. for C23H31F6N3O: 479; Found: 480 (M+H).

Step C

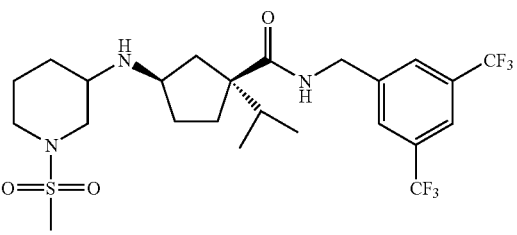

A solution of the intermediate from Step B above (68 mg, 0.12 mmol) and triethylamine (34 µL, 0.25 mmol) in 3 mL DCM was treated with methanesulfonyl chloride (10 µL, 0.12 mmol) and stirred at room temperature for 1 h. The reaction mixture was concentrated and the resulting residue was purified by preparative TLC (silica, 8% of 1/9 NH$_4$OH/methanol in DCM). The product was converted to its hydrochloride salt by dissolving in DCM, adding excess 1 N HCl in ether (~0.5 mL), and concentrating to afford 55 mg of product salt. ESI-MS calc. for C24H33F6N3O3S: 557; Found: 558 (M+H).

EXAMPLE 160

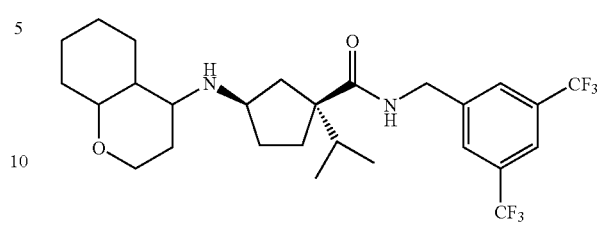

Step A

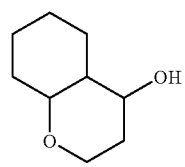

To a solution of 4-chromanone (5.00 g, 33.7 mmol) in methanol (50 mL) was added concentrated HCl solution (28 mL, 340 mmol) and PtO$_2$ (0.5 g). The resulting mixture was agitated while under 50 psi of hydrogen gas for 5 h using a Parr apparatus. The major products were those arising from over reduction (for example, 3-cyclohexyl-1-propanol), however purification by MPLC (silica, 50% ethyl acetate/hexane) did provide 136 mg of desired product as a mixture of isomers.

Step B

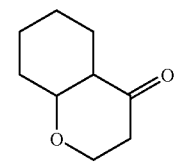

A solution of DMSO (0.244 mL, 3.43 mmol) in 2 mL DCM was added dropwise to a cooled (−78° C.) solution of oxalyl chloride (0.150 mL, 1.72 mmol) in 20 mL of DCM. After stirring for an additional 3 minutes, the alcohol prepared as described in Step A above (134 mg, 0.858) was added dropwise in 2 mL of DCM. After 15 minutes, neat triethylamine (0.956 mL, 6.86 mmol) was added dropwise. After 5 more minutes the reaction mixture was permitted to warm to room temperature and stir for 1 h. The reaction mixture was then diluted with DCM and washed successively with 1 N HCl solution, saturated NaHCO$_3$ solution, and brine, dried over anhydrous MgSO$_4$, filtered, and concentrated. The resulting crude product was purified by MPLC (silica, 50% ethyl acetate/hexane) to give 88 mg of the product as a 2:1 mixture of trans to cis isomers (see JOC (1974), 39, 2040.). $^1$H NMR (CDCl$_3$, 500 MHz): 4.30 (m), 3.81 (m, 1H from CHOH cis isomer), 3.75 (m), 3.23 (dt, J=10.5, 4.0 Hz, 1H from CHOH trans isomer), 2.74 (m), 2.39 (m, 1H from cis isomer), 2.34 (m, 1H from trans isomer), 2.22 (m), 2.10 (m), 2.03-1.95 (m), 1.88 (dq, J=12.5, 4.0 Hz), 1.84-1.75 (m), 1.70-1.61 (m), 1.59-1.44 (m), 1.35-1.19 (m).

Step C

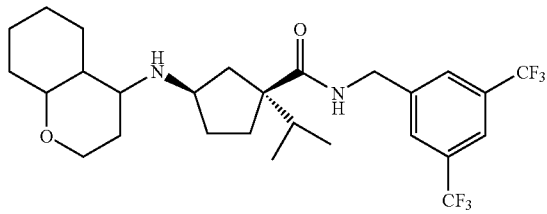

The ketone from Step B (29.9 mg, 0.194 mmol) was combined with Intermediate 16 (76.3 mg, 0.176 mmol), triethylamine (25 μL, 0.18 mmol), and sodium triacetoxyborohydride (187 mg, 0.880 mmol) in 3 mL DCM and the resulting mixture was stirred at room temperature for overnight. The reaction mixture was diluted with DCM and washed with saturated NaHCO$_3$ solution, then brine, dried over anhydrous MgSO$_4$, filtered, and concentrated. The crude product was purified and separated into three product bands (attributed to different isomer mixtures) by preparative TLC (silica, 5% of 1/9 NH$_4$OH/methanol in DCM). The following amounts were collected: Top band 25 mg, middle band 18 mg, bottom band 6 mg. All three bands showed the correct mass as indicated below. All three bands ESI-MS calc. for C27H36F6N2O2: 534; Found: 535 (M+H).

EXAMPLE 161

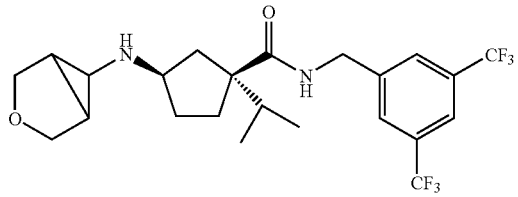

Step A

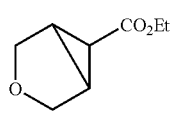

To a mixture of 2,5-dihydrofuran (5.31 mL, 70.1 mmol) and Rh(OAc)$_2$ (1.55 g, 7.01 mmol) in 250 mL of DCM was added via syringe pump under a nitrogen atmosphere a solution of ethyl diazoacetate (8.85 g, 84.1 mmol) in 40 mL of DCM at a rate of 2 mmol/h. After the addition was complete the reaction mixture was filtered through celite and concentrated. Purification by MPLC (silica, 25% ethyl acetate/hexane) afforded 6.35 g of product which appeared by HNMR to have purely the trans cyclopropane stereochemistry. $^1$H NMR (CDCl$_3$, 400 MHz) δ 4.14 (q, J=7.2 Hz, 2H), 3.94 (d, J=8.8 Hz, 2H), 3.76 (d, J=8.4 Hz, 2H), 2.17 (m, 2H), 1.62 (t, J=3.2 Hz, 1H), 1.28 (t, J=7.2 Hz, 3H).

Step B

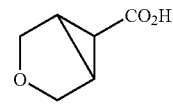

A solution of the ester prepared as described in Step A (5.35 g, 34.3 mmol) in 80 mL of methanol was treated with a solution of LiOH.H$_2$O in 30 mL of water. The reaction mixture was stirred overnight at room temperature. The reaction mixture was partially concentrated to remove the methanol and ~32 mL of 4 N HCl in 1,4-dioxane was added while cooling in an ice bath, bringing the pH to 5. The mixture was then concentrated almost to dryness and extracted twice with ethyl acetate. The combined organic layers were dried over anhydrous Na$_2$SO$_4$, filtered, and concentrated to give 2.41 g of product which required no further purification. $^1$H NMR (CDCl$_3$, 400 MHz): 3.97 (d, J=8.8 Hz, 2H), 3.78 (d, J=8.8 Hz, 2H), 2.25 (m, 2H), 1.64 (t, J=3.2 Hz, 1H).

Step C

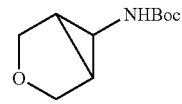

The acid from Step B (1.40 g, 10.9 mmol) was combined with diphenylphosphoryl azide (2.59 mL, 12.0 mmol) and triethylamine (3.19 mL, 22.9 mmol) in 90 mL of t-butanol and stirred at reflux for 3 days (timer failed to turn off). The reaction mixture was concentrated and the residue was dissolved in ethyl acetate and washed with 1 N HCl solution, saturated NaHCO$_3$ solution, and brine, dried over MgSO$_4$, filtered, and concentrated. Purification by MPLC (silica, 65% ethyl acetate/hexane) gave 1.14 g of the desired product. 1H NMR (CDCl$_3$, 400 MHz): 4.65 (br s, 1H), 3.98 (d, J=8.0 Hz, 2H), 3.72 (d, J=8.4 Hz, 2H), 2.41 (s, 1H), 1.78 (s, 2H), 1.46 (s, 9H).

Step D

A solution of the product from Step C (790 mg, 3.96 mmol) in 4 N HCl in 1,4-dioxane was stirred at room temperature for 0.5 h then concentrated to give 537 mg of amine hydrochloride product. 1H NMR (CD$_3$OD, 500 MHz): 3.94 (d, J=9.0 Hz, 2H), 3.69 (d, J=9.0 Hz, 2H), 2.38 (br t, J=2.5 Hz, 1H), 2.07 (m, 2H).

Step E

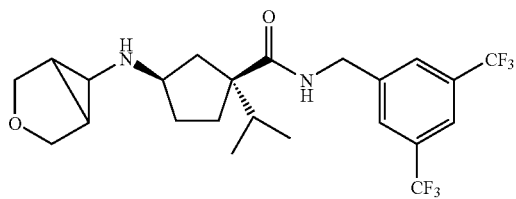

A solution of the amine salt prepared in Step D (62 mg, 0.46 mmol), Intermediate 8 (120 mg, 0.304 mmol), triethylamine (64 µL, 0.46 mmol), and sodium triacetoxyborohydride (322 mg, 1.52 mmol) was stirred at room temperature for 2 days. The reaction mixture was diluted with DCM, washed with saturated NaHCO$_3$ solution, then brine, dried over anhydrous MgSO$_4$, filtered, and concentrated. Purification by preparative TLC (silica, 5% of 1/9 NH$_4$—OH/methanol in DCM) afforded two bands corresponding to the cis isomer pair (top spot, 79.5 mg) and the trans isomer pair (bottom spot, 49.6 mg).

Top spot: ESI-MS calc. for C23H28F6N2O2: 478; Found: 479 (M+H).

Bottom spot: ESI-MS calc. for C23H28F6N2O2: 478; Found: 479 (M+H).

EXAMPLE 162

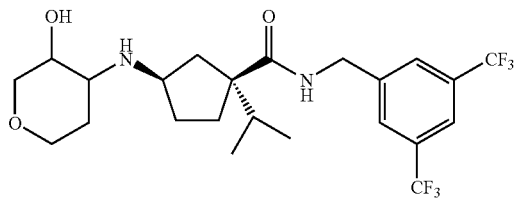

Step A

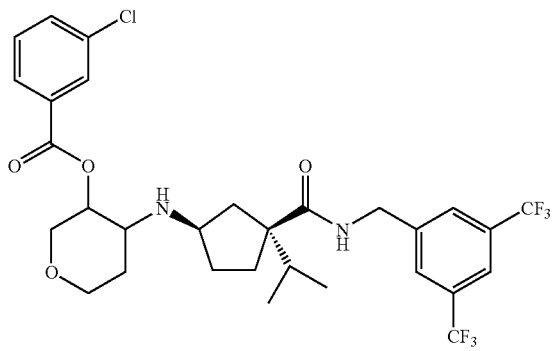

A solution of Intermediate 3 (59 mg, 0.23 mmol), intermediate 16 (100.0 mg, 0.231 mmol), diisopropylethylamine (40 µL, 0.23 mmol) and crushed molecular sieves (4 Å, 50 mg) in dichloroethane (5 mL) was treated with sodium triacetoxyborohydride (245 mg, 1.16 mmol) and stirred at room temperature overnight. The reaction was quenched with saturated sodium bicarbonate solution (10 mL) and diluted with an additional 10 mL of DCE. The organic layer was separated and the aqueous washed with dichloromethane (2×5 mL). The organics were combined, dried over anhydrous sodium sulfate, filtered and evaporated under reduced pressure. The residue was purified by preparative TLC (eluant: 0.5% NH$_4$OH: 5% MeOH: 94.5% CH$_2$Cl$_2$) to yield 135 mg (87%) of the product as a mixture of four diastereomers. LC-MS calculated for C$_{30}$H$_{33}$ClF$_6$N$_2$O$_4$ is 634.20, found (MH)$^+$ 635.1 and (MH+2)$^+$ 637.2.

Step B

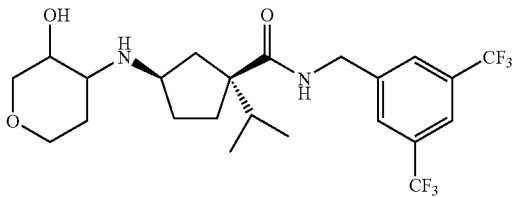

A solution of the product described in step A, example 162 (120 mg, 0.190 mmol) in methanol (3 mL) was treated with a 0.5 M solution of sodium methoxide in methanol (1 mL) and the resulting mixture stirred for 1 h at room temperature. The mixture was evaporated under vacuum and the residue purified by preparative TLC (eluant: 1.0% NH$_4$OH: 10% MeOH: 89% CH$_2$Cl$_2$) to yield 95 mg (87%) of the final product as a mixture of four diastereomers. The single isomers were obtained by using a Gilson HPLC equipped with a Preparatory ChiralCel OD column eluting with 5% ethanol and 95% hexane with a flow rate of 9 ml/min. LC-MS calculated for C$_{23}$H$_{30}$F$_6$N$_2$O$_3$ is 496.22, found (MH)$^+$ 497.3 for all 4 isomer.

EXAMPLE 163

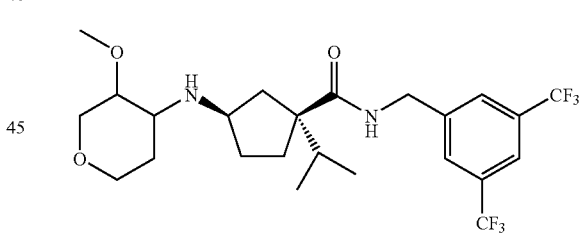

A solution of intermediate 24 (13 mg, 0.093 mmol), intermediate 16 (37 mg, 0.093 mmol), diisopropylethylamine (17 µL, 0.093 mmol) and crushed molecular sieves (4 Å, 20 mg) in dichloroethane (3 mL) was treated with sodium triacetoxyborohydride (100 mg, 0.465 mmol) and stirred at room temperature overnight. The reaction was quenched with saturated sodium bicarbonate solution (10 mL) and diluted with an additional 10 mL of DCE. The organic layer was separated and the aqueous washed with dichloromethane (2×5 mL). The organics were combined, dried over anhydrous sodium sulfate, filtered and evaporated under reduced pressure. The residue was purified by preparative TLC (eluant: 0.5% NH$_4$OH: 5% MeOH: 94.5% CH$_2$Cl$_2$) to yield 26 mg (63%) of the final product as a mixture of four diastereomers. LC-MS calculated for C$_{24}$H$_{32}$F$_6$N$_2$O$_3$ is 510.24, found (MH)$^+$ 511.2.

EXAMPLE 164

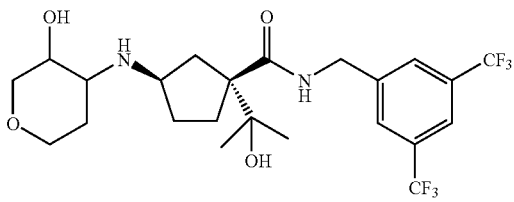

Step A

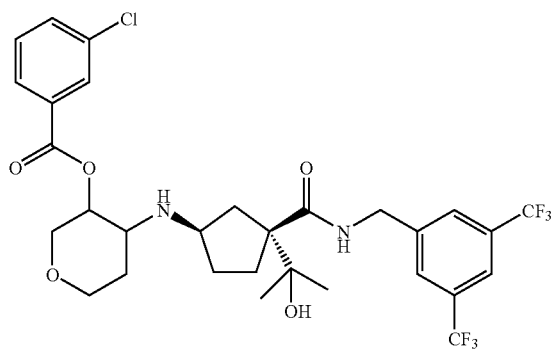

A solution of intermediate 3 (113 mg, 0.446 mmol), intermediate 14 (200.0 mg, 0.446 mmol), diisopropylethylamine (78 μL, 0.45 mmol) and crushed molecular sieves (4 Å, 100 mg) in dichloroethane (25 mL) was treated with sodium triacetoxyborohydride (473 mg, 2.23 mmol) and stirred at room temperature overnight. The reaction was quenched with saturated sodium bicarbonate solution (20 mL) and diluted with an additional 20 mL of DCE. The organic layer was separated and the aqueous washed with dichloromethane (2×10 mL). The organics were combined, dried over anhydrous sodium sulfate, filtered and evaporated under reduced pressure. The residue was purified by preparative TLC (eluant: 100% ethyl acetate) to yield 263 mg (98%) of the product as a mixture of four diastereomers. LC-MS calculated for $C_{30}H_{33}ClF_6N_2O_5$ is 650.26, found $(MH)^+$ 651.2 and $(MH+2)^+$ 653.3.

Step B

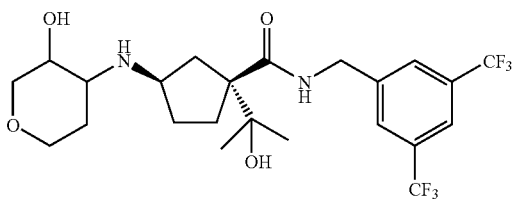

A solution of the product described in step A, example 164 (263 mg, 0.440 mmol) in methanol (5 mL) was treated with a 0.5 M solution of sodium methoxide in methanol (1 mL) and the resulting mixture was stirred for 1 h at room temperature. The mixture was evaporated under vacuum and the residue was purified by preparative TLC (eluant: 1.0% $NH_4OH$: 10% MeOH: 89% $CH_2Cl_2$) to yield 210 mg (86%) of the final product as a mixture of four diastereomers. The single isomers were obtained by using a Gilson HPLC equipped with a Preparatory ChiralCel OD column eluting with 7% ethanol and 93% hexane with a flow rate of 9 ml/min. LC-MS calculated for $C_{23}H_{30}F_6N_2O_4$ is 512.22, found $(MH)^+$ 513.3 for all 4 isomer.

EXAMPLE 165

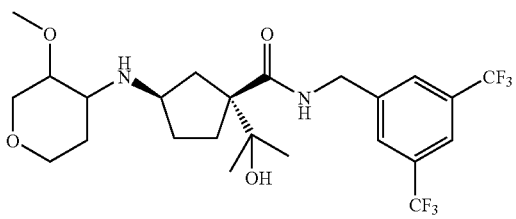

A solution of intermediate 24 (30 mg, 0.22 mmol), intermediate 14 (100 mg, 0223 mmol), diisopropylethylamine (39 μL, 0.22 mmol) and crushed molecular sieves (4 Å, 80 mg) in dichloroethane (15 mL) was treated with sodium triacetoxyborohydride (236 mg, 1.12 mmol) and stirred at room temperature overnight. The reaction was quenched with a saturated sodium bicarbonate solution (15 mL) and diluted with an additional 10 mL of DCE. The organic layer was separated and the aqueous layer was washed with dichloromethane (2×5 mL). The organics were combined, dried over anhydrous sodium sulfate, filtered and evaporated under reduced pressure. The residue was purified by preparative TLC (eluant: 0.5% $NH_4OH$: 5% MeOH: 94.5% $CH_2Cl_2$) to yield 84 mg (72%) of the final product as a mixture of four diastereomers. A second purification of this material by preparative TLC (eluant 7% MeOH: 93% $CH_2Cl_2$), developed twice, provided two bands which were assigned as less polar and more polar and were presumed to be a mixture of two isomers each. LC-MS calculated for $C_{24}H_{32}F_6N_2O_4$ is 526.24, found $(MH)^+$ 527.3 for both.

EXAMPLE 166

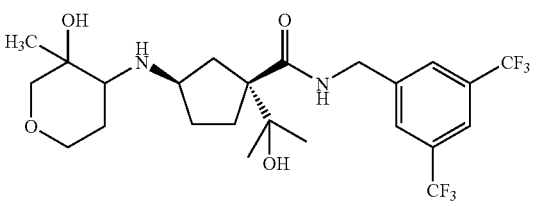

Step A

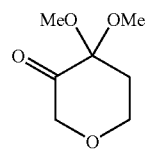

To a cooled (0° C.) solution of oxalyl chloride (237 μL, 2.72 mmol) and DMSO (386 μL, 5.44 mmol) in dichloromethane (15 mL), under nitrogen, was added dropwise a prepared solution of the product from step A, intermediate 24

(220 mg, 1.36 mmol) in DCM (10 mL) via syringe. The mixture was stirred for 30 minutes at 0° C. and then triethylamine (1.52 mL, 10.9 mmol) was added via syringe and the resulting mixture was stirred overnight allowing to warm to room temperature. The solution was evaporated in vacuo and the residue was purified by preparative TLC (eluant: 60% ethyl acetate: 40% hexane) to afford the product (133 mg, 66%) as a yellow oil.

Step B

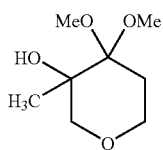

To a cooled (0° C.) solution of the product from step A, Example 166 (50 mg, 0.31 mmol) in ether (3 mL), under nitrogen, was added dropwise methylmagnesium chloride (208 µL, 0.625 mmol) via syringe and the resulting mixture was stirred at 0° C. for 3 h. The reaction was quenched by the slow addition of a saturated solution of ammonium chloride (2 mL) and then the organic layer was separated. The aqueous layer was extracted with ether (3×5 mL) and the organics were combined, dried over anhydrous sodium sulfate, filtered, and evaporated under vacuum. The material was used without further purification for the next reaction.

Yield was quantitative. $^1$H NMR (CDCl$_3$, 500 MHz): 3.78-3.74 (m, 1H), 3.45-3.38 (m, 2H), 3.42 (overlapped s, 3H), 3.31 (s, 3H), 3.26 (d, J=11 Hz, 1H), 1.93 (ddd, J=2.7, 5.3, 14.8 Hz, 1H), 1.72 (ddd, J=4.8, 11.9, 14.8 Hz, 1H), 1.34 (s, 3H).

Step C

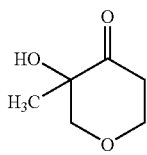

A solution of product from step B, Example 166 (50 mg, 0.31 mmol) in THF/water (1 mL/0.1 mL) was treated with concentrated hydrochloric acid (0.1 mL) and the resulting solution was stirred at room temperature for 1 h. The mixture was concentrated in vacuo to remove the THF and the aqueous layer was extracted with ether (6×5 mL). The organics were combined, dried over anhydrous sodium sulfate, filtered, and evaporated under reduced pressure to afford the product (7.5 mg, 18%) as a clear film. $^1$H NMR (CDCl$_3$, 500 MHz): 4.31 (ddd, J=3.2, 7.6, 11.2 Hz, 1H), 3.96 (dd, J=1.7, 11.0 Hz, H), 3.65 (ddd, J=3.0, 12.1, 14.0 Hz, 1H), 3.36 (dd, J=1.5, 11.2 Hz, 1H), 2.91 (ddd, J=7.6, 11.9, 14.2 Hz, 1H), 2.50 (ddd, J=1.6, 2.9, 14.2 Hz, 1H), 1.51 (s, 3H).

Step D

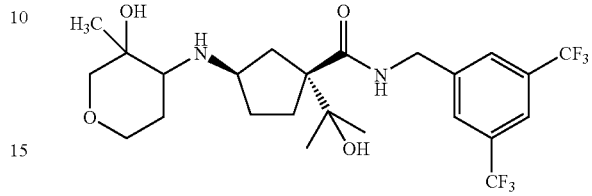

A solution of product described in step C, Example 166 (5 mg, 0.04 mmol), intermediate 14 (17 mg, 0039 mmol), diisopropylethylamine (7 µL, 0.039 mmol) and crushed molecular sieves (4 Å, 80 mg) in dichloroethane (2 mL) was treated with sodium triacetoxyborohydride (42 mg, 0.20 mmol) and stirred at room temperature overnight. The reaction was quenched with a saturated sodium bicarbonate solution (5 mL) and diluted with an additional 5 mL of DCE. The organic layer was separated and the aqueous layer was washed with dichloromethane (2×5 mL). The organics were combined, dried over anhydrous sodium sulfate, filtered and evaporated under reduced pressure. The residue was purified by preparative TLC (eluant: 0.5% NH$_4$OH: 5% MeOH: 94.5% CH$_2$Cl$_2$) to yield 8.8 mg (43%) of the final product as a mixture of four diastereomers. LC-MS calculated for C$_{24}$H$_{32}$F$_6$N$_2$O$_4$ is 526.24, found (MH)$^+$ 527.3.

EXAMPLE 167

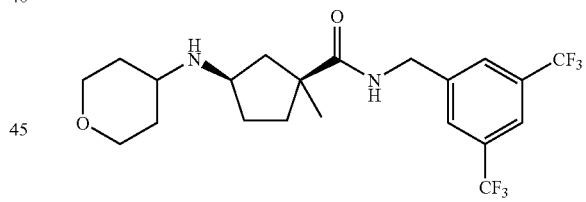

Step A

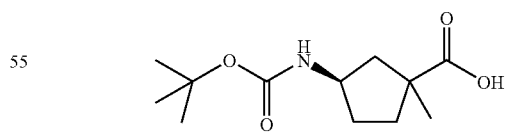

This intermediate was prepared in an analogous fashion to that of Intermediate 10, except iodomethane was used in place of 2-iodopropane. The cis and trans isomers were not separated; therefore, the compound was used as a mixture of two diastereomers. $^1$H NMR (CDCl$_3$, 500 MHz): 4.56 (br s, 1H), 4.18-4.10 (m, 1H) 4.03 (br s, 1H), 3.78-3.74 (m, 1H), 2.60 (dd, J=7.8, 13.3 Hz, 1H), 2.20-2.00 (m, 2H), 1.62-1.55 (m, 1H), 1.43 (s, 9H), 1.31 (s, 3H).

Step B

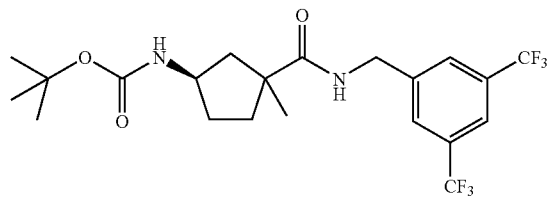

A mixture of the acid described in step A, Example 167 (500 mg, 2.06 mmol), 3,5-bis(trifluoromethyl)benzylamine hydrochloride (575 mg, 2.06 mmol), HOAt (280 mg, 2.06 mmol), N,N-diisopropylethylamine (356 µl, 2.06 mmol) in dichloromethane (25 mL) was treated with 1-[3-(dimethylamino)propyl]-3-ethylcarbodiimide hydrochloride (786 mg, 4.10 mmol) and stirred at room temperature overnight. The reaction mixture was diluted with dichloromethane (30 mL), washed with water (2×20 mL), brine (1×30 mL), dried over anhydrous sodium sulfate and the solvent was evaporated. The pure compound was obtained by purification with preparative TLC (eluant 30% ethyl acetate/70% hexane), 610 mg (64%). LC-MS calculated for $C_{21}H_{26}F_6N_2O_3$ is 468.18, found $(MH)^+$ 469.3. $^1$H NMR (CDCl$_3$, 500 MHz) δ 7.80 (s, 1H), 7.72 (s, 2H), 6.18 (br s, 1H), 4.60 (dd, J=6.1, 15.6 Hz, 1H), 4.52 (dd, J=6.0, 15.9 Hz, 1H), 4.03-4.00 (m, 1H), 2.62 (dd, J=7.8, 13.6 Hz, 1H), 2.22-2.05 (m, 3H), 1.60-1.54 (m, 1H), 1.45 (s, 9H), 1.39 (s, 3H).

Step C

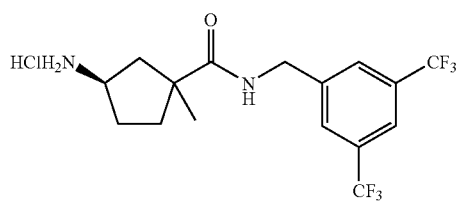

The product described in step B, Example 167 (610 mg, 1.30 mmol) was dissolved with 4 N HCl in dioxane (8 ml) and the resulting solution was stirred at room temperature for 1 h. The reaction was evaporated under vacuum to afford the product (484 mg, 92%) as a white powder. LC-MS calculated for $C_{16}H_{18}F_6N_2O$ is 368.18, found $(M+H)^+$ 369.3.

Step D

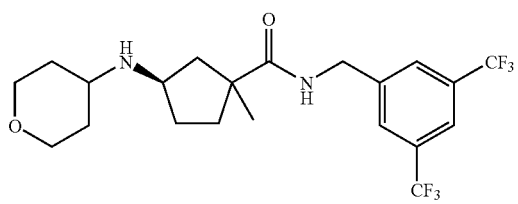

A solution of product described in step C, Example 167 (100 mg, 0.250 mmol), tetrahydro-4H-pyran-4-one (25 µL, 0.25 mmol), diisopropylethylamine (44 µL, 0.25 mmol) and crushed molecular sieves (4 Å, 50 mg) in dichloroethane (10 mL) was treated with sodium triacetoxyborohydride (265 mg, 1.25 mmol) and stirred at room temperature overnight. The reaction was quenched with a saturated sodium bicarbonate solution (15 mL) and diluted with an additional 10 mL of DCE. The organic layer was separated and the aqueous washed with dichloromethane (2×10 mL). The organics were combined, dried over anhydrous sodium sulfate, filtered and evaporated under reduced pressure. The residue was purified by preparative TLC (eluant: 0.5% NH$_4$OH: 5% MeOH: 94.5% CH$_2$Cl$_2$) to yield 105 mg (86%) of the final product (Example 271) as a mixture of two diastereomers. LC-MS calculated for $C_{21}H_{26}F_6N_2O_2$ is 452.19, found $(M+H)^+$ 453.2.

EXAMPLE 168

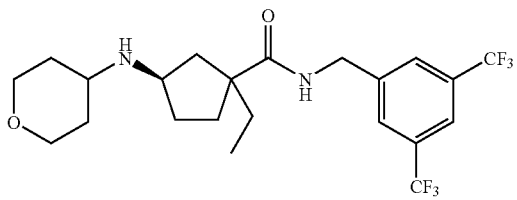

Step A

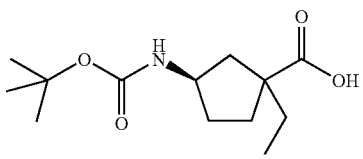

This intermediate was prepared in an analogous fashion to that of Intermediate 10, except iodoethane was used in place of 2-iodopropane. The cis and trans isomers were not separated; therefore, the compound was used as a mixture of two diastereomers. $^1$H NMR (CDCl$_3$, 500 MHz): 4.51 (br s, 1H), 3.98 (br s, 1H), 2.63 (dd, J=7.3, 13.0 Hz, 1H), 2.14 (ddd, J=6.8, 7.3, 13.0 Hz, 1H), 2.08-2.00 (m, 2H), 1.76-1.59 (m, 4H), 1.44 (s, 9H), 1.31 (s, 3H), 1.28-1.23 (m, 2H), 0.83 (t, J=7.4 Hz, 3H).

Step B

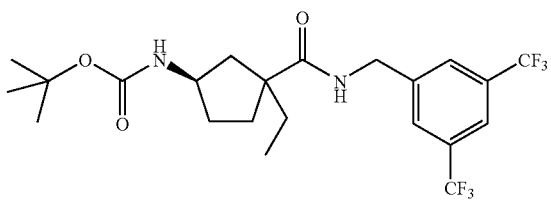

A mixture of the acid described in step A, Example 168 (528 mg, 2.06 mmol), 3,5-bis(trifluoromethyl)benzylamine hydrochloride (575 mg, 2.06 mmol), HOAt (280 mg, 2.06 mmol), N,N-diisopropylethylamine (356 µl, 2.06 mmol) in dichloromethane (25 mL) was treated with 1-[3-(dimethylamino)propyl]-3-ethylcarbodiimide hydrochloride (786 mg, 4.10 mmol) and stirred at room temperature overnight. The reaction mixture was diluted with dichloromethane (30 mL), washed with water (2×20 mL), brine (1×30 mL), dried over anhydrous sodium sulfate and the solvent was evaporated.

The pure compound was obtained by purification with preparative TLC (eluant 25% ethyl acetate/75% hexane), 380 mg (38%). LC-MS calculated for $C_{22}H_{28}F_6N_2O_3$ is 482.21, found $(M+H)^+$ 483.2.

Step C

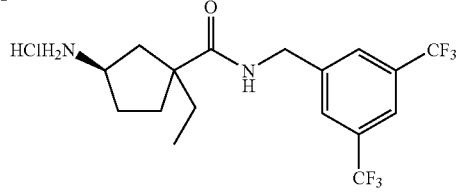

The product described in step B, Example 168 (380 mg, 0.79 mmol) was dissolved with 4 N HCl in dioxane (8 ml) and the resulting solution was stirred at room temperature for 1 h. The reaction was evaporated under vacuum to afford the product (321.4 mg, 97%) as a white powder. LC-MS calculated for $C_{17}H_{20}F_6N_2O$ is 382.20, found $(M+H)^+$ 383.2.

Step D

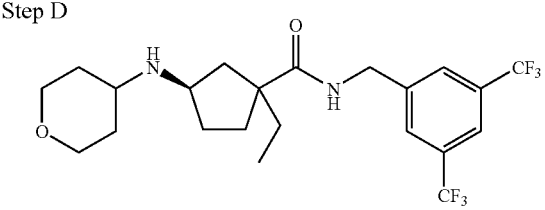

A solution of the product described in step C, Example 272 (103 mg, 0.250 mmol), tetrahydro-4H-pyran-4-one (25 mL, 0.25 mmol), diisopropylethylamine (44 µL, 0.25 mmol) and crushed molecular sieves (4 Å, 50 mg) in dichloroethane (10 mL) was treated with sodium triacetoxyborohydride (265 mg, 1.25 mmol) and stirred at room temperature overnight. The reaction was quenched with a saturated sodium bicarbonate solution (15 mL) and diluted with an additional 10 mL of DCE. The organic layer was separated and the aqueous layer was washed with dichloromethane (2×10 mL). The organics were combined, dried over anhydrous sodium sulfate, filtered and evaporated under reduced pressure. The residue was purified by preparative TLC (eluant: 0.5% $NH_4OH$: 5% MeOH: 94.5% $CH_2Cl_2$) to yield 114 mg (91%) of the final product (Example 272) as a mixture of two diastereomers. LC-MS calculated for $C_{22}H_{28}F_6N_2O_2$ is 466.19, found $(MH)^+$ 467.3.

EXAMPLE 169

Step A

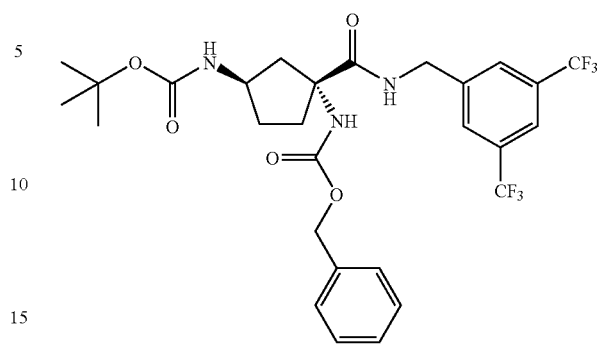

To a solution of intermediate 20 (10 mg, 0.020 mmol) and DIEA (7.2 µL, 0.040 mmol) in dichloromethane (2 mL) under nitrogen was added benzylchloroformate (3.8 µL, 0.026 mmol) and the resulting solution was stirred at room temperature overnight. The mixture was evaporated under reduced pressure and the residue purified by preparative TLC (eluant: 15% ethyl acetate/85% hexane) to afforded the product (6.3 mg, 52%) as a yellow film. LC-MS calculated for $C_{27}H_{29}F_6N_3O_5$ is 589.2, found $(M+H)^+$ 590.4.

Step B

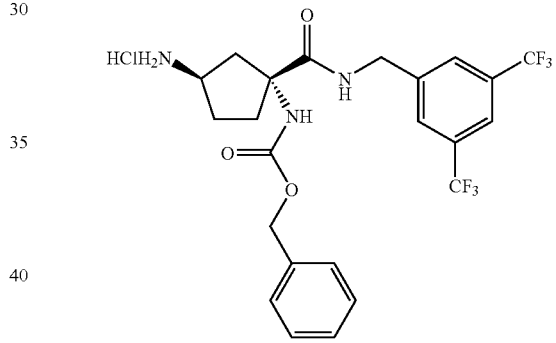

The product described in step A, Example 169 (6 mg, 0.01 mmol) was dissolved with 4 N HCl in dioxane (1 ml) and the resulting solution was stirred at room temperature for 1 h. The reaction was evaporated under vacuum to afford the product (5.88 mg, 97%) as a yellow powder. LC-MS calculated for $C_{27}H_{29}F_6N_3O_5$ is 489.2, found $(MH)^+$ 490.2.

Step C

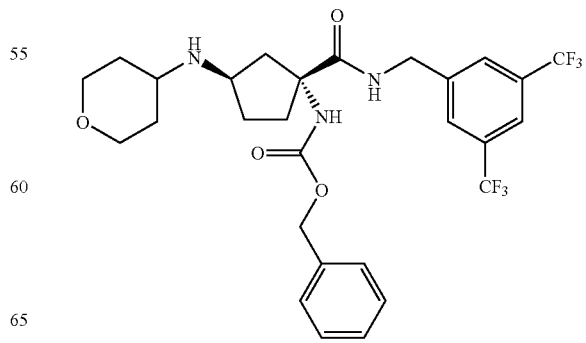

A solution of the product described in step B, Example 169 (5.9 mg, 0.0090 mmol), tetrahydro-4H-pyran-4-one (3 µL, 0.01 mmol), diisopropylethylamine (2 µL, 0.01 mmol) and crushed molecular sieves (4 Å, 5 mg) in dichloroethane (2 mL) was treated with sodium triacetoxyborohydride (10 mg, 0.05 mmol) and stirred at room temperature overnight. The reaction was quenched with a saturated sodium bicarbonate solution (5 mL) and diluted with an additional 5 mL of DCE. The organic layer was separated and the aqueous layer was washed with dichloromethane (2×5 mL). The organics were combined, dried over anhydrous sodium sulfate, filtered and evaporated under reduced pressure. The residue was purified by preparative TLC (eluant: 0.5% NH$_4$OH: 5% MeOH: 94.5% CH$_2$Cl$_2$) to yield 4.48 mg (87%) of the final product. LC-MS calculated for C$_{27}$H$_{29}$F$_6$N$_3$O$_4$ is 573.21, found (M+H)$^+$ 574.2.

EXAMPLE 170

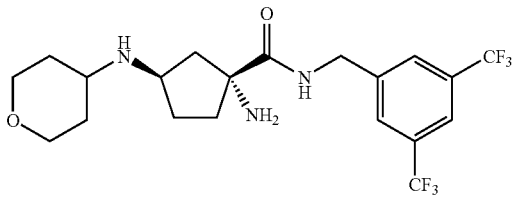

To a solution of the product described as Example 169 (2.1 mg, 0.0030 mmol) and 1 equivalent of concentrated HCl in ethanol (1 mL) was added 10% palladium on carbon (5 mg) and the resulting suspension was set under a hydrogen atmosphere introduced via a 5 L balloon of hydrogen gas. The mixture was stirred at room temperature for 2 h, then the hydrogen gas was evacuated and replaced with nitrogen. The mixture was filtered through a Gilman PTFE 0.45 µM syringe filter to remove the catalyst. The filtrate was evaporated to afford 0.83 mg (52%) of the final product (example 276) as a white powder. LC-MS calculated for C$_{20}$H$_{25}$F$_6$N$_3$O$_2$ is 453.21, found (M+H)$^+$ 454.3.

EXAMPLE 171

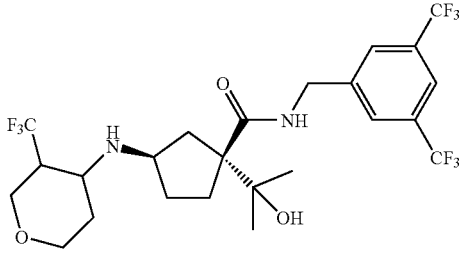

A solution of the ketone Intermediate 18 (200 mg, 1.0 mmol), amine Intermediate 14 (as a hydrochloride, 230 mg, 0.5 mmol), diisopropylethylamine (200 mg, 1.5 mmol), 4 Å molecular sieves (500 mg) in 10 mL of dry dichloroethane was treated with sodium triacetoxyborohydride (840 mg, 2.0 mmol) and the reaction mixture was stirred at room temperature 16 h. The crude reaction mixture was poured onto a saturated solution of sodium bicarbonate (50 mL), and the organic solvent was slowly evaporated under mildly reduced pressure (250 torr) and slight heating (40° C.). HPLC analysis of the aqueous phase indicated complete breakdown of the initial borane adduct after approximately 30 minutes. The crude product was extracted into dichloromethane, dried (anhydrous magnesium sulfate) and the solvent was removed in vacuo. The residue was further purified by preparative TLC to afford 50 mg (46%) of the higher eluting cis-isomeric mixture and 41 mg of the corresponding lower eluting trans-isomeric pair. The cis-isomeric pair was separated into single diastereomers by chiral semi-preparative HPLC using a ChiralPak OD column, eluted by a mixture of hexanes and ethyl alcohol (95:5) at 9 mL/min. The retention time of the isomers under the corresponding analytical conditions (1.0 mL/min flow rate) were 8.56 and 8.85 minutes, for the biologically less and more active isomer, respectively. LC MS for C24H29F9N2O3 for [M+H]$^+$ calc. 565, found 565.

EXAMPLE 172

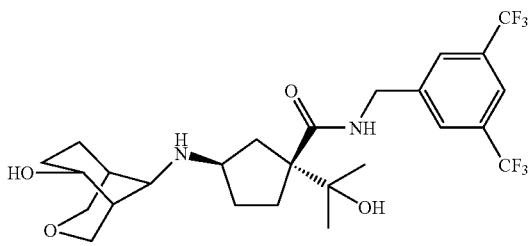

This compound, as a mixture of 4 isomers, was prepared starting from Intermediate 14 and the less polar endo hydroxyketone (Intermediate 21) according to the procedure described under Example 171. LC MS for C26H34F6N2O4 for [M+H]$^+$ calc. 523, found 523.

EXAMPLE 173

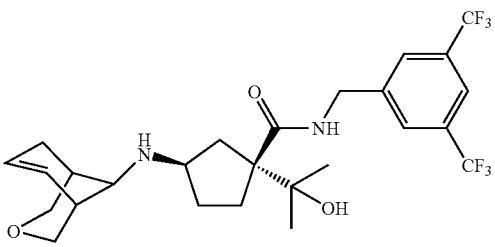

This compound (800 mg), as a mixture of 4 isomers, was prepared starting from the unsaturated ketone (850 mg) in step A of the Intermediate 22 and Intermediate 14 (900 mg) according to the same procedure described under Example 171. LC MS for C26H32F6N2O3 for [M+H]$^+$ calc. 535, found 535.

EXAMPLE 174

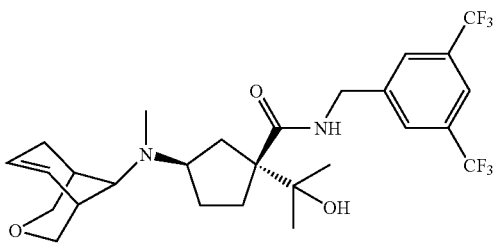

A solution of the unsaturated ketone (1.38 g, 10.0 mmol) in step a of Intermediate 22, amine Intermediate 14 (as a hydrochloride, 1.4 g mg, 3.0 mmol), diisopropylethylamine (0.52 g, 4 mmol), 4 Å molecular sieves (1.0 mg) in 20 mL of dry dichloroethane was treated with sodium triacetoxyborohydride (2.10 g, 10 mmol) and the reaction mixture was stirred at room temperature 48 h. 1.0 mL of a 30% aqueous formalin solution was added and followed by 1.0 g of 4 Å molecular sieves and 2.12 g of sodium triacetoxyborohydride. The mixture was stirred for 5 h. The crude reaction mixture was poured onto a saturated solution of sodium bicarbonate (50 mL), and the organic solvent was slowly evaporated under mildly reduced pressure (250 torr) and slight heating (60° C.). HPLC analysis of the aqueous phase indicated complete breakdown of the initial borane adduct after approximately 120 minutes. The crude product was extracted into dichloromethane, dried (anhydrous magnesium sulfate) and the solvent was removed in vacuo. The residue was further purified by preparative TLC to afford the desired endo and exo mixture as a gummy solid (2.0 g). LC MS for C27H34F6N2O3 for [M+H]+ calc. 549, found 549. Small quantities of (~150 mg) endo (less polar) and exo (more polar) isomers were separated on preparative TLC.

EXAMPLE 175

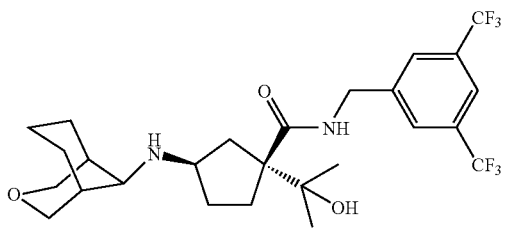

Procedure A

A mixture of the Example 172 (800 mg) and 10% Pd/C (200 mg) in 25 mL of methanol was shaken on a Parr shaker for 2 h under 45 psi of hydrogen. The catalyst was removed by filtration and the filtrate was evaporated to yield the desired product as a mixture of endo and exo isomers (790 mg). The mixture was separated into single isomers by chiral semi-preparative HPLC using a ChiralPak OD column, eluted by a mixture of hexanes and ethyl alcohol (95:5) at 9 mL/min. The retention time of the isomers under the corresponding analytical conditions (1.0 mL/min flow rate) were 12.48 and 14.65 minutes, for the biologically more and less active isomer, respectively. LC MS for C26H34F6N2O3 for [M+H]+ calc. 537, found 537.

Procedure B

The mixture of endo and exo isomers was also prepared starting from the Intermediate 22 and the Intermediate 14 according to the same procedure described under Example 171. LC MS for C26H34F6N2O3 for [M+H]+ calc. 537, found 537.

EXAMPLE 176

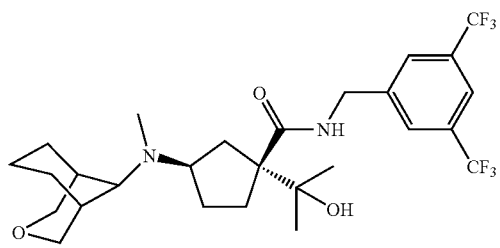

A mixture of the Example 174 (1.70 g) and 10% Pd/C (0.5 g) in 25 mL of methanol was shaken on a Parr shaker for 3 h under 50 psi of hydrogen. The catalyst was removed by filtration and the filtrate was evaporated to yield the desired product as a mixture of endo and exo isomers (1.30 g). The mixture was separated into single isomers by chiral semi-preparative HPLC using a ChiralPak OD column, eluted by a mixture of hexanes and ethyl alcohol (95:5) at 9 ml/min. The retention time of the isomers under the corresponding analytical conditions (1.0 mL/min flow rate) were 9.83 and 10.41 minutes, for the biologically more and less active isomer, respectively. LC MS for C27H36F6N2O3 for [M+H]+ calc. 551, found 551.

EXAMPLE 177

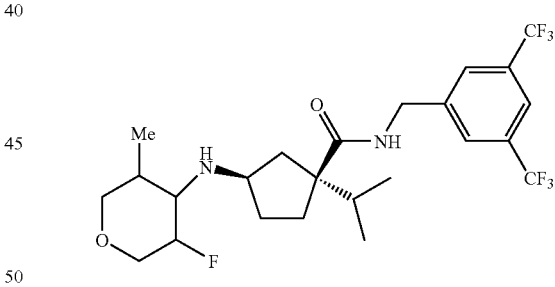

A solution of Intermediate 23 (50 mg, 0.4 mmol), amine Intermediate 16 (as a hydrochloride, 90 mg, 0.2 mmol), diisopropylethylamine (0.60 mg, 0.4 mmol), 4 Å molecular sieves (50 mg) in 5 mL of dry dichloroethane was treated with sodium triacetoxyborohydride (210 mg, 1.0 mmol) and the reaction mixture was stirred at room temperature 16 h. The crude reaction mixture was poured onto a saturated solution of sodium bicarbonate (10 mL). The crude product was extracted into dichloromethane, dried (anhydrous magnesium sulfate) and the solvent was removed in vacuo. The residue was further purified by preparative TLC to afford the desired product as an oil (75 mg). LC MS for C24H31F7N2O2 for [M+H]+ calc. 513, found 513. The four single diastereoisomers were obtained after twice chiral semi-preparative HPLC using a ChiralPak OD column (first run: 6.15, 7.52 minutes) and AD column (second run: 5.98, 6.92, 7.25, 8.32 minutes), eluted by a mixture of hexanes and ethyl alcohol (90:10) at 9 mL/min.

EXAMPLE 178

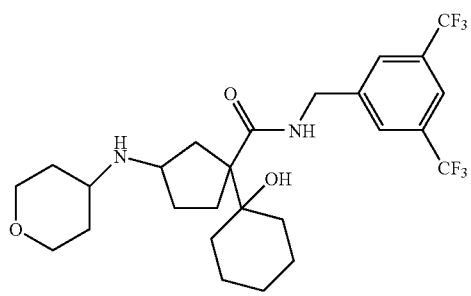

Step A

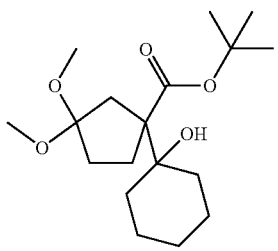

To a solution of 1.5 g (15 mmol) of diisopropylamine in 50 mL of THF at −78° C. under nitrogen was added a solution of n-butyllithium (2.5 M, 6.0 mL, 15 mmol) in hexane dropwise. The resulting mixture was warmed to 0° C. for 30 minutes and then recooled at −78° C. A solution of 2.3 g (10 mmol) of tert-butyl 3,3-dimethoxy-cyclopetanecarboxylate in 10 mL of THP was added dropwise. The resulting red solution was stirred at −78° C. for 30 minutes. A neat solution of 3.0 g (30 mmol) of cyclohexanone was added dropwise. After stirred for additional 1 h, the reaction was quenched with aqueous saturated ammonium chloride and extracted with ether. The title compound (1.60 g, 57%) was obtained as a colorless oil after flash chromatography purification (10% EtOAc/Hexane). $^1$H NMR (400 MHz, CDCl$_3$): 1.10 (m, 1H), 1.43 (ss, 9H), 1.60 (m, 8H), 1.78 (m, 5H), 2.30 (m, 1H), 2.40 (m, 1H), 3.42 (s, 3H), 3.46 (s, 3H).

Step B

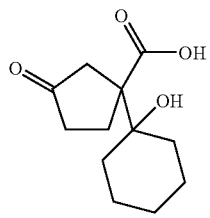

1.6 g (5.7 mmol) of the above ester (step A, Example 178) was mixed with 20 mL of 1:1 (v/v) TFA/CH$_2$Cl$_2$ and allowed to stand at room temperature for 30 minutes. The reaction was concentrated under reduced pressure and dried under high vacuum overnight. The title compound (1.50 g) was obtained as a yellow solid. $^1$H NMR (400 MHz, CDCl$_3$): 1.18 (m, 1H), 1.40-1.80 (m, 9H), 2.38 (m, 3H), 2.48 (d, 1H), 2.80 (d, 1H).

Step C

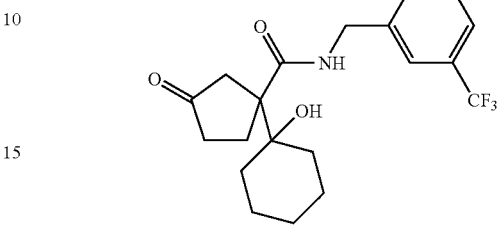

A mixture of 0.33 g (1.5 mmol) of 1-(2'-hydroxy-cyclohexyl)-3-oxo-cyclopentanecarboxylic acid (Step B, Example 178), 0.43 g (1.5 mmol) of (3,5-bis-trifluoromethyl)benzylamine hydrochloride, 0.23 g (1.6 mmol) of HOAt, 0.43 g (2.3 mmol) of EDC and 0.2 g (1.5 mmol) of DIEA in 20 mL of CH$_2$Cl$_2$ was stirred for 2 h, diluted with CH$_2$Cl$_2$, washed with water, 2 N aqueous HCl and brine, dried over Na$_2$SO$_4$, evaporated and dried under vacuum. The title compound (0.36 g) was obtained as a light yellow solid after being purified on preparative TLC (5% MeOH/CH$_2$Cl$_2$). $^1$H NMR (400 MHz, CDCl$_3$): 1.18 (m, 1H), 1.35 (m, 1H), 1.50 (m, 2H), 1.70 (m, 6H), 2.30 (m, 4H), 2.42 (d, 1H), 2.90 (d, 1H), 4.60 (m, 2H), 7.74 (s, 2H), 7.78 (s, 1H), 7.85 (broad, 1H). LC MS for C21H23F6NO3 for [M+H]$^+$ calc. 452, found 452.

Step D

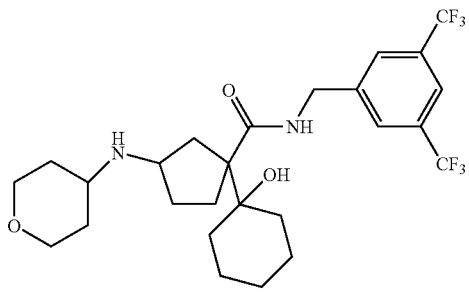

A mixture of 0.35 g (0.78 mmol) of, N-(3,5-bis-trifluoromethyl-benzyl)-1-(2'-hydroxy-cyclohexyl)-3-oxo-cyclopentanecarbamide (Step C, Example 178), 0.3 g (2 mmol) of tetrahydro-4H-pyran-4-yl ammonium chloride (Intermediate 2), 0.26 g (2.0 mmol) of DIEA, 0.4 g (2 mmol) of sodium triacetoxyborohydride and 0.5 g of molecular sieves (4 Å) in 10 mL of CH$_2$Cl$_2$ was stirred overnight and then quenched with 20 mL of saturated aqueous Na$_2$CO$_3$. The solid was removed by filtration and washing with CH$_2$Cl$_2$. CH$_2$Cl$_2$ was removed and the mixture was heated at 60° C. for 30 minutes. After being cooled, the aqueous solution was extracted with CH$_2$Cl$_2$ (3×) and the organic phases were dried with Na$_2$SO$_4$, and evaporated. The residue was purified by preparative TLC (10% [aq. NH$_4$OH/MeOH 1/9]/CH$_2$Cl$_2$). Two components were obtained. Less polar (0.13 g, cis isomer) $^1$H NMR (400 MHz, CDCl$_3$); 1.00-2.05 (m, 20H), 2.30 (m, 1H), 2.60 (m, 1H), 3.30 (m, 2H), 3.55 (broad, 1H), 3.95 (m, 2H), 4.48 (m, 2H), 5.40 (s, 1H), 7.71 (s, 2H), 7.78 (s, 1H), 9.95 (broad, 1H).

LC MS for C26H34F6N2O3 for [M+H]+ calc. 537, found 537. More polar (0.09 g, trans isomer) ¹H NMR (400 MHz, CDCl₃): 1.00-2.05 (m, 20H), 2.42 (m, 1H), 2.70 (m, 1H), 3.30 (m, 2H), 3.55 (broad, 1H), 3.90 (m, 2H), 4.50 (m, 2H), 5.40 (s, 1H), 7.71 (s, 2H), 7.78 (s, 1H), 9.95 (broad, 1H). LC MS for C26H34F6N2O3 for [M+H]+ calc. 537, found 537.

EXAMPLE 179

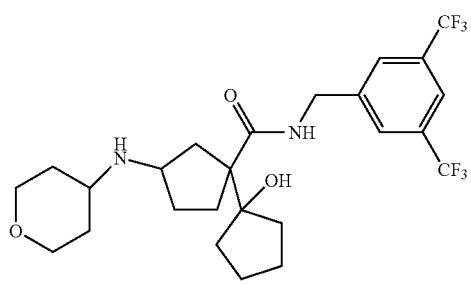

This compound, as a mixture of cis and trans isomers, was prepared starting from cyclopentanone according to the same procedure as described under Example 178. The cis (less polar) and trans (more polar) isomers were separated on preparative TLC. The cis isomer was further separated into single isomers by chiral semi-preparative HPLC using a ChiralPak OD column, eluted by a mixture of hexanes and ethyl alcohol (95:5) at 9 mL/min. The retention time of the isomers under the corresponding analytical conditions (1.0 mL/min flow rate) were 14.71 and 16.39 minutes, for the biologically less and more active isomer, respectively. LC MS for C25H32F6N2O3 for [M+H]+ calc. 523, found 523.

EXAMPLE 180

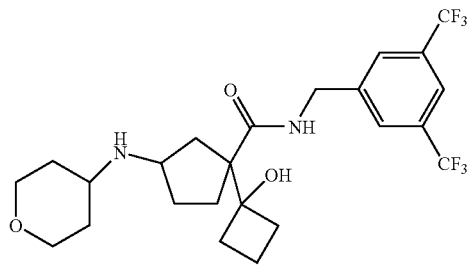

This compound, as a mixture of cis and trans isomers, was prepared starting from cyclobutanone according to the same procedure described under Example 178. The cis (less polar) and trans (more polar) isomers were separated on preparative TLC. The cis isomer was further separated into single isomers by chiral semi-preparative HPLC using a ChiralPak OD column, eluted by a mixture of hexanes and ethyl alcohol (95:5) at 9 ml/min. The retention time of the isomers under the corresponding analytical conditions (1.0 mL/min flow rate) were 15.18 and 25.46 minutes, for the biologically less and more active isomer, respectively. LC MS for C24H30F6N2O3 for [M+H]+ calc. 509, found 509.

EXAMPLE 181

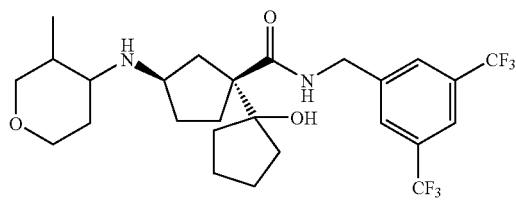

Step A

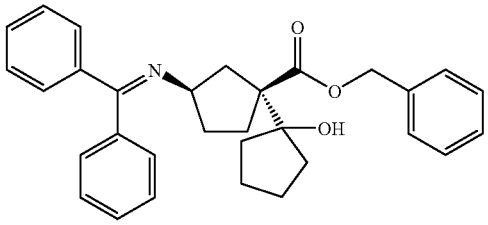

To a flame-dried 1000 mL round-bottomed flask, was added dry THF (150 mL). The solvent was cooled to −78° C. before diisopropylamine (8.04 mL, 57.4 mmol), 2.5 M n-butyllithium (22.95 mL, 57.37 mmol), and a solution of the Schiff base prepared in Step C, Intermediate 9 (20 g, 52 mmol) in dry THF (100 mL), were added sequentially. The reaction mixture was stirred at −78° C. for 0.5 h before cyclopentanone (13.84 mL, 156.5 mmol) was slowly added. After the reaction was stirred for another 2 h, the mixture was quenched with a saturated NH₄Cl solution, extracted with ether (three times), washed by brine, dried over Na₂SO₄, and concentrated. The crude product was purified by MPLC (15% EtOAc/Hexanes) to yield the desired product (2.35 g, 9.6%). ¹H-NMR (400 MHz, CDCl₃): 7.1-7.6 (m, 15H), 5.23 (s, 2H), 3.80 (m, 2H), 2.60 (m, 1H), 2.40 (m, 1H), 1.50-2.20 (m, 8H). LC-MS calc. For C31H33NO3: 467.25; Found: 468 (M+H).

Step B

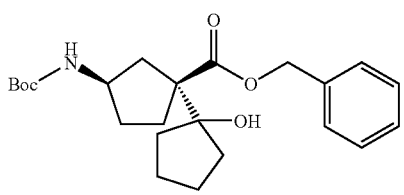

To a solution of the intermediate prepared in Step A, Example 181 (2.35 g, 5.03 mmol) in THP (20 mL), was slowly added 2 N HCl (8 mL, 0.02 mol) to form a homogeneous solution. The reaction mixture was stirred at room temperature overnight, and concentrated under vacuum. The residual solution was extracted with hexanes (three times) and the aqueous solution was diluted by water (80 mL), and made alkaline by the addition of solid NaHCO₃ (3.4 g, 40 mmol). The resulting product was dissolved in DCM (150 mL) and di-tert-butyl dicarbonate (3.29 g, 15.1 mmol) was added. The reaction was then stirred at room temperature for 24 h. The aqueous phase was separated and extracted by DCM (twice). The combined organic portion was washed with water and brine, dried over Na$_2$SO$_4$, filtered and concentrated. The residue was purified by flash column chromatography (silica gel, 20% EA/hexanes to 30% EA/hexanes) to yield the desired intermediate (1.03 g, 50.7%). $^1$H-NMR (500 MHz, CDCl$_3$) 7.36-7.42 (m, 5H), 5.20 (d, 2H), 4.67 (s, 1H), 4.27 (s, 1H), 3.17 (s, 1H), 2.18 (m, 2H), 2.05 (m, 2H), 1.82 (m, 2H), 1.45-1.64 (m, 8H), 1.45 (s, 9H).

Step C

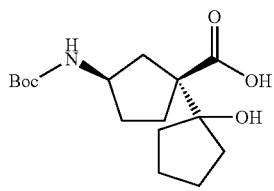

To a solution of the intermediate prepared in Step B, Example 181 (1.0 g, 2.5 mmol) in EtOAc (100 mL), was added 10% Pd/C (75 mg). The reaction mixture was placed in a Parr-shaker under 50 psi of H$_2$ for 8 h. The solution was filtered through celite and concentrated under vacuum to yield the desired intermediate (780 mg, 100%). $^1$H-NMR (400 MHz, CDCl$_3$): 4.10 (br s, 1H), 5.20 (d, 2H), 2.25 (m, 2H), 2.00 (m, 2H), 1.65-1.75 (m, 9H), 1.45 (s, 9H).

Step D

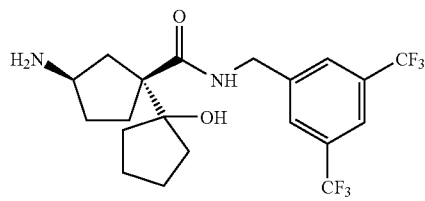

To a flask was added the intermediate prepared in Step C, Example 181 (400 mg, 1.28 mmol), 3,5-bis(trifluoromethyl) benzylamine HCl salt (713 mg, 2.55 mmol), EDC (488 mg, 2.55 mmol), HOAt (174 mg, 1.28 mmol) in DCM (10 mL). The reaction was stirred for 30 minutes and DIEA (444 µL, 2.55 mmol) was added into mixture. The resulting mixture was then stirred for 2 h. The reaction was diluted by DCM, washed by water, brine, dried over Na$_2$SO$_4$, filtered and concentrated. The residue was purified by flash column chromatography (silica gel, 30% EtOAc/Hexane to 40% EtOAc/Hexane) to yield the BOC protected Intermediate (1.01 g, 56.7%). $^1$H-NMR (500 MHz, CDCl$_3$): 8.60 (br s, 1H), 7.78 (s, 1H), 7.75 (s, 2H), 5.24 (br d, 1H), 4.58 (d, J=6.0 Hz, 2H), 3.96 (m, 1H), 3.18 (br s, 1H), 2.12-2.24 (m, 2H), 1.90-1.98 (m, 2H), 1.56-1.84 (m, 10H), 1.41 (s, 9H). ESI-MS calc. For C23H32F3N3O3: 455.24; Found: 356 (M+H-100). The BOC protected intermediate was treated with 4 N HCl/Dioxane to yield the desired intermediate (450 mg).

Step E

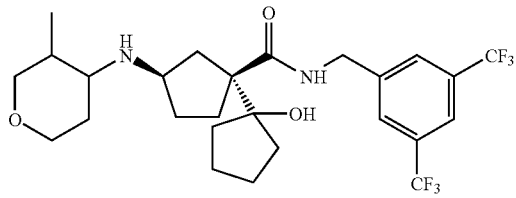

A mixture of the intermediate prepared in Step D, Example 181 (207 mg, 0.436 mmol), Intermediate 5 (174 mg, 1.53 mmol), molecular sieve (4 Å, 450 mg), DIEA (76 µL, 0.44 mmol) and sodium triacetoxyborohydride (323 mg, 1.53 mmol in DCM (10 mL) was stirred for 24 h. The reaction mixture was filtered, washing with DCM and MeOH, mixed with saturated aqueous NaHCO$_3$, and heated at 60° C. for 1.5 h before the DCM and methanol were evaporated. The resulted mixture was diluted with water (10 mL) and extracted with DCM (five times). The organic portion was separated, washed with water and brine, dried over Na$_2$SO$_4$, filtered and concentrated. The residue was purified on preparative TLC (1000 micron) (developed by 4% [aqueous NH$_4$OH/MeOH(1/9)] in DCM) to yield the final title compound as a free base. Its HCl salt Example 181 (112 mg) was formed by treatment with 4 N HCl/dioxane. $^1$H-NMR (400 MHz, CDCl$_3$): 10.14 (br s, 1H), 7.80 (s, 1H), 7.70 (s, 2H), 4.50 (m, 2H), 3.55-3.85 (m, 2H), 3.30-3.42 (m, 2H), 2.75 (br s, 1H), 1.82-2.24 (m, 8H), 1.45-1.75 (m, 12H), 0.92 (m, 3H). ESI-MS calc. for C26H34F6N2O3: 536.25; Found: 537 (M+H).

EXAMPLE 182

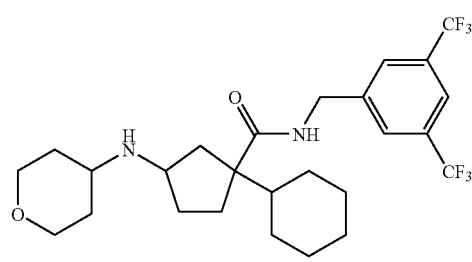

This compound, as a mixture of cis and trans isomers, was prepared via replacement of cyclohexanone with cyclohexyl iodide (5.0 eq.) in HMPA (1.0 eq.) (alkylation time: 12 h in Step A) according to the same procedure described under Example 178. The cis (less polar) and trans (more polar) isomers were separated on preparative TLC. LC MS for C26H34F6N2O2 for [M+H]$^+$ calc. 521, found 521.

EXAMPLE 183

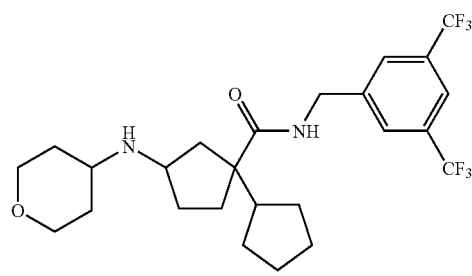

This compound, as a mixture of cis and trans isomers, was prepared via replacement of cyclohexanone with cyclopentyl iodide (5.0 eq.) in HMPA (1.0 eq.) (alkylation time: 12 h in Step A) according to the same procedure described under Example 178. The cis (less polar) and trans (more polar) isomers were separated on preparative TLC. LC MS for C25H32F6N2O2 for [M+H]$^+$ calc. 507, found 507.

EXAMPLE 184

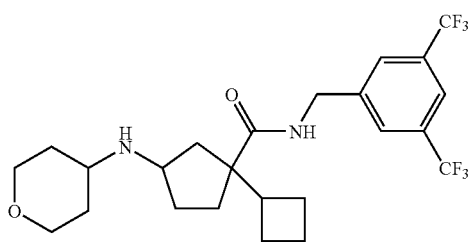

This compound, as a mixture of cis and trans isomers, was prepared via replacement of cyclohexanone with cyclobutyl bromide (5.0 eq.) in HMPA (1.0 eq.) (alkylation time: 12 h in Step A) according to the same procedure described under Example 178. The cis (less polar) and trans (more polar) isomers were separated on preparative TLC. LC MS for C24H30F6N2O2 for [M+H]+ calc. 493, found 493.

EXAMPLE 185

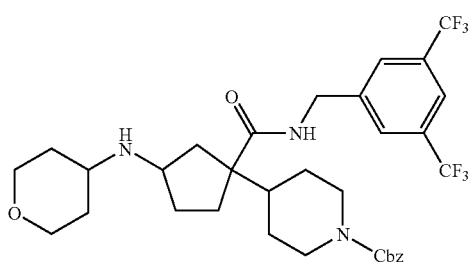

This compound, as a mixture of cis and trans isomers, was prepared via replacement of cyclohexanone with N-Cbz-piperidyl bromide (5.0 eq.) in HMPA (1.0 eq.) (alkylation time: 12 h in Step A) according to the same procedure described under Example 178. The cis (High Band) and trans (Low Band) isomers were separated on preparative TLC. LC MS for C33H39F6N3O4 for [M+H+ calc. 656, found 656.

EXAMPLE 186

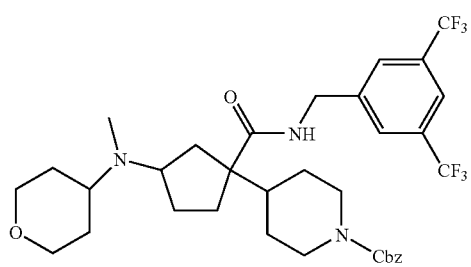

To a stirred mixture of Example 185 (high band, cis isomer, 660 mg, 1.0 mmol) and 4 Å molecular sieves (2.0 g) in 20 mL of dichloromethane was added 0.5 mL of a 30% aqueous formalin solution. The mixture was stirred for 5 minutes and sodium triacetoxyborohydride (420 mg, 2.0 mmol) was added. The mixture was stirred for 2 h, quenched with saturated aqueous sodium carbonate, filtered, and washed with dichloromethane. The crude product was extracted into dichloromethane, dried over Na2SO4, evaporated and purified on preparative TLC. The desired product was obtained as a gummy solid (520 mg, 78%). LC MS for C34H41F6N3O4 for [M+H]+ calc. 670, found 670.

EXAMPLE 187

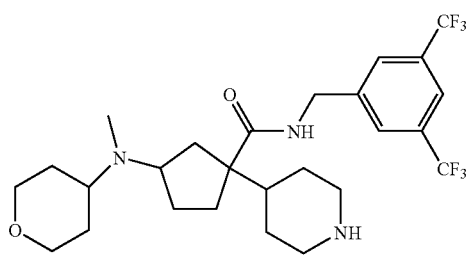

A mixture of Example 186 (500 mg) and 10% Pd/C (100 mg) in 20 mL of methanol was hydrogenated on a Parr-shaker for 5 h under 45 psi of hydrogen. The catalyst was removed by filtration. The filtrate was evaporated. The desired product was obtained as a light yellow solid (400 mg, 100%). LC MS for C26H35F6N3O2 for [M+H]+ calc. 536, found 536.

EXAMPLE 188

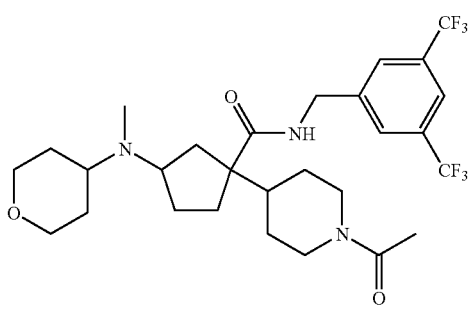

A mixture of Example 187 (54 mg, 0.10 mmol), pyridine (0.2 mL) and acetic anhydride (0.1 mL) in 1 mL of dichloromethane was stirred overnight. Preparative TLC afforded the desired product as a white solid (32 mg, 55%). LC MS for C28H37F6N3O3 for [M+H]+ calc. 578, found 578.

EXAMPLE 189

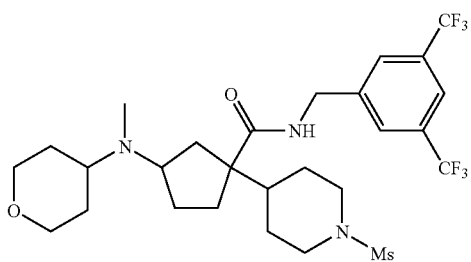

A mixture of Example 187 (54 mg, 0.10 mmol), pyridine (0.2 mL) and mesyl chloride (0.1 mL) in 1 mL of dichloromethane was stirred overnight. Preparative TLC afforded the desired product as a white solid (37 mg, 60%). LC MS for C27H37F6N3O4S for [M+H]+ calc. 614, found 614.

EXAMPLE 190

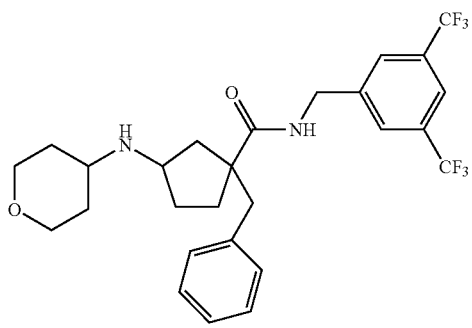

This compound, as a mixture of cis and trans isomers, was prepared via replacement of cyclohexanone with benzyl bromide (5.0 eq.) in HMPA (1.0 eq.) (alkylation time: 12 h in Step A, Example 178) according to the same procedure described under Example 178. LC MS for C27H30F6N2O2 for [M+H]+ calc. 529, found 529.

EXAMPLE 191

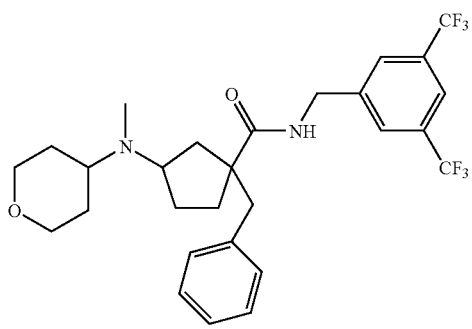

This compound, as a mixture of cis and trans isomers, was prepared starting from Example 190 according to the procedure described under Example 186. LC MS for C28H32F6N2O2 for [M+H]+ calc. 542, found 542.

EXAMPLE 192

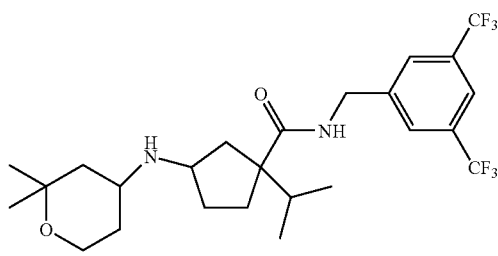

This compound, as a mixture of all possible isomers, was prepared starting from 2,2-dimethyltetrahydro-2-H-pyran-4-amine and Intermediate 8 according to the same procedure described under Example 1. LC MS for C25H34F6N2O2 for [M+H]+ calc. 509, found 509.

EXAMPLE 193

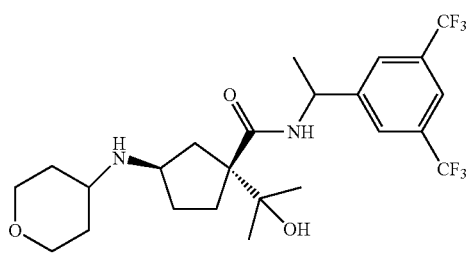

Step A

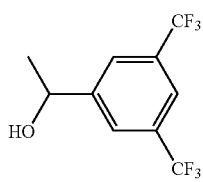

To a solution of bis(trifluoromethyl)benzaldehyde (20 g, 0.083 mol) in 200 mL of THF at −78 C was added dropwise a solution of 84 mL of methylmagnesium bromide (1 M, 0.08 mol) in butyl ether. The temperature was raised up to room temperature and the entire mixture was poured into a stirred mixture of ammonium chloride, ice and water (1000 mL) and extracted with ethyl acetate (2×1000 mL). The organic phases were dried over $Na_2SO_4$. Evaporation in vacuo afforded the title compound as a light yellow liquid (20.64 g, 98%), which was used directly for further conversion.

Step B

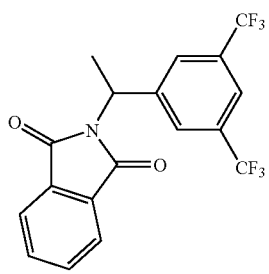

To a stirred solution of bis-(trifluoromethyl)phenylethanol (20.6 g, 80.0 mmol), phthalimide (11.8 g, 80.0 mmol) and triphenylphosphine (22.6 g, 100 mmol) in 150 mL of THF at 0° C. was added dropwise a solution of DEAD (17.4 g, 100 mmol) in 100 mL of THF over 30 minutes. The mixture was then stirred at room temperature overnight and condensed in vacuo. Flash chromatography on silica gel (500 g) afforded the title compound as a light yellow solid. $^1$H NMR (400 MHz, CDCl$_3$): 1.96 (d, 3H), 5.64 (q, 1H), 7.70 (m, 2H), 7.79 (s, 1H), 7.80 (m, 2H), 7.96 (s, 2H).

Step C

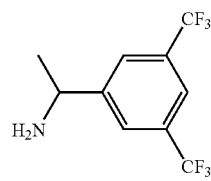

A mixture of N-(bis-[trifluoromethyl]phenylethyl)phthalimide (all material, ~0.076 mol) and hydrazine (3.2 g, 100 mmol) in 500 mL of ethanol was stirred at 80° C. for 2 h. The flask was put into the refrigerator overnight. The solid was removed by filtration and washing with ethanol. The filtrates were combined and evaporated in vacuo to afford the crude product which was stirred with di-tert-butyl dicarbonate (17 g, 80 mmol) in 200 mL of dioxane for 30 minutes and then evaporated in vacuo. The residue was purified by flash chromatography on silica gel (400 g) using 30% EtOAc/hexanes. The BOC-Amide (20.7 g) was obtained as a white solid. $^1$H NMR (400 MHz, CD$_3$OD): 1.40 (s, 9H), 1.71 (d, 3H), 4.50 (m, 1H), 7.75 (s, 3H). This material was stirred with a solution of 100 mL of 4 N HCl in dioxane for 2 h. The mixture was evaporated and dried in vacuo to afford the title compound as a white solid (15.6 g). $^1$H NMR (400 MHz, CD$_3$OD): 1.69 (d, 2H), 4.75 (q, 1H), 8.05 (s, 1H), 8.16 (s, 2H).

Step D

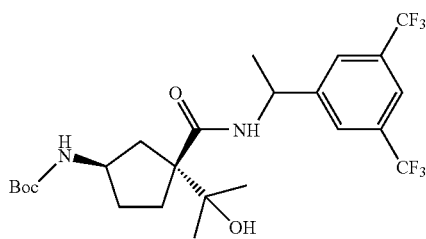

This compound, as a mixture of two diastereoisomers, was prepared from Intermediate 9 and the amine prepared in Step C of Example 193, according to the same procedure as described under Step A, Example 20. LC MS for C24H32F6N2O4 for [M+H]$^+$ calc. 527, found 527.

Step E

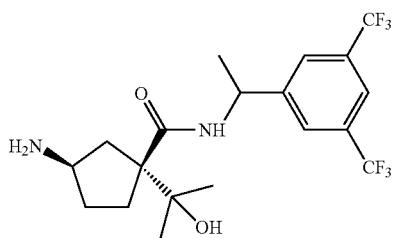

This compound, as a mixture of two diastereoisomers, was prepared following the procedure described under Step B, Example 20. LC MS for C19H24F6N2O2 for [M+H]$^+$ calc. 427, found 427.

Step F

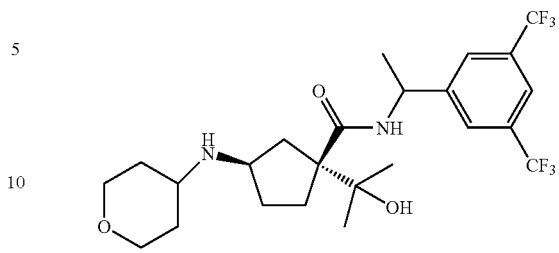

This compound, as a mixture of two diastereoisomers, was prepared according to the procedure described under Step C, example 20. LC MS for C24H32F6N2O3 for [M+H$^+$ calc. 511, found 511.

EXAMPLE 194

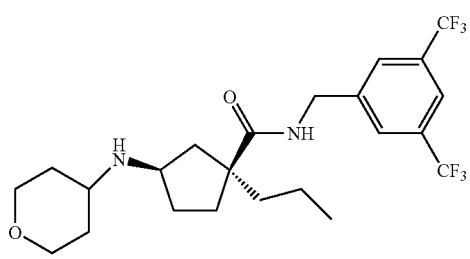

Step A

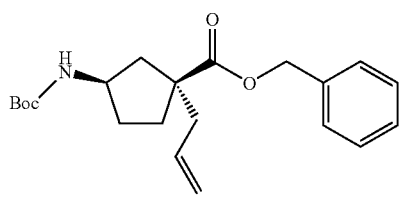

To a stirred, −78° C. solution of the Schiff base prepared in Step C, Intermediate 9 (38.4 g, 100 mmol) in 200 mL of THF was added a solution of LDA (2.0 M, 55 mL, 110 mmol) in THF. The mixture was stirred for 30 minutes at −78° C., then a solution of allyl bromide (20 mL, 200 mmol) in HMPA (18 mL, 100 mmol) was added dropwise. The resulting red solution was stirred at −78° C. for 1 h, warmed to room temperature by removing the cooling bath, diluted with water, and extracted with ether. The ether layer was washed with water and brine, dried over Na$_2$SO$_4$ and evaporated. The residue was dissolved in 300 mL of THF. To this solution was added 150 mL of 2 N aqueous HCl and stirred for 1 h, evaporated to remove THF, and extracted with hexane (3×). The aqueous solution was made alkaline to pH>9 with a saturated aqueous sodium carbonate solution and immediately was mixed and stirred with a solution of di-tert-butyl dicarbonate (42 g, 200 mmol) in 200 mL of dichloromethane. After 30 minutes, the organic phase was separated and the aqueous layer was extracted with dichloromethane (2×). The combined organic phases were washed with water and brine, dried over Na$_2$SO$_4$ and evaporated. The residue was purified on by flash chromatography (10% EtOAc/Hexane) to yield a mixture of cis and trans isomers (24.0 g, 65%). The mixture was separated into single cis (fast-eluted) and trans (slow-eluted) isomers on MPLC (5% EtOAc/Hexane). $^1$H NMR (400 MHz, CDCl$_3$): cis: 7.40 (m, 5H), 5.68 (m, 1H), 5.18 (s, 2H), 5.04 (m, 2H), 4.85 (br s, 1H), 4.10 (br s, 1H), 2.50 (dd, J=7.2 Hz, 1H), 2.30 (dd, J=7.3 Hz, 1H), 2.20 (m, 1H), 2.00 (m, 3H), 1.70-1.43 (m, 2H), 1.44 (s, 9H). trans: 7.38 (m, 5H), 5.65 (m, 1H), 5.12 (s, 2H), 5.03 (m, 2H), 4.50 (br s, 1H), 4.00 (br s, 1H), 2.62 (dd, J=6.1 Hz, 1H), 2.24 (m, 2H), 2.10 (m, 2H), 1.70 (m, 1H), 1.41 (s, 9H), 1.42-1.30 (m, 2H).

Step B

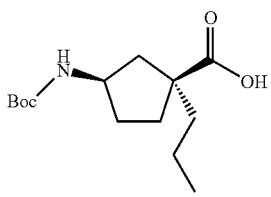

A mixture of the cis ester prepared in Step A, Example 194 (0.65 g) and 10% Pd/C (0.2 g) in methanol (mL) was shaken on a Parr apparatus for 2 h under 50 psi of hydrogen. The catalyst was removed by filtration, the filtrate was evaporated and dried under vacuum to yield the desired acid as a white solid which was used in next step without further purification.

Step C

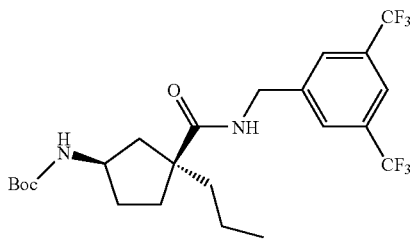

A mixture of the cis acid prepared in Step B, Example 194 (101 mg, 0.4 mmol), the amine prepared in Intermediate 6, as a HCl salt (216 mg, 0.8 mmol) and EDC (190 mg, 1.0 mmol) in 2 mL of dichloromethane was stirred at room temperature overnight., diluted with dichloromethane, washed with water, 1 N aqueous HCl and brine, dried over Na$_2$SO$_4$, evaporated and purified on preparative TLC (5% MeOH/Hexane). The desired product was obtained as a gummy solid (100 mg, 51%). $^1$H NMR (400 MHz, CDCl$_3$): 7.76 (s, 1H), 7.71 (s, 2H), 6.72 (br s, 1H), 5.29 (br s, 1H), 4.56 (d, J=6.1 Hz, 2H), 4.02 (m, 1H), 2.10 (m, 2H), 2.00 (m, 1H), 1.80 (dd, J=3.0, 5.2 Hz, 1H), 1.68 (m, 1H), 1.50 (m, 3H), 1.40 (s, 9H), 1.20 (m, 2H), 0.92 (t, J=7.2 Hz, 3H).

Step D

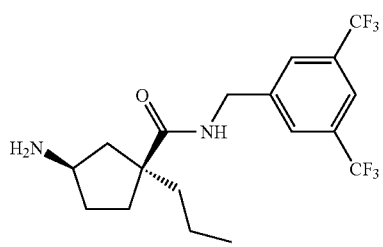

The BOC-Amide from Step C, Example 194 (100 mg, 0.2 mmol) was treated with 4 N HCl/dioxane (5 mL) for 5 h, evaporated and dried under vacuum to afford a white solid (86 mg, 99%). LC MS for C18H22F6N2O for [M+H]$^+$ calc. 397, found 397.

Step E

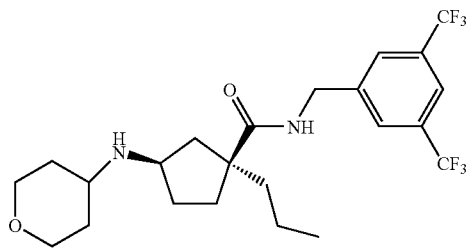

The amino amide prepared in Step D, Example 194 (86 mg, 0.2 mmol), tetrahydro-4H-pyran-4-one (100 mg, 1.0 mmol), sodium triacetoxyborohydride (210 mg, 1.0 mmol), DIEA (130 mg, 1.0 mmol) and 4 Å molecular sieves (100 mg) in 5 mL of dichloromethane was stirred overnight, quenched with saturated aqueous sodium carbonate and filtered. The crude product was extracted into dichloromethane, dried over Na$_2$SO$_4$ and evaporated. Purification on preparative TLC (10% [aq. NH$_4$OH/MeOH 1/9]/DCM) gave the desired product as an oil (72 mg, 75%). LC MS for C23H30F6N2O2 for [M+H]$^+$ calc. 481, found 481.

EXAMPLE 195

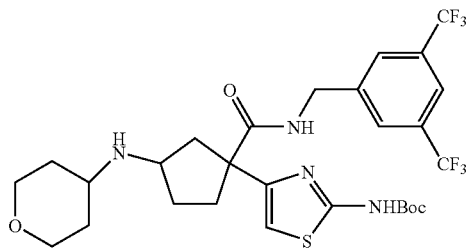

Step A

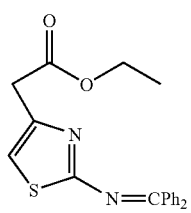

A neat mixture of 54 g (0.29 mole) ethyl (2-aminothiazol-4-yl)acetate and 50 g (0.28 mole) benzophenone imine was stirred at 190° C. for 5 h and then cooled to room temperature and diluted with 100 mL of CH$_2$Cl$_2$. The entire mixture was transferred onto a silica gel column and eluted with 20% EtOAc/Hexane. The title compound was obtained as light-yellow solid (70 g, 69% yield). $^1$H NMR (300 MHz, CDCl$_3$): 1.26 (t, 3H), 3.74 (s, 2H), 4.15 (q, 2H), 6.87 (s, 1H), 77.25-7.86 (m, 10H). LC MS for C20H18N2O2S for [M+H]$^+$ calc. 351, found 351.

Step B

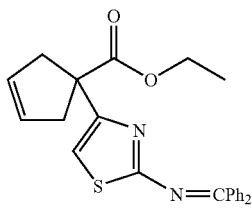

To a mixture of 35 g (0.10 mol) of ethyl (2-diphenylmethyleneamino-thiazol-4-yl)acetate (Step A, Example 195), cis-1,3-dichloro-2-butene (13 mL, 0.11 mol) in 500 mL of DME at room temperature was added in multiple portions solid NaH (60% oil, 10 g, 0.25 mol). The resulting mixture was stirred for 2 days, poured into 2000 mL of ice-water and extracted with 1500 mL of ether. The ether layer was washed with water (3×500 mL), dried over $Na_2SO_4$ and evaporated. Flash chromatography (silica gel, 5% EtOAc/Hexane) afforded the title compound as an oil (24 g, 59%). $^1$H NMR (300 MHz, $CDCl_3$): 1.20 (t, 3H), 2.87 (d, 2H), 3.19 (d, 2H), 4.14 (q, 2H), 5.29 (s, 2H), 6.71 (s, 1H), 7.26-7.81 (m, 10H). LC MS for C24H22N2O2S for [M+H]$^+$ calc. 403, found 403.

Step C

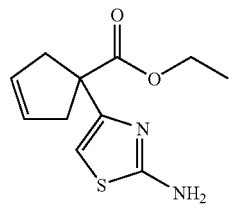

24 g (0.059 mol) of ethyl 1-(2-diphenylmethyleneamino-thiazol-4-yl)-3-cyclopentenecarboxylate (Step B, Example 195) was dissolved in 100 mL of 4 N HCl/dioxane. After 1 h, 1.8 mL of water was added. The mixture was stirred for 3 h and evaporated to dryness. The residue was dissolved in 100 mL of $CH_2Cl_2$ and 15 mL of DIEA was added. The entire mixture was dumped onto a silica gel column, eluted with 20% EtOAc/hexanes to remove benzophenone, then eluted with 40% EtOAc/hexane to give the title compound as a light yellow solid (12.0 g, 85%). $^1$H NMR (300 MHz, $CDCl_3$): 1.19 (t, 3H), 2.79 (d, 12H), 3.15 (d, 2H), 4.13 (q, 2H), 5.66 (s, 2H), 5.82 (wide, 2H), 6.19 (s, 1H).

Step D

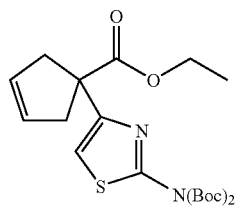

A mixture of 12 g (50 mmol) of ethyl 1-(2-amino-thiazol-4-yl)-3-cyclopentenecarboxylate (Step C, Example 195), 28 g (0.13 mol) of di-tert-butyl dicarbonate and 0.6 g of DMAP in 250 mL of $CH_2Cl_2$ was stirred overnight, and evaporated.

The title compound (21.0 g, 96%) was obtained as a yellow oil after flash chromatography purification on silica gel (10% EtOAc/Hexane). $^1$H NMR (300 MHz, $CDCl_3$): 1.18 (t, 3H), 1.49 (d, 18H), 2.88 (d, 2H), 3.18 (d, 2H), 4.13 (q, 2H), 5.65 (s, 2H), 6.83 (s, 1H). LC MS for C21H30N2O6S for [M+H]$^+$ calc. 439, found 439.

Step E

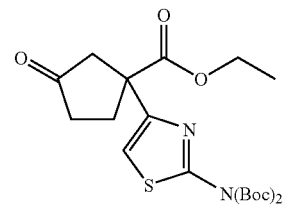

To a solution of 13 g (30 mmol) of ethyl 1-(2-Bis-Boc-amino-thiazol-4-yl)-3-cyclopentenecarboxylate (Step D, Example 195) in 50 mL of anhydrous ether at −78° C. was added dropwise a solution of borane-dimethyl sulfide in THF (14 mL, 0.024 mmol). The cooling bath was removed and the mixture was stirred at room temperature for 3 h, diluted with 250 mL of $CH_2Cl_2$, and 25 g of sodium acetate and 55 g of PCC were added. The mixture was stirred overnight. The entire mixture was dumped onto a silica gel column and eluted with in 10% EtOAc/hexane and then 30% EtOAc/hexane. Two components were obtained. The fast-eluted isomer (yellow oil, 6.0 g) was identified as the title compound. $^1$H NMR (300 MHz, $CDCl_3$): 1.21 (t, 3H), 1.50 (s, 18H), 2.33 (t, 2H), 2.42-2.70 (m, 2H), 2.78-3.10 (dd, 2H), 4.18 (q, 3H), 6.88 (s, 1H). LC MS for C21H30N2O7S for [M+H]$^+$ calc. 455, found 455.

Step F

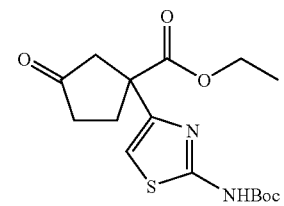

The slow-eluted component from the flash chromatography in Step E, Example 195 was proved to be the title compound (gummy material, 1.80 g). $^1$H NMR (300 MHz, $CDCl_3$): 1.16 (t, 3H), 1.46 (s, 9H), 2.27 (3, 2H), 2.38-2.62 (m, 2H), 2.64-3.00 (dd, 2H), 4.11 (q, 2H), 6.66 (s, 1H). LC MS for C16H22N2O5S for [M+H]$^+$ calc. 355, found 355.

Step G

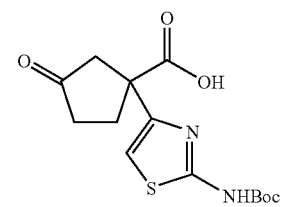

A mixture of 1.4 g (4.0 mmol) of ethyl 1-(2-tert-butoxycarbonyl-amino-thiazol-4-yl)-3-oxo-cyclopentanecarboxylate (Step F, Example 195) and 0.82 g (13 mmol) of lithium hydroxide monohydrate in a solution of 20 mL of MeOH and 2 mL of water was stirred at room temperature overnight. The entire mixture was poured onto a silica gel column and eluted with 10% MeOH/CH$_2$Cl$_2$. Evaporation in vacuo afforded a light yellow solid. 1.30 g of the title product was obtained as a fluffy solid. $^1$H NMR (300 MHz, CDCl$_3$): 1.52 (t, 9H), 2.10-3.20 (m, 8H), 6.60 (s, 1H).

Step H

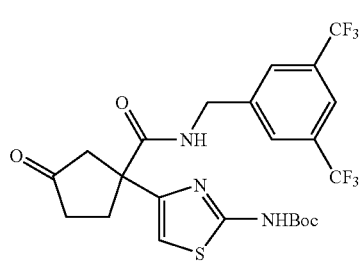

A mixture of 0.65 g (2.0 mmol) of 1-(2-tert-butoxycarbonyl-amino-thiazol-4-yl)-3-oxo-cyclopentane carboxylic acid (Step H, Example 195), 0.70 g (2.5 mmol) of (3,5-bis-trifluoromethyl)benzylamine hydrochloride and 0.95 g EDC (5.0 mmol) in 50 mL of CH$_2$Cl$_2$ was stirred for 2 h. The reaction mixture was diluted with 100 mL of CH$_2$Cl$_2$ and washed with 3 N aqueous HCl (3×50 mL), saturated aqueous NaHCO$_3$ (50 mL), and water (100 mL) and dried over Na$_2$SO$_4$ and evaporated in vacuo. 1.0 g of the title compound was obtained as a yellow solid. $^1$H NMR (400 MHz, CDCl$_3$): 1.55 (s, 9H), 2.10-2.22 (m, 2H), 2.38-2.64 (m, 2H), 2.70-3.23 (dd, 2H), 4.48-4.64 (m, 2H), 6.74 (s, 1H), 7.36 (broad, 1H), 7.63 (s, 2H), 7.77 (s, 1H), 7.98 (broad, 1H). LC MS for C23H23F6N3O4S for [M+H]$^+$ calc. 552, found 552.

Step I

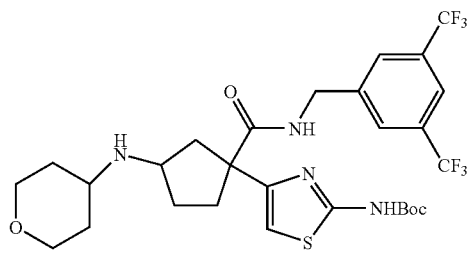

A mixture of 0.55 g (1.0 mmol) of, N-(3,5-bis-trifluoromethyl-benzyl)-1-(2-tert-butoxycarbonyl-amino-thiazol-4-yl)-3-oxo-cyclopentanecarbamide (Step H, Example 195), 0.27 g (2.0 mmol) of tetrahydro-4H-pyran-4-yl ammonium chloride (Intermediate 2), 0.3 g (2 mmol) of DIEA, 0.83 g (4.0 mmol) of sodium triacetoxyborohydride and 3.0 g of molecular sieves (4 Å) in 50 mL of CH$_2$Cl$_2$ was stirred overnight and quenched with 50 mL of saturated aqueous Na$_2$CO$_3$. The solid was removed by filtration and washing with CH$_2$Cl$_2$. The organic phase was separated and dried with Na$_2$SO$_4$ and evaporated. The residue was purified by preparative TLC (10% [aq. NH$_4$OH/MeOH 1/9]/CH$_2$Cl$_2$). The title compound (0.52 g, 82%) was obtained as a mixture of cis and trans isomers. $^1$H NMR (400 MHz, CDCl$_3$): 1.30-2.60 (m, 25H), 3.97 (m, 2H), 4.50 (m, 2H), 6.72 (s, 1H), 6.93 (broad, 1H), 7.30 (broad, 1H), 7.58 (d, 2H), 7.75 (s, 1H). LC MS for C28H34F6N4O4S for [M+H]$^+$ calc. 637, found 637.

EXAMPLE 196

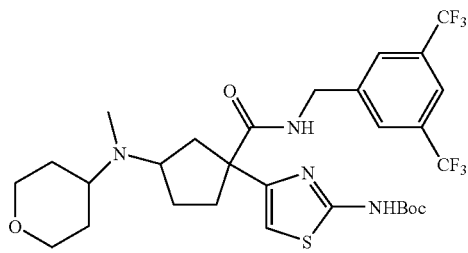

A mixture of 0.32 g (0.50 mmol) of N-(3,5-bis-trifluoromethyl-benzyl)-1-(2-tert-butoxycarbonyl-amino-thiazol-4-yl)-3-(tetrahydro-4H-pyran-4-ylamino]-cyclopentane-carbamide (Example 195), 0.3 g of a 37% aqueous formalin solution and 3.0 g of molecular sieves (4 Å) in 50 mL of CH$_2$Cl$_2$ was stirred for 30 minutes, then 0.84 g of sodium triacetoxyborohydride was added. The mixture was stirred overnight and quenched with 50 mL of saturated aqueous Na$_2$CO$_3$. The solid was removed by filtration and washing with CH$_2$Cl$_2$. The organic phase was separated and dried with Na$_2$SO$_4$ and evaporated. The residue was purified by preparative TLC (10% [aq. NH$_4$OH/MeOH 1/9]/CH$_2$Cl$_2$). The title compound (0.250 g, 77%) was obtained as a mixture of cis and trans isomers. $^1$H NMR (400 MHz, CDCl$_3$): 1.20-3.49 (m, 28H), 4.00 (m, 2H), 4.50 (m, 2H), 6.70, 6.73 (ss, 1H), 6.93, 7.12 (broad, broad, 1H), 7.57 (d, 2H), 7.78 (s, 1H), 8.27 (broad,1H). LC MS for C29H36F6N4O4S for [M+H]$^+$ calc. 651, found 651.

EXAMPLE 197

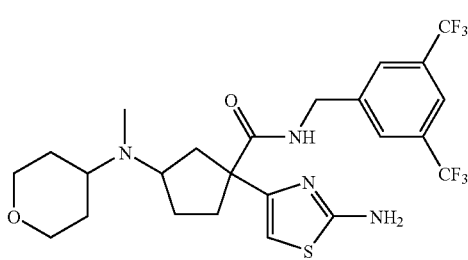

A mixture of 0.22 g (0.34 mmol) of N-(3,5-bis-trifluoromethyl-benzyl)-1-(2-tert-butoxycarbonyl-amino-thiazol-4-yl)-3-(N-methyl, N-tetrahydro-4H-pyran-4-ylamino]-cyclopentanecarbamide (Example 196) and 5.0 mL of TFA was allowed to stand at room temperature for 30 minutes, evaporated and dried in vacuo. The residue was dissolved in 5 mL of 4 N HCl in dioxane, evaporated and dried in vacuo. The hydrochloride salt of the title compound (mixture of cis and trans isomers, 210 mg, 100%) was obtained as a light brown solid. LC MS for C24H28F6N4O2S for [M+H]$^+$ calc. 551, found 551.

EXAMPLE 198

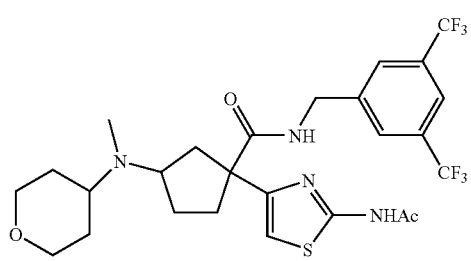

A mixture of 0.055 g (0.10 mmol) of N-(3,5-bis-trifluoromethyl-benzyl)-1-(2-amino-thiazol-4-yl)-3-(tetrahydro-4H-pyran-4-ylamino]-cyclopentanecarbamide hydrochloride salt (Example 197), 0.20 g of acetic anhydride and 0.40 g of pyridine in 1.0 mL of $CH_2Cl_2$ was stirred overnight, evaporated and dried in vacuo. The residue was purified by preparative TLC (10% [aqueous $NH_4OH$/MeOH 1/9]/ $CH_2Cl_2$). The title compound (0.35 g, 59%) was obtained as a mixture of cis and trans isomers. $^1$H NMR (400 MHz, $CDCl_3$): 1.50-3.40 (m, 20H), 4.00 (m, 2H), 4.50 (m, 2H), 6.70, 7.05 (tt, 1H), 6.80 (d, 1H), 7.60 (d, 2H), 7.75 (s, 1H), 9.10 (broad,1H). LC MS for $C_{26}H_{30}F_6N_4O_3S$ for $[M+H]^+$ calc. 593, found 593.

EXAMPLE 199

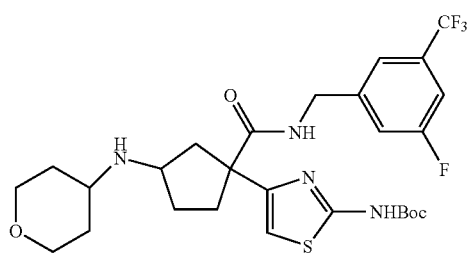

Step A

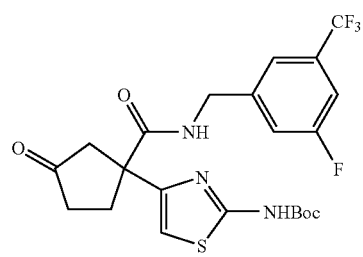

A mixture of 0.65 g (2.0 mmol) of 1-(2-tert-butoxycarbonyl-amino-thiazol-4-yl)-3-oxo-cyclopentanecarboxylic acid (Step G, Example 195), 0.65 g (2.5 mmol) of 3-fluoro-5-trifluoromethylbenzylamine hydrochloride and 0.95 g EDC (5.0 mmol) in 50 mL of $CH_2Cl_2$ was stirred for 2 h. The reaction mixture was diluted with 100 mL of $CH_2Cl_2$ and washed with 3 N aqueous HCl (3×50 mL), saturated aqueous $NaHCO_3$ (50 mL), water (100 mL), dried over $Na_2SO_4$ and evaporated in vacuo. 0.9 g of the title compound was obtained as a yellow solid. $^1$H NMR (400 MHz, $CDCl_3$): 1.56 (s, 9H), 2.18 (m, 1H), 2.38-2.65 (m, 3H), 2.70 (d, 1H), 3.12 (d, 1H), 4.48 (m, 2H), 6.74 (s, 1H), 7.10 (d, 1H), 7.20-7.35 (m, 3H), 7.99 (broad, 1H). LC MS for $C_{22}H_{23}F_4N_3O_4S$ for $[M+H]^+$ calc. 502, found 502.

Step B

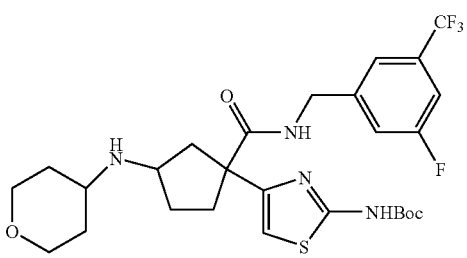

This compound was prepared starting from the keto-amide (Step A, Example 199) and Intermediate 2 according to the same procedure described under Example 195. LC MS for $C_{27}H_{34}F_4N_4O_4S$ for $[M+H]^+$ calc. 587, found 587.

EXAMPLE 200

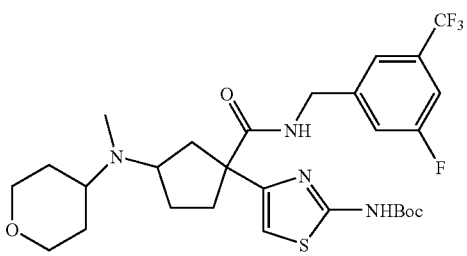

This compound was prepared starting from Example 199 according to the same procedure described under Example 196. LC MS for $C_{28}H_{36}F_4N_4O_4S$ for $[M+H]^+$ calc. 601, found 601.

EXAMPLE 201

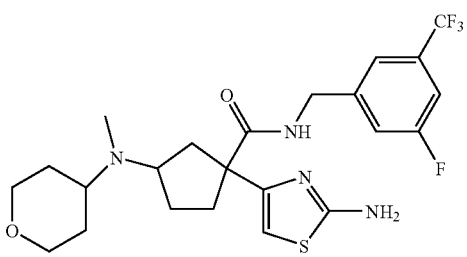

This compound was prepared starting from Example 200 according to the same procedure described under Example 197. LC MS for $C_{23}H_{28}F_4N_4O_2S$ for $[M+H]^+$ calc. 501, found 501.

EXAMPLE 202

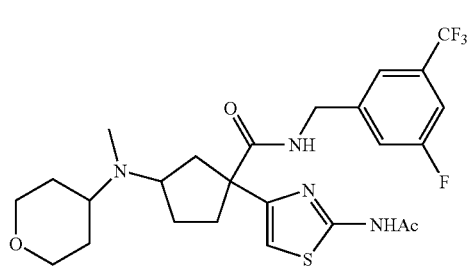

This compound was prepared starting from Example 201 according to the same procedure described under Example 198. LC MS for C25H30F4N4O3S for [M+H]+ calc. 543, found 543.

EXAMPLE 203

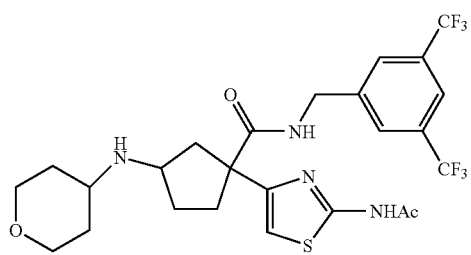

Step A

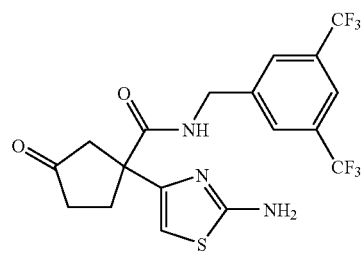

A mixture of 1.1 g (2.0 mmol) of N-(3,5-Bis-trifluoromethyl-benzyl)-1-(2-tert-butoxycarbonyl-amino-thiazol-4-yl)-3-oxo-cyclopentanecarbamide (Step H, Example 195) and 5 mL of neat TFA was stirred at room temperature for 1 h and evaporated. The residue was dissolved in 50 mL of EtOAc, washed with saturated aqueous sodium bicarbonate, dried over Na₂SO₄, evaporated and dried under vacuum. The title compound (0.85 g, 94%) was obtained as a yellow solid. $^1$H NMR (400 MHz, CDCl₃): 2.20 (m, 1H), 2.38 (m, 1H), 2.52 (m, 2H), 2.60 (d, 1H), 3.18 (d, 1H), 4.58 (m, 2H), 5.34 (broad, 2H), 6.31 (s, 1H), 7.65 (2, 2H), 7.75 (s, 1H), 7.80 (broad, 1H). LC MS for C18H15F6N3O2S for [M+H]+ calc. 452, found 452.

Step B

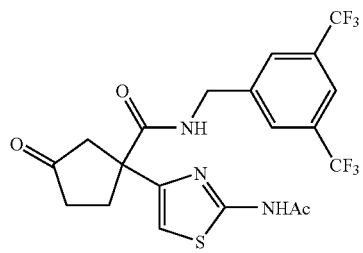

A mixture of 0.85 g (1.9 mmol) of N-(3,5-bis-trifluoromethyl-benzyl)-1-(2-amino-thiazol-4-yl)-3-oxo-cyclopentanecarbamide (Step A, Example 203), 1.0 mL of acetic anhydride and 2.0 mL of pyridine in 20 mL of CH₂Cl₂ was stirred overnight, diluted with 50 mL of CH₂Cl₂, washed with water and 2 N aqueous HCl, dried over Na₂SO₄ and evaporated. The title compound (0.74 g) was obtained as a light yellow solid after purification on prep TLC (10% MeOH/CH₂Cl₂). LC MS for C20H17F6N3O3S for [M+H]+ calc. 494, found 494.

Step C

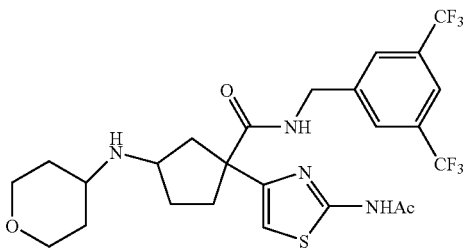

A mixture of 0.50 g (1.0 mmol) of, N-(3,5-bis-trifluoromethyl-benzyl)-1-(2-acetyl-amino-thiazol-4-yl)-3-oxo-cyclopentanecarbamide (Step B, Example 203), 0.27 g (2.0 mmol) of tetrahydro-4H-pyranyl ammonium chloride (Intermediate 2), 0.26 g (2.0 mmol) of DIEA, 0.84 g (4.0 mmol) of sodium triacetoxyborohydride and 0.5 g of molecular sieves (4 Å) in 20 mL of CH₂Cl₂ was stirred overnight, quenched with 50 mL of saturated aqueous Na₂CO₃. The solid was removed by filtration and washing with CH₂Cl₂. Organic phase was separated and dried with Na₂SO₄, evaporated. The residue was purified by preparative TLC (10% [aq. NH₄OH/MeOH 1/9]/CH₂Cl₂). The title compound (0.34 g, 58%) was obtained as a mixture of cis and trans isomers. LC MS for C25H28F6N4O3S for [M+H]+ calc. 579, found 579.

EXAMPLE 204

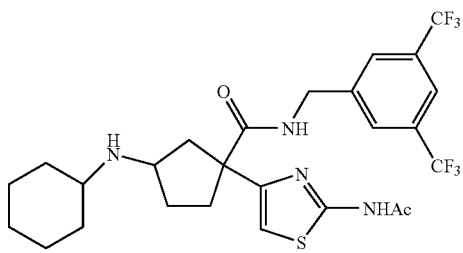

This compound, as a mixture of cis and trans isomers, was prepared starting from the intermediate prepared in Step B, Example 203 and cyclohexyl amine according to the same procedure described under Step C, Example 203. LC MS for C26H30F6N4O2S for [M+H]+ calc. 577, found 577.

EXAMPLE 205

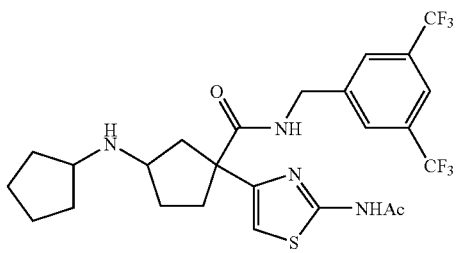

This compound, as a mixture of cis and trans isomers, was prepared starting from the intermediate prepared in Step B, Example 203 and cyclopentyl amine according to the same procedure described under Step C, Example 203. LC MS for C25H28F6N4O2S for [M+H]+ calc. 563, found 563.

EXAMPLE 206

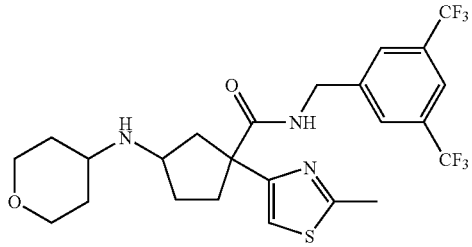

Step A

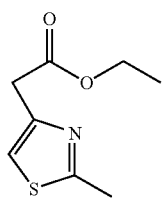

A mixture of 5.0 g (32 mmol) 2-methylthiazol-4-yl acetic acid, 2.4 g (50 mmol) ethanol and 7.3 g (38 mmol) EDC in 50 mL of CH$_2$Cl$_2$ was stirred at room temperature overnight. The entire mixture was loaded on a silica gel column and eluted with 30% EtOAc/hexane. The title compound was obtained as a colorless oil. (4.5 g, 76% yield). $^1$H NMR (300 MHz, CDCl$_3$): 1.24 (t, 3H), 2.66 (s, 3H), 3.75 (s, 2H), 4.15 (q, 4H), 6.98 (s, 1H).

Step B

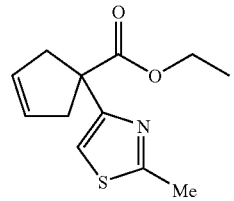

To a mixture of 4.5 g (0.024 mol) of ethyl (2-methylthiazol-4-yl)acetate (Step A, Example 206), cis-1,4-dichloro-2-butene (3.2 mL, 0.030 mol) in 100 mL of DME at room temperature was added in multiple portions solid NaH (60% oil, 2.5 g, 0.062 mol). The resulting mixture was stirred for 2 days, poured into 300 mL of ice-water and extracted with 500 mL of ether. The ether layer was washed with water (3×100 mL), dried over Na$_2$SO$_4$ and evaporated. Flash chromatography (silica gel, 10% EtOAc/hexane) afforded the title compound as an oil (3.0 g, 52%). $^1$H NMR (400 MHz, CDCl$_3$): 1.20 (t, 3H), 2.66 (s, 3H), 2.90 (d, 2H), 3.27 (d, 2H), 4.15 (q, 2H), 5.69 (s, 2H), 6.87 (1, 1H).

Step C

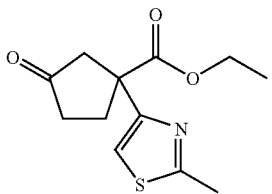

To a solution of 2.4 g (0.01 mol) of ethyl 1-(2-methylthiazol-4-yl)-3-cyclopentenecarboxylate (Step B, Example 206) in 30 mL of anhydrous ethyl ether at −78° C. was added dropwise a solution of BH$_3$.DMS in THF (5.0 mL, 0.015 mmol). The cooling bath was removed and the mixture was stirred at room temperature for 3 h, diluted with 100 mL of CH$_2$Cl$_2$, and 8.5 g of PCC was added. The mixture was stirred overnight. The entire mixture was dumped onto a silica gel column and eluted with 10% EtOAc/hexane. and then 30% EtOAc/hexane. Partial starting material (1.2 g, less polar) was recovered and the title compound (0.65 g, more polar) was obtained as an oil. $^1$H NMR (300 MHz, CDCl$_3$): 1.21 (t, 3H), 2.34 (m, 2H), 2.58 (m, 1H), 2.66 (s, 3H), 2.82 (d, 1H), 3.05 (d, 2H), 4.19 (q, 4H), 6.95 (s, 1H).

Step D

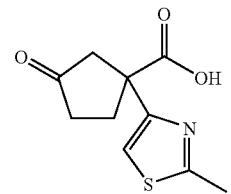

A mixture of 0.51 g (2.0 mmol) of ethyl 1-(2-methylthiazolyl)-3-oxo-cyclopentanecarboxylate (Step C, Example 206) and 200 mg (5 mmol) of lithium hydroxide monohydrate in a solution of 5 mL of MeOH and 1 mL of water was stirred at room temperature overnight, acidified with 2 N aqueous HCl, diluted with 50 mL of water and extracted with ethyl acetate (2×50 mL). The combined organic layers were dried over Na$_2$SO$_4$, filtered, evaporated and dried in vacuum. 0.12 g of the title product was obtained as a fluffy solid. $^1$H NMR (300 MHz, CDCl$_3$): 2.30 (m, 1H), 2.22 (m, 1H), 2.50 (m, 1H), 2.65 (m, 1H), 2.72 (s, 3H), 2.74 (d, 1H), 3.13 (d, 1H), 7.00 (s, 1H).

Step E

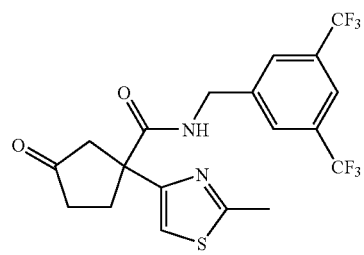

A mixture of 0.12 g (0.50 mmol) of 1-(2-methyl-thiazol-4-yl)-3-oxo-cyclopentanecarboxylic acid (Step D, Example 206), 0.2 g (0.7 mmol) of (3,5-bis-trifluoromethyl)benzylamine hydrochloride and 0.19 g EDC (1.0 mmol) in 5 mL of CH$_2$Cl$_2$ was stirred overnight. The reaction mixture was loaded on prep TLC and developed with 10% MeOH/CH$_2$Cl$_2$. 0.17 g of the title compound was obtained as a yellow solid. $^1$H NMR (400 MHz, CDCl$_3$): 2.18 (m, 1H), 2.40 (m, 1H), 2.60 (m, 2H), 2.70 (s, 3H), 2.77 (d, 1H), 3.25 (d, 1H), 4.58 (m, 2H), 6.97 (s, 1H), 7.60 (s, 2H), 7.75 (s, 1H), 7.87 (broad, 1H). LC MS for C19H16F6N2O2S for [M+H]$^+$ calc. 451, found 451.

Step F

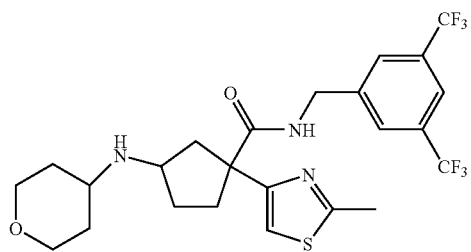

A mixture of 0.17 g (0.37 mmol) of, N-(3,5-bis-trifluoromethyl-benzyl)-1-(2-methyl-thiazol-4-yl)-3-oxo-cyclopentanecarbamide (Step E, Example 206), 0.27 g (2.0 mmol) of tetrahydro-4H-pyran-4-yl ammonium chloride, 0.13 g (1.0 mmol) of DIEA, 0.8 g (4 mmol) of sodium triacetoxyborohydride and 0.5 g of molecular sieves (4 Å) in 30 mL of CH$_2$Cl$_2$ was stirred overnight, quenched with 30 mL of saturated aqueous Na$_2$CO$_3$. The solid was removed by filtration and washing with CH$_2$Cl$_2$. The organic phase was separated and dried with Na$_2$SO$_4$ and evaporated. The residue was purified by preparative TLC (10% [aqueous NH$_4$OH/MeOH 1/9]/CH$_2$Cl$_2$). The title compound (0.11 g, 56%) was obtained as a mixture of cis and trans isomers. Further separation on prep TLC (10% MeOH/CH$_2$Cl$_2$) afforded two components. Less polar (trans isomer) $^1$H NMR (400 MHz, CDCl$_3$): 1.30-1.35 (m, 3H), 1.80 (m, 3H), 2.10 (m, 1H), 2.30 (m, 1H), 2.50 (m, 1H), 2.67 (s, 3H), 2.75 (m, 1H), 2.92 (m, 1H), 3.40 (t, 3H), 3.58 (m, 1H), 3.98 (m, 2H), 4.56 (m, 2H), 7.00 (s, 1H), 7.46 (broad, 1H), 7.54 (s, 2H), 7.73 (s, 1H). LC MS for C24H27F6N3O2S for [M+H]$^+$ calc. 563, found 563.

More polar (cis isomer) $^1$H NMR (400 MHz, CDCl$_3$): 1.50 (m, 2H), 1.65 (m, 1H), 1.80 (m, 2H), 2.10 (m, 1H), 2.20 (m, 1H), 2.50 (d, 2H), 2.60 (m, 1H), 2.69 (s, 3H), 2.82 (m, 1H), 3.38 (t, 2H), 3.50 (m, 1H), 3.98 (m, 2H), 4.58 (m, 2H), 6.99 (s, 1H), 7.57 (s, 2H), 7.76 (s, 1H), 7.84 (broad, 1H). LC MS for C24H27F6N3O2S for [M+H]$^+$ calc. 563, found 563.

EXAMPLE 207

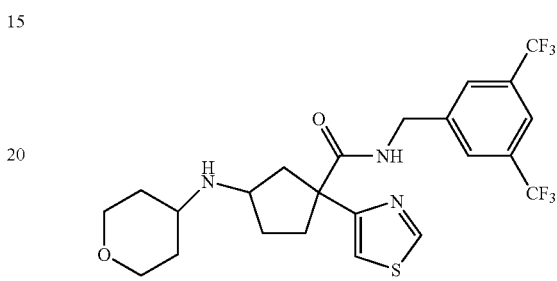

This compound, as a mixture of cis and trans isomers, was prepared starting from 2-thiazol-4-yl acetic acid following the same procedure described under Example 206. LC MS for C23H25F6N3O2S for [M+H]$^+$ calc. 522, found 522.

EXAMPLE 208

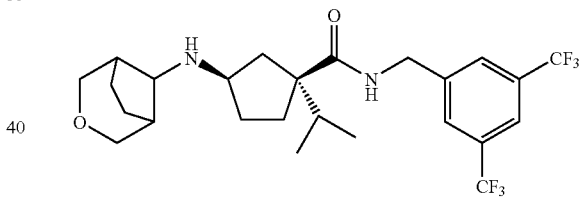

Step A

To a stirred solution of phenyl magnesium bromide (3 M solution in ether, 680 mL, 2.05 mol) in ethyl ether (500 mL) was added exo-epoxynorbornane (150 g, 1.36 mol) in ethyl ether (250 mL) slowly. After the initial exotherm, the reaction was heated to reflux for 3 h, after which time it was cooled in an ice bath and quenched with water (25 mL). The resulting solution was diluted with ethyl ether and washed with aqueous 3 N HCl twice. The combined aqueous layers where back extracted with ethyl ether twice and the combined organic layers where washed with brine, dried over MgSO$_4$, filtered, and concentrate under reduced pressure (100 mmHg, 30° C.) to give 230 g of a crude orange oil. This material was subject to flash chromatography (silica gel, 40% ethyl ether/hexanes)

to give 67 g of pure product (45%). ¹H NMR (CDCl₃, 500 MHz): 6.06 (d, J=1.0 Hz, 2H), 3.76 (s, 1H), 2.75 (d, J=2.0 Hz, 2H), 1.86 (bs, 2H), 1.71-1.68 (m, 2H).

Step B

To a cooled (−78° C.) solution of oxalyl chloride (83 g, 660 mmol) in DCM (500 mL) was added DMSO (78 mL, 1.1 mol) in DCM (200 mL) rapidly but keeping the temperature below −50° C. To this solution was immediately added the product from Step A (67 g, 610 mmol) in DCM (600 mL) rapidly, but keeping the temperature below −50° C. After stirring for 15 minutes at −78° C. this solution was treated with triethylamine (310 mL, 2.1 mol) and allowed to warm to room temperature. After 1 h at room temperature, the reaction was quenched with water and concentrated under reduced pressure. The crude residue was dissolved in a 3:1 solution of ethyl ether and petroleum ether and washed 3 times with aqueous 1 N HCl then with brine. The organic layer was dried over Na₂SO₄, filtered, and concentrated under reduced pressure. The resulting residue was quickly chromatographed (short column—silica gel, 15% ethyl ether/hexanes) and concentrated under reduced pressure. Final purification was achieved by distillation (collecting the 60° C. to 70° C. fractions at 30 mm Hg) to give 18.5 g of pure product as a colorless liquid (28%). ¹H NMR (CDCl₃, 500 MHz): 6.53 (bs, 2H), 2.82 (bs, 2H), 1.97 (d, J=7.0 Hz, 2H), 1.21 (dd, J=4.5, 6.5 Hz, 2H).

Step C

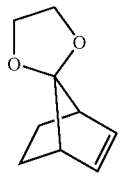

The product from Step B (17.5 g, 162 mmol) was combined with p-toluenesulfonic acid (4.9 g, 26 mmol) and ethylene glycol (13.1 mL, 243 mmol) in benzene (200 mL) and heated to reflux. After 5 h, the solution was allowed to cool to room temperature and stir overnight, after which time it was partitioned between ethyl ether and aqueous saturated NaHCO₃. The organic phase was washed with brine, dried over MgSO₄, filtered and concentrated. The product was purified by flash chromatography (silica gel, 10% ethyl ether/hexanes) to give 19.0 g of a colorless oil (83%). ¹H NMR (CDCl₃, 500 MHz): 6.18 (bs, 2H, 3.92 (t, J=6.0 Hz, 2H), 3.85 (t, J=6.0 Hz, 2H), 2.53 (bs, 2H), 1.92 (d, J=7.5 Hz, 2H), 0.97 (dd, J=3.5, 10.5 Hz, 2H).

Step D

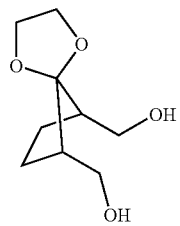

A solution of the product from Step C (2.0 g, 13 mmol) in a mixture of methanol (30 mL) and DCM (24 mL) was cooled to −78° C. and treated with ozone gas (7.5 psi, 2 L/min) until a blue tint to the solution was apparent. At this time, the reaction was purged with nitrogen gas to remove the excess ozone and sodium borohydride (600 mg, 16 mmol) was added to the reaction. The reaction was allowed to warm to 0° C. on an ice bath before acetone was added to quench the excess reducing agent. The resulting solution was concentrated under reduced pressure and the product was purified by flash chromatography (silica gel, eluting with EA) to give 1.9 g of a colorless oil which upon cooling to −20° C. became a colorless solid (78%). ¹H NMR (CDCl₃, 500 MHz): 4.02 (m, 4H), 3.67 (m, 4H), 2.22 (t, J=6.0 Hz, 2H), 1.83 (m, 2H), 1.63 (m, 2H).

Step E

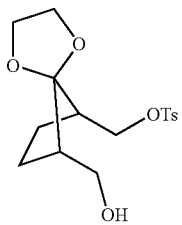

To a cooled (−15° C.) solution of the product from Step D (1.26 g, 6.71 mmol) in THF (21 mL) was added n-butyllithium (2.5 M in hexanes, 2.8 mL, 7.0 mmol). After the reaction was stirred for 30 minutes at −15° C., tosyl chloride (1.28 g, 6.71 mmol) in THF (10 mL) was added dropwise and the reaction was warmed to room temperature and stirred for an additional 30 minutes before being concentrated under reduced pressure. The mono-tosylate product was separated from small amounts of starting material and di-tosylation product by medium pressure liquid chromatography (silica gel, 40-100% EA/hexanes) to give 900 mg of a colorless oil (39%) which was used directly in the next step.

Step F

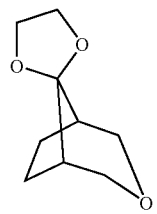

The product from Step E (707 mg, 2.07 mmol) was combined with sodium hydride (60% dispersion in mineral oil, 250 mg) in THF and stirred at room temperature. After 2 h the reaction was quenched with hydrogen chloride (2 N solution in ethyl ether, 4 mL) and the resulting precipitate was filtered off. The filtrate was concentrated and purified by flash chromatography (silica gel, 20% ethyl ether/hexanes) to give 320 mg of product (91%). $^1$H NMR (CDCl$_3$, 500 MHz): 3.97 (m, 4H), 3.93 (d, J=10.5 Hz, 2H), 3.57 (dd, J=2.5, 11.0 Hz, 2H), 1.84-1.81 (m, 2H), 1.75 (m, 4H).

Step G

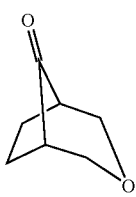

The product from Step F (250 mg, 1.47 mmol) was dissolved in a mixture of THF (4 mL) and aqueous 5% HCl (2 mL) and stirred at room temperature. After 18 h the reaction was diluted with ethyl ether, washed with brine, and dried over MgSO$_4$, filtered and concentrated under reduced pressure. The product was purified by flash chromatography (silica gel, 30% ethyl ether/hexanes) to give 51 mg of a volatile liquid (28%). $^1$H NMR (CDCl$_3$, 500 MHz): 3.99 (dd, J=2.5, 11.0 Hz, 2H), 3.87 (d, J=1 Hz, 2H), 2.28 (bs, 2H), 2.03 (m, 2H), 1.99 (m, 2H).

Step H

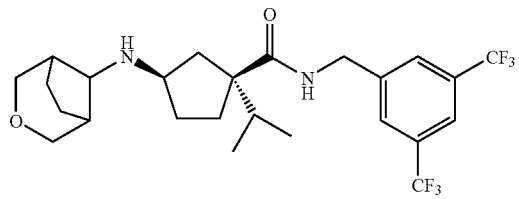

Intermediate 16 (30 mg, 0.07 mmol) was combined with the product from Step G (9 mg, 0.07 mmol), N,N-diisopropylethylamine (25 µL, 0.15 mmol), 4 Å powdered molecular sieves (50 mg), and sodium triacetoxyborohydride (75 mg, 0.35 mmol) in 5 mL DCM. The reaction mixture was stirred at room temperature for 6 days, then filtered through celite, and concentrated under reduced pressure. The product was purified by preparative TLC (silica gel, 0.3% NH$_4$OH/3.7% MeOH/97% DCM) and converted to its hydrochloride salt by the addition of hydrogen chloride (2 N solution in ethyl ether) to give 9 mg of a white solid (25%). ESI-MS calc. for C25H32F6N2O2: 506; found 507 (M+H).

EXAMPLE 209

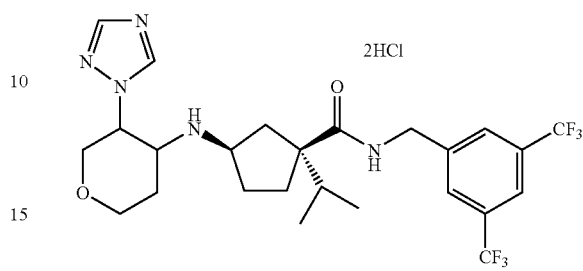

Step A:

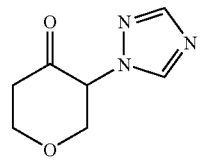

Intermediate 19 (860 mg, 4.8 mmol) was added to a stirred solution of 1,2,4-triazole (280 mg, 4.0 mmol) in THF (5 mL) and DMF (5 mL). K$_2$CO$_3$ (690 mg, 5.0 mmol) was added to the solution and the reaction was allowed to stir at room temperature for 18 h at which time it was filtered and the concentrated to dryness. The product was purified by medium pressure liquid chromatography (silica gel, 10-100% EA/hexanes) to give 430 mg of a single isomer (54%). $^1$H NMR (CDCl$_3$, 500 MHz) 8.26 (s, 1H), 7.98 (s, 1H), 5.18 (dd, J=6.5, 17.5 Hz, 1H), 4.57 (m, 1H), 4.37 (m, 1H), 4.05 (t, J=10.5 Hz, 1H), 3.86 (m, 1H), 2.84 (m, 1H), 2.69 (m, 1H).

Step B

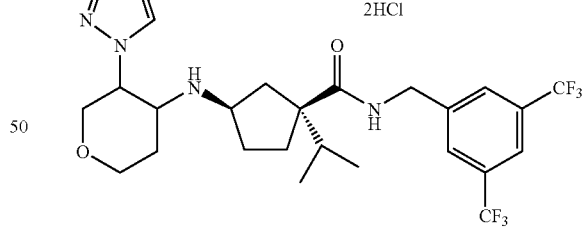

The product from Step A (24 mg, 0.15 mmol) was added to a solution of Intermediate 16 (52 mg, 0.12 mmol) and triethylamine (17 µL, 0.12 mmol) in DCM (5 mL). After 5 minutes at room temperature this solution was treated portionwise with 4 Å molecular sieves (100 mg) and sodium triacetoxyborohydride (100 mg). After 72 h at room temperature the reaction was treated with an additional amount of the product from Step A (24 mg, 0.15 mmol) and allowed to stir for an additional 72 h. The reaction was filtered through celite washing with DCM, and concentrated under reduced pressure. The product was purified by preparative TLC (silica gel, 1000 µm, 0.5% NH$_4$OH/4.5% MeOH/95% DCM) and converted to its hydrochloride salt by the addition of 2 N HCl in ethyl ether to give 22 mg of a white solid (30%). ESI-MS calc. for C25H31F6N5O2: 547; found 548 (M+H).

EXAMPLE 210

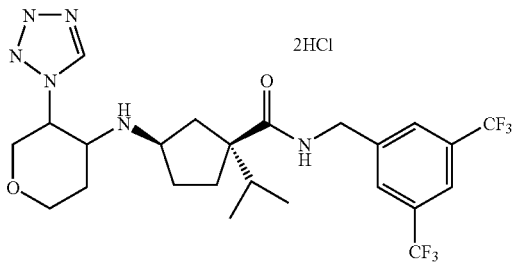

Step A

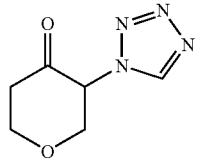

Intermediate 19 (860 mg, 4.8 mmol) was added to a stirred solution tetrazole (280 mg, 4.0 mmol) in THF (5 mL) and DMF (5 mL). K$_2$CO$_3$ (690 mg, 5.0 mmol) was added to the solution and the reaction was allowed to stir at room temperature for 18 h at which time it was filtered and the concentrated to dryness. The product was purified by medium pressure liquid chromatography (silica gel, 30-100% EA/hexanes) to give 260 mg of a single isomer (38%). $^1$H NMR (CDCl$_3$, 500 MHz) 8.85 (s, 1H), 5.51 (dd, J=6.5, 17.5 Hz, 1H), 4.75 (m, 1H), 4.45 (m, 1H), 4.00 (t, J=9.5 Hz, 1H), 3.86 (m, 1H), 2.93 (m, 1H), 2.75 (m, 1H).

Step B

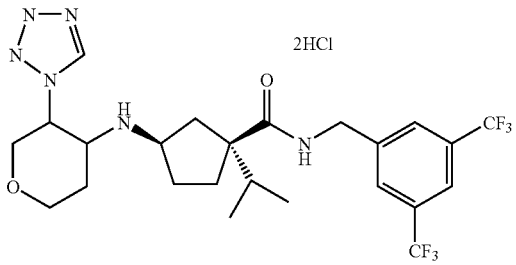

The product from Step A (25 mg, 0.15 mmol) was added to a solution of Intermediate 16 (52 mg, 0.12 mmol) and triethylamine (17 µL, 0.12 mmol) in DCM (5 mL). After 5 minutes at room temperature this solution was treated portionwise with 4 Å molecular sieves (100 mg) and sodium triacetoxyborohydride (100 mg). After 72 h at room temperature the reaction was treated with an additional amount of the product from Step A (24 mg, 0.15 mmol) and allowed to stir for an additional 72 h. The reaction was filtered through celite, washing with DCM, and concentrated under reduced pressure. The product was purified by preparative TLC (silica gel, 1000 µm, 0.5% NH$_4$OH/4.5% methanol/95% DCM) and converted to its hydrochloride salt by the addition of 2 N HCl in ethyl ether to give 1.8 mg of a white solid (2%). ESI-MS calc. for C24H30F6N6O2: 548; found 549 (M+H).

EXAMPLE 211

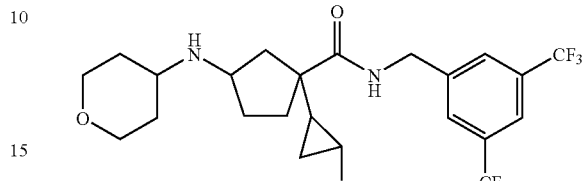

Step A

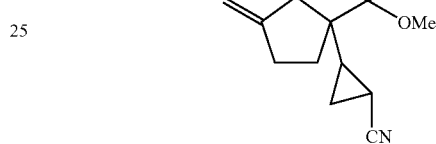

A cooled (−78° C.) THF (80 mL) solution of commercially available methyl-(3-methylenecyclopentane) carboxylate (3.90 g, 27.8 mmol) was treated dropwise with 1.5 M LDA in cyclohexane (22.3 mL, 33 mmol) over 10 minutes. The reaction mixture was stirred for an additional 35 minutes., then a solution of 4-bromocrotononitrile (1:2 trans/cis, prepared according to Zindel, J.; de Meijere, A., *Synthesis* (1994), 190-194. 4.26 g, 29.2 mmol) in THF (5 mL) was added dropwise over 10 minutes. The reaction mixture was stirred at −78° C. for 1.5 h., then poured into a 10% aqueous citric acid solution. This mixture was extracted twice with ether (300 mL), the ethereal layers were combined, and these in turn were washed with saturated NaHCO$_3$ solution, followed by brine. The ethereal layer was then dried over anhydrous MgSO$_4$, filtered, and concentrated. Purification by MPLC (silica, 40% ether/hexane) afforded two product mixtures (6:1 ratio), corresponding to the four isomers with trams-cyclopropyl stereochemistry (3.07 g) and the four with cis-cyclopropyl stereochemistry (504 mg), respectively.

Step B

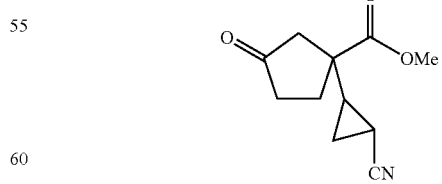

Ozone gas was bubbled through a cooled solution (−78° C.) of the olefin prepared as described in Step A above (top spot, trans-cyclopropyl, 3.07 g, 15.0 mmol) in DCM (50 mL) until the reaction mixture became blue in color. Then nitrogen gas was bubbled through the solution until it was colorless again. Triphenylphosphine (4.33 g, 16.5 mmol) was then added and the reaction mixture was permitted to warm to room temperature and stir for three h. The reaction mixture was then concentrated and purified by flash chromatography (silica, eluted with DCM, then 1% methanol/DCM, then 3% methanol/DCM) to give 1.31 g of product as a mixture of 4 diastereomers (trans cyclopropyl). The olefin prepared in Step A having the cis-cyclopropyl stereochemistry (bottom spot) was converted to its corresponding ketone in the same fashion as that described immediately above.

Step C

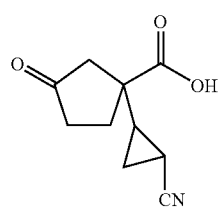

The trans-cyclopropyl ketone from Step B above (790 mg, 3.8 mmol) was dissolved in 1:1 THF/methanol (16 mL) and treated with a solution of LiOH.H$_2$O (800 mg, 19 mmol) in 8 mL of water. The resulting reaction mixture was stirred at room temperature for 1 h, then neutralized with 3 N HCl solution, and concentrated to remove the organic solvents. The aqueous product mixture was then extracted three times with chloroform, the organic layers were combined and dried over anhydrous MgSO$_4$, filtered, and concentrated to give 604 mg of carboxylic acid product (82%).

Step D

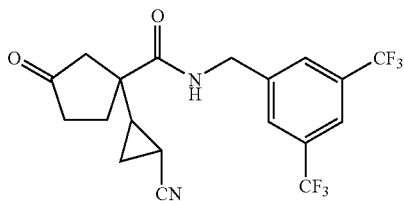

The trans-cyclopropyl keto-acid from Step C above (570 mg, 2.9 mmol) was added to a stirred solution of 1-ethyl-3-(3-dimethylaminopropyl)carbodiimide (1.1 g, 5.9 mmol) in DCM (30 mL). To this was added 3,5-bistrifluorobenzylamine hydrochloride (1.2 g, 4.4 mmol), triethylamine (440 mg, 4.4 mmol), and N,N-dimethylamino pyridine (5 mg). The reaction was stirred at room temperature for 18 h before being diluted with DCM and washed three times with aqueous 1 N HCl, once with water, three times with saturated aqueous sodium bicarbonate, and once with brine. The organic layer was dried over MgSO$_4$, filtered and concentrated under reduced pressure. The product was purified by medium pressure liquid chromatography (silica gel, 70% EA/Hexanes) to give 229 mg of a colorless oil. ESI-MS calc. for C19H16F6N2O2: 418; found 419 (M+H).

Step E

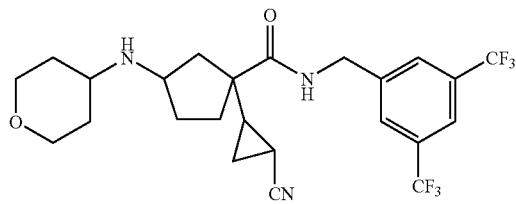

The trans-cyclopropyl keto-amide from Step D above (200 mg, 0.47 mmol) was combined with 4-amino-4H-tetrahydropyran (78 mg, 0.57 mmol), triethylamine (57 mg, 0.56 mmol), 4° A powdered molecular sieves (100 mg), and sodium triacetoxyborohydride (400 mg, 1.9 mmol) in 5 mL DCM. The reaction mixture was stirred at room temperature for 3 days, then filtered through celite, diluted with DCM, and washed with saturated NaHCO$_3$ solution and brine. The organic layer was dried over anhydrous MgSO$_4$, filtered and concentrated. The product was purified by reverse phase HPLC (C18, 20-100% MeCN/H$_2$O) to give 119 mg of a mixture of 8 isomers. Preparatory TLC (0.5% NH$_4$OH/4.5% MeOH/95% DCM) of this product gave 2 separate mixtures of 4 isomers. 40 mg of the top spot, cis-racemate cyclopentyl/trans-cyclopropyl was recovered: ESI-MS calc for C24H27F6N3O2: 503; found 504 (M+H). 5.6 mg of the bottom spot, trans-racemate cyclopentyl/trans-cyclopropyl was recovered: ESI-MS calc for C24H27F6N3O2: 503; found 504 (M+H).

EXAMPLE 212

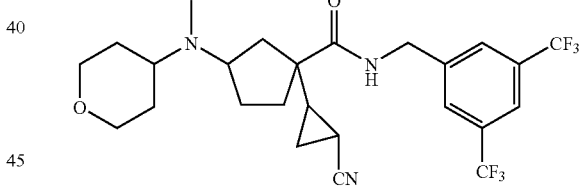

N-methylation of Example 211 (34 mg, 0.068 mmol) was carried out according to the standard procedure (Example 2) to give 21 mg of product (61%). ESI-MS calc. for C25H29F6N3O2: 517; found 517 (M+H).

EXAMPLE 213

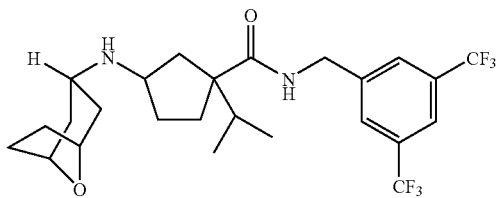

Step A

Intermediate 37 (210 mg, 1.7 mmol) was dissolved in THF (10 mL) and cooled to −78° C. A 1.0 M solution of LS-Selectride in THF (3.4 mL, 3.4 mmol) was added dropwise and the solution was allowed to warm to room temperature over 4 h at which time it was left at room temperature for 12 h before being concentrated under reduced pressure. The resulting oil was dissolved in DCM, washed with an aqueous 1 N HCl solution, then with brine, dried over MgSO$_4$, filtered and concentrated. The product was purified by flash chromatography (silica, 45% petroleum ether/ethyl ether) to give 144 mg of a colorless oil (66%). $^1$H NMR (CDCl$_3$, 500 MHz): 4.35 (bs, 2H), 4.12 (t, J=4.5 Hz, 1H), 2.24-2.13 (m, 2H), 2.12-2.08 (m, 2H), 1.98-1.90 (m, 2H), 1.63 (d, J=11.5 Hz, 2H).

Step B

To a cooled (0° C.) solution of the product from Step A (120 mg, 0.95 mmol), triethylamine (144 μL, 1.04 mmol) and DMAP (2-3 crystals) in DCM (10 mL), was added methane sulfonyl chloride (80 μL, 1.0 mmol) dropwise. The solution was stirred at 0° C. for 2.5 h before an additional portion of methane sulfonyl chloride (80 μL, 1.0 mmol) was added. The solution was warmed to room temperature and stirred for 16 h. The reaction was washed with saturated sodium bicarbonate solution, washed with brine, dried over MgSO$_4$, filtered and concentrated to give 205 mg of a yellow oil (99%+). The product was used in the next step without further purification.

Step C

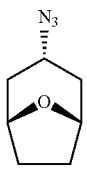

To a solution of the product form Step B (112 mg, 0.546 mmol) in DMSO (2 mL) was added sodium azide (177 mg, 2.73 mmol). The solution was heated to 50° C. for 18 h then diluted with DCM, washed with water twice, washed with brine, dried over MgSO$_4$, filtered and concentrated to give 80 mg of a yellow oil (96%). $^1$H NMR (CDCl$_3$, 500 MHz): 4.48 (bs, 2H), 3.66-3.60 (m, 1H), 2.64 (bs, 2H), 2.04-1.98 (m, 2H), 1.85-1.77 (m, 2H), 1.75-1.65 (m, 2H).

Step D

To a solution of the product from Step C (80 mg, 0.54 mmol) in methanol (2 mL) was added 20% Pd(OH)$_2$ (w/w) on C (16 mg). The solution was placed under a hydrogen balloon for 5.5 h. The solution was filtered through celite and concentrated to give 44 mg of a yellow oil (65%).

Step E

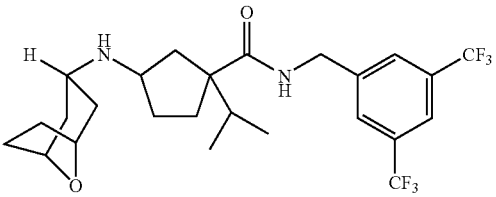

The product from step D (44 mg, 0.35 mmol) was combined with Intermediate 8 (100 mg, 0.25 mmol), 4 Å powdered molecular sieves (~200 mg), and sodium triacetoxyborohydride (212 mg, 1.00 mmol) in DCM (5 mL). The resulting mixture was stirred at room temperature for 5 d. The reaction mixture was filtered through celite and concentrated. The product was purified by preparative TLC (silica, 7% NH$_3$/MeOH in DCM) to give a top and bottom spot. The bottom spot was converted to its HCl salt by addition of a solution of HCl in dioxane to give 31.2 mg of a white solid (25%). The top spot was further purified by preparative TLC (silica, 7% NH$_3$/MeOH in DCM) and converted to its HCl salt by the addition of a solution of HCl in dioxane to give 28.6 mg of a white solid (20%).

Top Spot, cis racemate: ESI-MS calc. for C25H32F6N2O2: 506; Found: 507 (M+H).

Bottom Spot, trans racemate: ESI-MS calc. for C25H32F6N2O2: 506; Found: 507 (M+H).

EXAMPLE 214

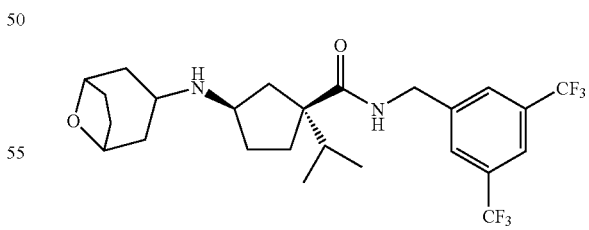

Intermediate 37 (43 mg, 0.35 mmol) was combined with Intermediate 16 (100 mg, 0.23 mmol), triethylamine (32 μL, 0.23 mmol), 4 Å powdered molecular sieves (50 mg), and sodium triacetoxyborohydride (200 mg, 0.92 mmol) in 10 mL of DCM. The reaction mixture was stirred at room temperature for 3 days, then filtered through celite, diluted with DCM, and washed with a saturated NaHCO$_3$ solution and brine. The organic layer was dried over anhydrous MgSO$_4$, filtered and concentrated. The product was purified preparative TLC (0.7% NH4OH/6.3% MeOH/93% DCM) and converted to its hydrochloride salt by addition of 2 N HCl in ethyl to give 47 mg of a white solid as an unknown endo/exo mixture. ESI-MS calc. for C25H32F6N2O2: 506; Found: 507 (M+H).

EXAMPLE 215

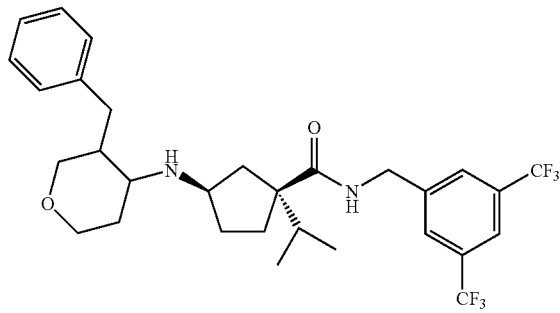

Step A

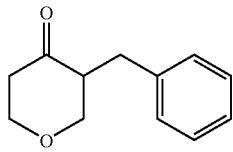

To a cooled (−78° C.) solution of LDA (1.5 M solution in cyclohexane, 16 mL, 24 mmol) in THF (80 mL) was added a solution of tetrahydro-4H-pyran-4-one (2 g, 20 mmol) and HMPA (3.6 mL, 21 mmol) in THF (20 mL). After 1 h at −78° C. the solution was treated with benzyl bromide (4.7 mL, 40 mmol) and allowed to warm to room temperature where it was allowed to stir overnight. The reaction was poured over ice and extracted 3 times with diethyl ether. The combined organic layers where washed with brine, dried over MgSO4, filtered, and concentrated under reduced pressure. The product was purified by flash chromatography (silica gel, 30% ether/hexanes) to give 800 mg of the desired mono-alkylation product and 1.16 g of an un-desired di-alkylation product. $^1$H NMR (desired mono-alkylation product): (CDCl3, 500 MHz) 7.35-7.15 (m, 5H), 4.21 (m, 1H), 4.06 (dd, J=5.5, 11.5 Hz, 1H), 3.81 (t, J=10 Hz), 3.22 (dd, J=5.0, 15.5 Hz, 1H), 2.85 (m, 1H), 2.63 (m, 1H), 2.50 (m, 2H).

Step B

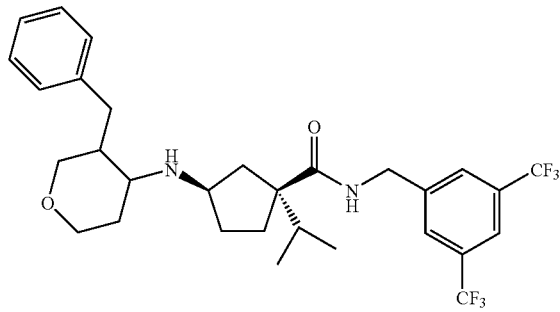

The product from Step A (88 mg, 0.46 mmol) was combined with Intermediate 16 (100 mg, 0.23 mmol), triethylamine (32 μL, 0.23 mmol), 4 Å powdered molecular sieves (60 mg), and sodium triacetoxyborohydride (240 mg, 1.1 mmol) in 10 mL DCM. The reaction mixture was stirred at room temperature for 3 days, then filtered through celite, diluted with DCM, and washed with saturated NaHCO3 solution and brine. The organic layer was dried over anhydrous MgSO4, filtered and concentrated. The product was purified preparative TLC (0.7% NH4OH/6.3% MeOH/93% DCM) and converted to its hydrochloride salt by the addition of 2 N HCl in ethyl ether to give 6 mg of a white solid as a mixture of 4 isomers. ESI-MS calc. for C30H36F6N2O2: 570; Found: 571 (M+H).

EXAMPLE 216

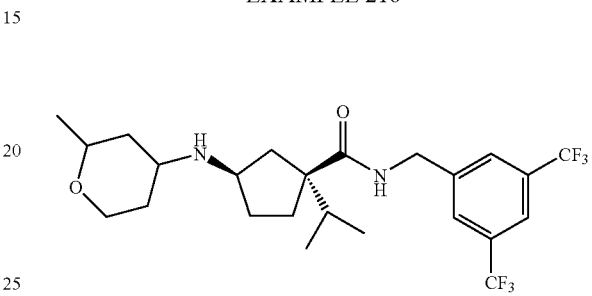

Example 128 was resolved into its 4 single diastereomers using a ChiralCel OD column, eluting with 3% ethanol/hexanes.

241A: First peak: ESI-MS calc. for C24H32F6N2O2: 494; found 495 (M+H).

241B: Second peak: ESI-MS calc. for C24H32F6N2O2: 494; found 495 (M+H).

241C: Third peak: ESI-MS calc. for C24H32F6N2O2: 494; found 495 (M+H).

241D: Fourth peak: ESI-MS calc. for C24H32F6N2O2: 494; found 495 (M+H).

EXAMPLE 217

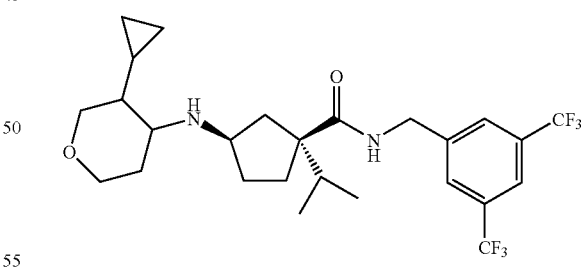

The Top Spot from Example 154 was resolved into 3 single diastereomers using a ChiralCel OD column, eluting with 20% isopropanol/hexanes.

242A: ESI-MS calc. for C26H34F6N2O2: 520; found 521 (M+H).

242B: ESI-MS calc. for C26H34F6N2O2: 520; found 521 (M+H).

242C: ESI-MS calc. for C26H34F6N2O2: 520; found 521 (M+H).

EXAMPLE 218

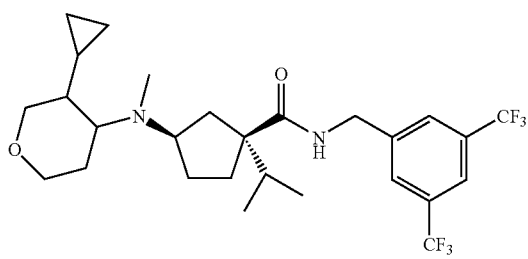

N-methylation of Example 242C (5.0 mg, 0.01 mmol) was carried out according to the standard procedure (see Example 2) to give 1.4 mg of product (28%). ESI-MS calc. for $C_{27}H_{36}F_6N_2O_2$: 534; found 535 (M+H).

EXAMPLE 219

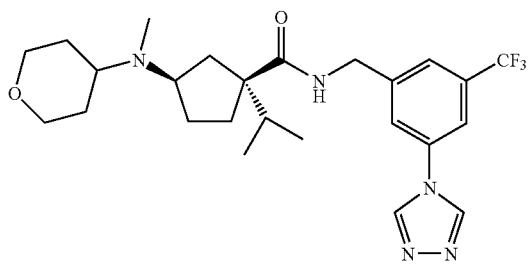

Step A

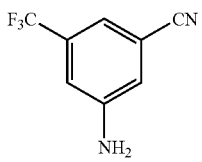

A mixture of 3-bromo-5-trifluoromethylbenzonitrile (9.9 g, 41 mmol), zinc cyanide (9.7 g, 82 mmol), and $Pd(PPh_3)_4$ (2.4 g, 2 mmol) in anhydrous N,N-dimethylformamide (120 ml) was degassed then heated at 90° C. for 6 h. The cooled reaction mixture was poured into water (600 ml) and extracted with ethyl acetate (3×150 ml). The combined ethyl acetate layers were washed with water (3×200 ml), saturated NaCl (100 ml), dried over $MgSO_4$, filtered and evaporated. The residue was purified by column chromatography on silica eluting with 20% ethyl acetate in hexanes to give the desired product (6.31 g, 84%); $^1$H NMR 500 MHz ($CDCl_3$): 4.21 (2H, s), 7.05 (1H, s), 7.09 (1H, s), 7.23 (1H, s).

Step B

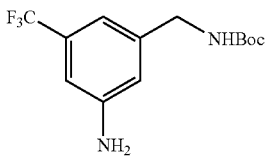

A solution of the product from Step A (4.75 g, 25.5 mmol) in a mixture of ethanol (50 mL) and ammonium hydroxide (10 mL) was hydrogenated at 40 psi over Raney Nickel (0.5 g) for 18 h on a Parr apparatus. The catalyst was removed by filtration thru celite, and the filtrate was evaporated to dryness. The resultant residue was dissolved in DCM, dried over $MgSO_4$, filtered and treated with di-tert-butyl dicarbonate (6.12 g, 28.0 mmol). The reaction was stirred at room temperature for 3 h before N,N-dimethyl ethylenediamine was added. After 30 minutes, the reaction was washed with aqueous 1 M citric acid, followed by aqueous saturated $NaHCO_3$, and brine. The organic layer was dried over $MgSO_4$, filtered and concentrated to give 4.5 g of product (62%). $^1$H NMR ($CDCl_3$, 500 MHz): 6.85 (s, 1H), 6.75 (s, 1H), 6.70 (s, 1H), 5.10 (bs, 1H), 4.20 (bs, 2H), 3.85 (bs, 2H), 1.60-1.20 (m, 9H).

Step C

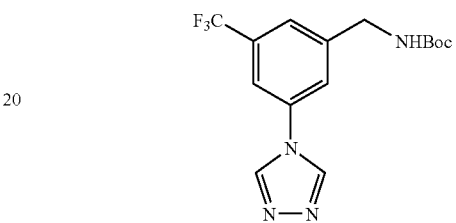

To a mixture of the product from Step B (3.5 g, 12 mmol) and N,N-dimethyl formamide azine (3.5 g) in toluene (100 mL) was added p-toluene sulfonic acid, and the resulting mixture was heated to reflux. After 18 h at reflux the reaction was cooled, washed with saturated aqueous $NaHCO_3$, dried over $K_2CO_3$, filtered, and concentrated under reduced pressure. The residue was purified using a Biotage flash 40 (silica gel, 0.5% $NH_4OH$/4.5% methanol/DCM) to give 2.1 g of product (51%). ESI-MS calc. for $C_{15}H_{17}F_3N_4O_2$: 342.1; found 343.1 (M+H).

Step D

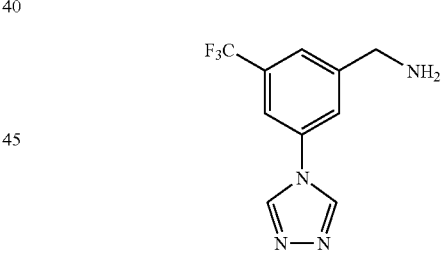

To a solution of the product from Step C (2.1 g, 6.1 mmol) in DCM (20 mL) was added trifluoroacetic acid (5 mL) and the mixture was stirred at room temperature. After 2 h the reaction was concentrated under reduced pressure and the residue was made alkaline with saturated aqueous $NaHCO_3$ and washed three times with DCM. The aqueous layer was evaporated to dryness and the resulting residue was triturated with methanol. The methanol triturate was evaporated under reduced pressure, and the crude product was purified by reverse phase HPLC (C18, 20-100% $MeCN/H_2O$). The resulting TFA salt was loaded onto Dowex 50 W×8 resin and washed with water then eluted with 10% aqueous $NH_4OH$ to give 700 mg of a yellow oil (47%). $^1$H NMR ($CDCl_3$, 500 MHz): 9.22 (s, 2H), 8.60 (bs, 2H), 8.20 (s, 1H), 8.19 (s, 1H), 7.97 (s, 1H), 4.20 (s, 2H).

Step E

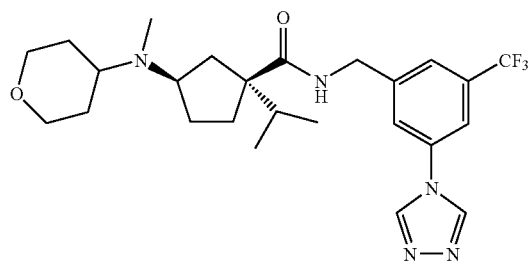

Intermediate 17 (700 mg, 2.6 mmol) was dissolved in DCM (10 mL) and treated with oxalyl chloride (230 µL, 5.2 mmol) and 1 drop of DMF. After 2 h at room temperature the reaction was concentrated to dryness and dried for 1.5 under high vacuum. 160 mg of this acid chloride (0.56 mmol) was dissolved in DCM (5 mL) and added dropwise to a stirred solution of the product from Step D (70 mg, 0.29 mmol) in triethylamine (2 mL). After 15 minutes an additional 100 mg of the acid chloride was added to the reaction and stirring was continued at room temperature. After 1 h the reaction was concentrated under reduced pressure and passed through a Spe-ed SCX column, washing with methanol and eluting with 2 M $NH_3$ solution in methanol. This crude product was twice further purified by reverse phase HPLC (C18, 25-100% MeCN/$H_2O$) and converted to its hydrochloride salt by the addition of hydrogen chloride (2 N solution in ethyl ether) to give 13 mg of a white solid (9%). ESI-MS calc. for $C_{25}H_{34}F_3N_5O_2$: 493; found 494 (M+H).

EXAMPLE 220

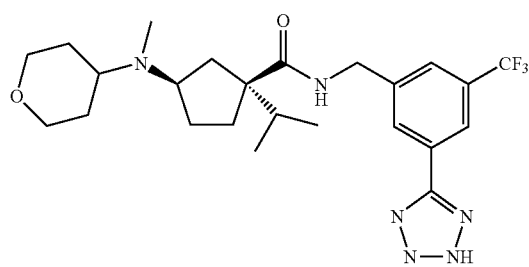

Step A

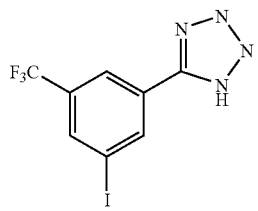

A solution of the iodo-nitrile prepared in Step A of Intermediate 7 (220 mg, 0.74 mmol) in toluene (2.5 mL) was treated with sodium azide (160 mg, 2.5 mmol) and triethylamine hydrochloride (350 mg, 2.5 mmol) and heated to 100° C. After 18 h the reaction was cooled to room temperature and extracted twice with $H_2O$. The aqueous layer was acidified with concentrated aqueous HCl, and the resulting precipitate was filtered, washed with water and dried under high vacuum to give 250 mg of a white solid (99%). ESI-MS calc. for $C_8H_4F_3IN_4$: 340; found 341.

Step B

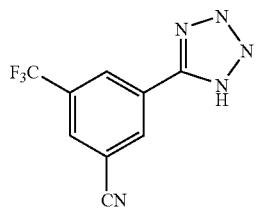

The product from Step A (230 mg, 0.68 mmol) was combined with tetrakis(triphenylphosphine) palladium (47 mg, 0.041 mmol) and zinc cyanide (110 mg, 0.95 mmol) in DMF (deoxygenated) and heated at 80°. After 18 h, an additional 50 mg of zinc cyanide was added and the reaction was stirred at 80° C. for an additional 3 h before being cooled to room temperature and extracted twice with aqueous 2 N $NH_4OH$. The combined aqueous layers were acidified with concentrated aqueous HCl and extracted 4 times with ethyl ether. The combined organic layers where washed with brine, dried over $MgSO_4$, filtered and concentrated under reduced pressure. The product was purified by medium pressure liquid chromatography (silica gel, 50 to 100% EA/hexanes) to give 100 mg of an oil (62%). ESI-MS calc. for $C_9H_4F_3N_5$: 239; found 240.

Step C

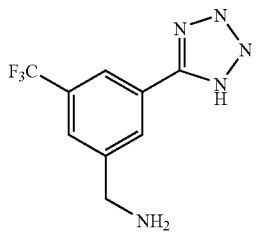

The product from Step B (90 mg, 0.38 mmol) was dissolved in THF (3 mL) and treated with borane (1.0 M solution in THF, 3.8 mL, 3.8 mmol). After 18 h at room temperature, the reaction was quenched with a 1% hydrogen chloride solution in methanol (10 mL) and heated to 50° C. After 18 h. the reaction was concentrated under reduced pressure and the residue was re-dissolved in a 1% hydrogen chloride solution in methanol (10 mL). After 4 h the solution was concentrated under reduced pressure to give 120 mg of product which was used directly in the next step. ESI-MS calc. for C9H8F3N5: 243; found 244 (M+H)

Step D

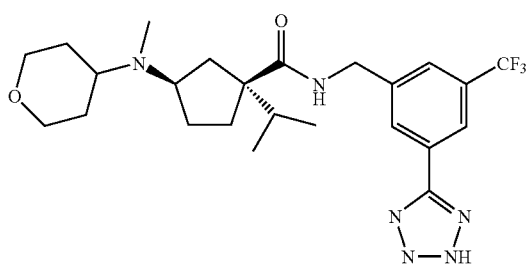

Intermediate 17 (700 mg, 2.6 mmol) was dissolved in DCM (10 mL) and treated with oxalyl chloride (230 μL, 5.2 mmol) and 1 drop of DMF. After 2 h at room temperature the reaction was concentrated to dryness and dried for 1.5 under high vacuum. 20 mg of this acid chloride (0.07 mmol) was dissolved in DCM (1 mL) and added dropwise to a stirred solution of the product from Step C (10 mg, 0.04 mmol) in triethylamine (1 mL). After 18 h the reaction was concentrated under reduced pressure and passed through a Spe-ed SCX column, washing with methanol and eluting with 2 M NH$_3$ solution in methanol. This crude product was further purified by reverse phase HPLC (C18, 25-100% MeCN/H$_2$O) and converted to its hydrochloride salt by addition of hydrogen chloride (2 N solution in ethyl ether) to give 10 mg of a white solid (50%). ESI-MS calc. for C24H33F3N6O2: 494; found 495 (M+H).

EXAMPLE 221

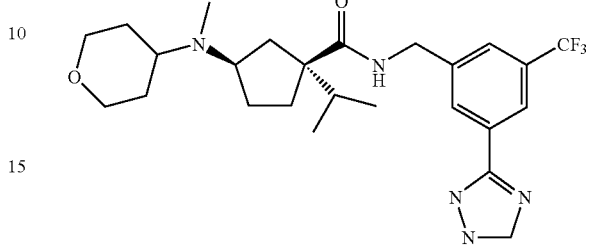

Step A

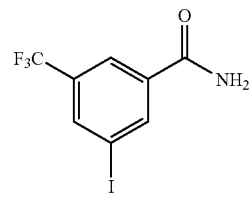

To a cooled (0° C.) solution of the iodo-nitrile prepared in Step A of Intermediate 7 (500 mg, 1.7 mmol) in DMSO (2 mL) was added with a solution of K$_2$CO$_3$.1.5H$_2$O (33 mg, 0.20 mmol) and H$_2$O$_2$ (30% solution in water, 340 μL, 3.1 mmol) in water (4 mL) and the resulting solution was allowed to warm to room temperature. After 18 h additional quantities of both K$_2$CO$_3$ (280 mg, 1.7 mmol) and H$_2$O$_2$ (610 μL, 5.4 mmol) where added and the reaction was stirred at room temperature for an additional 30 minutes. The reaction was diluted with water (10 mL) and extracted with EA. The organic layer was washed twice with water, then brine, and dried over MgSO$_4$, filtered and concentrated under reduced pressure to give 450 mg of product (85%).

Step B

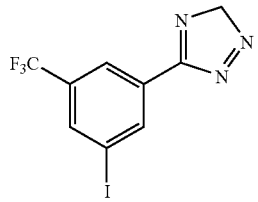

The product from Step A (410 mg, 1.3 mmol) was dissolved in N,N-dimethylformamide dimethyl acetal (10 mL) and heated to 120° C. for 4 h before the N,N-dimethylformamide dimethyl acetal was distilled off under reduced pressure. The resulting residue was treated with a solution of hydrazine hydrate (76 μL, 1.6 mmol) in glacial acetic acid (10 mL) and heated to 90° C. After 1 h the reaction was concentrated under reduced pressure to give 442 mg of product (99%). ESI-MS calc. for C9H5F31N3: 339; found 340 (M+H).

Step C

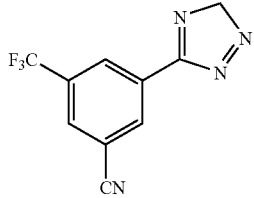

The product from Step B (440 mg, 1.3 mmol) was combined with Tetrakis(triphenylphosphine) palladium (90 mg, 0.078 mmol) and zinc cyanide (300 mg, 2.6 mmol) in DMF (deoxygenated) and heated to reflux. After 110 h, the reaction was cooled to room temperature and partitioned between ethyl ether and aqueous 2 N NH$_4$OH. The aqueous layer was extracted twice with ether and the combined organic layers where washed with brine, dried over MgSO$_4$, filtered and concentrated under reduced pressure to give 350 mg of product which was used directly in the next step. ESI-MS calc. for C10H5F3N4: 238; found: 239 (M+H).

Step D

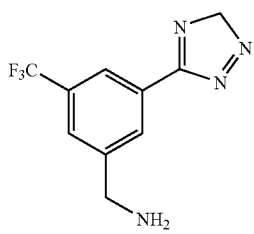

The product from Step C (350 mg, 1.5 mmol) was dissolved in THF (10 mL) and treated with borane (1.0 M solution in THF, 7.4 mL, 7.4 mmol). After 2 h at room temperature, the reaction was quenched with a 1% hydrogen chloride solution in methanol (20 mL) and heated to 50° C. After 18 h. the reaction was concentrated under reduced pressure and the residue was re-dissolved in a 1% hydrogen chloride solution in methanol (20 mL). After 2 h the solution was concentrated under reduced pressure to give 410 mg a white salt (98%). ESI-MS calc. for C10H9F3N4: 242; found 243 (M+H).

Step E

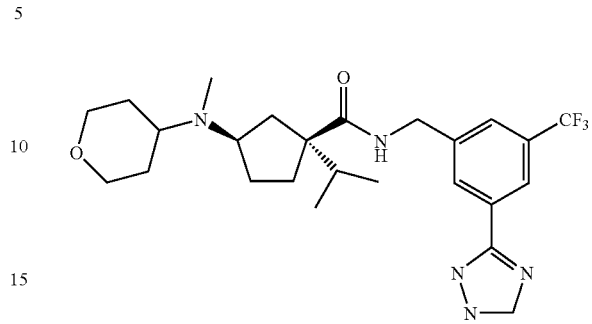

Intermediate 17 (700 mg, 2.6 mmol) was dissolved in DCM (10 mL) and treated with oxalyl chloride (230 µL, 5.2 mmol) and 1 drop of DMF. After 2 h at room temperature the reaction was concentrated to dryness and dried for 1.5 under high vacuum. 90 mg of this acid chloride (0.31 mmol) was dissolved in DCM (2 mL) and added dropwise to a stirred solution of the product from Step D (45 mg, 0.19 mmol) in triethylamine (2 mL). After 3.5 h the reaction was concentrated under reduced pressure and passed through a Spe-ed SCX column, washing with methanol and eluting with 2 M NH$_3$ solution in methanol. This crude product was further purified by reverse phase HPLC (C18, 25-100% MeCN/H$_2$O) and converted to its hydrochloride salt by the addition of hydrogen chloride (2 N solution in ethyl ether) to give 3.7 mg of a white solid (4%). ESI-MS calc. for C25H34F3N5O2: 493; found 494 (M+H).

EXAMPLE 222

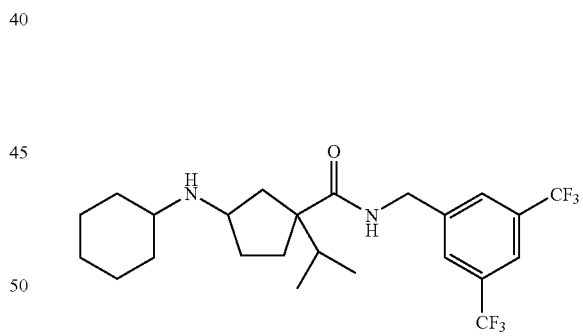

A mixture of the Intermediate 8 (79 mg, 0.20 mmol), cyclohexylamine (46 µL, 0.40 mmol), molecular sieve (4 Å, 90 mg), DIEA (70 µL, 0.40 mmol) and sodium triacetoxyborohydride (127 mg, 0.60 mmol) in DCE (5 mL) was stirred for 24 h. The reaction mixture was diluted by DCM, filtered, and washed with saturated aqueous NaHCO$_3$, water and brine. The DCM layers were dried over Na$_2$SO$_4$, filtered and concentrated. The residue was purified on preparative TLC (1000 micron) (developed by 100% EtOAc) to yield the title compound as a free base. Its HCl salt (56.2 mg) was formed by treatment with 4 N HCl/dioxane. ESI-MS calc. for C24H32F6N2O: 478.24; Found: 479 (M+H).

EXAMPLE 223

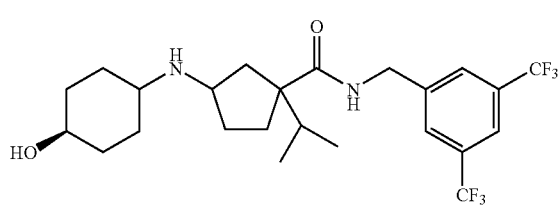

Example 223 was prepared starting from Intermediate 8 and trans-4-aminocyclohexanol as detailed in Example 222. LC-MS calc. For C24H32F6N2O2: 494.24; Found: 495 (M+H).

EXAMPLE 224

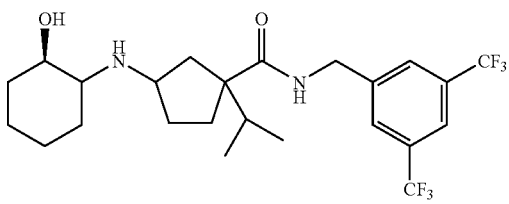

Example 224 was prepared starting from Intermediate 8 and trans-2-aminocyclohexanol as detailed in Example 222. LC-MS calc. For C24H32F6N2O2: 494.24; Found: 495 (M+H).

EXAMPLE 226

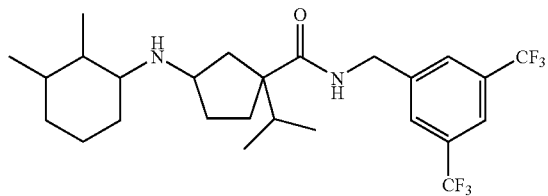

Step A

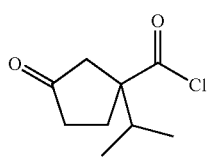

To a solution of Intermediate 1 (22 g, 130 mmol) in benzene (140 mL), was added thionyl chloride (21 mL, 290 mmol). The reaction mixture was stirred at 40° C. for 4.5 h and then the solvent and volatile materials were evaporated. Distillation under vacuum yielded Intermediate chloride (Step A, Example 226) (7.186 g, 30%) (bp. 105-107° C./3 mmHg). $^1$H-NMR (500MHz, CDCl$_3$): 2.82 (d, 1H), 2.50-2.56 (m, 1H), 2.3-2.42 (m, 4H), 2.07-2.15 (m, 1H), 1.00-1.04 (m, 6H).

Step B

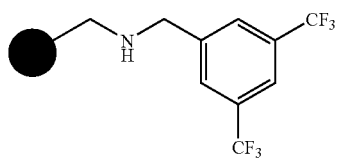

A mixture of DCE/trimethyl orthoformate (1:1, 200 mL) was used to swell the 4-(4-formyl-3-methoxy-phenoxy)butylryl AM resin (01-64-0209, NovaBiochem, 0.55 mmol/g, 13 g) for 2.45 h. After filtration, the resin was suspended in DCE/trimethyl orthoformate (1:1, 180 mL) and the 3,5-bis(trifluoromethyl)benzyl amine (22 g, 89 mmol) and sodium triacetoxyborohydride (22.7 g, 107 mmol) was added into the suspension. The suspension was left to spin for 48 h with periodic release of the pressure for the first 6 h. The resin was then filtered off, washed by MeOH (three times), DCM (three times), DMF (three times) and then washed again by MeOH (three times), DCM (three times), DMF (three times). It was dried under vacuum and used in the next step (Step B, Example 226).

Step C

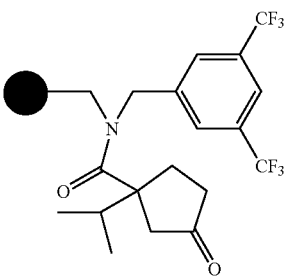

To a suspension of the intermediate from the previous step (10.5 g, 5.25 mmol) in DCM (100 mL), was added the intermediate from Step A, Example 226 (4.95 g, 26.3 mmol), and DIEA (4.57 mL, 26.3 mmol) under nitrogen. The reaction was left to spin for 48 h. The resin was filtered, washed by DCM (12 times), dried under vacuum and used as obtained in the next step.

Step D

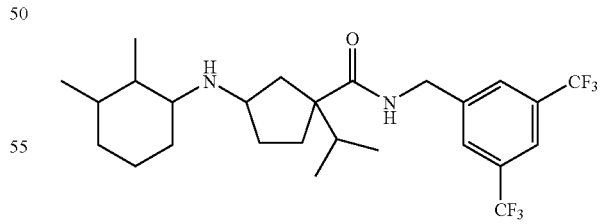

The intermediate from Step C, Example 226 (100 mg, 0.05 mmol) was swelled in 5% trimethyl orthoformate/DCE for 30 minutes and then the solvent was drained off. After 5% trimethyl orthoformate/DCE (1.5 mL), 2,3-dimethyl-cyclohexylamineamine (0.25 mmol) and sodium triacetoxyborohydride (110 mg, 0.50 mmol) was added, the suspension was spun for 48 h and pressure was released every 15 minutes for 3 h. The resin was then filtered out, washed by MeOH (twice), DCM (five times), DMF (five times) and then washed again by MeOH (twice), DMF (five times) and DCM (five times). The resin was dried under vacuum and mixed with 25% TFA/DCM (2 mL), and spun for 1 h, was filtered, and washed twice with DCM. The filtrate was evaporated to yield the final compound as a TFA salt (7.8 mg). LC-MS calc. For C26H36F6N2O calc.: 506.27; Found: 507 (M+H).

EXAMPLE 227

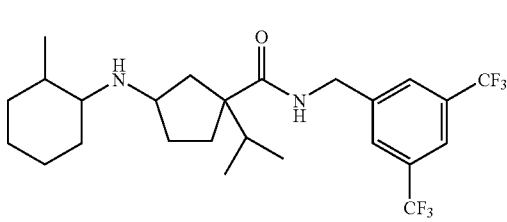

Example 227 was prepared starting from the intermediate prepared in Step C, Example 226 and 2-methylcyclohexylamine as detailed in Example 226-Step D. LC-MS calc. For C25H34F6N2O: 492.26; Found: 493 (M+H).

EXAMPLE 228

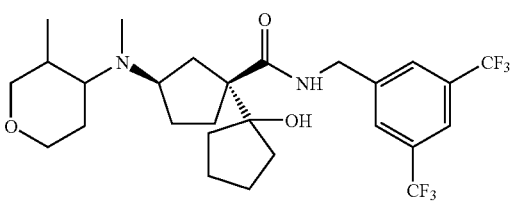

To a solution of the secondary amine described in Example 181 (60 mg, 0.11 mmol) in DCM (4 mL), was added formalin (37% aqueous solution, 96 mg, 1.1 mmol), molecular sieve (4 Å, 500 mg), and sodium triacetoxyborohydride (120 mg, 0.56 mmol). The reaction mixture was stirred over 48 h, it was filtered, washing with DCM and MeOH. Saturated aqueous NaHCO$_3$ was added and the mixture was heated at 60° C. for 1.5 h, and evaporated to remove the volatiles. The resulting mixture was diluted with water (10 mL) and extracted with DCM (four times). The organic portion was separated, washed with water, brine, dried over Na$_2$SO$_4$, filtered and concentrated. The residue was purified by preparative TLC (1000 micron) (developed by 5% [aqueous NH$_4$OH/MeOH (1/9)] in DCM) to yield the final compound as a free base. Its HCl salt (47 mg) was formed by treatment with 4 N HCl/dioxane. LC-MS calc. for C27H36F6N2O3: 550.26; Found: 551 (M+H).

EXAMPLE 229

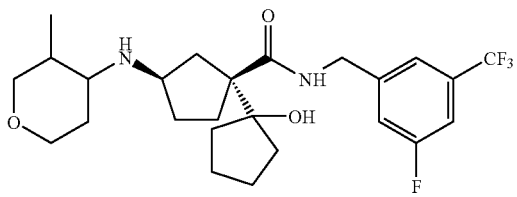

Example 229 was prepared starting from the intermediate prepared in Step C, Example 181 and 3-fluoro-5-trifluoromethylbenzylamine as detailed in Example 181. LC-MS for calc. C25H34F4N2O3: 486.25; Found: 487 (M+H).

EXAMPLE 230

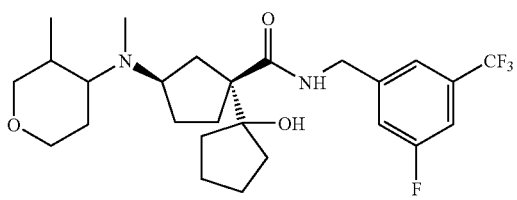

Example 230 was prepared starting from Example 229 as detailed in Example 181. LC-MS for calc. C26H36F4N2O3: 500.27; Found: 501 (M+H).

EXAMPLE 231

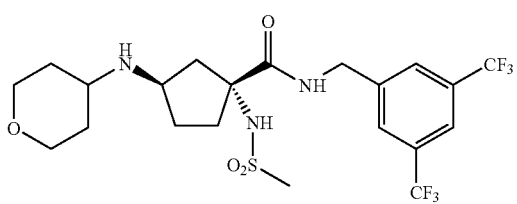

Example 231 was prepared as detailed in Example 169 except that benzylchloroformate in Step A was replaced by methanesulfonyl chloride. LC-MS for. C21H27F6N3O4 for [M+H]$^+$ calc. 532.16; Found: 532.30.

EXAMPLE 232

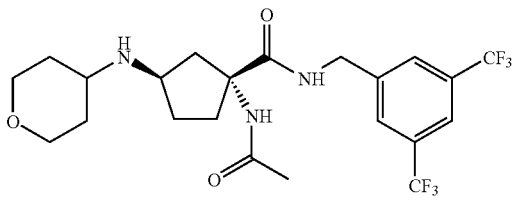

Example 232 was prepared as detailed in Example 169 except that benzylchloroformate in Step A was replaced by acetic anhydride. LC-MS for. C22H27F6N2O3 for [M+H]+ calc. 496.20; Found: 496.20.

EXAMPLE 233

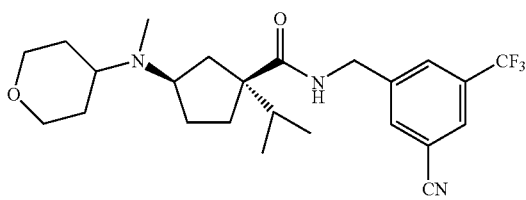

Step A

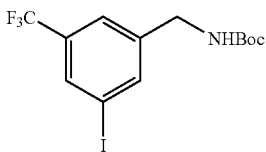

To a cooled (0° C.) solution of the hydrochloride salt of Intermediate 7 (600 mg, 1.8 mmol) and triethylamine (370 µL, 1.8 mmol) in DCM (15 mL) was added di-tert butyl dicarbonate (470 mg, 2.2 mmol). The reaction was allowed to warm to room temperature. After 4.5 h, the reaction was diluted with DCM and washed with saturated aqueous NaHCO$_3$ and brine. The organic layer was dried over MgSO$_4$, filtered and concentrated to give 700 mg of product (93%). ESI-MS calc. for C13H15F31NO2: 401; found 346 (M-tert-Butyl), 402 (M+H).

Step B

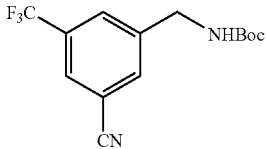

The product from Step A (840 mg, 2.1 mmol) was combined with tetrakis(triphenylphosphine)palladium (150 mg, 0.13 mmol) and zinc cyanide (170 mg, 1.5 mmol) in DMF (deoxygenated) and heated to 80° C. After 4 h, the reaction was cooled to room temperature and partitioned between EA and aqueous 2 N NH$_4$OH. The organic layer was washed twice with aqueous 2 N NH$_4$OH, then brine, and dried over MgSO$_4$, filtered and concentrated under reduced pressure. The product was purified by medium pressure liquid chromatography (silica gel, 0-50% EA/hexanes) to give 500 mg of product (80%). ESI-MS calc. for C14H15F3N2O2: 300; found 245 (M-tert-Butyl).

Step C

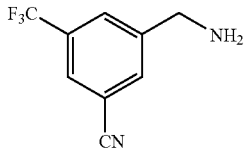

The product from Step B (500 mg, 1.7 mmol) was treated with hydrogen chloride (4 N in dioxane, 15 mL) and stirred at room temperature. After 2 h the reaction was concentrated under reduced pressure to give 360 mg of a white solid (90%). ESI-Ms calc. for C9H7F3N2: 200; found 201 (M+H).

Step D

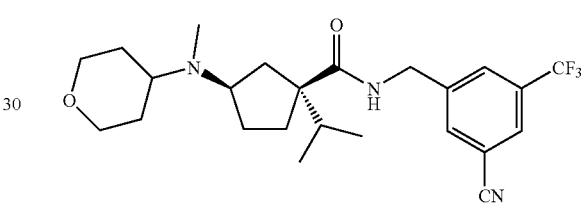

Intermediate 17 (230 mg, 0.84 mmol) was combined with the product from Step C (300 mg, 1.3 mmol), PyBrop (390 mg, 0.84 mmol), DMAP (61 mg, 0.5 mmol), and triethylamine (180 µL, 1.2 mmol) in DCM (50 mL). After 72 h at room temperature the reaction was diluted with DCM, washed with saturated aqueous NaHCO$_3$ and brine. The organic layer was dried over MgSO$_4$, filtered and concentrated under reduced pressure. The product was purified by reverse phase HPLC (C18, 20-100% MeCN/H$_2$O) and converted to its hydrochloride salt by addition of 2 N HCl in ethyl ether to give 160 mg of a white solid (43%). ESI-MS calc. for C24H32F3N3O2: 451; found 452 (M+H).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

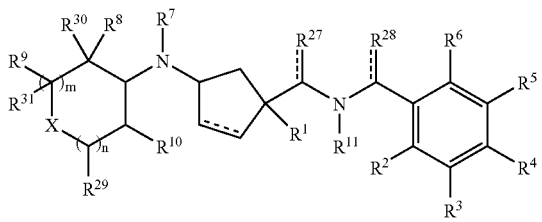

wherein:

X is selected from the group consisting of:
—O—, —NR$^{20}$—, —S—, —SO—, —SO$_2$—, and —CR$^{21}$R$^{22}$—, —NSO$_2$R$^{20}$—, —NCOR$^{20}$—, —NCO$_2$R$^{20}$—, —CR$^{21}$CO$_2$R$^{20}$—, —CR$^{21}$OCOR$^{20}$—, —CO—, —O—C(CH$_3$)$_2$—O—, where R$^{20}$ is selected from: hydrogen, C$_{1-6}$ alkyl, benzyl, phenyl, C$_{3-6}$ cycloalkyl where the alkyl, phenyl, benzyl, and cycloalkyl groups can be unsubstituted or substituted with 1-3 substituents where the substituents are independently selected from: halo, hydroxy, C$_{1-3}$alkyl, C$_{1-3}$alkoxy, —CO$_2$H, —CO$_2$—C$_{1-6}$ alkyl, and trifluoromethyl, where R$^{21}$ and R$^{22}$ are independently selected from: hydrogen, hydroxy, C$_{1-6}$ alkyl, —O—C$_{1-6}$alkyl, benzyl, phenyl, C$_{3-6}$ cycloalkyl where the alkyl, phenyl, benzyl, and cycloalkyl groups can be unsubstituted or subsituted with 1-3 substituents where the substituents are independently selected from: halo, hydroxy, C$_{1-3}$alkyl, C$_{1-3}$alkoxy, —CO$_2$H, —CO$_2$—C$_{1-6}$ alkyl, and trifluoromethyl;

R$^1$ is selected from:
—C$_{1-6}$alkyl, —C$_{0-6}$alkyl—O—C$_{1-6}$alkyl, —C$_{0-6}$alkyl-S—C$_{1-6}$alkyl, —C$_{0-6}$alkyl-SO$_{1-2}$—C$_{1-6}$alkyl, —C$_{0-6}$alkyl-SO$_2$—NR$^{26}$—C$_{1-6}$alkyl, —(C$_{0-6}$alkyl)—(C$_{3-7}$ cycloalkyl)-(C$_{0-6}$alkyl), hydroxy, —CO$_2$R$^{20}$, heterocycle, —CN, —NR$^{20}$R$^{26}$, —NR$^{26}$SO$_2$R$^{20}$, —NR$^{26}$COR$^{21}$, —OCOR$^{20}$, and phenyl, where R$^{26}$ is selected from: hydrogen, C$_{1-6}$ alkyl, benzyl, phenyl, C$_{3-6}$ cycloalkyl where the alkyl, phenyl, benzyl, and cycloalkyl groups can be unsubstituted or substituted with 1-3 substituents where the substituents are independently selected from: halo, hydroxy, C$_{1-3}$alkyl, C$_{1-3}$alkoxy, —CO$_2$H, —CO$_2$—C$_{1-6}$ alkyl, and trifluoromethyl, where the alkyl and the cycloalkyl are unsubstituted or substituted with 1-7 substituents where the substituents are independently selected from: halo, hydroxy, —O—C$_{1-3}$alkyl, trifluoromethyl, C$_{1-3}$alkyl, —O—C$_{1-3}$alkyl, —CO$_2$R$^{20}$, —SO$_2$R$^{20}$, —NHCOCH$_3$, —NHSO$_2$CH$_3$, -heterocycle, =O, and —CN, and where the phenyl and heterocycle are unsubstituted or substituted with 1-3 substituents where the substituents are independently selected from: halo, hydroxy, C$_{1-3}$alkyl, C$_{1-3}$alkoxy and trifluoromethyl;

R$^2$ is selected from: hydrogen, C$_{1-6}$alkyl, trifluoromethyl trifluoromethoxy, chloro, bromo, and phenyl;

R$^3$ is selected from: hydrogen, hydroxy, halo, C$_{1-6}$alkyl, —O—C$_{1-6}$alkyl, —NR$^{20}$R$^{21}$, —NR$^{20}$CO$_2$R$^{21}$, —NR$^{20}$CONR$^{20}$R$^{21}$, —NR$^{20}$—SO$_2$—NR$^{20}$R$^{21}$, —NR$^{20}$—SO$_2$—R$^{21}$, heterocycle, —CN, —CONR$^{20}$R$^{21}$, —CO$_2$R$^{20}$, —NO$_2$, —S—R$^{20}$, —SO—R$^{20}$, —SO$_2$—R$^{20}$, and —SO$_2$—NR$^{20}$R$^{21}$;

R$^4$ is selected from: hydrogen, C$_{1-6}$alkyl, trifluoromethyl, trifluoromethoxy, chloro, bromo, and phenyl;

R$^5$ is selected from: C$_{1-6}$alkyl substituted with 1-6 fluoro and optionally substituted with hydroxyl, —O—C$_{1-6}$alkyl substituted with 1-6 fluoro, —CO—C$_{1-6}$alkyl substituted with 1-6 fluoro, —S—C$_{1-6}$alkyl, -pyridyl, fluoro, chloro, bromo, and phenyl;

R$^6$ is selected from: hydrogen, C$_{1-6}$alkyl, trifluoromethyl, trifluoromethoxy, chloro, bromo, and phenyl;

R$^7$ is selected from: hydrogen, C$_{1-6}$alkyl, and trifluoromethyl;

R$^8$ is selected from: hydrogen, C$_{1-6}$alkyl, where alkyl may be unsubstituted or substituted with 1-6 substituents where the substituents are chosen from the group: fluoro, C$_{1-3}$alkoxy, hydroxy, —CO$_2$R$^{20}$, fluoro, —O—C$_{1-3}$alkyl, where alkyl may be unsubstituted or substituted with 1-3 fluoro, and C$_{3-6}$ cycloalkyl, —O—C$_{3-6}$cycloalkyl, hydroxy, —CO$_2$R$^{20}$, —OCOR$^{20}$, and phenyl, or R$^7$ and R$^8$ may be joined together via a C$_{2-4}$alkyl or a C$_{0-2}$alkyl-O—C$_{1-3}$alkyl chain to form a 5-7 membered ring;

R$^9$ is selected from: hydrogen, C$_{1-6}$alkyl, where alkyl may be unsubstituted or substituted with 1-6 substituents where the substituents are chosen from the group: fluoro, C$_{1-3}$alkoxy, hydroxy, —CO$_2$R$^{20}$, CO$_2$R$^{20}$, hydroxy, and —O—C$_{1-6}$alkyl, where alkyl may be unsubstituted or substituted with 1-6 substituents where the substituents are chosen from the group: fluoro, C$_{1-3}$alkoxy, hydroxy, and —CO$_2$R$^{20}$,
or R$^8$ and R$^9$ may be joined together by a C$_{1-4}$alkyl chain or a C$_{0-3}$alkyl-O—C$_{0-3}$alkyl chain to form a 3-6 membered ring;

R$^{10}$ is selected from: hydrogen, and C$_{1-6}$alkyl, where alkyl may be unsubstituted or substituted with 1-6 fluoro, fluoro, —O—C$_{3-6}$cycloalkyl, and —O—C$_{1-3}$alkyl, where alkyl may be unsubstituted or substituted with 1-6 fluoro,
or R$^8$ and R$^{10}$ may be joined together by a C$_{1-3}$alkyl chain or a single bond to form a 3-6 membered ring; where the alkyl are unsubstituted or substituted with 1-3 substituents where the substiuents are independently selected from: halo, hydroxy, —CO$_2$R$^{20}$, C$_{1-3}$alkyl, and C$_{1-3}$alkoxy,
or R$^8$ and R$^{10}$ may be joined together by a C$_{1-2}$alkyl-O—C$_{1-2}$alkyl chain to form a 6-8 membered ring, where the alkyl are unsubstituted or substituted with 1-3 substituents where the substiuents are independently selected from: halo, hydroxy, —CO$_2$R$^{20}$, C$_{1-3}$alkyl, and C$_{1-3}$alkoxy,
or R$^8$ and R$^{10}$ may be joined together by a —O—C$_{1-2}$alkyl-O— chain to form a 6-7 membered ring, where the alkyl are unsubstituted or substituted with 1-3 substituents where the substiuents are independently selected from: halo, hydroxy, —CO$_2$R$^{20}$, C$_{1-3}$alkyl, and C$_{1-3}$alkoxy;

R$^{11}$ is selected from: hydrogen, C$_{1-6}$alkyl, and trifluoromethyl;

R$^{27}$ and R$^{28}$ are independently selected from: =O, where R$^{27}$, R$^{28}$, or both, is oxygen and is connected via a double bond, hydrogen, phenyl, and C$_{1-6}$alkyl which may be substituted or unsubstituted with 1-6 of the following substituents:

—COR$^{11}$, hydroxy, fluoro, chloro, and —O—C$_{1-3}$alkyl;
R$^{29}$, R$^{30}$, and R$^{31}$ are independently selected from: hydrogen, methyl, hydroxyl, trifluoromethyl, methoxy, and trifluoromethoxy;
or R$^{29}$ and R$^9$ are connected by a C$_{1-3}$alkyl bridge;
m is selected from 0, 1, and 2;
n is selected from 0, 1 and 2; and
the dashed line represents a single or a double bond; and
or a pharmaceutically acceptable salt thereof.

2. The compound of claim 1 of the formula Ia:

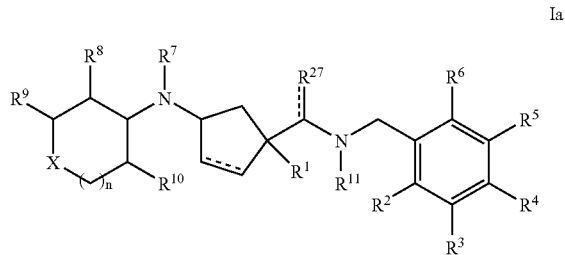

Ia or a pharmaceutically acceptable salt thereof.

3. The compound of claim 1 or a pharmaceutically acceptable salt thereof, wherein:
X is selected from the group consisting of: —O—, and —CH$_2$—.

4. The compound of claim 1 or pharmaceutically acceptable salt thereof, wherein X is —O—.

5. The compound of claim 1 or a pharmaceutically acceptable salt thereof, wherein R$^1$ is selected from:
(1) —C$_{1-6}$alkyl, which is unsubstituted or substituted with 1-6 substituents where the substituents are independently selected from: halo, hydroxy, —O—C$_{1-3}$alkyl, and trifluoromethyl,
(2) —C$_{0-6}$alkyl-O—C$_{1-6}$alkyl-, which is unsubstituted or substituted with 1-6 substituents where the substituents are independently selected from: halo, and trifluoromethyl,
(3) —C$_{0-6}$alkyl-S—C$_{1-6}$alkyl-, which is unsubstituted or substituted with 1-6 substituents where the substituents are independently selected from: halo, and trifluoromethyl, and
(4) —(C$_{3-5}$cycloalkyl)-(C$_{0-6}$alkyl), which is unsubstituted or substituted with 1-7 substituents where the substituents are independently selected from: halo, hydroxy, —O—C$_{1-3}$alkyl, and trifluoromethyl.

6. The compound of claim 1 or a pharmaceutically acceptable salt thereof, wherein R$^1$ is C$_{1-6}$alkyl which is unsubstituted or substituted with 1-5 substituents where the substituents are independently selected from: hydroxy, and fluoro.

7. The compound of claim 1 or a pharmaceutically acceptable salt thereof, wherein:
R$^1$ is selected from: isopropyl, —CH(OH)CH$_3$, and —CH$_2$CF$_3$.

8. The compound of claim 1 or a pharmaceutically acceptable salt thereof, wherein:
R$^2$ is selected from: hydrogen, hydroxy, and trifluoromethyl.

9. The compound of claim 1 or a pharmaceutically acceptable salt thereof, wherein:
R$^2$ is selected from: hydrogen, and hydroxy.

10. The compound of claim 1 or a pharmaceutically acceptable salt thereof, wherein:
R$^3$ is selected from: C$_{1-6}$alkyl unsubstituted or substituted with 1-6 substituents independently selected from fluoro, chloro, and bromo.

11. The compound of claim 1 or a pharmaceutically acceptable salt thereof, wherein:
R$^3$ is selected from: trifluoromethyl, cyclopropyl, and fluoro.

12. The compound of claim 1 or a pharmaceutically acceptable salt thereof, wherein:
R$^5$ is selected from: C$_{1-6}$alkyl unsubstituted or substituted with 1-6 substituents independently selected from fluoro, chloro, and bromo.

13. The compound of claim 1 or a pharmaceutically acceptable salt thereof, wherein:
R$^5$ is selected from: trifluoromethyl, cyclopropyl, and fluoro.

14. The compound of claim 1 or a pharmaceutically acceptable salt thereof, wherein:
R$^5$ is trifluoromethyl.

15. The compound of claim 1 or a pharmaceutically acceptable salt thereof, wherein R$^6$ is hydrogen.

16. The compound of claim 1 or a pharmaceutically acceptable salt thereof, wherein R$^7$ is hydrogen.

17. The compound of claim 1 or a pharmaceutically acceptable salt thereof, wherein R$^8$ is selected from: hydrogen, C$_{1-3}$alkyl, which is unsubstituted or substituted with 1-6 fluoro, —O—C$_{1-3}$alkyl, fluoro, and hydroxy.

18. The compound of claim 1 or a pharmaceutically acceptable salt thereof, wherein R$^8$ is selected from: hydrogen, methyl, ethyl, trifluoromethyl, fluoro, and —O—CH$_3$.

19. The compound of claim 1 or a pharmaceutically acceptable salt thereof, wherein R$^9$ is hydrogen and R$^{10}$ is hydrogen.

20. The compound of claim 1 or a pharmaceutically acceptable salt thereof, wherein R$^8$ and R$^{10}$ are joined together by a —CH$_2$CH$_2$— chain or a —CH$_2$CH$_2$CH$_2$— chain to form a cyclopentyl ring or a cyclohexyl ring.

21. The compound of claim 1 or a pharmaceutically acceptable salt thereof, wherein R$^{27}$ is =O, where R$^{27}$ is oxygen and is connected via a double bond.

22. The compound of claim 1 or a pharmaceutically acceptable salt thereof, wherein R$^9$ and R$^{29}$ are joined together by a C$_{1-3}$alkyl chain to form a ring.

23. The compound of claim 1 or a pharmaceutically acceptable salt thereof, wherein R$^{29}$ is hydrogen, R$^{30}$ is hydrogen, and R$^{31}$ is hydrogen.

24. A compound which is selected from the group consisting of:

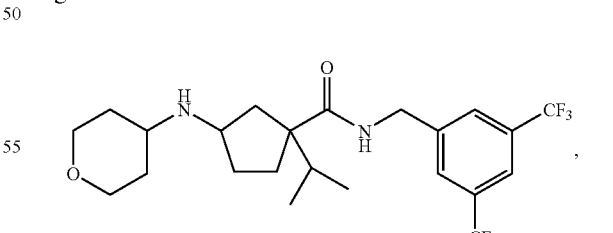

,

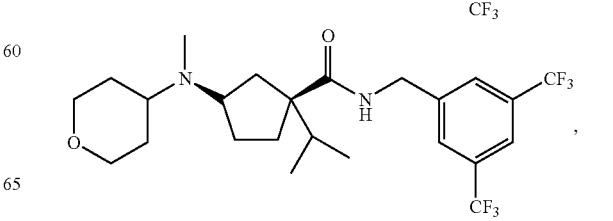

,

225
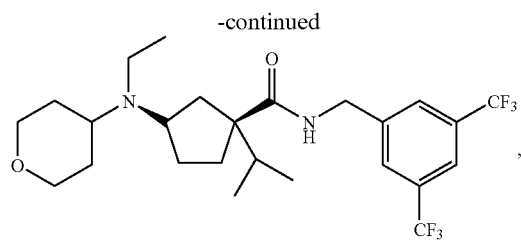
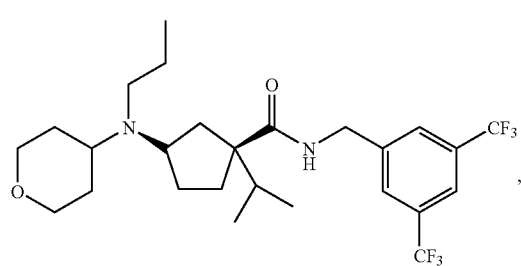
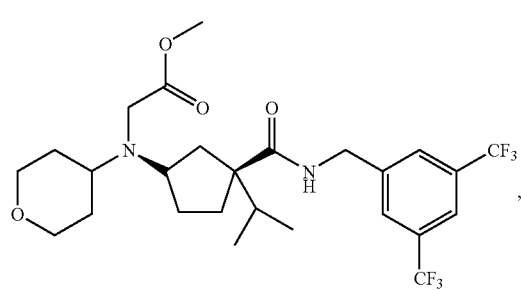
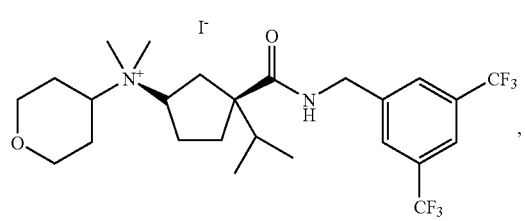
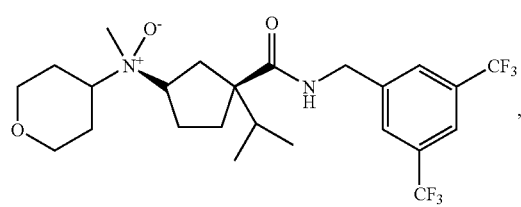
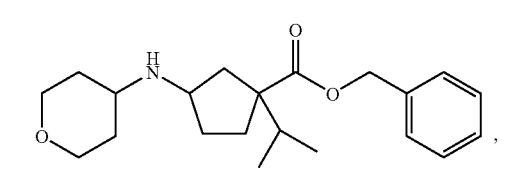
226
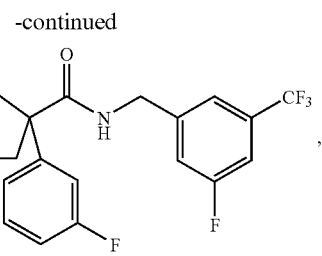
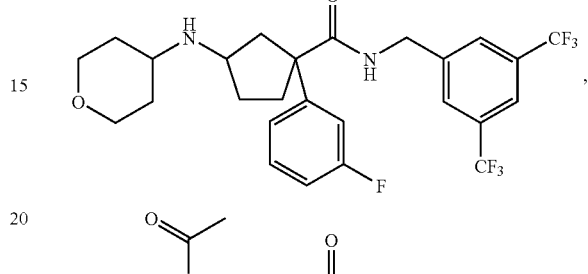
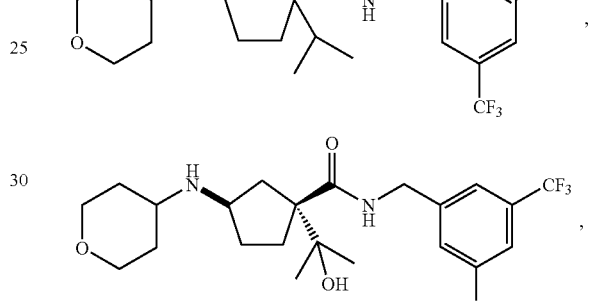
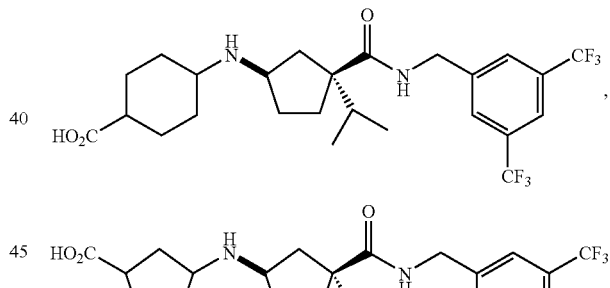
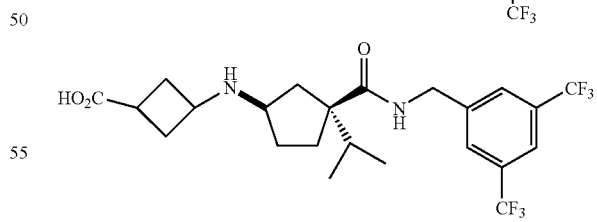
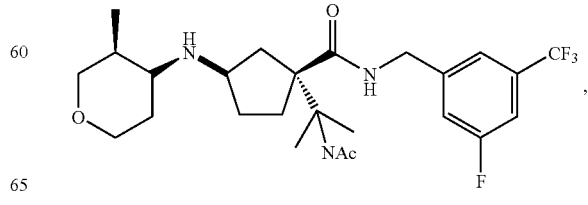

227
-continued
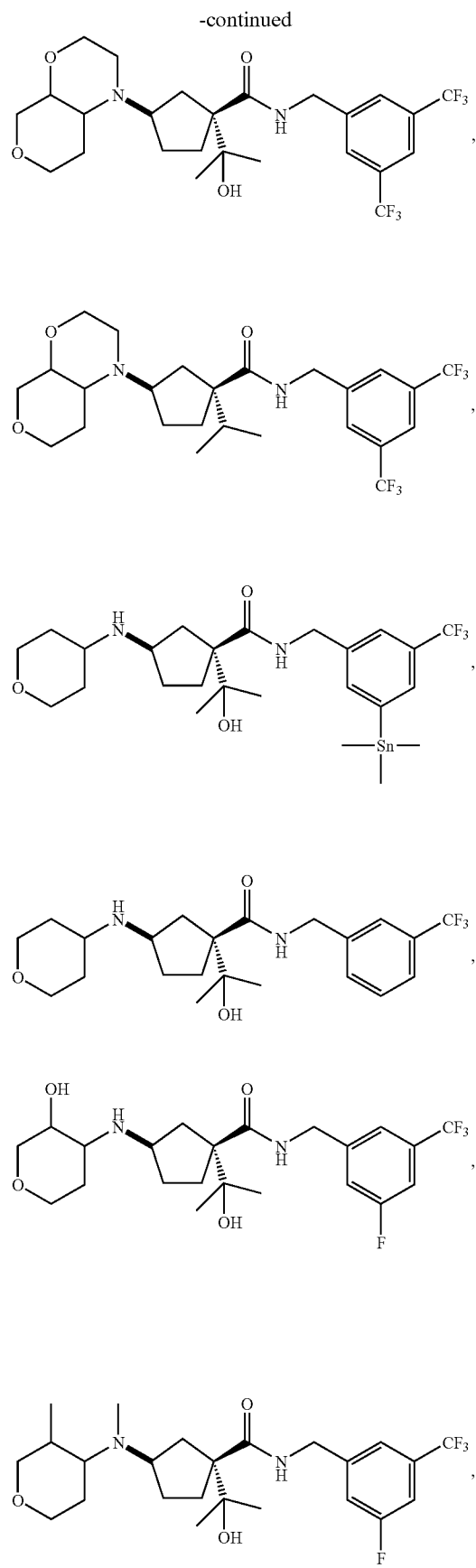
228
-continued
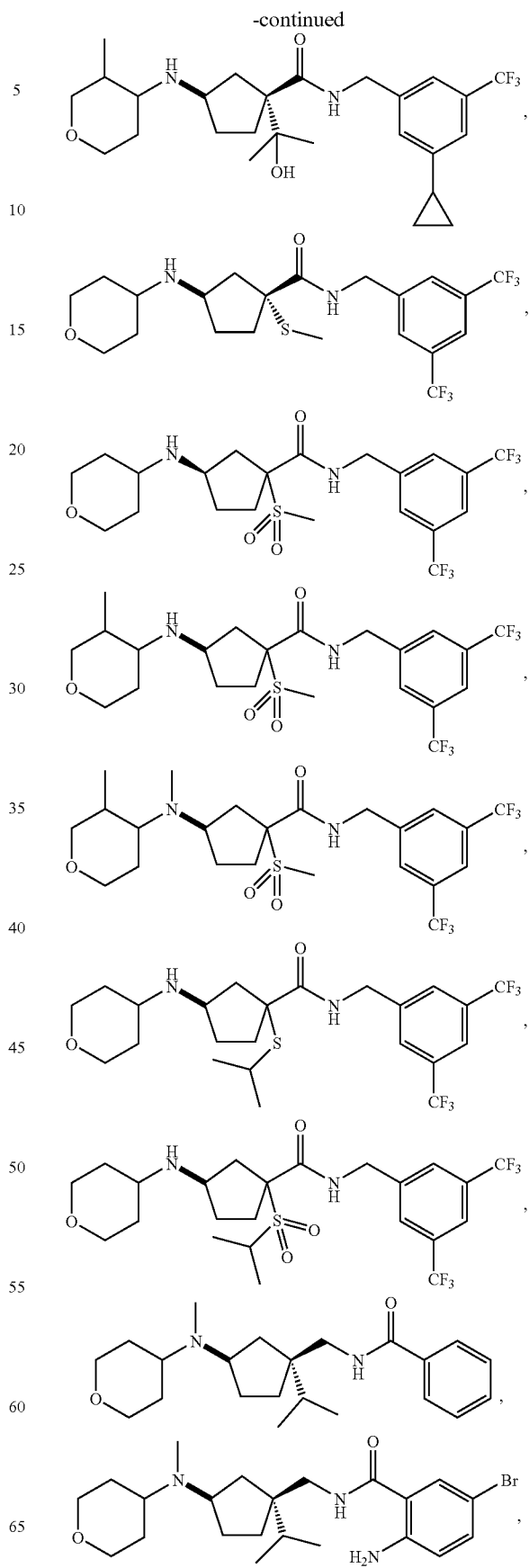

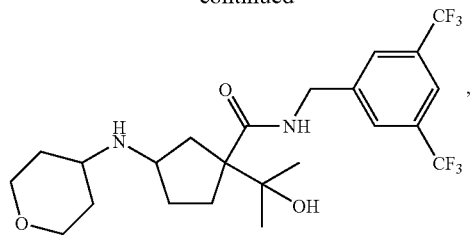
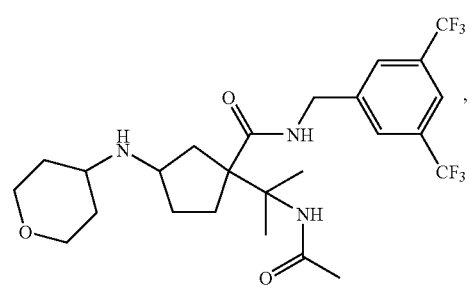
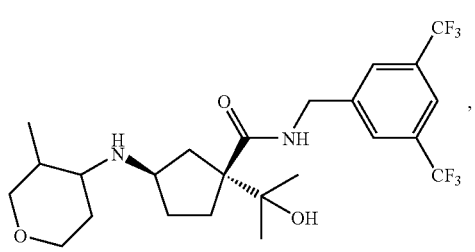
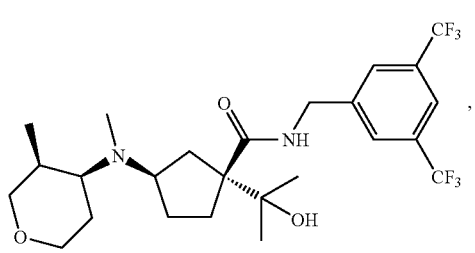
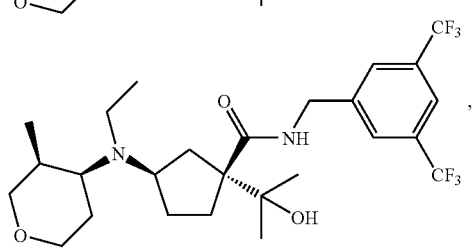
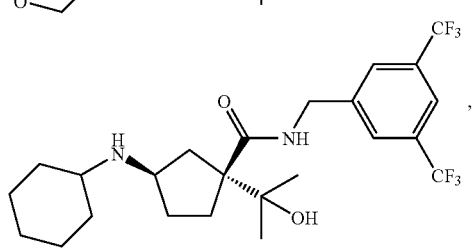
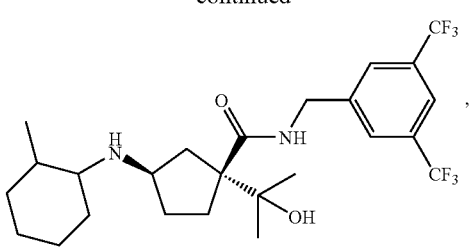
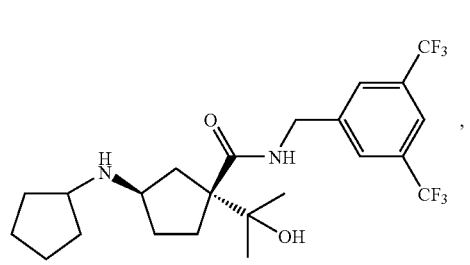
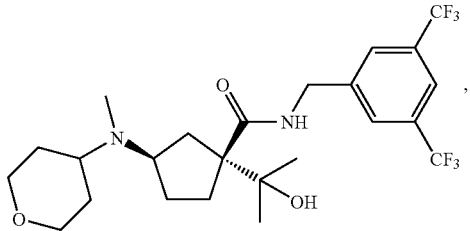
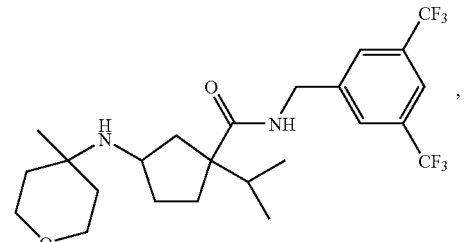
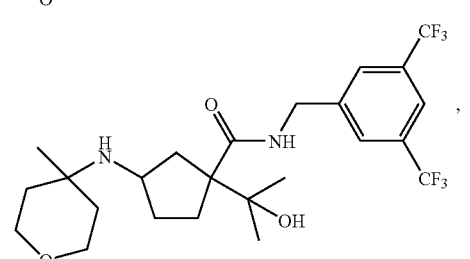
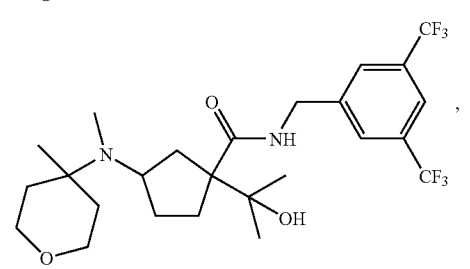

231
-continued
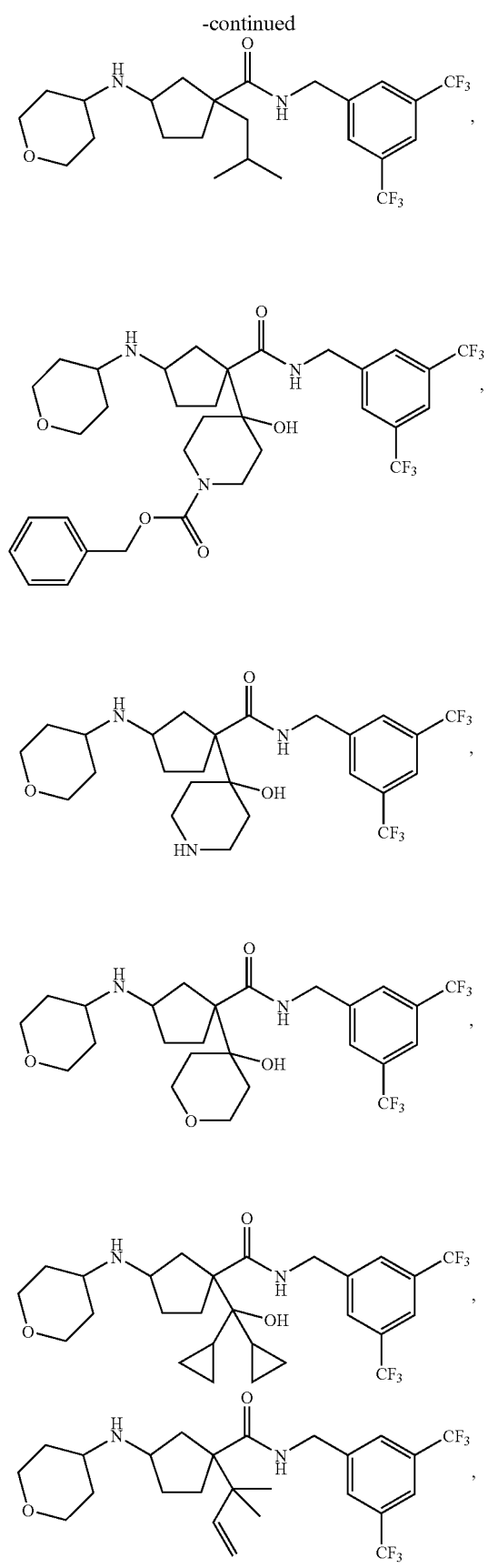
232
-continued
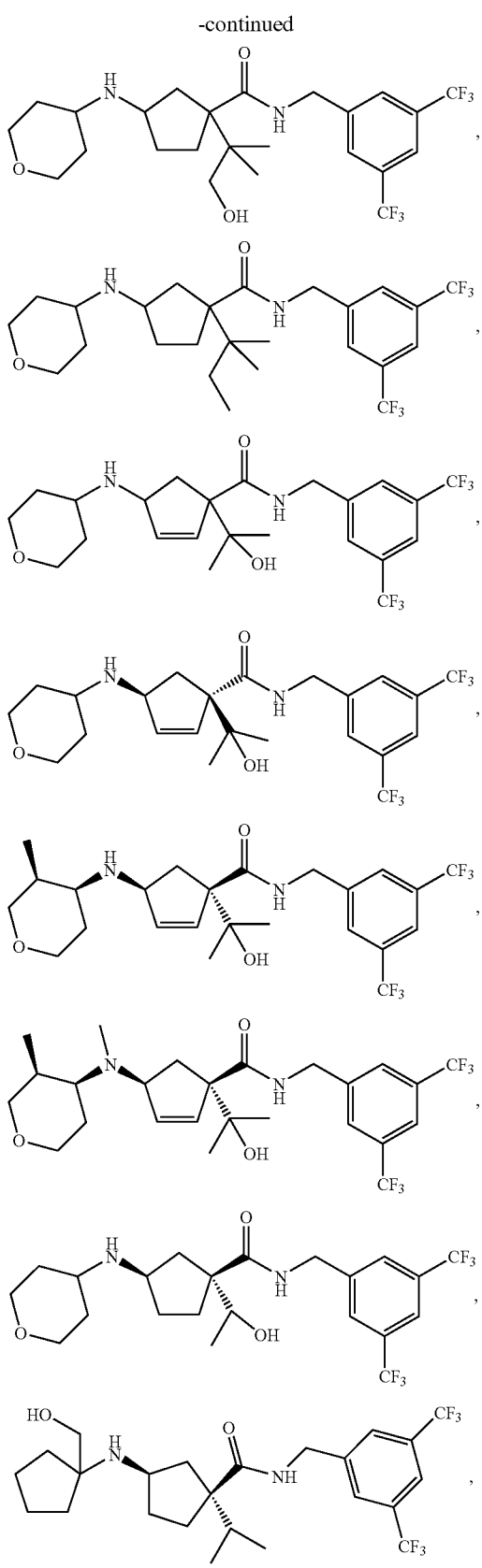

-continued
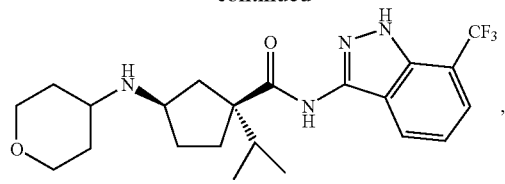
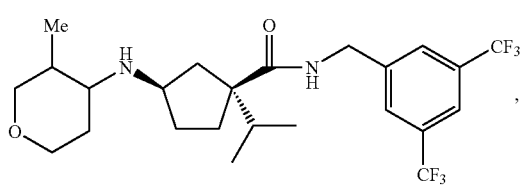
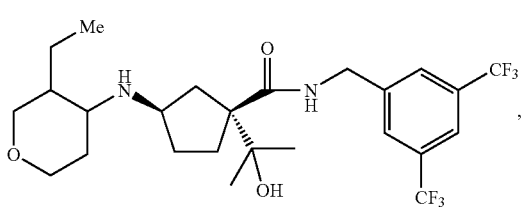
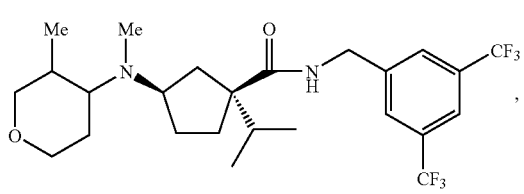
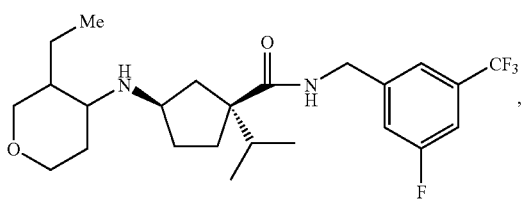
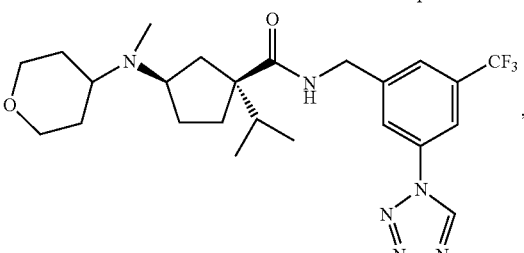
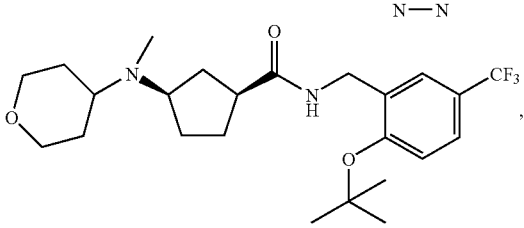
-continued
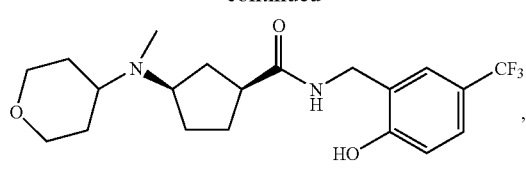
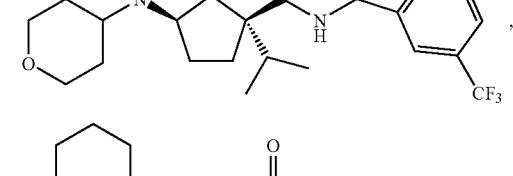
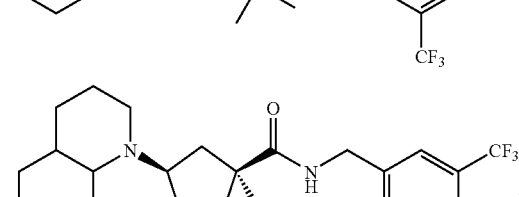
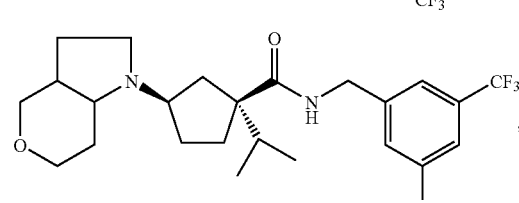
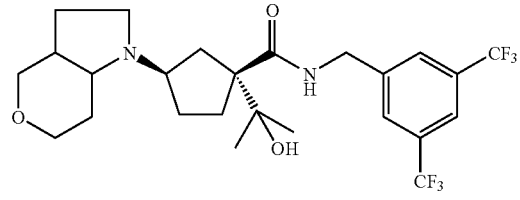
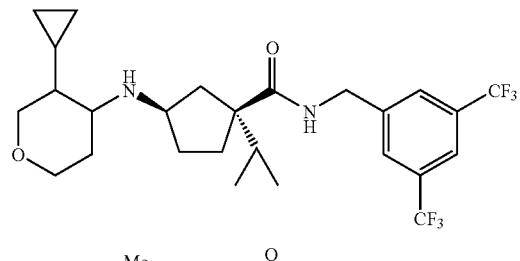
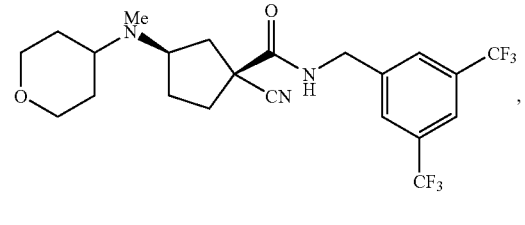

-continued
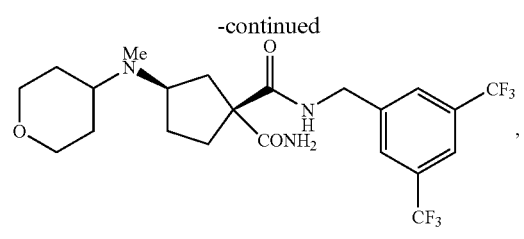
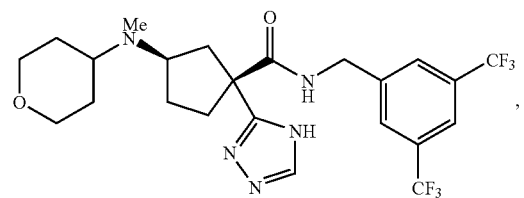
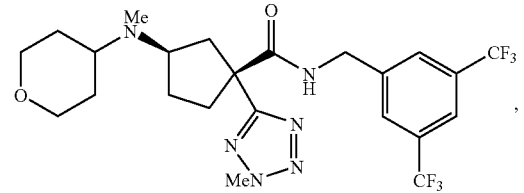
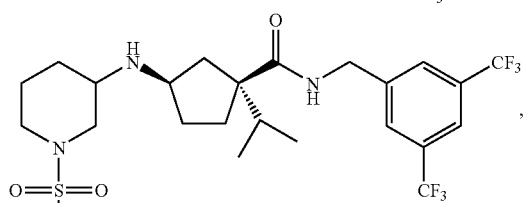
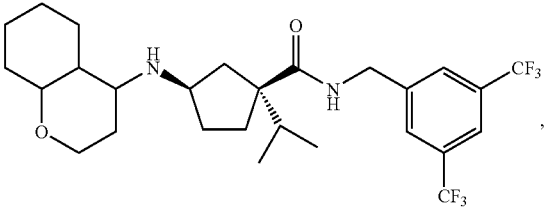
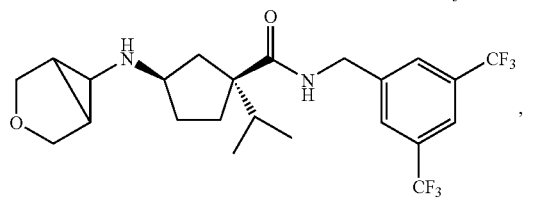
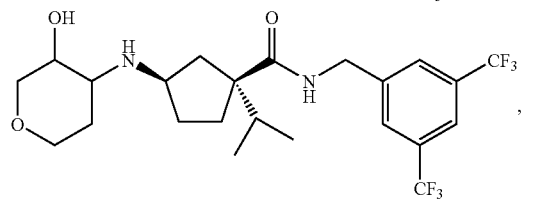
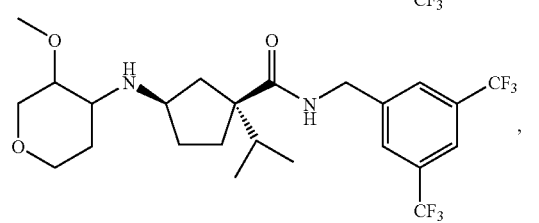
-continued
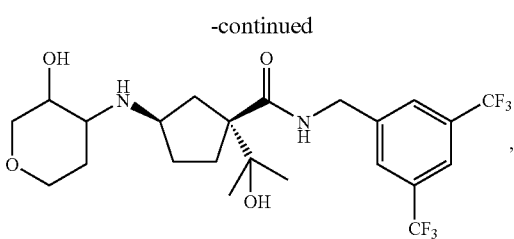
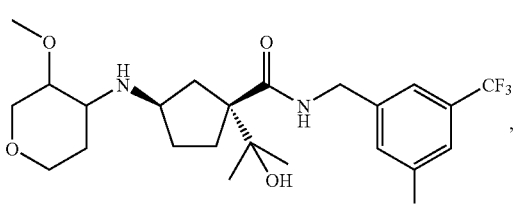
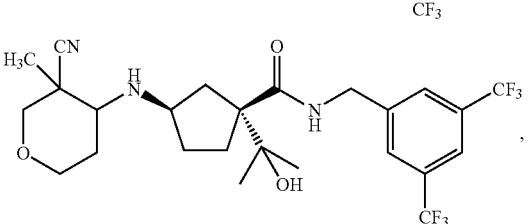
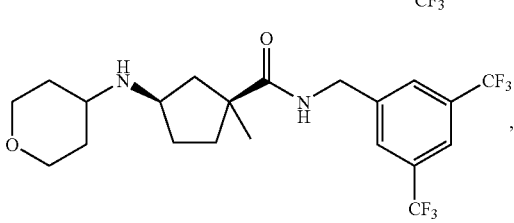
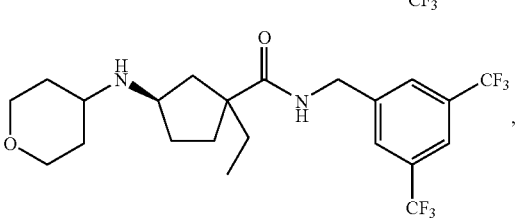
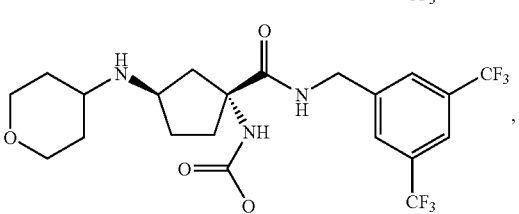
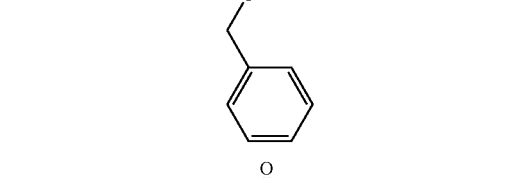
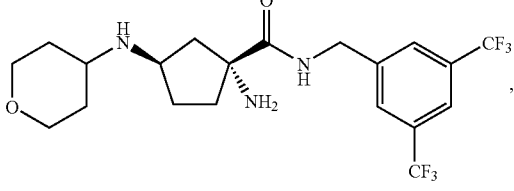

237
-continued
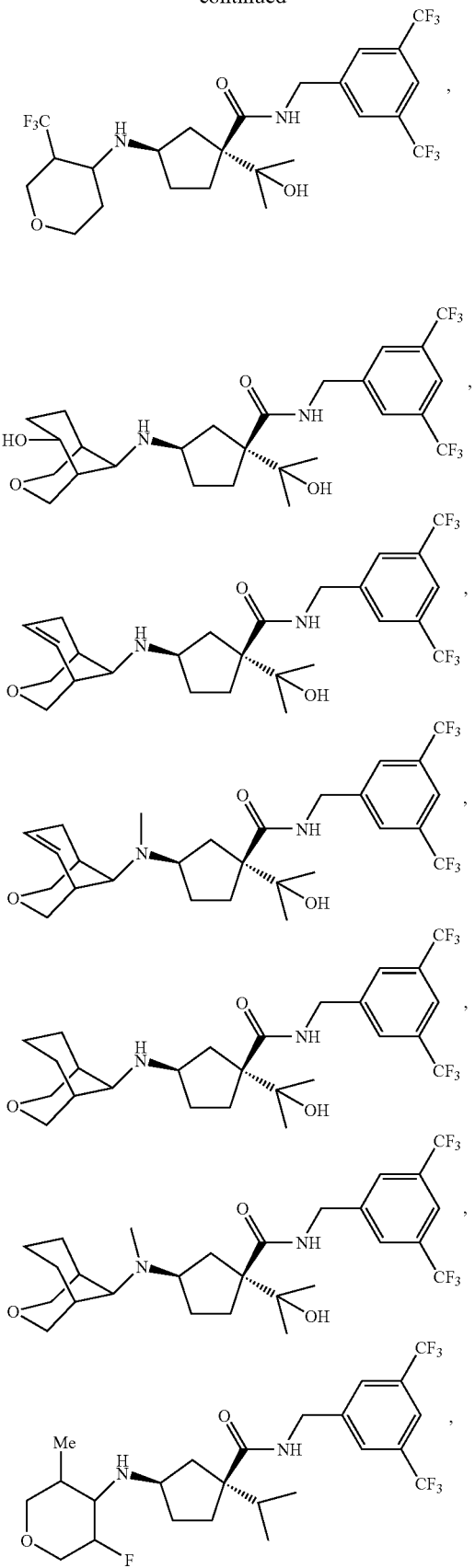
238
-continued
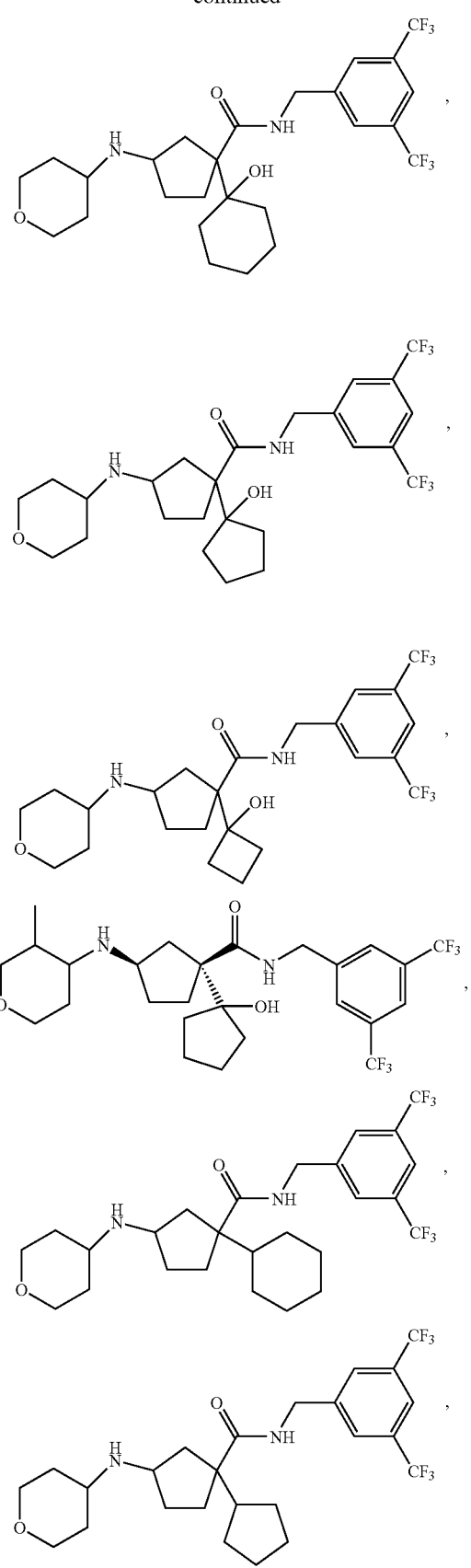

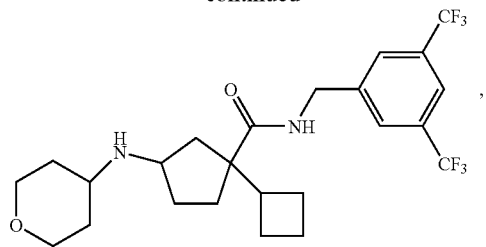
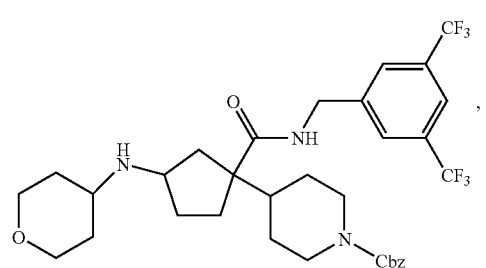
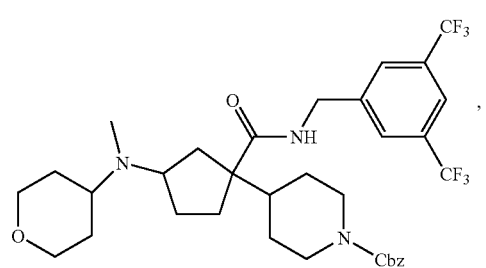
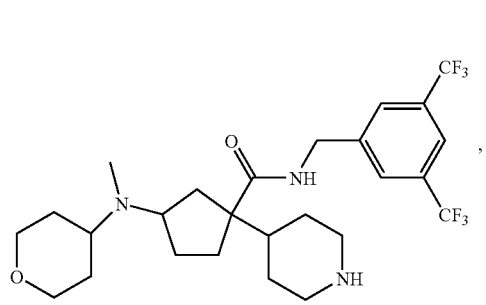
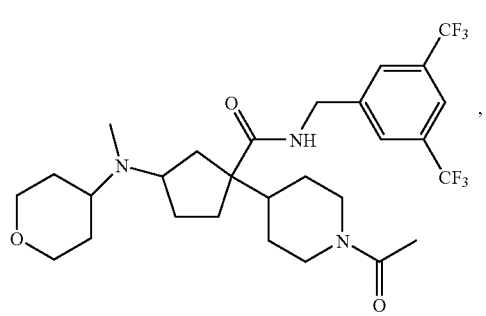
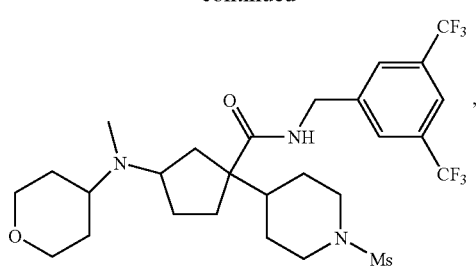
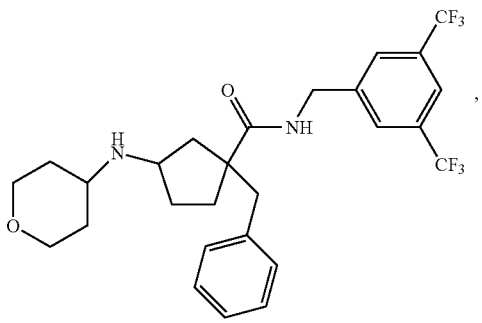
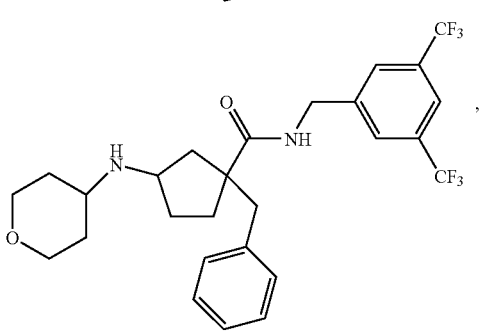
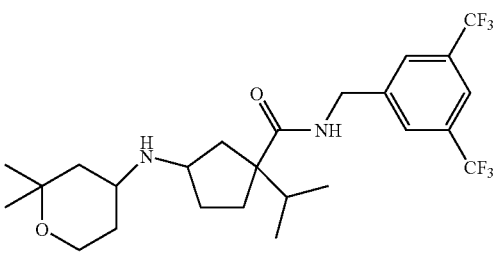
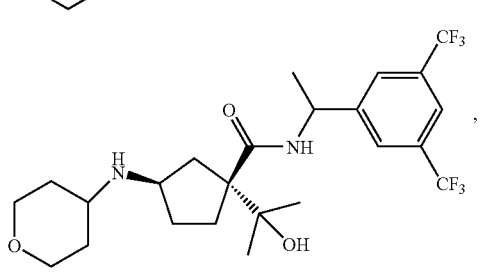
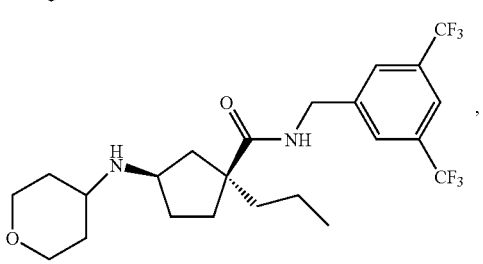

-continued
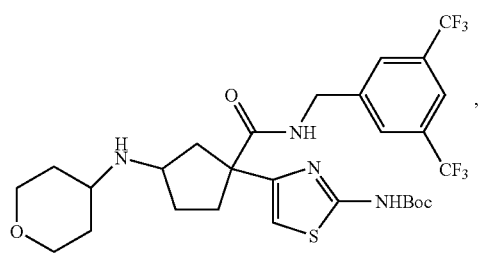
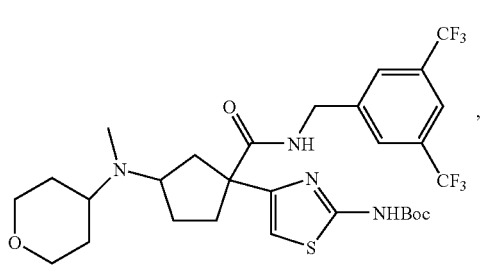
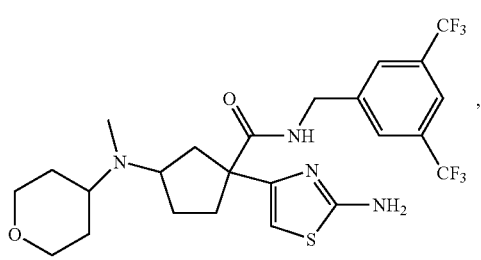
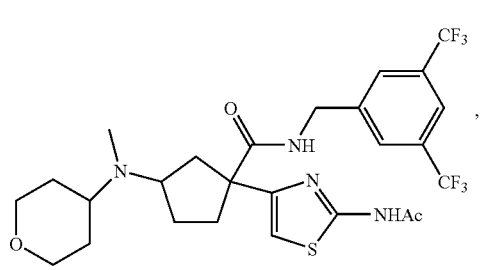
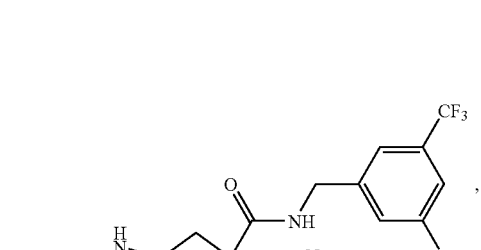
-continued
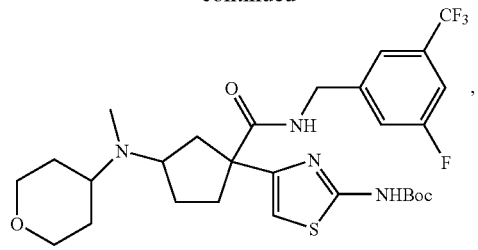
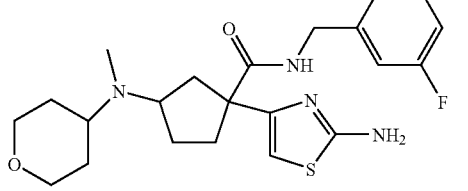
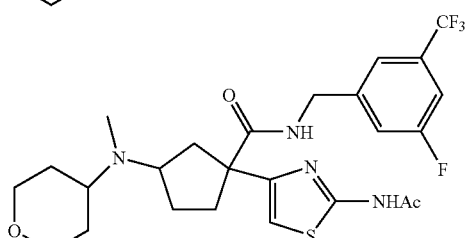
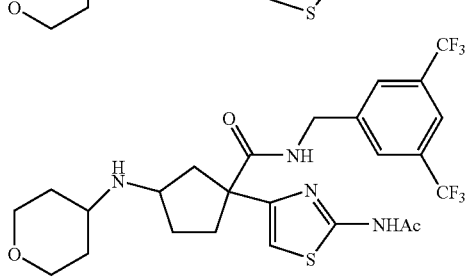
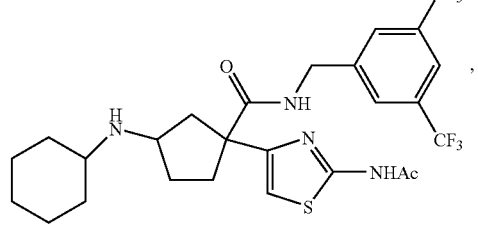
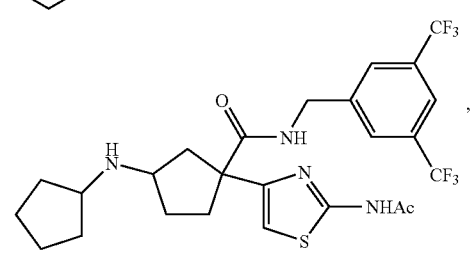
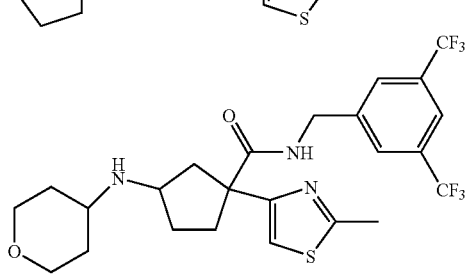

-continued
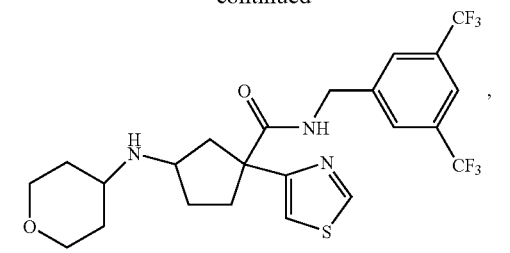
,
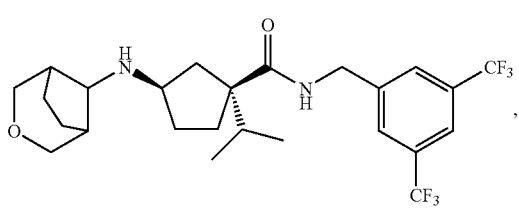
,
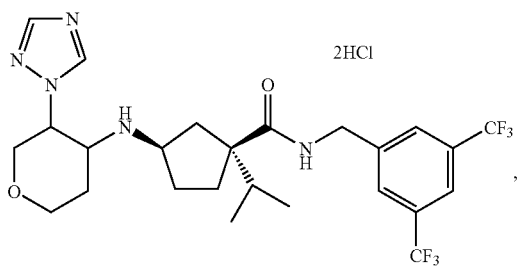
2HCl
,
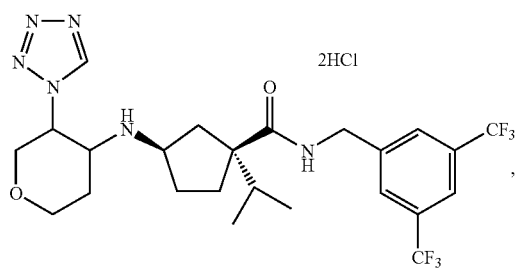
2HCl
,
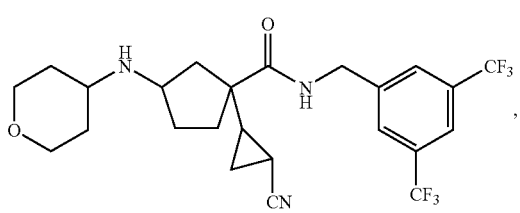
,
-continued
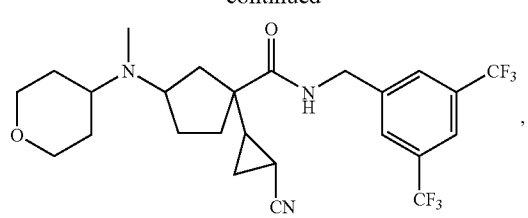
,
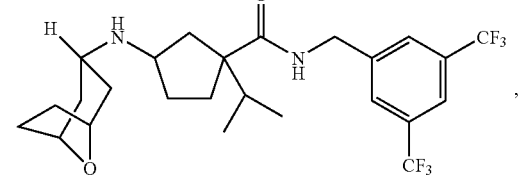
,
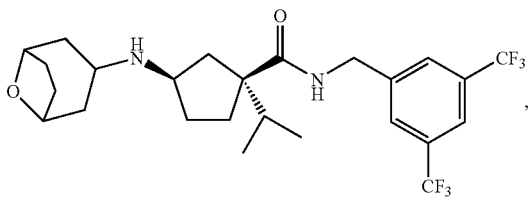
,
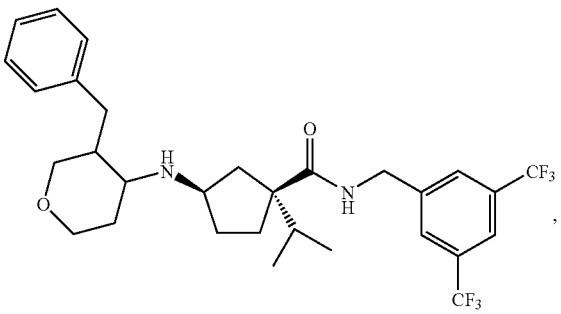
,
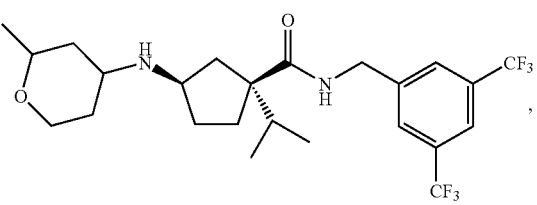
,
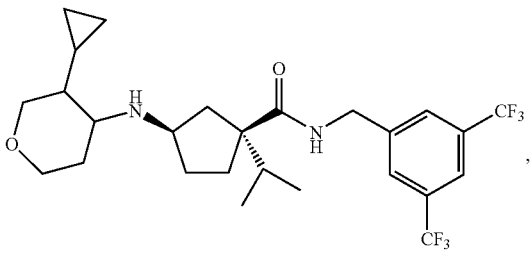
,
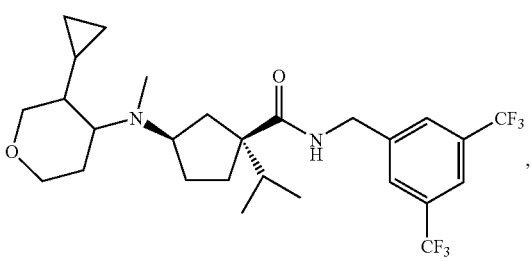
, -continued
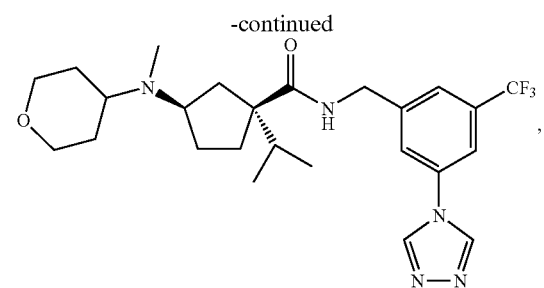
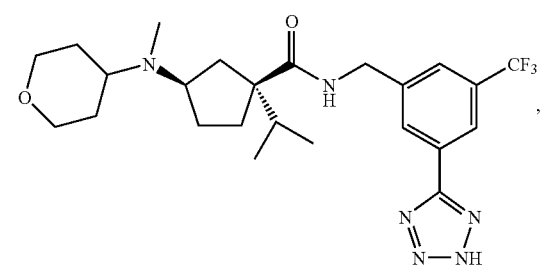
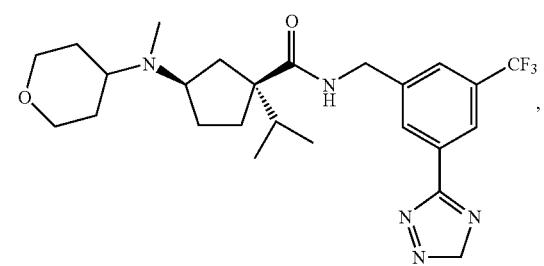
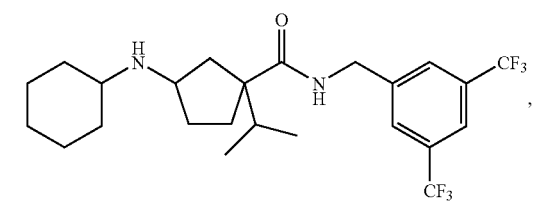
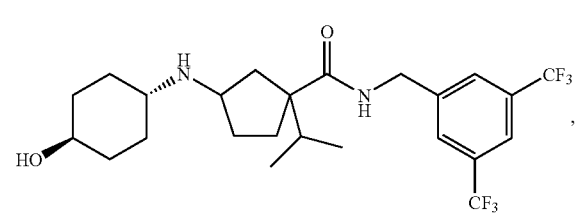
-continued
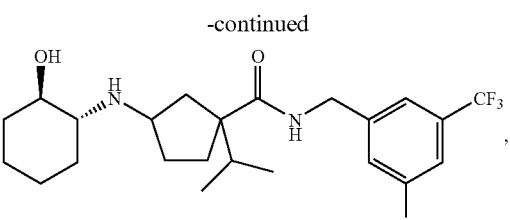
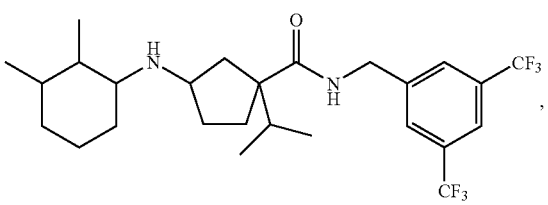
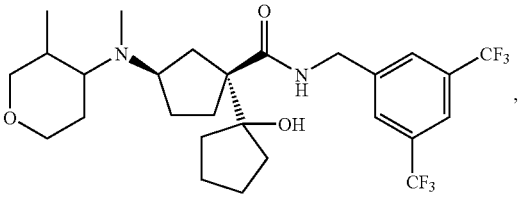
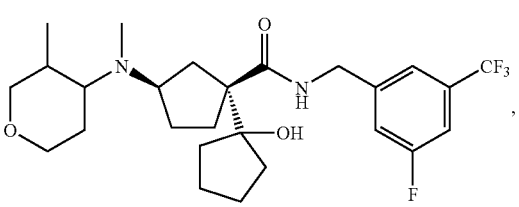
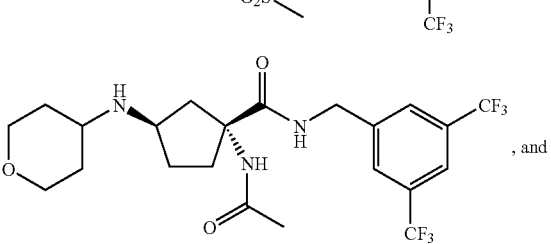

-continued

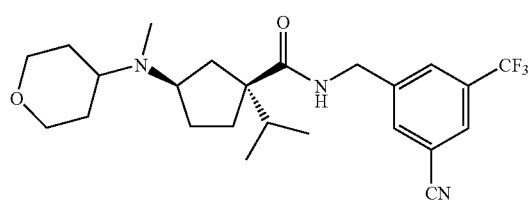

and pharmaceutically acceptable salts thereof and individual diastereomers thereof.

25. A compound of the formula:

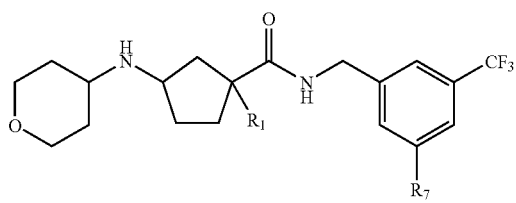

wherin $R_7$ is F or $CF_3$, and wherein $R^1$ is selected from:

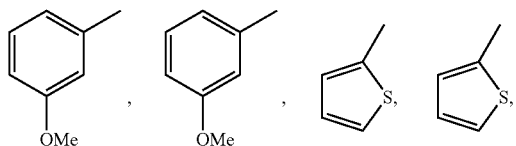

and pharmaceutically acceptable salts thereof and individual diastereomers thereof.

26. A compound of the formula:

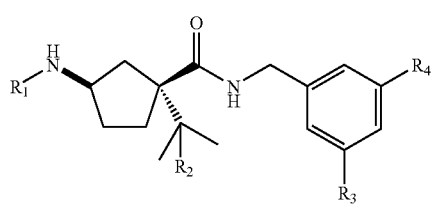

wherein $R_2$ is H or OH, wherein $R_3$ is F or $CF_3$, wherein $R_4$ is $CF_3$, Ph, $OCF_3$, Cl, or

and wherein $R_1$ is selected from:

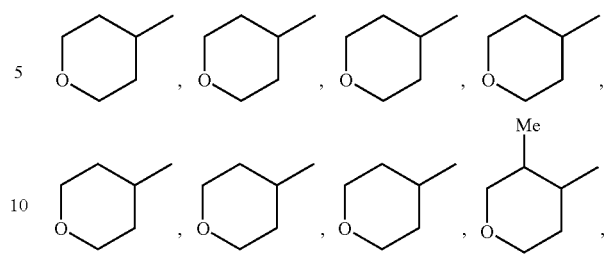

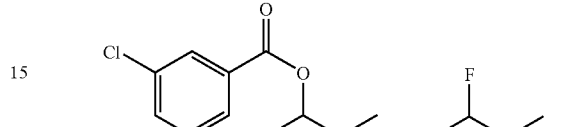

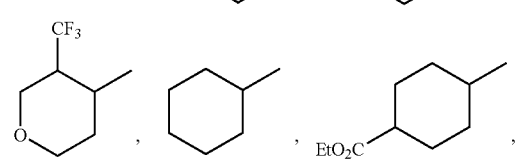

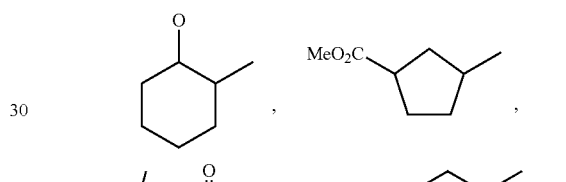

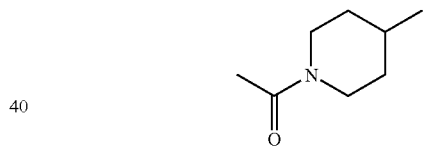

and pharmaceutically acceptable salts thereof and individual diastereomers thereof.

27. A compound of the formula:

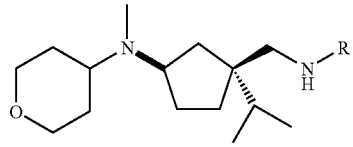

wherein R is selected from:

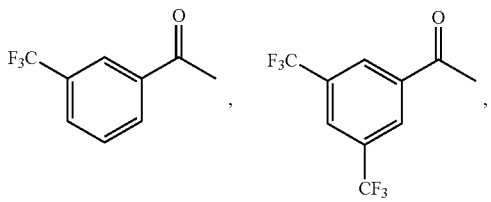

and pharmaceutically acceptable salts thereof and individual diastereomers thereof.
28. A compound of the formula:
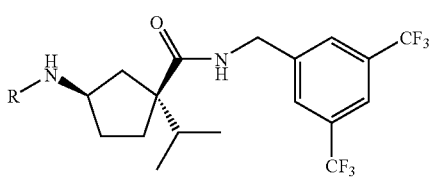
wherein R is selected from:
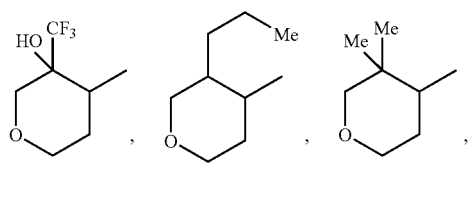
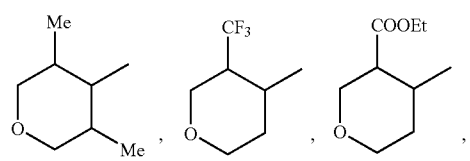
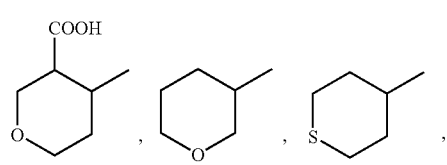
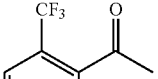
and pharmaceutically acceptable salts thereof and individual diastereomers thereof.
29. A compound of the formula:
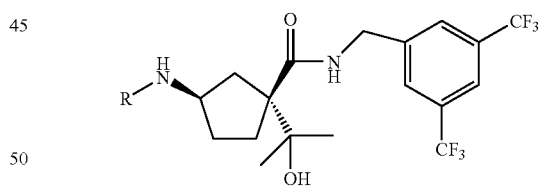
wherein R is selected from:
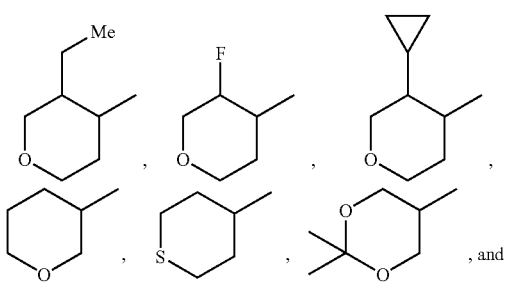

-continued

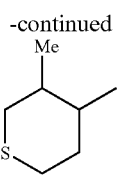

and pharmaceutically acceptable salts thereof and individual diastereomers thereof.

30. A compound of the formula:

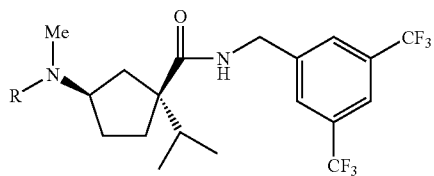

wherein R is selected from:

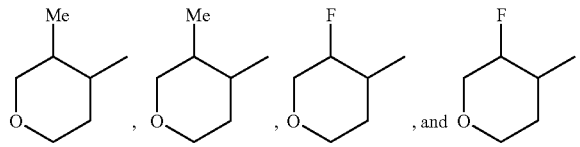

and pharmaceutically acceptable salts thereof and individual diastereomers thereof.

31. A pharmaceutical composition which comprises an inert carrier and the compound of claim 1, or a pharmaceutically acceptable salt thereof.

32. A method for treating, ameliorating or controlling an inflammatory or immunoregulatory disorder or disease which comprises administering to a patient in need thereof an effective amount of the compound of claim 1, or a pharmaceutically acceptable salt thereof.

33. A method for reducing the risk of an inflammatory or immunoregulatory disorder or disease which comprises administering to a patient in need thereof an effective amount of the compound of claim 1, or a pharmaceutically acceptable salt thereof.

34. A method for treating, ameliorating or controlling rheumatoid arthritis which comprises administering to a patient in need thereof an effective amount of the compound of claim 1, or a pharmaceutically acceptable salt thereof.

\* \* \* \* \*